US012459918B2

(12) United States Patent
Liu et al.

(10) Patent No.: US 12,459,918 B2
(45) Date of Patent: Nov. 4, 2025

(54) ISOQUINOLINONE DERIVATIVES SERVING AS ROCK PROTEIN KINASE INHIBITORS AND USE THEREOF

(71) Applicant: GUANGZHOU OCUSUN OPHTHALMIC BIOTECHNOLOGY CO., LTD., Guangzhou (CN)

(72) Inventors: Yizhi Liu, Guangzhou (CN); Yandong Wang, Guangzhou (CN); Lingyun Wu, Guangzhou (CN); Xu You, Guangzhou (CN); Zheming Xiao, Guangzhou (CN); Shuhui Chen, Guangzhou (CN)

(73) Assignee: GUANGZHOU OCUSUN OPTHALMIC BIOTECHNOLOGY CO., LTD., Guangzhou (CN)

( * ) Notice: Subject to any disclaimer, the term of this patent is extended or adjusted under 35 U.S.C. 154(b) by 988 days.

(21) Appl. No.: 17/621,502

(22) PCT Filed: Jun. 22, 2020

(86) PCT No.: PCT/CN2020/097503
§ 371 (c)(1),
(2) Date: Dec. 21, 2021

(87) PCT Pub. No.: WO2020/253882
PCT Pub. Date: Dec. 24, 2020

(65) Prior Publication Data

US 2023/0024516 A1 Jan. 26, 2023

(30) Foreign Application Priority Data

Jun. 21, 2019 (CN) ......................... 201910544202.5
Nov. 6, 2019 (CN) ......................... 201911078066.1

(51) Int. Cl.
*C07D 401/12* (2006.01)
*A61P 27/06* (2006.01)
*C07D 405/14* (2006.01)
*C07D 409/14* (2006.01)

(52) U.S. Cl.
CPC ............ *C07D 401/12* (2013.01); *A61P 27/06* (2018.01); *C07D 405/14* (2013.01); *C07D 409/14* (2013.01)

(58) Field of Classification Search
None
See application file for complete search history.

(56) References Cited

FOREIGN PATENT DOCUMENTS

| | | | |
|---|---|---|---|
| CN | 101253166 | A | 8/2008 |
| CN | 101622243 | A | 1/2010 |
| CN | 105085478 | A | 11/2015 |
| CN | 105085525 | A | 11/2015 |
| EP | 1818329 | A1 | 8/2007 |
| JP | S62111981 | A | 5/1987 |
| JP | 2006290827 | A | 10/2006 |
| JP | 2017513919 | A | 6/2017 |
| WO | 2004106325 | A1 | 12/2004 |
| WO | 2022135421 | A1 | 6/2022 |

OTHER PUBLICATIONS

Chemical Abstract Registry No. 928706-06-3, indexed in the Registry File on STN CAS Online Mar. 29, 2007.*
International Search Report and Written Opinion for PCT/CN2020/097503, pp. 1-6. Mailing date of Search Report, Sep. 10, 2020.

* cited by examiner

*Primary Examiner* — Po-Chih Chen
(74) *Attorney, Agent, or Firm* — BOND, SCHOENECK & KING, PLLC; George R. McGuire

(57) ABSTRACT

Disclosed are a series of isoquinolone derivatives as ROCK protein kinase inhibitors and uses thereof in preparing medicaments for ROCK protein kinase inhibitor-related glaucoma or ocular hypertension diseases. Specially, disclosed are a compound of formula (I), an isomer thereof or a pharmaceutically acceptable salt thereof.

(I)

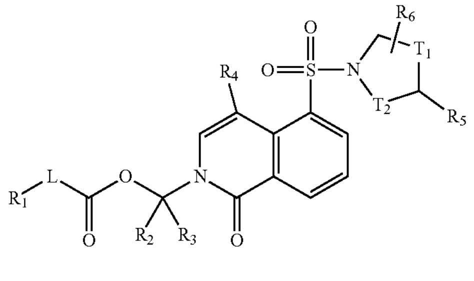

25 Claims, No Drawings

ISOQUINOLINONE DERIVATIVES SERVING AS ROCK PROTEIN KINASE INHIBITORS AND USE THEREOF

The present application claims the following priorities: This is a National Stage Application filed under 35 U.S.C. 371 based on International Patent Application No. PCT/CN2020/097503, filed on Jun. 22, 2020, which claims priority to Chinese Patent Application Nos. 201910544202.5 filed Jun. 21, 2019, and 201911078066.1 filed Nov. 6, 2019.

TECHNICAL FIELD

The present disclosure relates to a series of isoquinolone derivatives as ROCK protein kinase inhibitors and uses thereof in preparation of ROCK protein kinase inhibitor-related medicaments for treating glaucoma or ocular hypertension, and particularly relates to a compound of formula (I), an isomer thereof or a pharmaceutically acceptable salt thereof.

BACKGROUND

RHO associated kinase (ROCK), belonging to a serine/threonine protein kinase, is a downstream target molecule of RHO and is widely expressed in human body. ROCK is involved in regulation of myosin light chain (MLC) and is suitable for treatment of vasodilation; ROCK kinase can also act on trabecular outflow tract cells to relax trabecular cells and reduce aqueous outflow resistance. Recent studies have shown that ROCK kinase inhibitors can also promote damage repair of corneal endothelial cells and prevent fibrosis, showing great application prospects.

Isoquinoline sulfonamide compounds are an important type of ROCK kinase inhibitors. The currently launched Fasudil and K-115 (WO2006057397A1) are both isoquinoline sulfonamide compounds. Wherein, Fasudil, as a new drug with extensive pharmacological effects, is a RHO kinase inhibitor, which dilates blood vessels by increasing the activity of myosin light chain phosphatase, reduces the tension of endothelial cells, improves brain tissue microcirculation, but does not induce or aggravate cerebral steal, and at the same time can antagonize the inflammatory factor, protect the nerve against apoptosis and promote the nerve regeneration. K-115 has a wide range of approved and potential applications, including treatment of glaucoma, ocular hypertension, diabetic retinal injury complications, age-related macular degeneration, corneal injury, cataract and glaucoma recovery after surgery and so on, and at the same time may be further extended to systemic drugs.

WO2007026664A1 reported a series of compounds with ROCK kinase inhibition effects, for example, control compound 1 and control compound 2. The series of compounds have good enzyme activity, but need to be improved on membrane permeability, pharmacokinetics, druggability and other aspects. The present disclosure reports a kind of structurally modified similar compounds with the properties significantly improved.

K-115

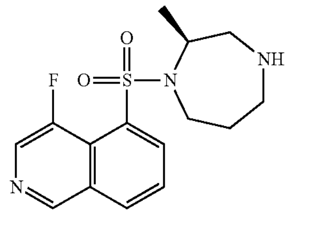

-continued

Control compound 1

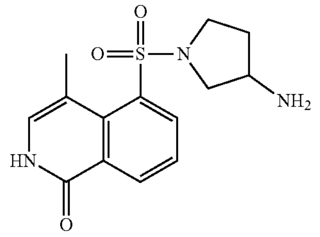

Control compound 2

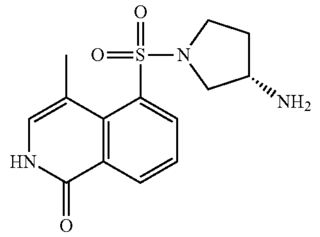

SUMMARY

The present disclosure provides a compound of formula (I), an isomer thereof or a pharmaceutically acceptable salt thereof, (I)

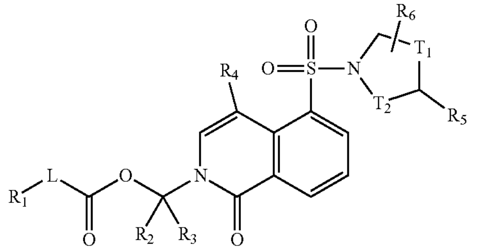

wherein, $T_1$ is $-(CH_2)_n-$;

$T_2$ is selected from a group consisting of $-(CH_2)_m-$ and $-C(R_7)(R_8)-$;

$R_1$ is selected from a group consisting of $C_{1-16}$ alkyl, phenyl, $C_{3-7}$ cycloalkyl, 3-8 membered heterocycloalkyl and 5-10 membered heteroaryl, wherein, each of $C_{1-16}$ alkyl, phenyl, $C_{3-7}$ cycloalkyl, 3-8 membered heterocycloalkyl and 5-10 membered heteroaryl is optionally substituted by 1, 2 or 3 $R_a$;

each of $R_2$ and $R_3$ is independently selected from a group consisting of H, F, Cl, Br, I, OH, $NH_2$, CN and $C_{1-3}$ alkyl;

$R_4$ is selected from a group consisting of H, F, Cl, Br, I, OH, $NH_2$, CN, and $C_{1-3}$ alkyl which is optionally substituted by 1, 2 or 3 $R_b$;

$R_5$ is $NR_9R_{10}$;

$R_6$ is selected from a group consisting of H, F, Cl, Br, I, OH, $NH_2$, CN and $C_{1-3}$ alkyl; each of $R_7$ and $R_8$ is independently selected from a group consisting of H, F, Cl, Br, I, OH, $NH_2$, CN, and $C_{1-3}$ alkyl which is optionally substituted by 1, 2 or 3 $R_c$;

or, $R_7$ and $R_8$ together with the atom that they attached to form a $C_{3-5}$ cycloalkyl which is optionally substituted by 1, 2 or 3 $R_d$;

each of $R_9$ and $R_{10}$ is independently selected from a group consisting of H, and $C_{1-3}$ alkyl which is optionally substituted by 1, 2 or 3 $R_e$;

L is selected from a group consisting of a single bond, —O— and —$NR_{11}$—;

$R_{11}$ is selected from a group consisting of H and $C_{1-3}$ alkyl;

n is selected from a group consisting of 0, 1 and 2;

m is selected from a group consisting of 0, 1, 2 and 3;

$R_a$ is selected from a group consisting of F, Cl, Br, I, OH, $NH_2$, CN, $C_{1-3}$ alkyl and $C_{1-3}$ alkoxy, wherein each of $C_{1-3}$ alkyl and $C_{1-3}$ alkoxy is optionally substituted by 1, 2 or 3 R;

each of $R_b$, $R_c$, $R_d$ and $R_e$ is independently selected from a group consisting of H, F, Cl, Br, I, OH, $NH_2$, CN and $C_{1-3}$ alkyl;

R is selected from a group consisting of F, Cl, Br, I, OH, $NH_2$, CN and $CH_3$;

wherein, each of the 3-8 membered heterocycloalkyl and 5-10 membered heteroaryl is independently include 1, 2, 3 or 4 heteroatom(s) or heteroatom group(s) which is/are independently selected from a group consisting of —NH—, —O—, —S— and N.

The present disclosure provides a compound of formula (I) or a pharmaceutically acceptable salt thereof, (I)

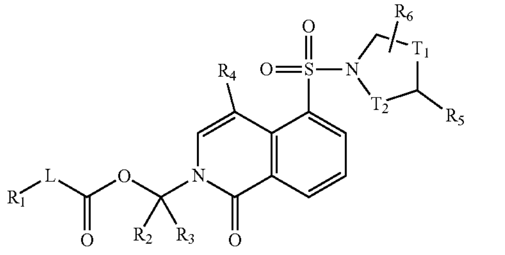

wherein,

T1 is —(CH2)n-;

T2 is selected from a group consisting of —(CH2)m- and —C(R7)(R8)-;

R1 is selected from a group consisting of C1-16 alkyl, phenyl, C3-7 cycloalkyl, 3-8 membered heterocycloalkyl and 5-10 membered heteroaryl, wherein, each of C1-16 alkyl, phenyl, C3-7 cycloalkyl, 3-8 membered heterocycloalkyl and 5-10 membered heteroaryl is optionally substituted by 1, 2 or 3 Ra;

each of R2 and R3 is independently selected from a group consisting of H, F, Cl, Br, I, OH, NH2, CN and C1-3 alkyl;

R4 is selected from a group consisting of H, F, Cl, Br, I, OH, NH2, CN, and C1-3 alkyl which is optionally substituted by 1, 2 or 3 Rb;

R5 is NR9R10;

R6 is selected from a group consisting of F, Cl, Br, I, OH, NH2, CN and C1-3 alkyl;

each of R7 and R8 is independently selected from a group consisting of H, F, Cl, Br, I, OH, NH2, CN, and C1-3 alkyl which is optionally substituted by 1, 2 or 3 Rc;

or, R7 and R8 together with the atom that they attached to form a C3-5 cycloalkyl which is optionally substituted by 1, 2 or 3 Rd;

each of R9 and R10 is independently selected from a group consisting of H, and $C_{1-3}$ alkyl which is optionally substituted by 1, 2 or 3 $R_e$;

L is selected from a group consisting of a single bond, —O— and —NR11-;

R11 is selected from a group consisting of H and $C_{1-3}$ alkyl;

n is selected from a group consisting of 0, 1 and 2;

m is selected from a group consisting of 0, 1, 2 and 3;

Ra is selected from a group consisting of H, F, Cl, Br, I, OH, NH2, CN, C1-3 alkyl and C1-3 alkoxy, wherein each of C1-3 alkyl and C1-3 alkoxy is optionally substituted by 1, 2 or 3 R;

each of Rb, Rc, Rd and Re is independently selected from a group consisting of H, F, Cl, Br, I, OH, NH2, CN and C1-3 alkyl;

R is selected from a group consisting of F, Cl, Br, I, OH, NH2, CN and CH3;

wherein, each of the 3-8 membered heterocycloalkyl and 5-10 membered heteroaryl is independently include 1, 2, 3 or 4 heteroatom(s) or heteroatom group(s) which is/are independently selected from a group consisting of —NH—, —O—, —S— and N.

In some embodiments of the present disclosure, Ra is selected from a group consisting of F, Cl, Br, I, OH, NH2, CN, CH3, CF3, CH2F, CHF2, CH2CH3 and OCH3, other variables are as defined in the present disclosure.

In some embodiments of the present disclosure, Ra is selected from a group consisting of H, F, Cl, Br, I, OH, NH2, CN, CH3, CF3, CH2F, CHF2, CH2CH3 and OCH3, other variables are as defined in the present disclosure.

In some embodiments of the present disclosure, R1 is selected from a group consisting of C1-12 alkyl, phenyl, cyclobutyl, cyclopentyl, cyclohexyl, tetrahydrofuranyl, tetrahydropyranyl, piperidinyl, thienyl, furyl, pyrrolyl and benzofuryl, wherein, each of C1-12 alkyl, phenyl, cyclobutyl, cyclopentyl, cyclohexyl, tetrahydrofuranyl, tetrahydropyranyl, piperidinyl, thienyl, furyl, pyrrolyl and benzofuryl is optionally substituted by 1, 2 or 3 Ra, other variables are as defined in the present disclosure.

In some embodiments of the present disclosure, $R_1$ is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$,

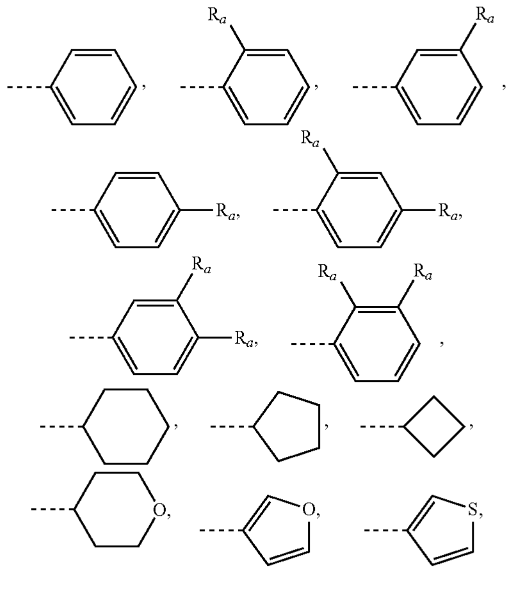

-continued

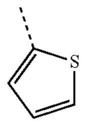

and

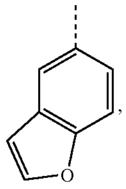

other variables are as defined in the present disclosure.

In some embodiments of the present disclosure, $R_1$ is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$,

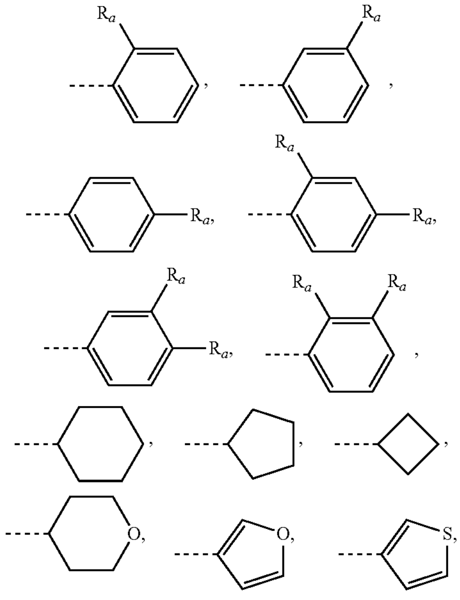

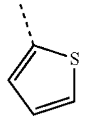

and

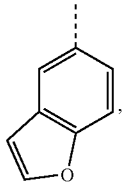

other variables are as defined in the present disclosure.

In some embodiments of the present disclosure, $R_1$ is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$,

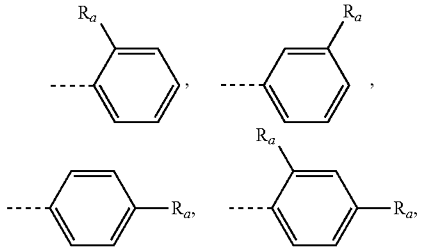

-continued

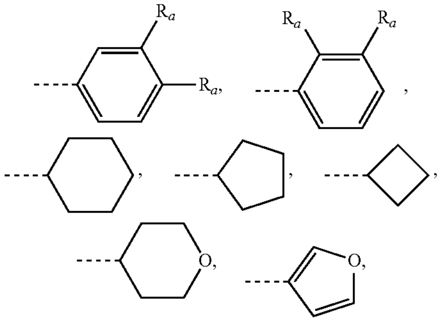

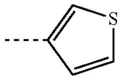

and

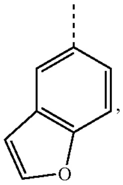

other variables are as defined in the present disclosure.

In some embodiments of the present disclosure, $R_1$ is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$,

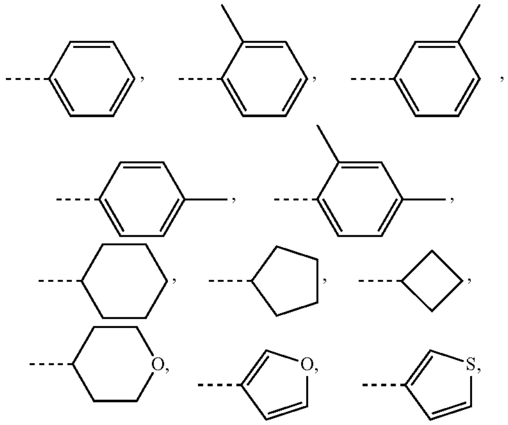

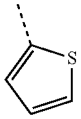

and

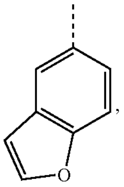

other variables are as defined in the present disclosure.

In some embodiments of the present disclosure, $R_1$ is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$,

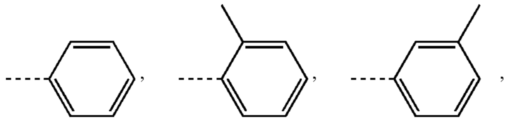

-continued

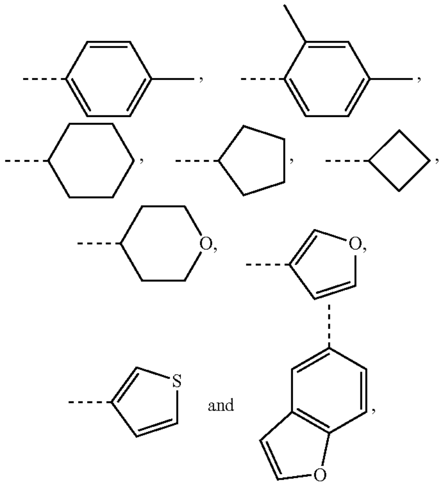

other variables are as defined in the present disclosure.

In some embodiments of the present disclosure, each of $R_2$ and $R_3$ is independently selected from a group consisting of H, F, Cl, Br, I, OH and $NH_2$, other variables are as defined in the present disclosure.

In some embodiments of the present disclosure, each of R2 and R3 is independently selected from a group consisting of H, F, Cl, Br, I, OH, NH2, other variables are as defined in the present disclosure.

In some embodiments of the present disclosure, R4 is selected from a group consisting of H, F, Cl, Br, I, OH, NH2, CN, CH3 and CH2CH3, other variables are as defined in the present disclosure.

In some embodiments of the present disclosure, each of R9 and R10 is independently selected from a group consisting of H, CH3 and CH2CH3, other variables are as defined in the present disclosure.

In some embodiments of the present disclosure, R5 is selected from a group consisting of NH2, NH(CH3) and N(CH3)2, other variables are as defined in the present disclosure.

In some embodiments of the present disclosure, R6 is selected from a group consisting of H, F, Cl, Br, I, OH, NH2, CN and CH3, other variables are as defined in the present disclosure.

In some embodiments of the present disclosure, R6 is selected from a group consisting of F, Cl, Br, I, OH, NH2, CN and CH3, other variables are as defined in the present disclosure.

In some embodiments of the present disclosure, each of R7 and R8 is independently selected from a group consisting of F, Cl, Br, I, OH, NH2, CN and CH3, other variables are as defined in the present disclosure.

In some embodiments of the present disclosure, each of $R_7$ and $R_8$ is independently selected from a group consisting of H, F, Cl, Br, I, OH, $NH_2$, CN and $CH_3$, other variables are as defined in the present disclosure.

In some embodiments of the present disclosure, $R_7$ and $R_8$ together with the atom that they attached to form a cyclopropyl which is optionally substituted by 1, 2 or 3 Rd, other variables are as defined in the present disclosure.

In some embodiments of the present disclosure, R7 and R8 together with the atom that they attached to form a cyclopropyl, other variables are as defined in the present disclosure.

In some embodiments of the present disclosure, L is selected from a group consisting of a single bond, —O—, —NH— and —N(CH3)-, other variables are as defined in the present disclosure.

In some embodiments of the present disclosure, T2 is selected from a group consisting of —$CH_2$—, —$(CH_2)_2$— and

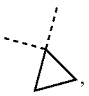

other variables are as defined in the present disclosure.

In some embodiments of the present disclosure, the structure unit

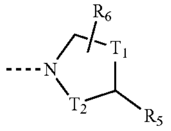

is selected from a group consisting of

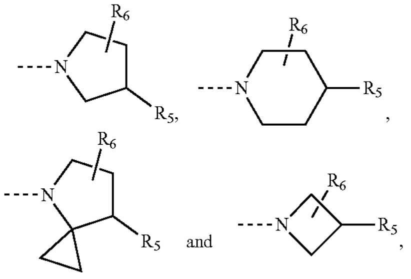

other variables are as defined in the present disclosure.

In some embodiments of the present disclosure, the structure unit

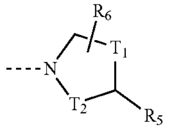

is selected from a group consisting of

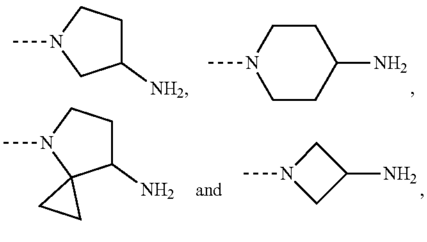

other variables are as defined in the present disclosure.

In some embodiments of the present disclosure, the structure unit

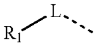

is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$, $OCH_3$, $OCH_2CH_3$, $O(CH_2)_2CH_3$, $O(CH_2)_3CH_3$, $(CH_2)_4CH_3$, $O(CH_2)_5CH_3$, $O(CH_2)_6CH_3$, $OCH(CH_3)_2$, $OC(CH_3)_3$, $N(CH_3)_2$,

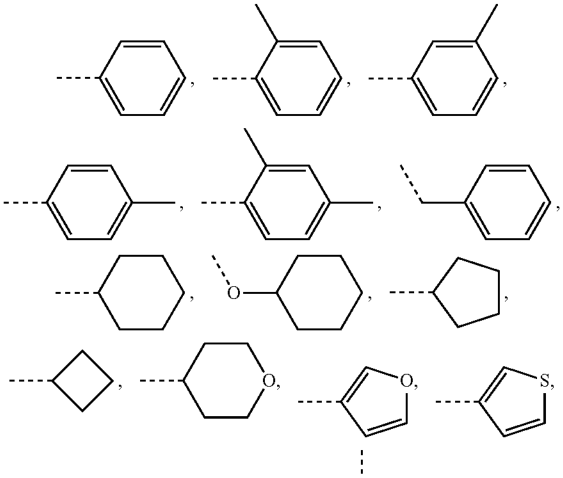

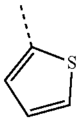 and 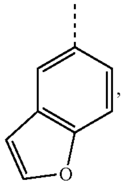

other variables are as defined in the present disclosure.

In some embodiments of the present disclosure, the structure unit

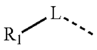

is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$, $OCH_3$, $OCH_2CH_3$, $O(CH_2)_2$, $CH_3$, $O(CH_2)_3$, $CH_3$, $O(CH_2)_4CH_3$, $O(CH_2)_5CH_3$, $O(CH_2)_6CH_3$, $OCH(CH_3)_2$, $OC(CH_3)_3$, $N(CH_3)_2$,

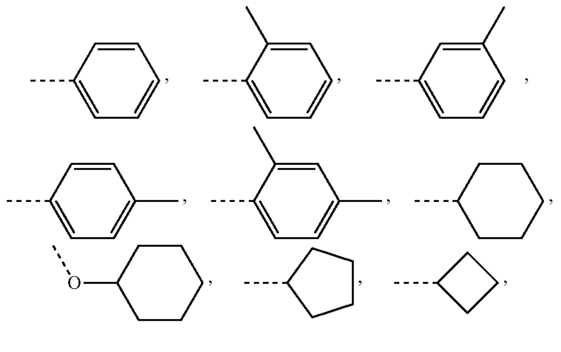

-continued

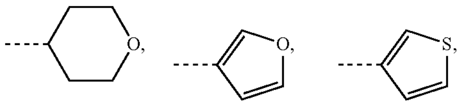

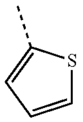 and 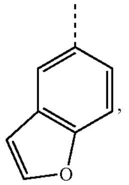

other variables are as defined in the present disclosure.

In some embodiments of the present disclosure, the structure unit

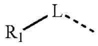

is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$, $OCH_3$, $OCH_2$, $CH_3$, $O(CH_2)_2$, $CH_3$, $O(CH_2)_3$, $CH_3$, $O(CH_2)_4CH_3$, $O(CH_2)_5$ $CH_3$, $O(CH_2)_6CH_3$, $OCH(CH_3)_2$, $OC(CH_3)_3$, $N(CH_3)_2$,

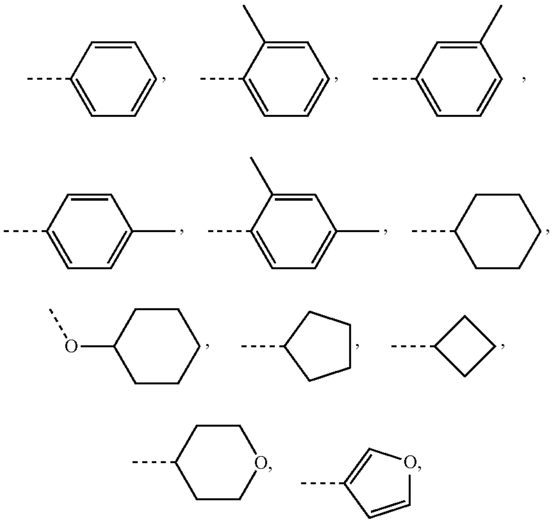

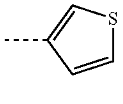 and 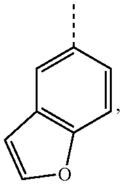

other variables are as defined in the present disclosure.

Some other embodiments of the present disclosure are derived from any combination of the above variables.

In some embodiments of the present disclosure, the compound, the isomer thereof or the pharmaceutically acceptable salt thereof is selected from a group consisting of:

(I-1)

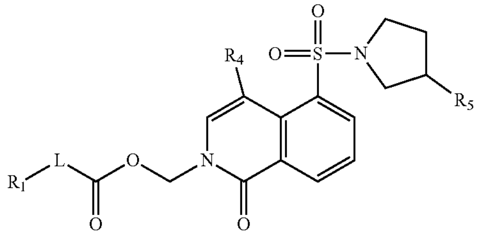

(I-2)

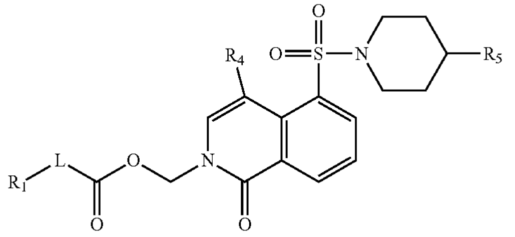

(I-3)

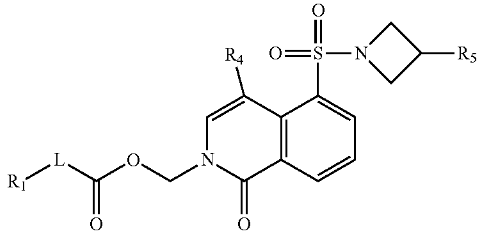

(I-4)

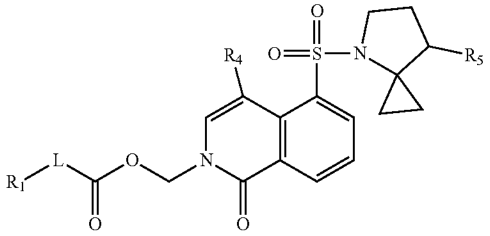

wherein, $R_1$, $R_4$, $R_5$ and L are as defined in the present disclosure.

In some embodiments of the present disclosure, the compound, the isomer thereof or the pharmaceutically acceptable salt thereof is selected from a group consisting of:

(I-1a)

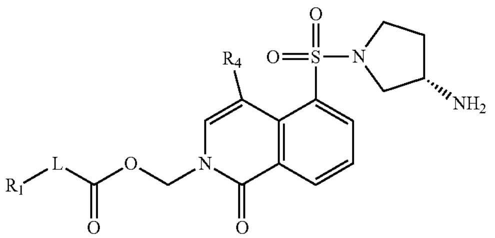

-continued (I-1b)

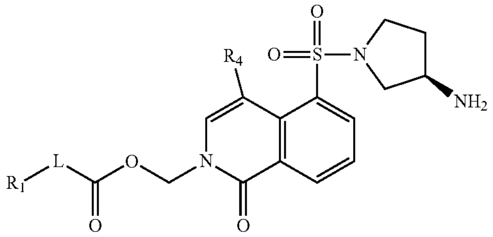

(I-2)

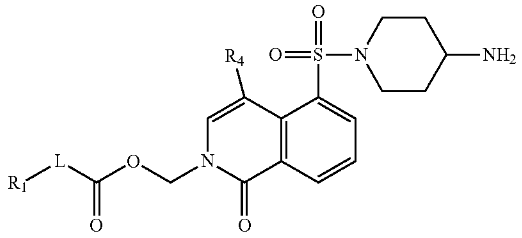

(I-3)

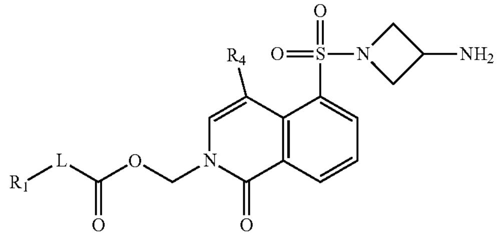

(I-4a)

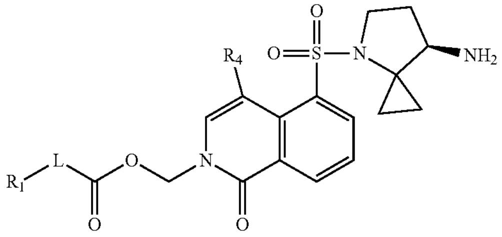

(I-4b)

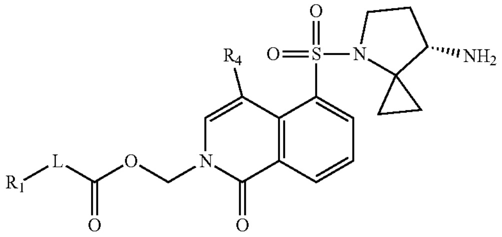

wherein, $R_1$, $R_4$ and L are as defined in the present disclosure.

The present disclosure also provides a compound of the following formula, an isomer thereof or a pharmaceutically acceptable salt thereof, wherein the compound is selected from a group consisting of:

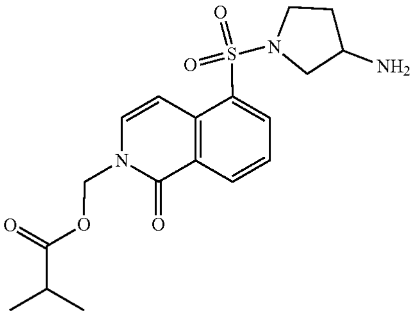
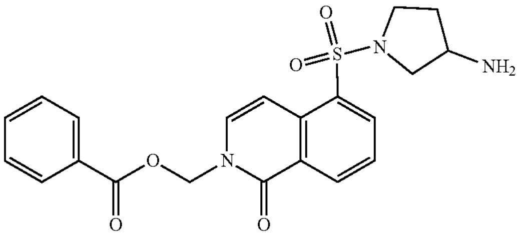
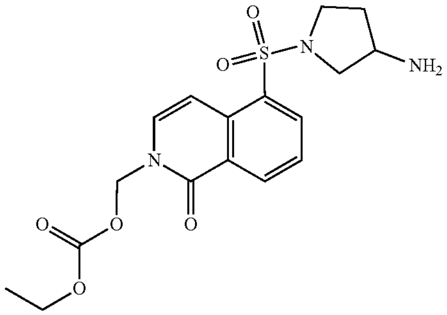
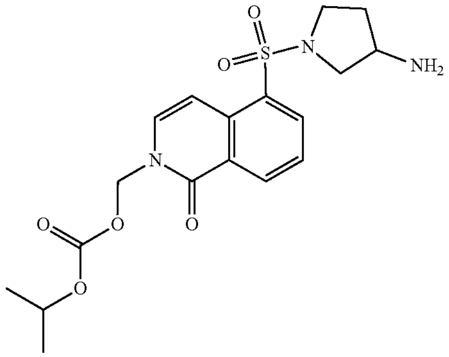
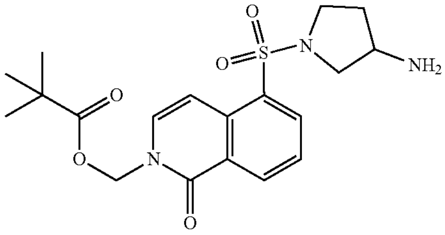
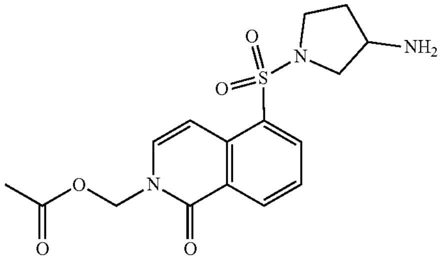
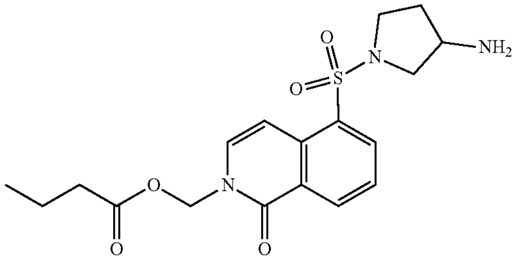
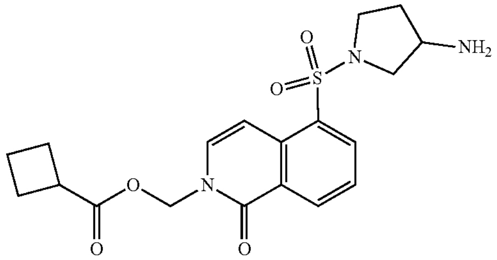
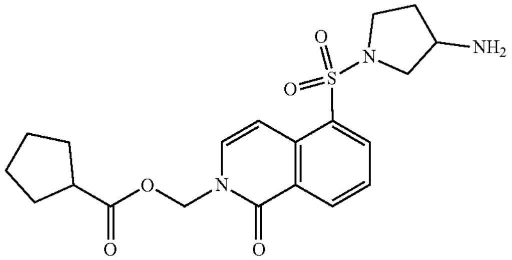
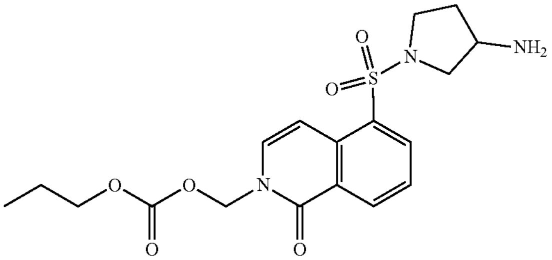
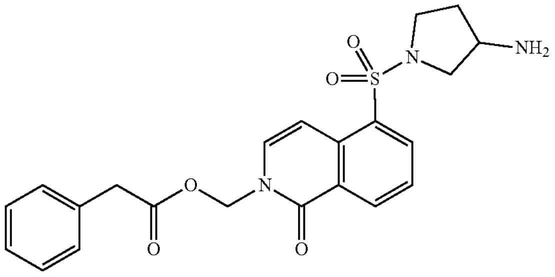
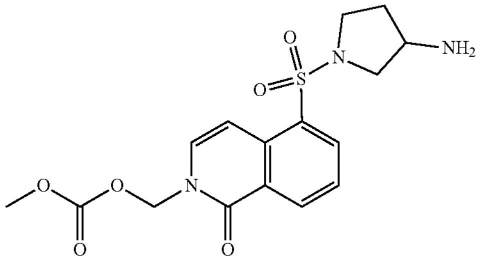

-continued
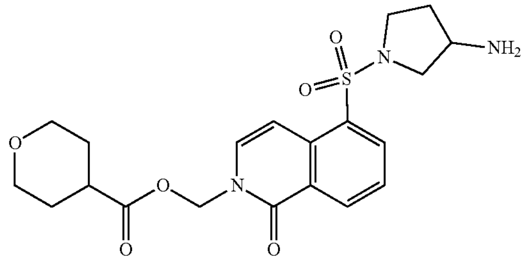
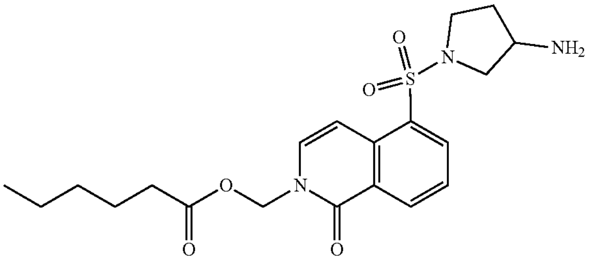
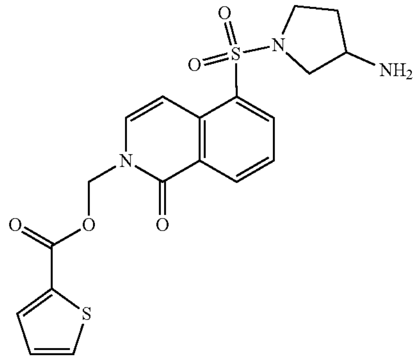
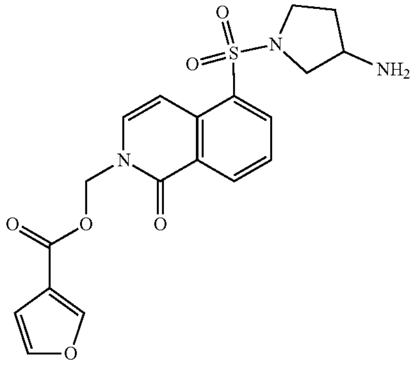
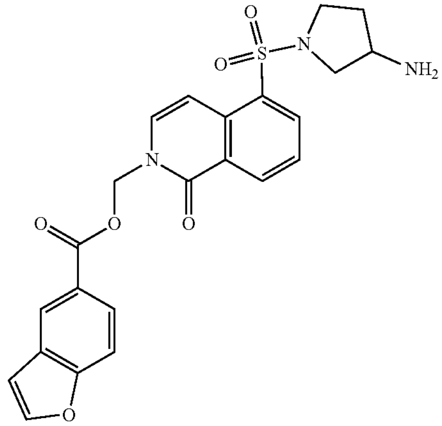
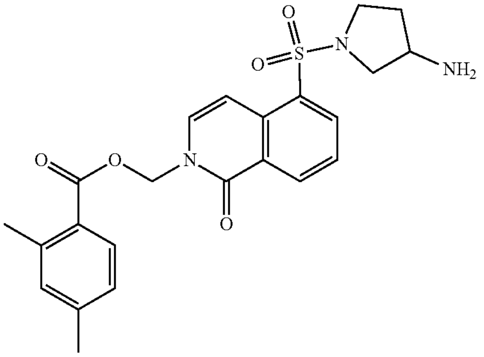
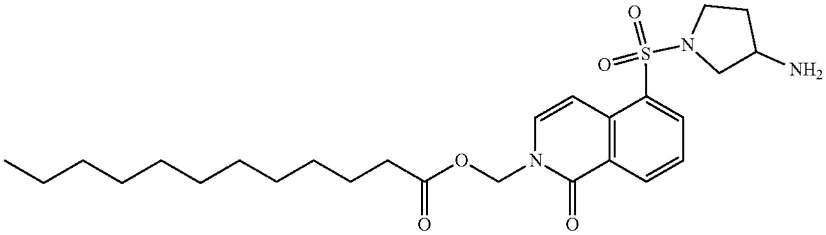
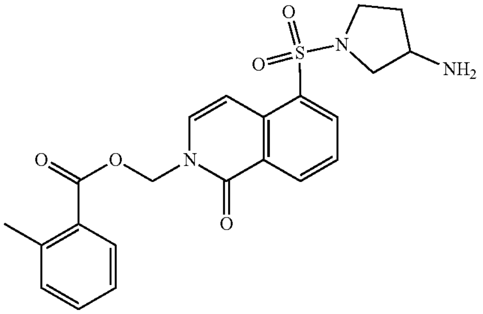
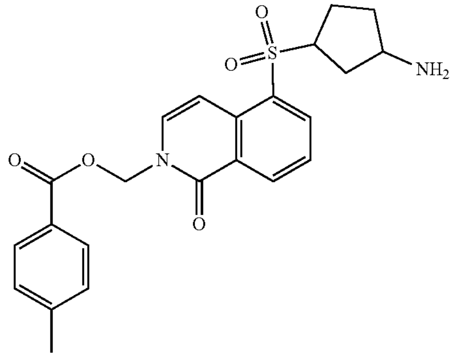

-continued
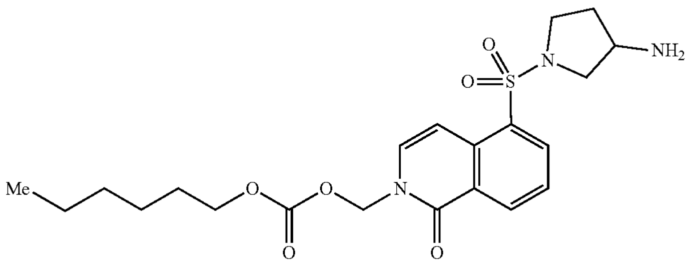
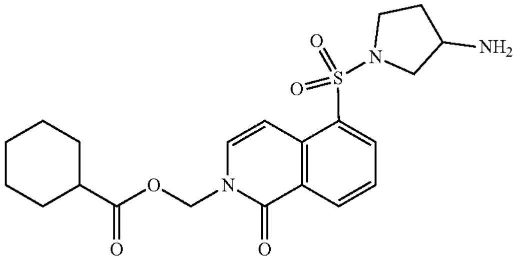
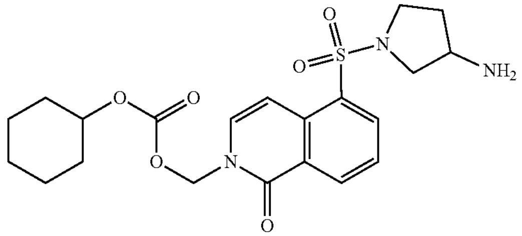
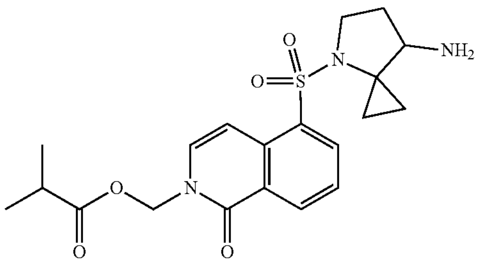
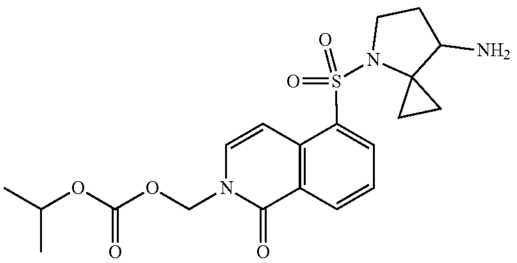
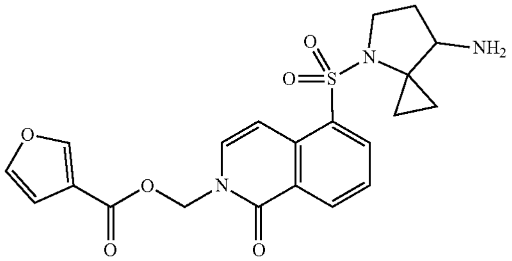
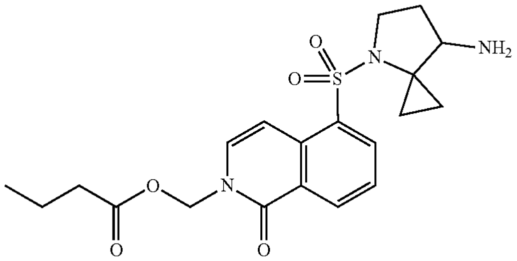
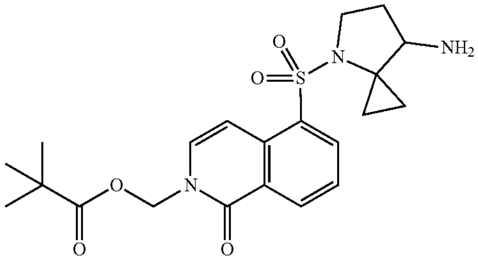
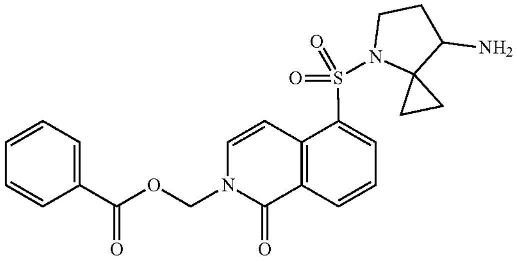
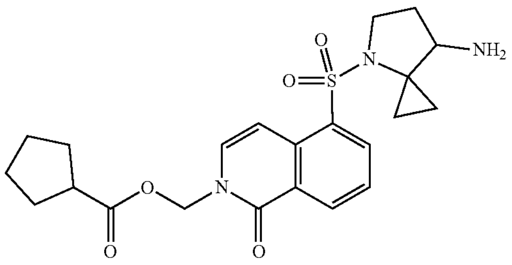
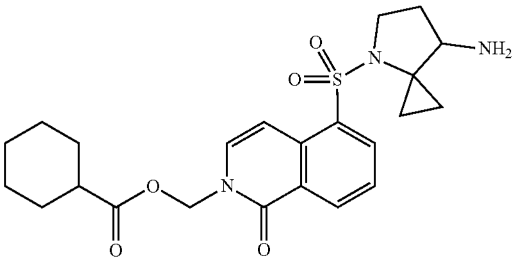

-continued
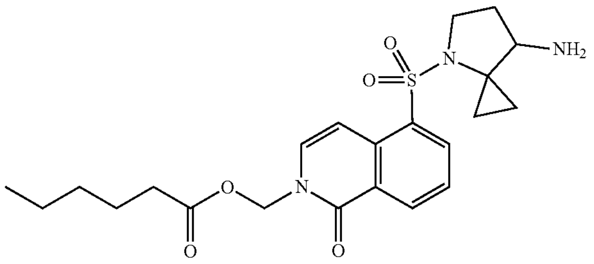
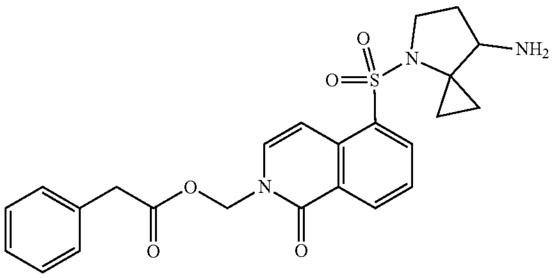
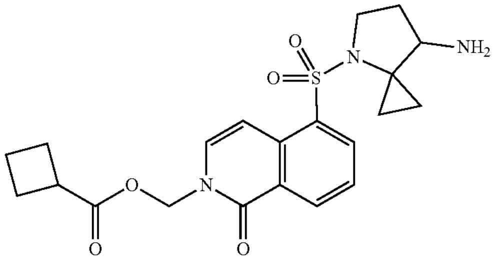
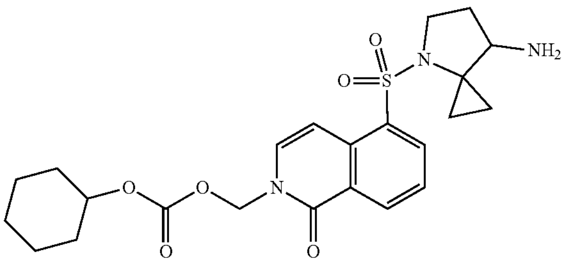
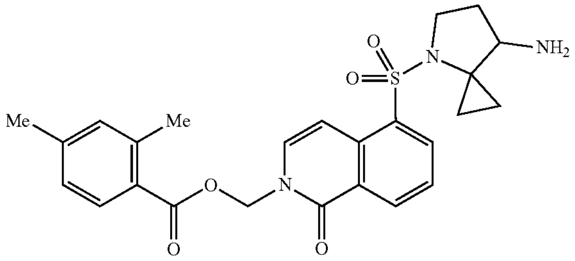
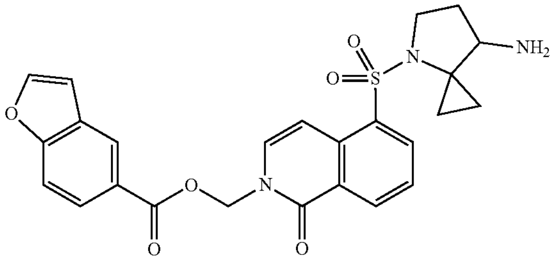
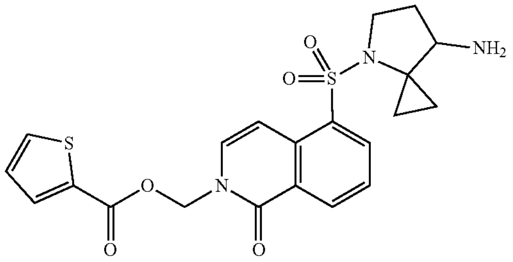
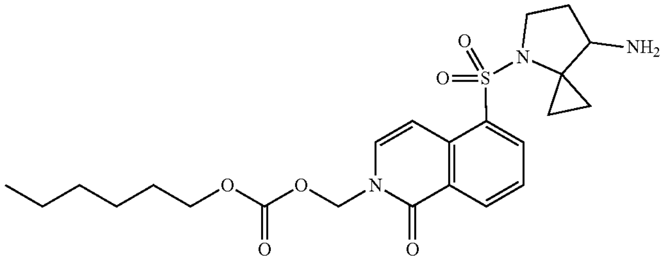
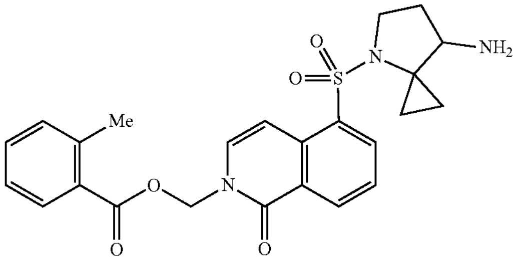
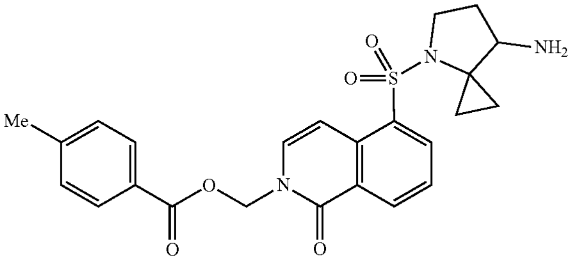

-continued
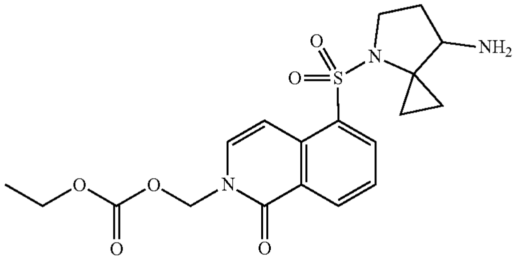
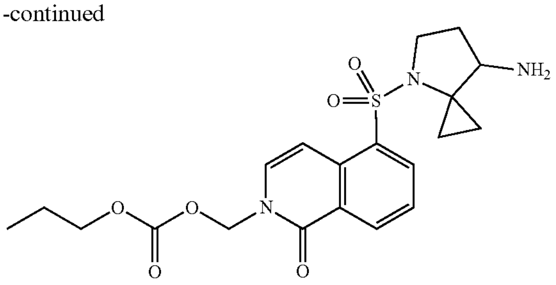
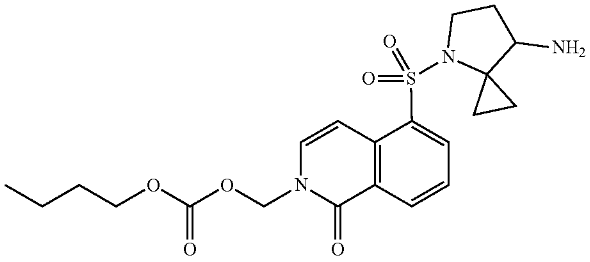
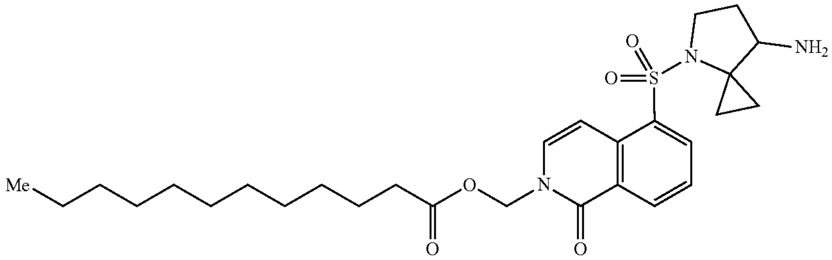
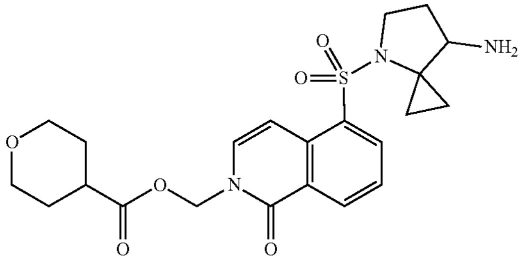
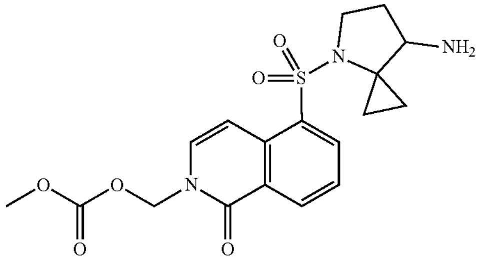
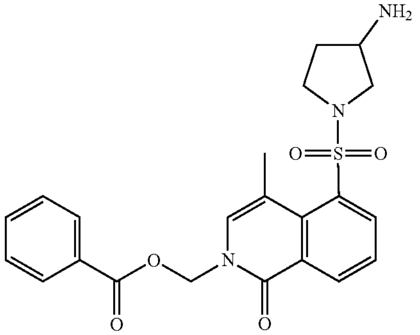
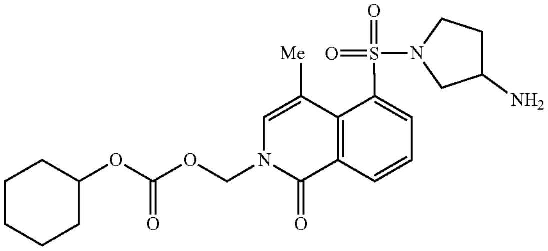
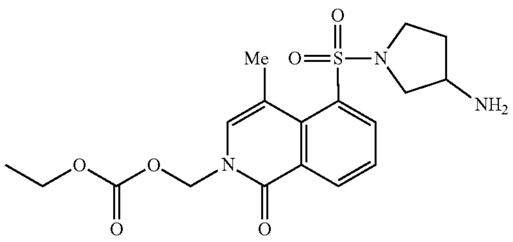
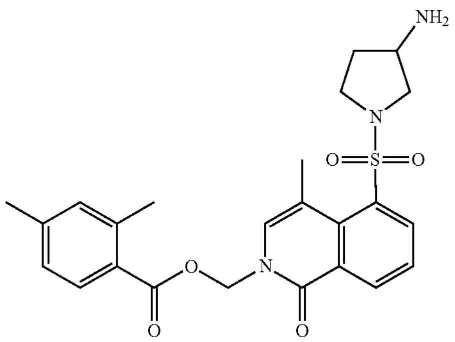

-continued
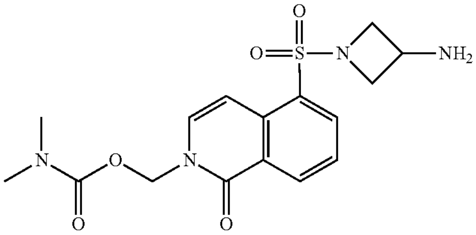
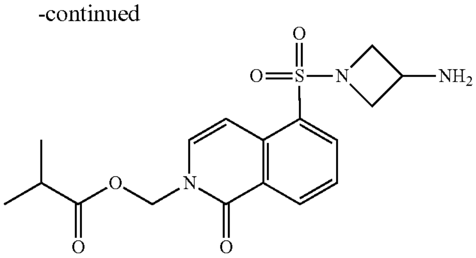
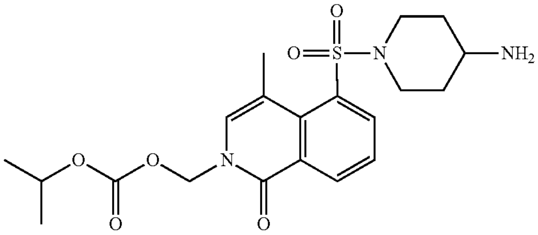
and
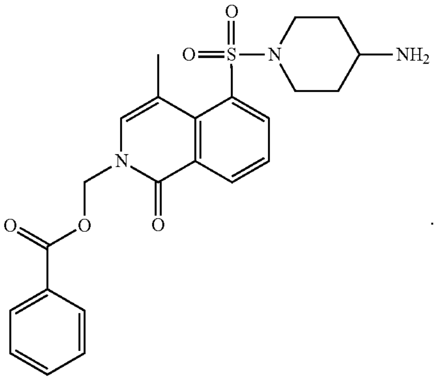
.
In some embodiments of the present disclosure, the compound, the isomer thereof or the pharmaceutically acceptable salt thereof is selected from a group consisting of:
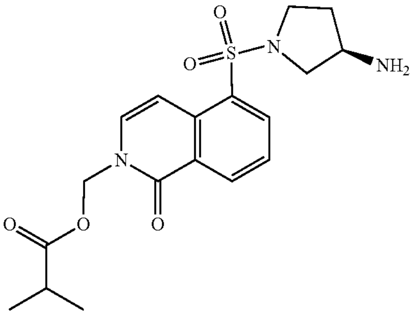
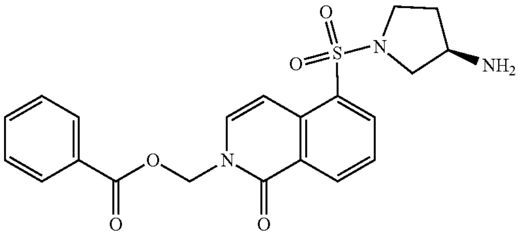
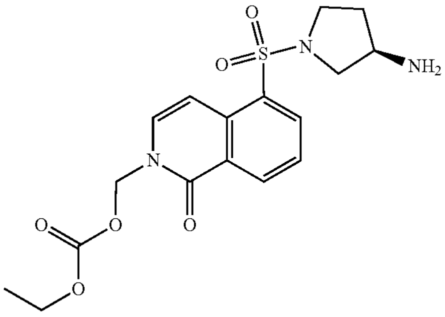
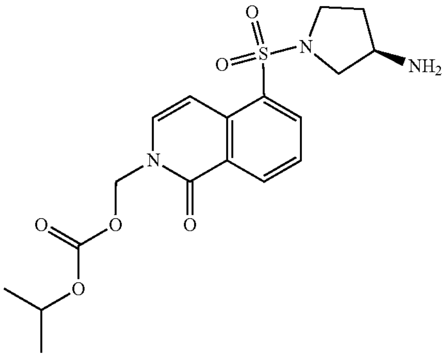

-continued
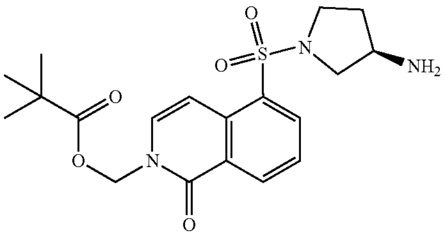
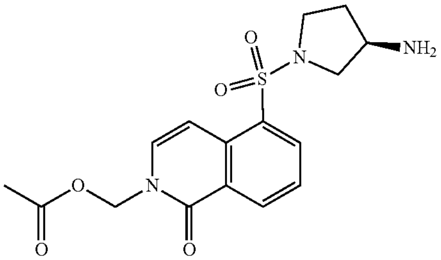
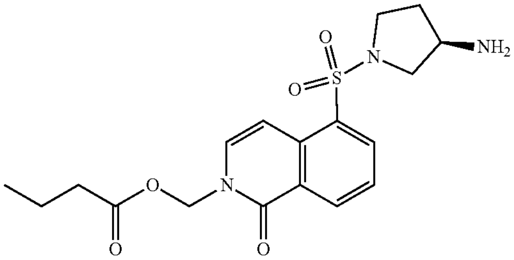
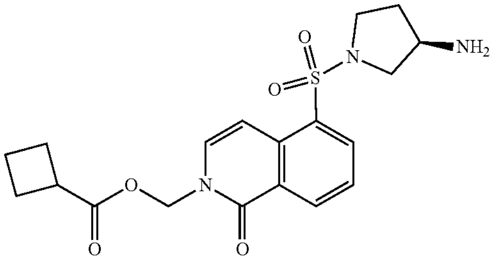
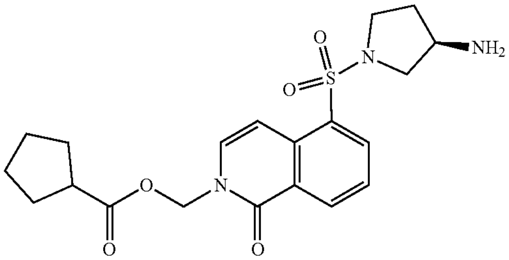
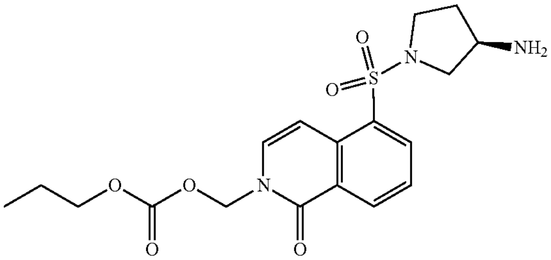
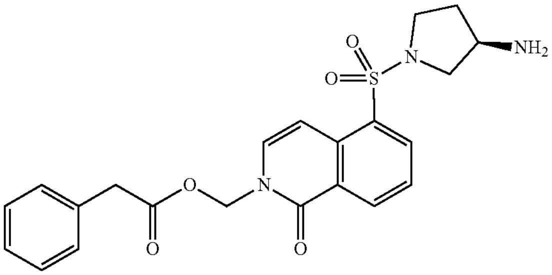
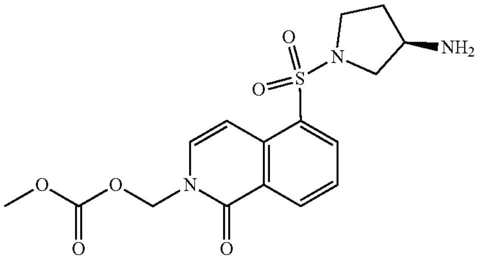
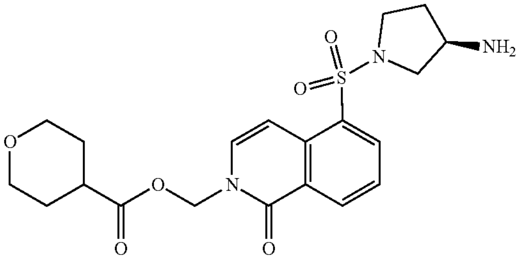
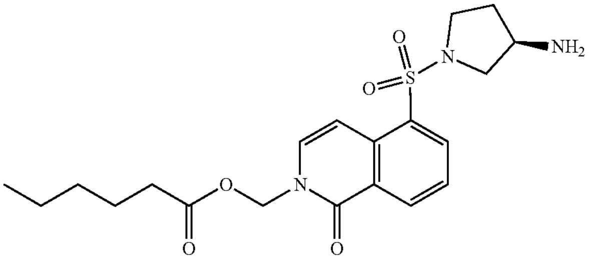
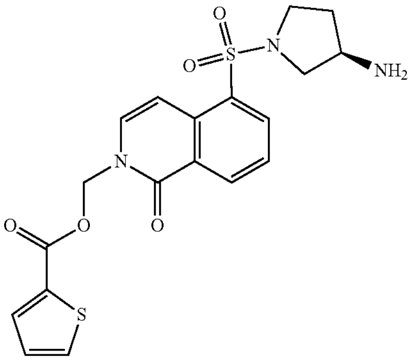
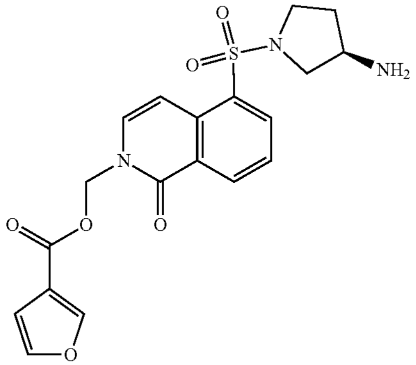

-continued
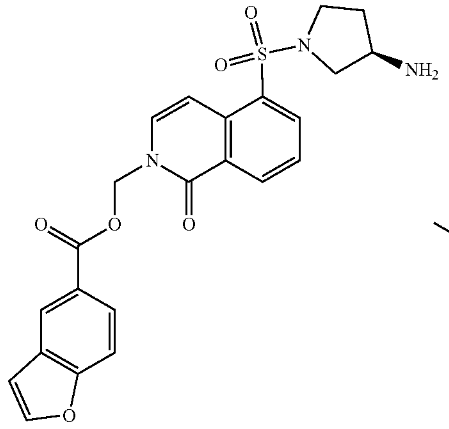
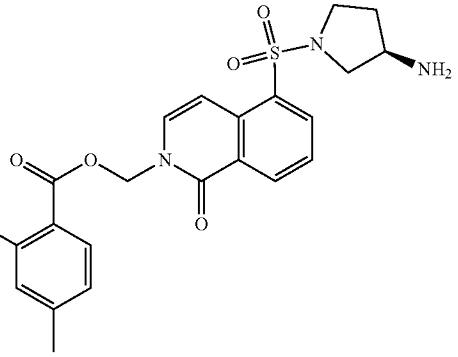
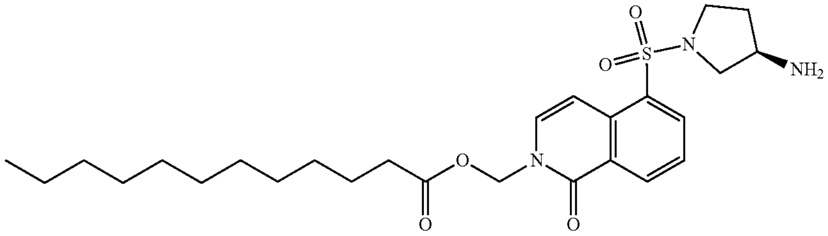
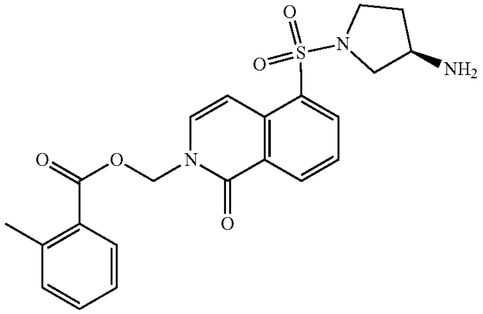
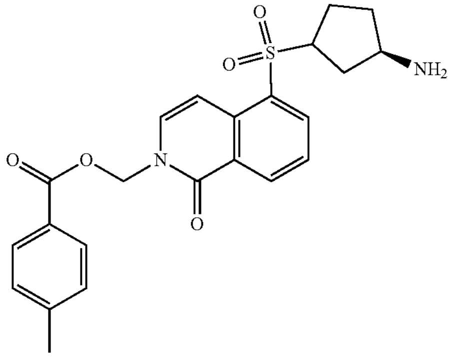
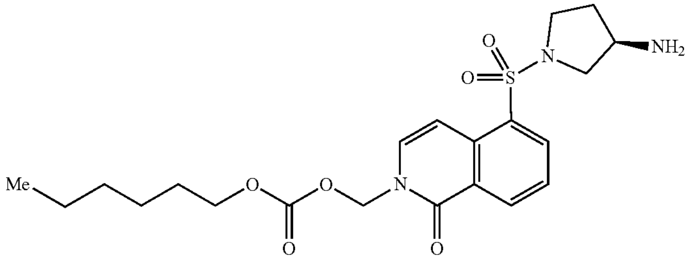
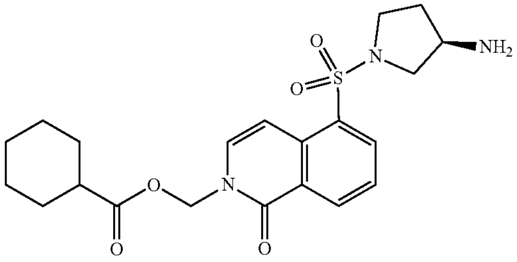
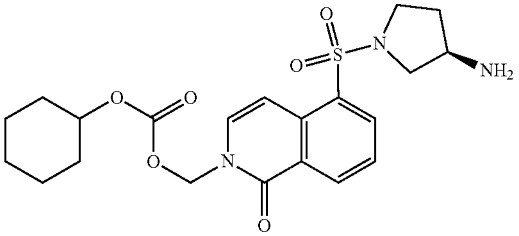

-continued
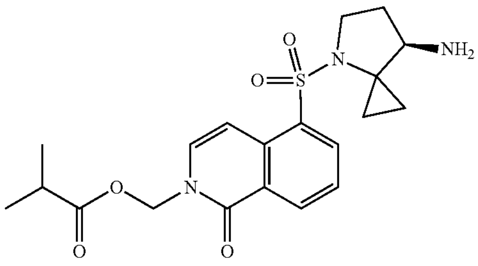
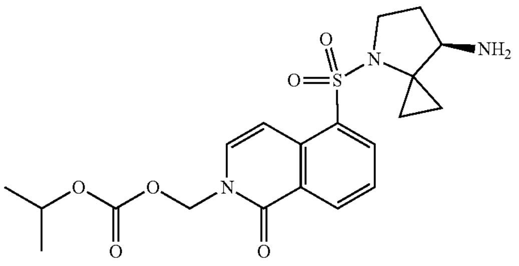
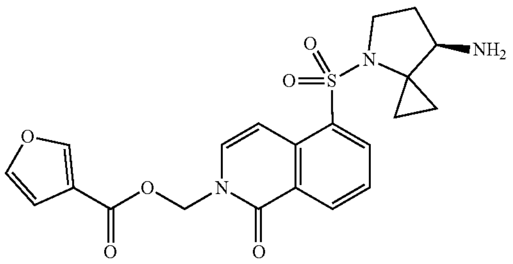
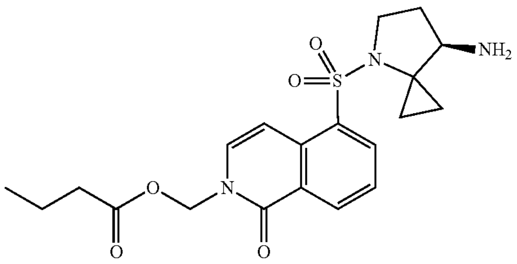
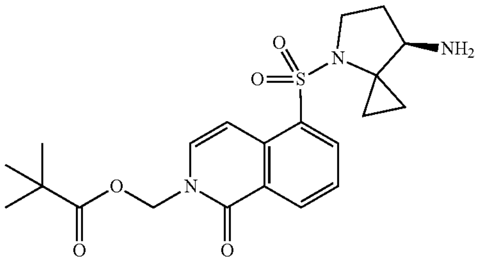
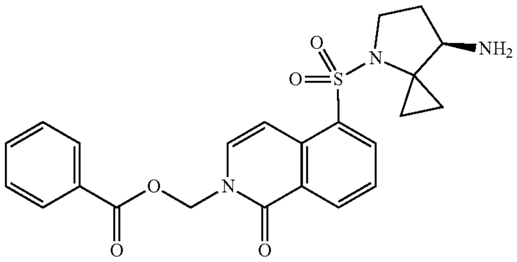
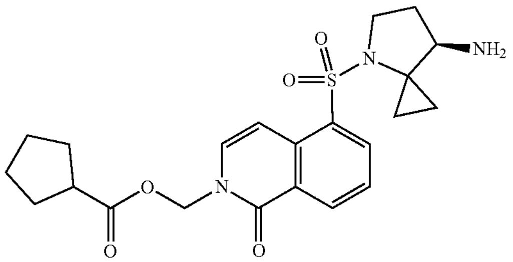
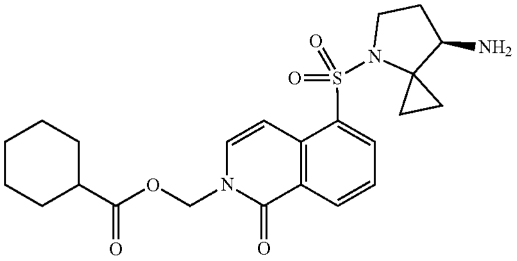
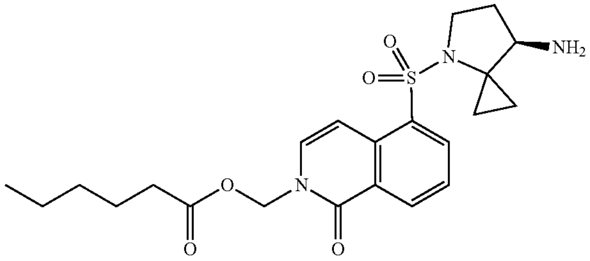
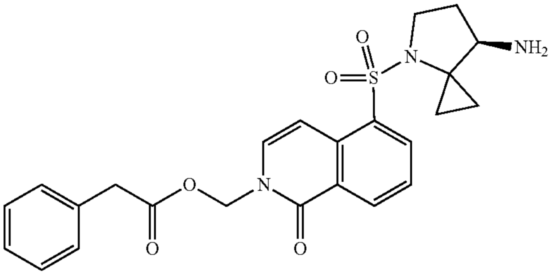
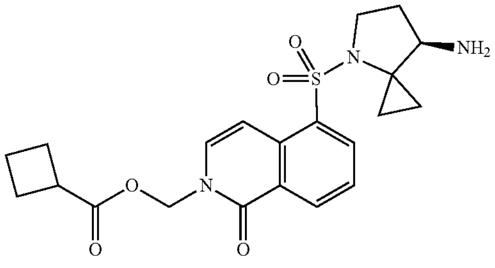
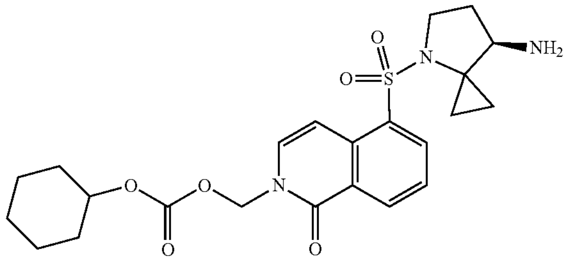

-continued
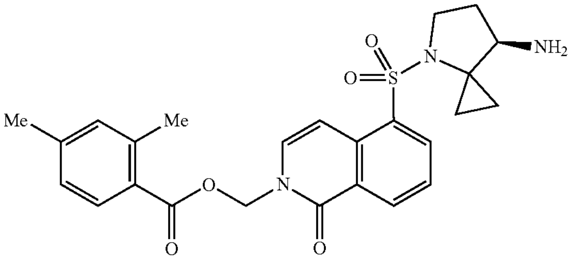
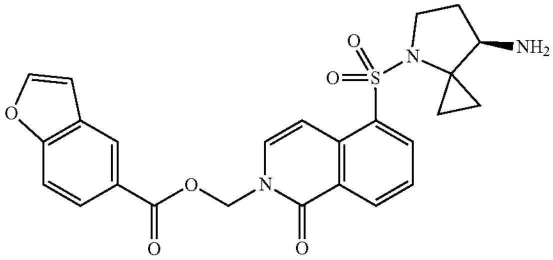
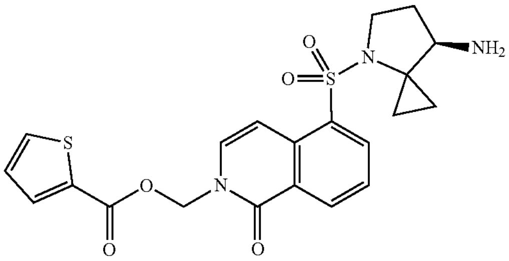
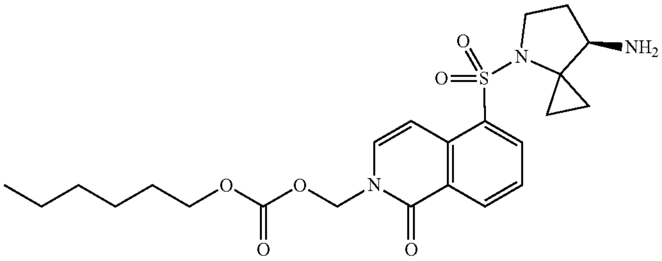
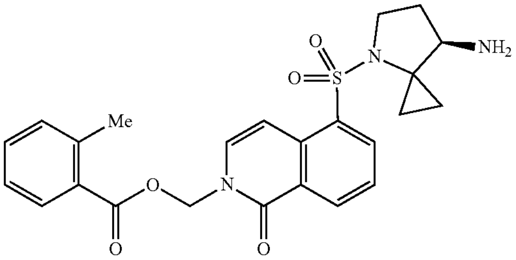
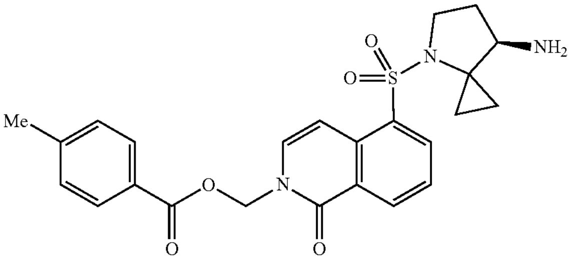
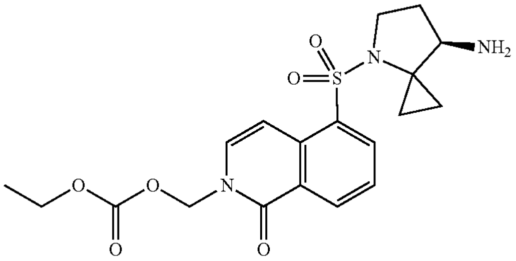
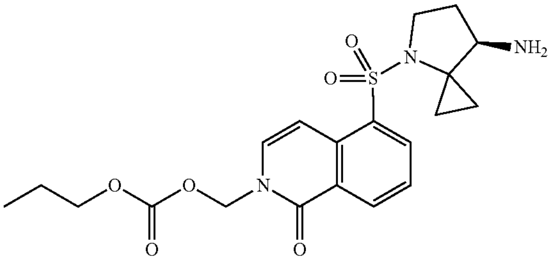
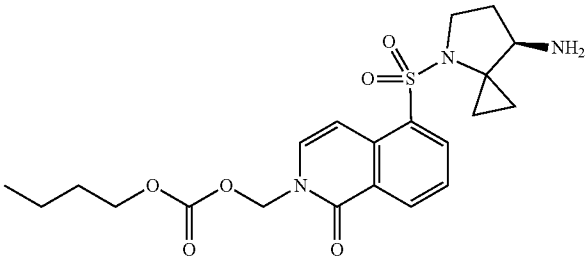

-continued
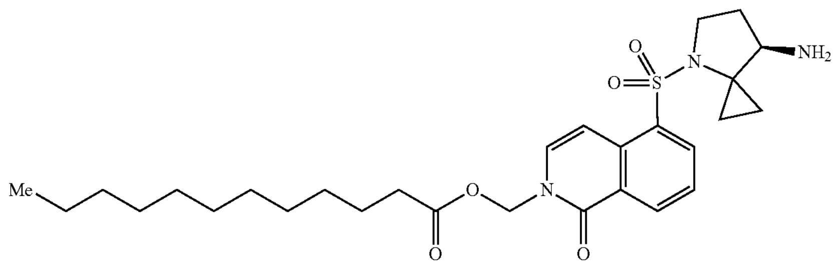
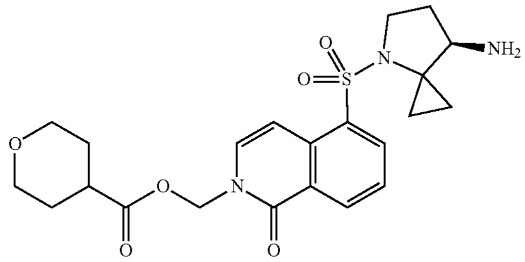
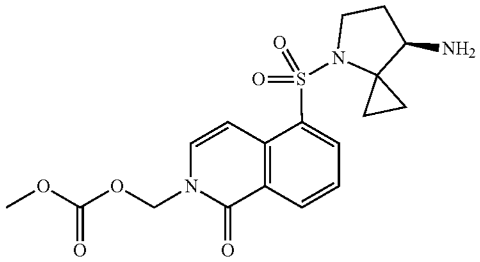
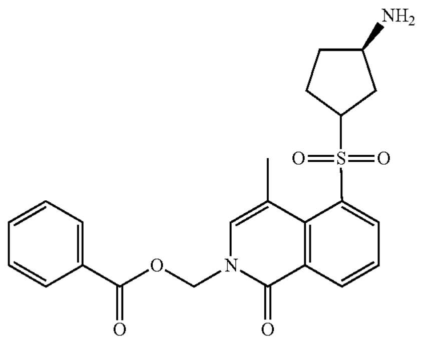
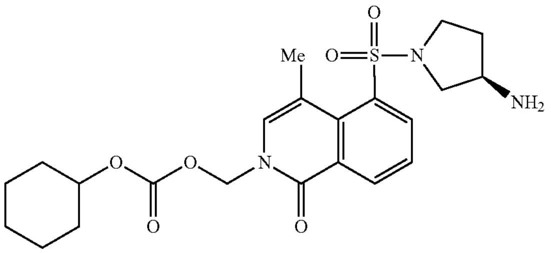
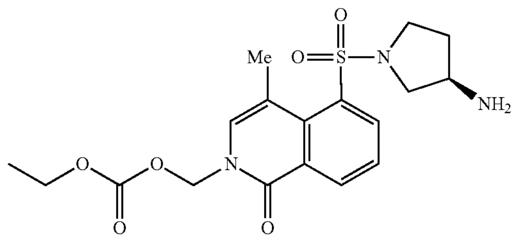
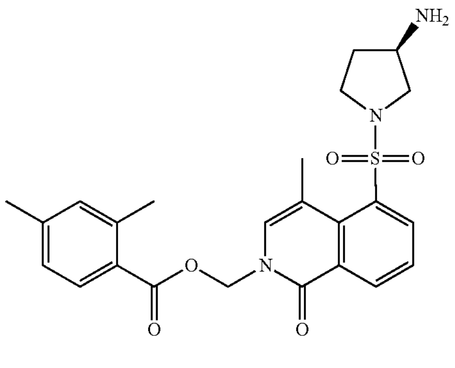
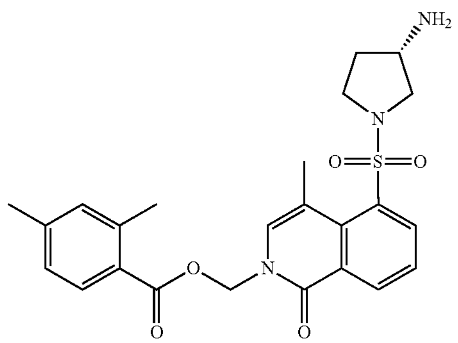
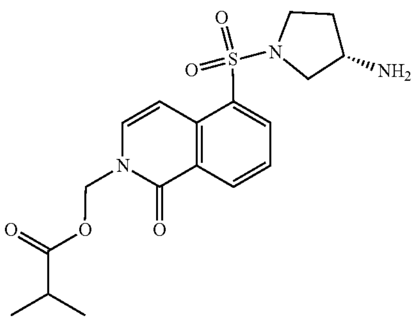

-continued
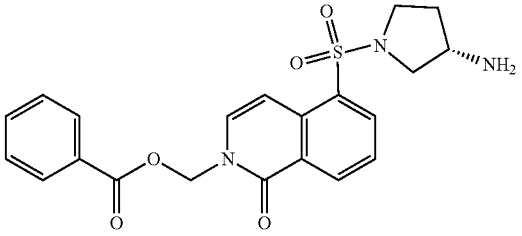
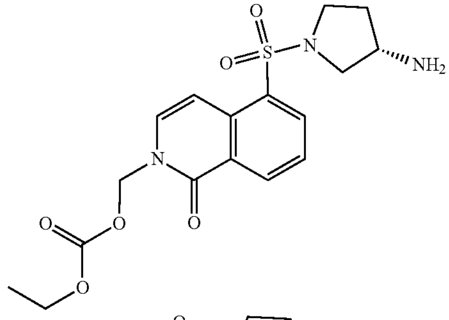
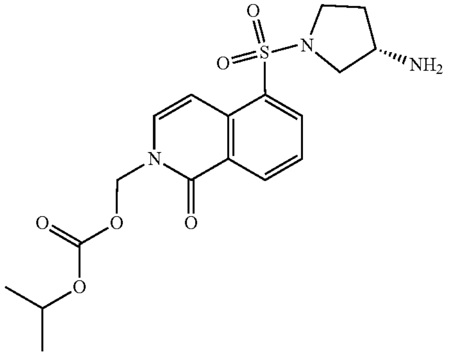
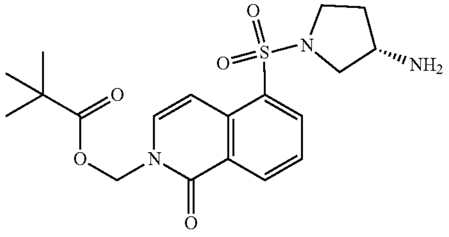
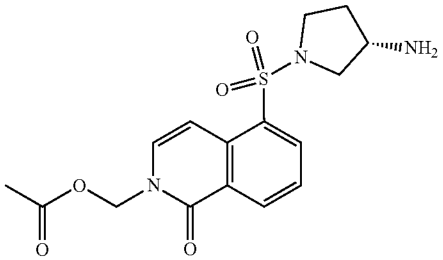
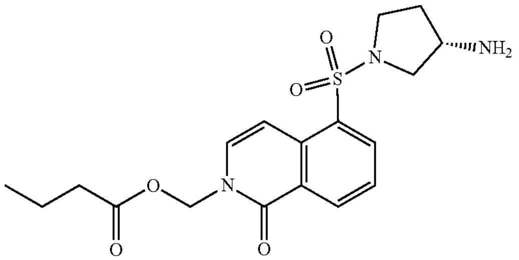
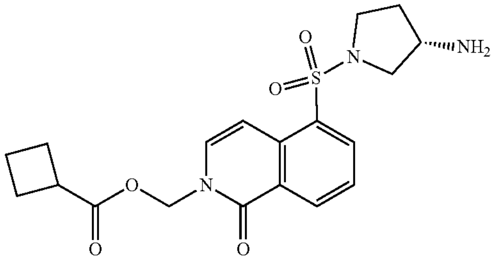
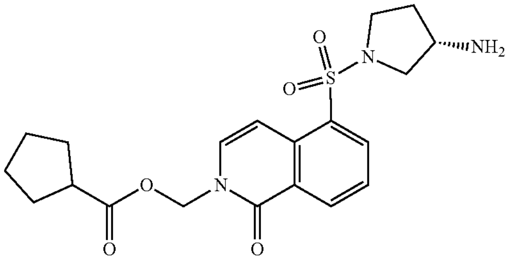
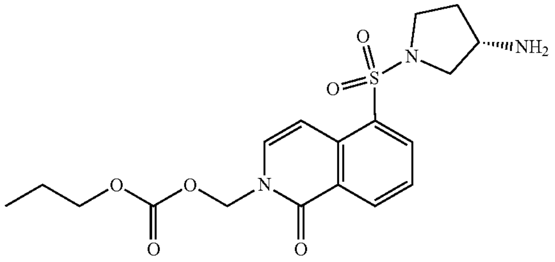
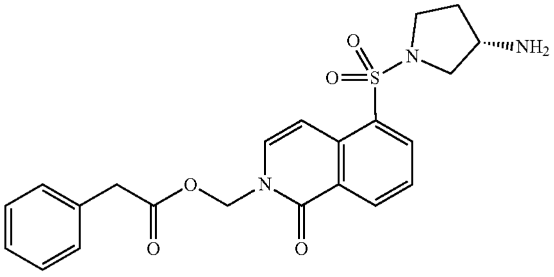
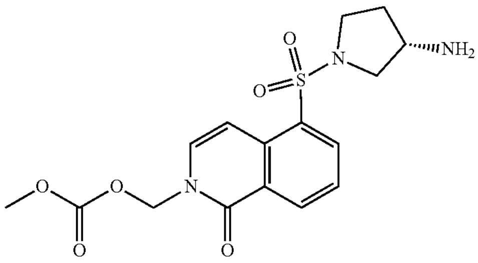
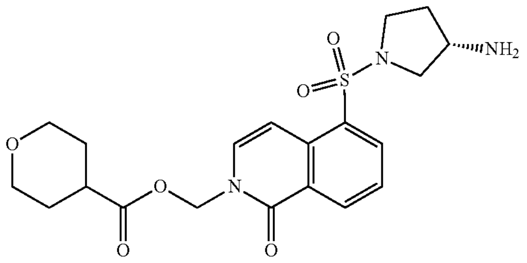

-continued
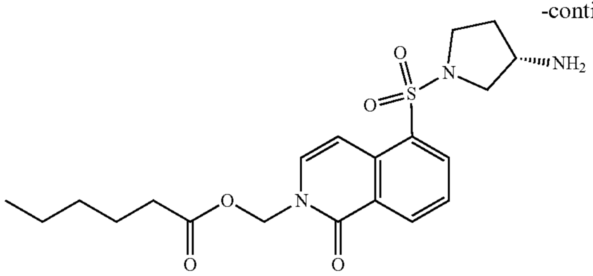
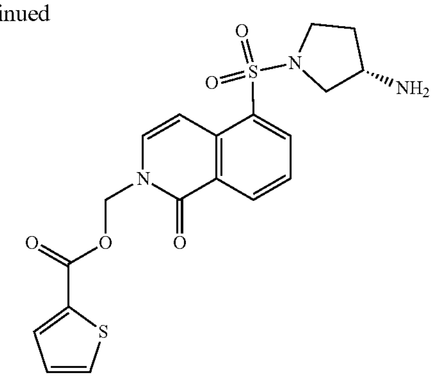
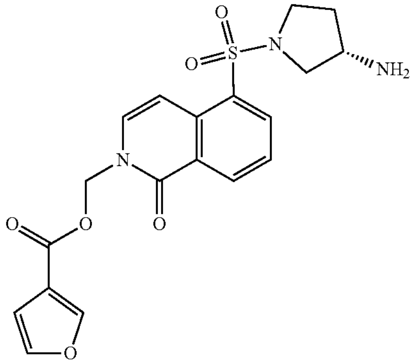
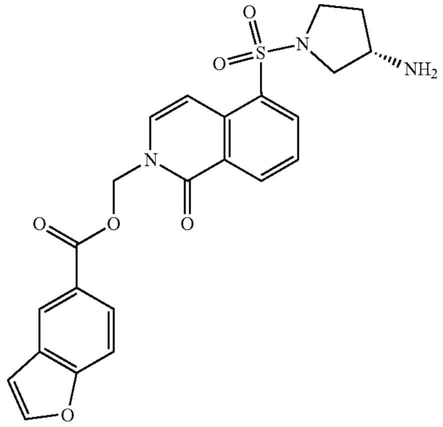
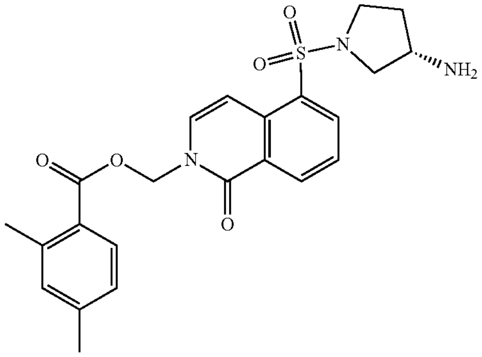
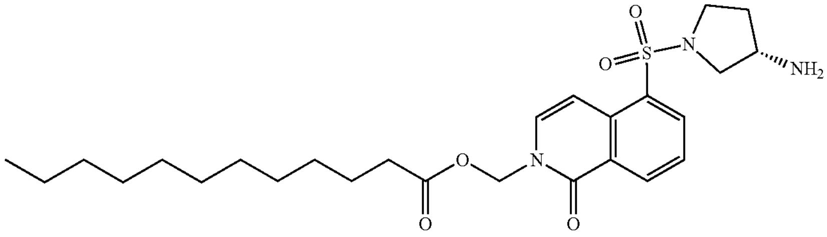
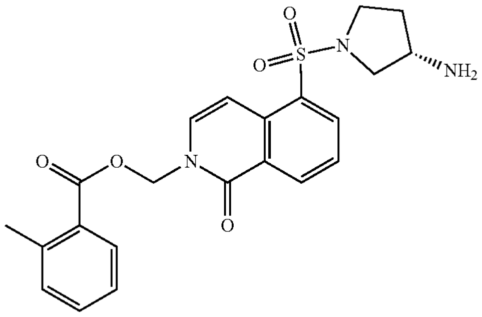
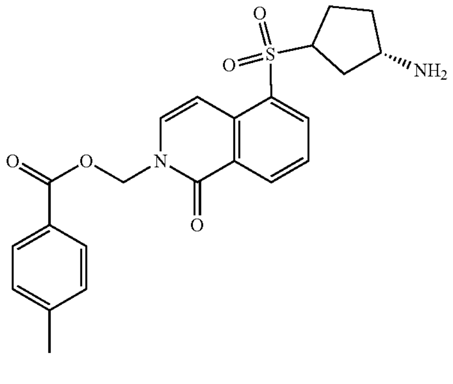

-continued
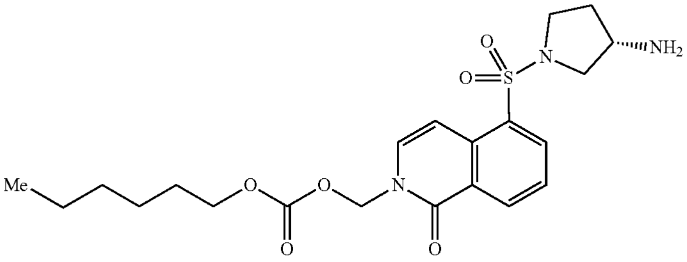
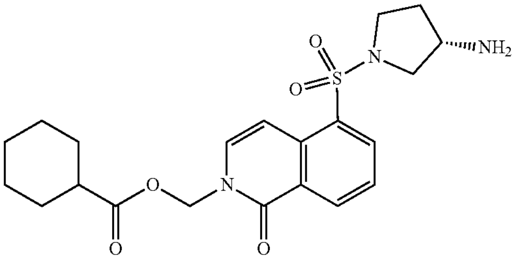
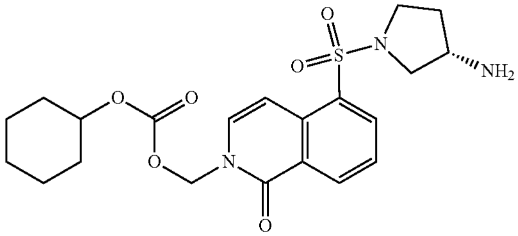
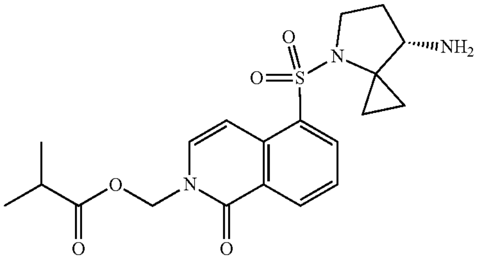
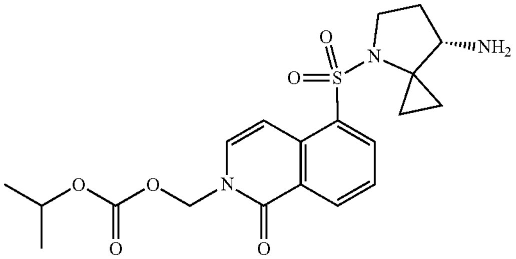
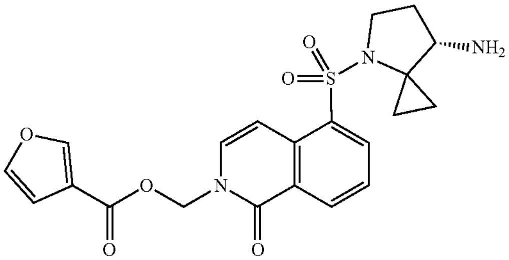
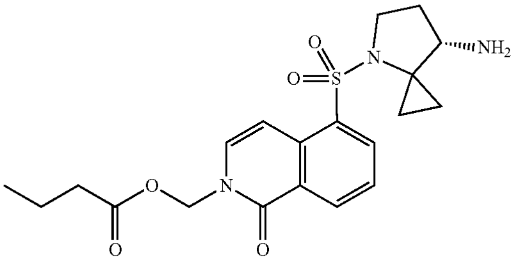
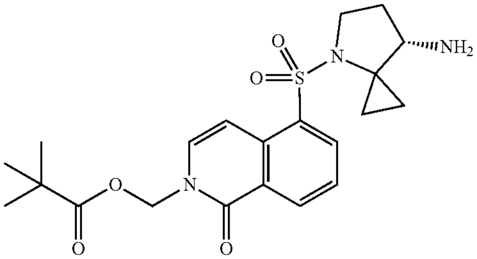
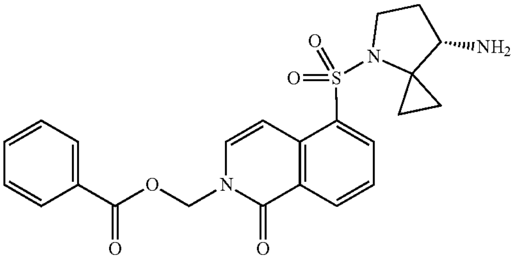
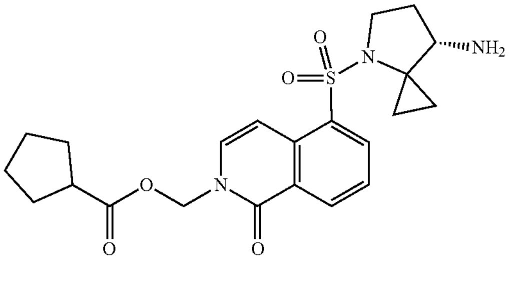
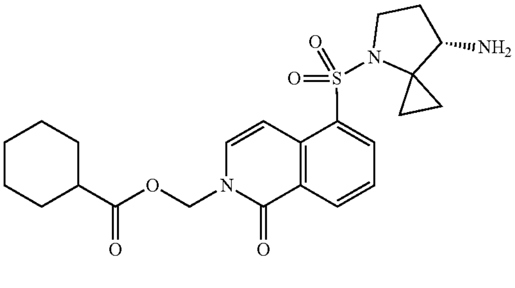

-continued
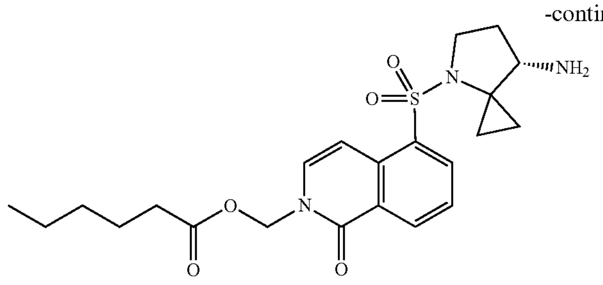
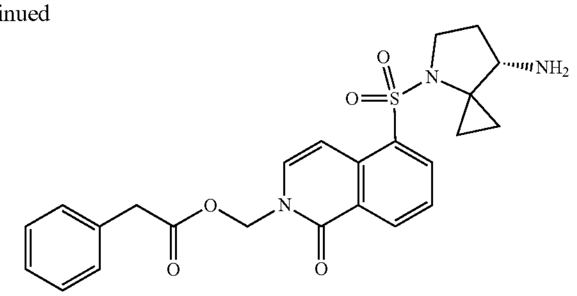
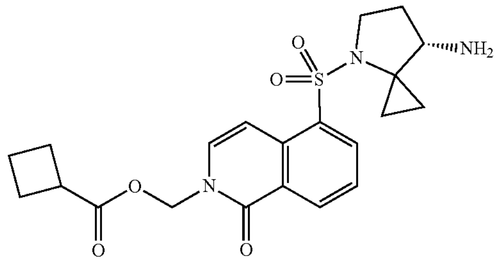
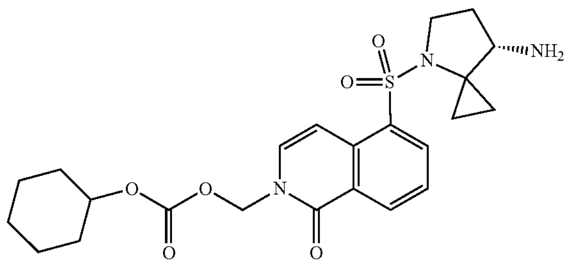
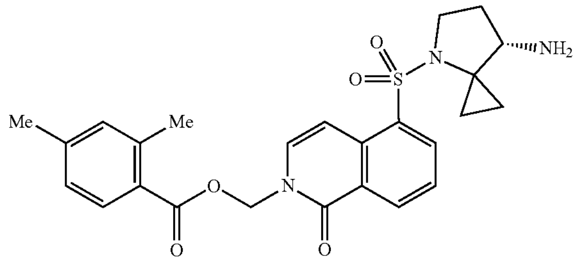
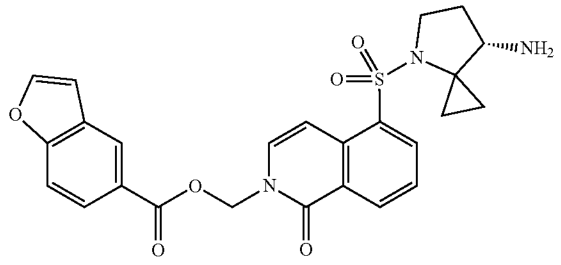
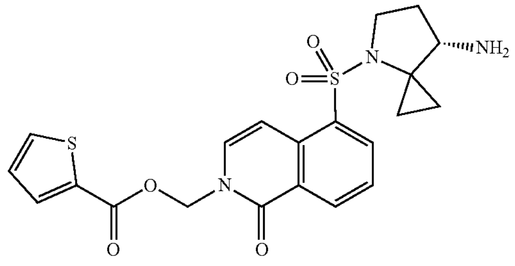
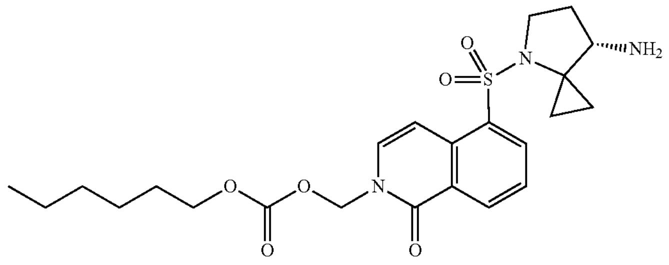
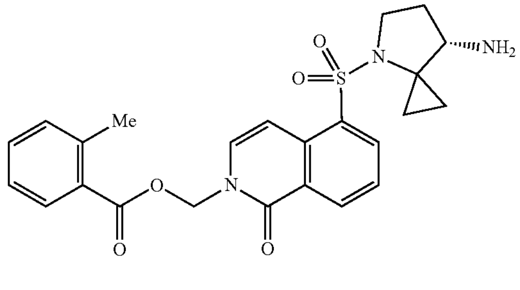
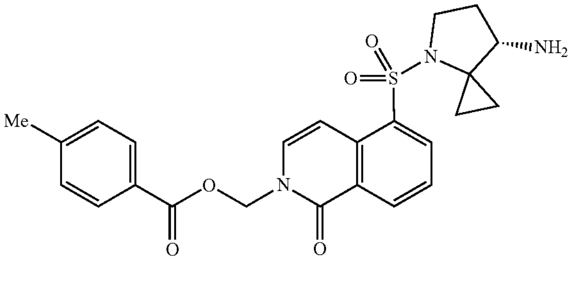

-continued
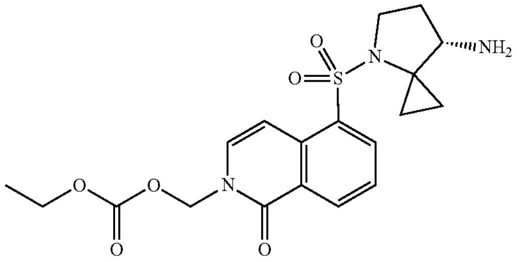
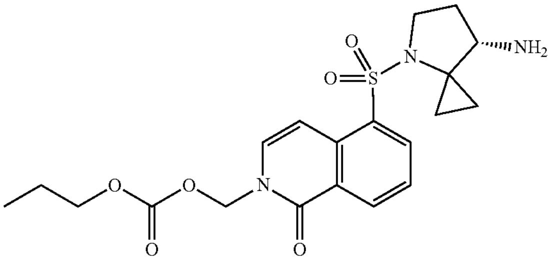
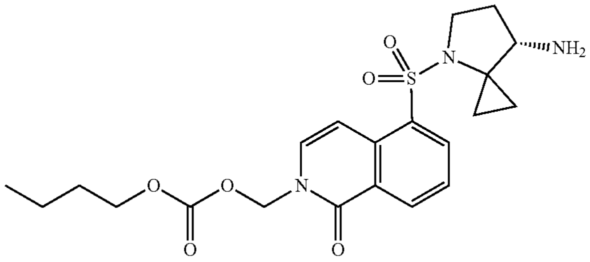
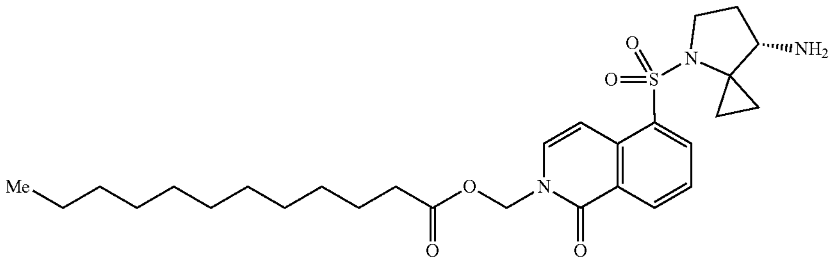
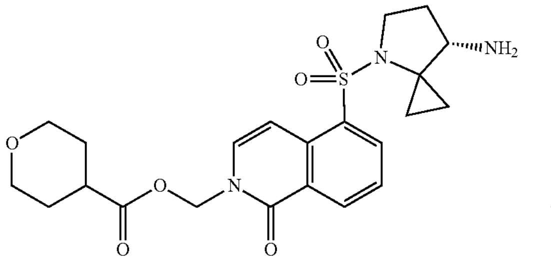
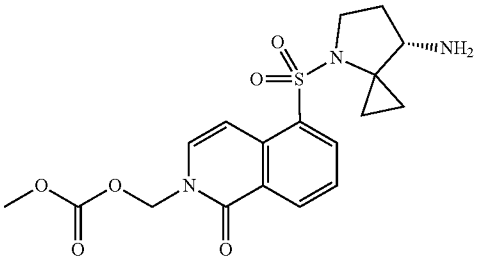
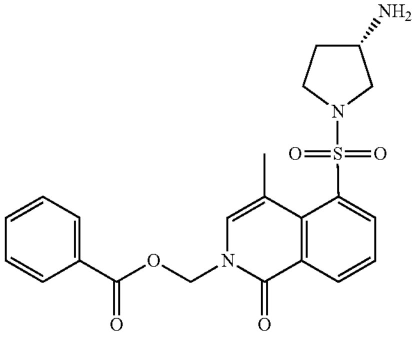
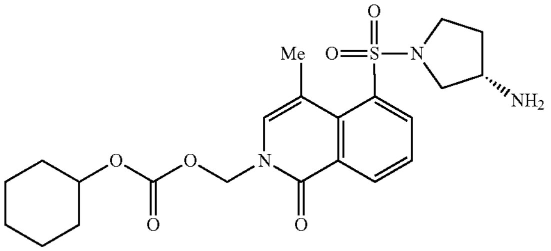
and
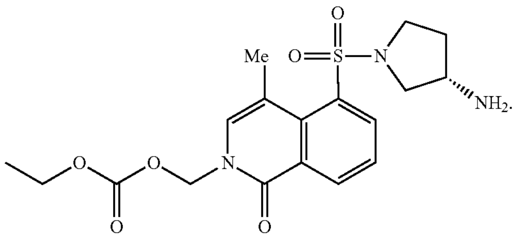

The present disclosure also provides a pharmaceutical composition, comprising a therapeutically effective amount of the compound, the isomer thereof or the pharmaceutically acceptable salt thereof and a pharmaceutically acceptable carrier.

In some embodiments of the present disclosure, providing a method of treating a disease associated with an ROCK protein kinase, comprising administrating a therapeutically effective amount of the compound, the isomer thereof or the pharmaceutically acceptable salt thereof.

In some embodiments of the present disclosure, the disease associated with an ROCK protein kinase is selected from glaucoma or ocular hypertension.

Definitions and Explanations

Unless otherwise stated, the following terms and phrases used herein shall have the following meanings. A specific term or phrase shall not be considered as uncertain or unclear without a special definition, but shall be understood in its plain meaning. When a trade name appears herein, it is meant to refer to its corresponding commodity or its active ingredient. The term "pharmaceutically acceptable" employed herein refers to those compounds, materials, compositions, and/or dosage forms which are within the scope of sound medical judgement, suitable for use in contact with tissues of human beings and animals without excessive toxicity, irritation, allergic response, or other problem or complications, and commensurate with a reasonable benefit/risk ratio.

The term "pharmaceutically acceptable salt" refers to salts of the compounds of the present disclosure, which are prepared from the compounds with specific substituents discovered in the present disclosure and a relatively non-toxic acid or base. When the compounds of the present disclosure contain a relatively acidic functional group, a base addition salt can be obtained by contacting a neutral form of the compounds with a sufficient amount of base in a pure solution or a suitable inert solvent. The pharmaceutically acceptable base addition salts include sodium, potassium, calcium, ammonium, organic amine or magnesium salts or similar salts. When the compounds of the present disclosure contain a relatively basic functional group, an acid addition salt can be obtained by contacting a neutral form of the compounds with a sufficient amount of acid in a pure solution or a suitable inert solvent. Examples of the pharmaceutically acceptable acid addition salts include salts of inorganic acid, including, for example, hydrochloric acid, hydrobromic acid, nitric acid, carbonic acid, bicarbonate, phosphoric acid, monohydrogen phosphate, dihydrogen phosphate, sulfuric acid, hydrogen sulphate, hydroiodic acid, phosphorous acid, etc.; salts of organic acid, including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and other similar acids; and salts of amino acid (such as arginine) and salts of organic acids such as glucuronic acid. Certain specific compounds of the present disclosure contain basic and acidic functional groups, and therefore can be converted into any base or acid addition salts.

The pharmaceutically acceptable salts of the present disclosure can be synthesized from parent compounds which contain acidic radicals or basic groups by conventional chemical methods. Generally, such salts can be prepared by a reaction of the compounds in the form of free acid or base and a stoichiometric amount of appropriate base or acid in water or in an organic solvent, or in a mixture of the two.

In addition to the form of salt, the compounds provided by the present disclosure also exist in the form of prodrugs. The prodrugs of the compounds described herein are prone to chemical changes under physiological conditions to be converted into the compounds of the present disclosure. In addition, the prodrugs may be converted into the compounds of the present disclosure by a chemical or biochemical method in an in-vivo environment.

Some compounds of the present disclosure may exist in a non-solvated form or a solvated form, including a hydrate form. In general, the solvated form is equivalent to the non-solvated form, and both are included in the scope of the present disclosure.

The compounds of the present disclosure may exist in specific geometric or stereoisomeric forms. The present disclosure contemplates all the compounds, including cis- and trans-isomers, (−)- and (+)-enantiomers, (R)- and (S)-enantiomers, diastereoisomers, (D)-isomers, (L)-isomers, and racemic mixtures and other mixtures thereof, such as enriched mixtures of the enantiomers or diastereoisomers, and all of the mixtures are within the scope of the present disclosure. Additional asymmetric carbon atoms may exist in substituents such as alkyl. All these isomers and mixtures thereof are included in the scope of the present disclosure.

Unless otherwise stated, the term "enantiomer" or "optical isomer" refers to stereoisomers which are in a mutual mirrored relationship.

Unless otherwise stated, the term "cis-trans isomer" or "geometric isomer" is caused by inability of double bonds or single bonds of ring-constituting carbon atoms to rotate freely.

Unless otherwise stated, the term "diastereoisomers" refers to stereoisomers in which molecules have two or more chiral centers and the molecules are in a non-mirrored relationship.

Unless otherwise stated, "(D)" or "(+)" means right-handed, "(L)" or "(−)" means left-handed, and "(DL)" or "(+/−)" means racemic.

Unless otherwise stated, a wedge-shaped solid line bond () and a wedge-shaped dashed line bond () represent an absolute configuration of a stereocenter, a straight solid line bond () and a straight dashed line bond () represent a relative configuration of a stereocenter, a wavy line () represents a wedge-shaped solid line bond () or a wedge-shaped dashed line bond () or a wavy line () represents a straight solid line bond () or a straight dashed line bond ().

The compounds of the present disclosure can exist in the specific form of tautomers. Unless otherwise stated, the term "tautomer" or "tautomeric form" refers to that at the room temperature, isomers with different functional groups are in a dynamic equilibrium and can be transformed one another quickly. If tautomers are possible (for example in a solution), a chemical equilibrium of the tautomers can be reached. For example, a proton tautomer, also referred to as a prototropic tautomer, includes an intertransformation through proton migration, for example, keto-enol isomerization and imine-enamine isomerization. A valence tautomer includes recombination of some bonding electrons for an intertransformation. A specific example of a keto-enoltautomerization is the tautomerization between two tautomers of pentane-2,4-dione and 4-hydroxypent-3-en-2-one.

Unless otherwise stated, the terms "enriched in one isomer", "enriched in isomers", "enriched in one enantiomer" or "enriched in enantiomers" refers to that the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to a difference between relative percentages of two isomers or two enantiomers. For example, if the content of one isomer or enantiomer is 90%, and the content of the other isomer or enantiomer is 10%, the isomer or enantiomeric excess (ee value) is 80%.

The optically active (R)- and (S)-isomers and D and L isomers can be prepared by chiral synthesis or chiral reagents or other conventional techniques. If desired, an enantiomer of a compound of the present disclosure can be prepared by asymmetric synthesis or derivatization with a chiral auxiliary, the resulting diastereomeric mixture is separated and auxiliary groups are cleaved to provide the desired pure enantiomer. Alternatively, when a molecule contains a basic functional group (such as an amino group) or an acidic functional group (such as a carboxyl group), a diastereomeric salt is formed with a suitable optically active acid or base, then diastereoisomers are resolved through a conventional method known in the art, and the pure enantiomer is recovered. In addition, separation of the enantiomer and a diastereomer is usually accomplished through chromatography which employs a chiral stationary phase and is optionally combined with chemical derivatization (for example, formation of carbamate from amines). The compounds of the present disclosure may contain atomic isotopes in an unnatural proportion on one or more of atoms constituting the compounds. For example, the compounds can be labeled with radioisotopes, such as tritium ($^3H$), iodine-125 ($^{125}I$), or C-14 ($^{14}C$). For another example, deuterated drugs can be formed by replacing hydrogen with deuterium. A bond formed by deuterium and carbon is stronger than that formed by ordinary hydrogen and carbon. Compared with undeuterated drugs, the deuterated drugs have advantages of reducing toxic and side effects, increasing drug stability, enhancing efficacy, prolonging biological half-life of drugs and the like. All changes in isotopic composition of the compounds of the present disclosure, whether radioactive or not, are included in the scope of the present disclosure.

The term "optional" or "optionally" means that the event or condition described later may but does not necessarily occur and the description includes a situation in which the event or condition occurs and a situation in which the event or condition does not occur.

The term "substituted" means that any one or more hydrogen atoms on a specific atom are replaced by substituents, including deuterium and hydrogen variants, as long as the valence of the specific atom is normal and the substituted compound is stable. When the substituent is oxygen (i.e. =O), it means that two hydrogen atoms are substituted. Oxygen substitution does not occur on aromatic groups. The term "optionally substituted" means that it can be substituted or unsubstituted. Unless otherwise stated, the type and number of substituents can be arbitrary on the basis that they can be chemically realized.

When any variable (such as R) occurs more than once in the composition or structure of a compound, its definition in each case is independent. Thus, for example, if a group is substituted by 0-2 R, the group can optionally be substituted by up to two R, and the R has independent options in each case. In addition, combinations of substituents and/or variants thereof are only allowed if such combinations result in stable compounds.

When the number of a linking group is 0, such as —(CRR)0-, it means that the linking group is a single bond.

When one of the variables is selected from a single bond, it means that the two groups connected by the single bond are directly connected. For example, when L in A-L-Z represents a single bond, it means that the structure is actually A-Z.

When a substituent is vacant, it means that the substituent is absent. For example, when X in A-X is vacant, it means that the structure is actually A. When the listed substituents do not indicate through which atom it is connected to the substituted group, such substituents can be bonded by any atoms. For example, pyridyl can be connected to the substituted group through any one carbon atom of a pyridine ring as a substituent. When the listed linking group does not indicate its linking direction, the linking direction is arbitrary. For example, the linking group L in

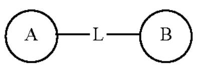

is -M-W—, on this occasion, the -M-W— can link ring A and ring B in a left-to-right reading direction to form

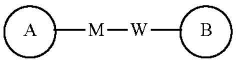

and can also link ring A and ring B in a direction opposite to the left-to-right reading direction to form

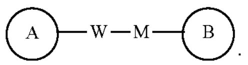

Combinations of the linking group, substituents and/or variants thereof are only allowed if such combinations result in stable compounds.

Unless otherwise stated, the term "$C_{1-16}$ alkyl" is used to indicate a linear or branched saturated hydrocarbon group composed of 1 to 16 carbon atoms. The $C_{1-16}$ alkyl includes $C_{1-15}$, $C_{1-14}$, $C_{1-12}$, $C_{1-10}$, $C_{1-9}$, $C_{1-8}$, $C_{1-6}$, $C_{1-5}$, $C_{1-4}$, $C_{1-3}$, $C_{1-2}$, $C_{2-6}$, $C_{2-4}$, $C_{10}$, $C_8$, $C_7$, $C_6$, $C_5$ alkyl, and so on, and can be monovalent (such as methyl), divalent (such as methylene) or multivalent (such as methine). Examples of the $C_{1-16}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, heptyl, octyl, and so on.

Unless otherwise stated, the term "C1-12 alkyl" is used to indicate a linear or branched saturated hydrocarbon group composed of 1 to 12 carbon atoms. The C1-12 alkyl includes C1-10, C1-9, C1-8, C1-6, C1-5, C1-4, C1-3, C1-2, C2-6, C2-4, C10, C8, C7, C6, C5 alkyl, and so on, and can be monovalent (such as methyl), divalent (such as methylene) or multivalent (such as methine). Examples of the C1-12 alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, heptyl, octyl, and so on. Unless otherwise stated, the term "C1-3 alkyl" is used to indicate a linear or branched saturated hydrocarbon group composed of 1 to 3 carbon atoms. The C1-3 alkyl includes C1-2, C2-3 alkyl, and so on, and can be monovalent (such as methyl), divalent (such as methylene) or multivalent (such as methine). Examples of the C1-3 alkyl include, but are not limited to, methyl (Me), ethyl (Et), propyl (including n-propyl and isopropyl), and so on.

Unless otherwise stated, the term "C1-3 alkoxy" represents alkyl groups containing 1 to 3 carbon atoms linked to the rest of the molecule through an oxygen atom. The $C_{1-3}$ alkoxy includes $C_{1-2}$, $C_{2-3}$, $C_3$, $C_2$ alkoxy, and so on. Examples of the $C_{1-3}$ alkoxy include, but are not limited to, methoxy, ethoxy, propoxy (including n-propoxy and isopropoxy), and so on.

Unless otherwise stated, "$C_{3-7}$ cycloalkyl" represents a saturated cyclic hydrocarbon group composed of 3 to 7 carbon atoms and the saturated cyclic hydrocarbon group is a monocyclic ring system. The $C_{3-7}$ cycloalkyl includes $C_{5-7}$, $C_{3-4}$ and $C_{4-5}$ cycloalkyl, and so on, and can be monovalent, divalent or multivalent. Examples of the $C_{3-7}$ cycloalkyl include, but are not limited to, cyclopropyl, cyclobutyl, cyclopentyl, and so on.

Unless otherwise stated, "$C_{3-5}$ cycloalkyl" represents a saturated cyclic hydrocarbon group composed of 3 to 5 carbon atoms and the saturated cyclic hydrocarbon group is a monocyclic ring system. The $C_{3-5}$ cycloalkyl includes $C_{3-4}$ and $C_{4-5}$ cycloalkyl, and so on, and can be monovalent, divalent or multivalent. Examples of the $C_{3-5}$ cycloalkyl include, but are not limited to, cyclopropyl, cyclobutyl, cyclopentyl, and so on.

Unless otherwise stated, the term "3-8 membered heterocycloalkyl" by itself or in combination with other terms respectively represents a saturated cyclic group composed of 3 to 8 ring atoms, wherein 1, 2, 3 or 4 ring atoms are heteroatoms independently selected from a group consisting of O, S and N, and the rest are carbon atoms, wherein the nitrogen atom is optionally quaternized, and the nitrogen and sulfur heteroatoms can be optionally oxidized (i.e., NO and $S(O)_p$, p is 1 or 2). The saturated cyclic group includes monocyclic and bicyclic systems, wherein the bicyclic system includes spiro, fused, and bridged rings. In addition, for the "3-8 membered heterocycloalkyl", a heteroatom may occupy a linking position of the heterocycloalkyl with the rest of the molecule. The 3-8 membered heterocycloalkyl includes 3-6 membered, 3-5 membered, 4-6 membered, 5-6 membered, 4 membered, 5 membered, 6 membered heterocycloalkyl, and so on. Examples of the 3-8 membered heterocycloalkyl include, but are not limited to, azacyclobutyl, oxacyclobutyl, thiacyclobutyl, pyrrolidinyl, pyrazolidinyl, imidazolidinyl, tetrahydrothienyl (including tetrahydrothiophen-2-yl and tetrahydrothiophen-3-yl, and so on), tetrahydrofuranyl (including tetrahydrofuran-2-yl, and so on), tetrahydropyranyl, piperidinyl (including 1-piperidinyl, 2-piperidinyl, 3-piperidinyl, and so on), piperazinyl (including 1-piperazinyl, 2-piperazinyl, and so on), morpholinyl (including 3-morpholinyl, 4-morpholinyl, and so on), dioxanyl, dithiazinyl, isoxazolidinyl, isothiazolidinyl, 1,2-oxazinyl, 1,2-thiazinyl, hexahydropyridazinyl, homopiperazinyl, homopiperidinyl or dioxepan, and so on.

Unless otherwise stated, the terms "5-10 membered heteroaryl ring" and "5-10 membered heteroaryl" can be used interchangeably in the present disclosure. The term "5-10 membered heteroaryl" represents a ring group composed of 5 to 10 ring atoms and having a conjugated π-electron system, wherein 1, 2, 3 or 4 ring atoms are heteroatoms independently selected from a group consisting of O, S and N, and the rest are carbon atoms. The ring group can be monocyclic, fused bicyclic or fused tricyclic systems, wherein each ring is aromatic, wherein the nitrogen atom is optionally quaternized, the nitrogen and sulfur heteroatoms can be optionally oxidized (i.e. NO and $S(O)_p$, p is 1 or 2). The 5-10 membered heteroarylgroup can be linked to the rest of the molecule through a heteroatom or a carbon atom. The 5-10 membered heteroaryl group includes 5-8 membered, 5-7 membered, 5-6 membered, 5 membered, 6 membered heteroaryl, and so on. Examples of the 5-10 membered heteroaryl include, but are not limited to, pyrrolyl (including N-pyrrolyl, 2-pyrrolyl, 3-pyrrolyl, and so on), pyrazolyl (including 2-pyrazolyl, 3-pyrrolyl, and so on), imidazolyl (including N-imidazolyl, 2-imidazolyl, 4-imidazolyl, 5-imidazolyl, and so on), oxazolyl (including 2-oxazolyl, 4-oxazolyl, 5-oxazolyl, and so on), triazolyl (1H-1,2,3-triazolyl, 2H-1,2,3-triazolyl, 1H-1,2,4-triazolyl, 4H-1,2,4-triazolyl, and so on), tetrazolyl, isoxazolyl (3-isoxazolyl, 4-isoxazolyl, 5-isoxazolyl, etc.), thiazolyl (including 2-thiazolyl, 4-thiazolyl, 5-thiazolyl, and so on), furyl (including 2-furyl, 3-furyl, and so on), thienyl (including 2-thienyl, 3-thienyl, and so on), pyridyl (including 2-pyridyl, 3-pyridyl, 4-pyridyl, and so on), pyrazinyl, pyrimidinyl (including 2-pyrimidinyl, 4-pyrimidinyl, and so on), benzothiazolyl (including 5-benzothiazolyl, and so on), purinyl, benzimidazolyl (including 2-benzimidazolyl, and so on), benzoxazolyl, indolyl (including 5-indolyl, and so on), isoquinolinyl (including 1-isoquinolinyl, 5-isoquinolinyl, and so on), quinoxalinyl (including 2-quinoxalinyl, 5-quinoxalinyl, and so on) or quinolinyl (including 3-quinolinyl, 6-quinolinyl, and so on).

Unless otherwise stated, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$. $C_{n-n+m}$ or $C_n$-$C_{n+m}$ also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, and so on; in the same way, n membered to n+m membered represents that the number of atoms on the ring ranges from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring. Any range from n to n+m is also included. For example, 3-12 membered ring includes 3-6 membered ring, 3-9 membered ring, 5-6 membered ring, 5-7 membered ring, 6-7 membered ring, 6-8 membered ring, 6-10 membered ring, and so on.

The term "leaving group" refers to a functional group or atom that can be substituted by another functional group or atom through a substitution reaction (for example, a nucleophilic substitution reaction). For example, representative leaving groups include trifluoromethanesulfonate; chlorine, bromine, and iodine; sulfonate such as mesylate, tosylate, p-bromobenzenesulfonate, p-toluenesulfonate, and so on; and acyloxy, such as acetoxy, trifluoroacetoxy, and so on.

The term "protecting group" includes, but is not limited to, "amino protecting group", "hydroxy protecting group" or "thiol protecting group". The term "amino protecting group" refers to a protecting group suitable for preventing a side reaction at an amino nitrogen position. Representative amino protecting groups include, but are not limited to, formyl; acyl, such as alkanoyl (e.g., acetyl, trichloroacetyl or trifluoroacetyl); alkoxycarbonyl, such as tert-butoxycarbonyl (Boc); arylmethoxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; silyl, such as trimethylsilyl (TMS), tert-butyldimethylsilyl (TBS), and so on. The term "hydroxyl protecting group" refers to a protecting group suitable for preventing a side reaction of a hydroxyl. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); and silyl, such as trimethylsilyl (TMS), tert-butyldimethylsilyl (TBS), and so on.

The compound of the present disclosure can be prepared by various synthetic methods well known to those skilled in the art, including the specific embodiments listed below, the embodiments formed in combination with other chemical synthesis methods, and equivalent alternatives well known to those skilled in the art. Preferred embodiments include, but are not limited to, the embodiments of the present disclosure.

The solvents used in the present disclosure are commercially available. The present disclosure uses the following abbreviations: aq represents aqueous; HATU represents 0-(7-aza-1H-benzotriazole-1-yl)-N,N,N',N'-tetramethyluroniumhexafluorophosphate; EDCI represents N-(3-dimethylaminopropyl)-N'-ethylcarbodiimide hydrochloride; m-CPBA represents 3-chloroperoxybenzoic acid; eq represents equivalent; CDI represents carbonyldiimidazole; DCM represents dichloromethane; PE represents petroleum ether; DIAD represents diisopropylazodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butyloxycarbonyl, which is an amine protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; $SOCl_2$ represents thionyl chloride; $CS_2$ represents carbon disulfide; TsOH represents p-toluenesulfonic acid; NFSI represents N-fluoro-N-(phenylsulphonyl)benzenesulfonamide; NCS represents 1-chloropyrrolidine-2,5-dione; $n\text{-}Bu_4NF$ represents tetrabutylammonium fluoride; iPrOH represents 2-propanol; mp represents melting point; LDA represents lithium diisopropylamide; LiHMDS represents lithium hexamethyldisilazide; Xantphos represents 4,5-bis(diphenylphosphino)-9,9-dimethyl-xanthne; $LiAlH_4$ represents lithium aluminum hydride; $Pd_2(dba)_3$ represents tris(dibenzylideneacetone)dipalladium; $Pd(dppf)Cl_2$ represents [1,1'-bis(diphenylphosphino)ferrocene]dichloropalladium; DIEA represents N,N-diisopropylethylamine; $Pd(PPh_3)_4$ represents tetrakistriphenylphosphine palladium; IPA represents isopropanol; and DEA represents diethylamine.

The compounds are named according to conventional naming principles in the field or using ChemDraw® software, and commercially available compounds are expressed in names in a supplier catalog.

Technical Effects

Compared with the control compounds, the compounds of the present disclosure witness a significant increase of the exposure amount of active drugs, the peak blood concentration and the action duration. The compounds of the present disclosure exhibit a larger reduction magnitude of intraocular pressure and a longer intraocular pressure reduction action duration. In the model of acute ocular hypertension, the compounds of the present disclosure all exhibited good hypotensive effects at different test doses and also showed certain dose correlation, and the hypotensive amplitude and the action duration were both superior to K-115. The metabolite concentration of the compounds of the present disclosure was 0.934 ng/mL in 4 hours after the administration at a high dose of 8 mg/mL; and in 8 hours after the administration, the metabolite concentration of the compounds was below the detection limit, indicating high system safety.

DETAILED DESCRIPTION OF THE EMBODIMENTS

The following examples will describe the present disclosure in detail, but are not intended to impose any unfavorable limitation on the present disclosure. The present disclosure has been described in detail herein, and its specific examples are also disclosed. It will be obvious for those skilled in the art that various changes and modifications may be made to the examples of the present disclosure without departing from the spirit and scope of the present disclosure.

Synthesis of Fragments of the Technical Concentrate

Intermediate 1

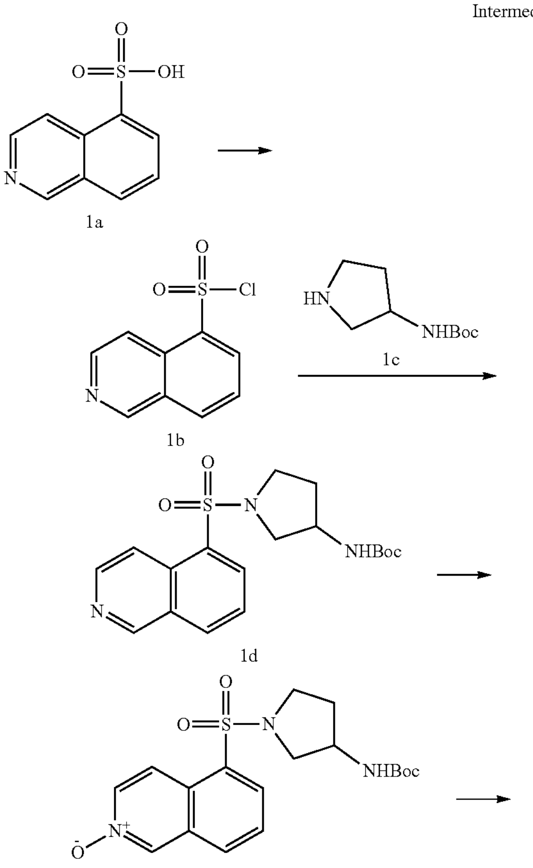

1a

1b

1c

1d

1e

-continued

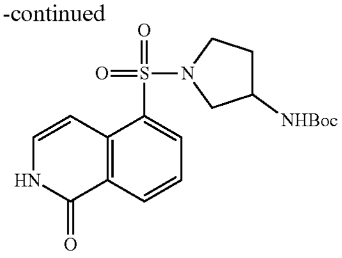

1

Step 1

To a solution of compound 1a (15.0 g, 71.7 mmol) in thionyl chloride (164.0 g, 1.38 mol) was added N,N-dimethylformamide (0.55 mL), stirred for 12 hours at 80° C. After the reaction was completed, the reaction mixture was concentrated under reduced pressure to obtain a crude compound 1b. MS-ESI calculated value $[M+H]^+$ 228, actually measured value 228.

Step 2

At 0° C., to a solution of compound 1b (18.9 g, 62.0 mmol) in dichloromethane (150 mL) was added compound 1c (12.7 g, 68.2 mmol) and N,N-diisopropylethylamine (124 mL) under a nitrogen atmosphere, stirred for 0.5 hours at 25° C. After the reaction was completed, the reaction solution, after being concentrated under reduced pressure, was diluted with water (100 mL), and extracted with dichloromethane (60 mL×3), and the combined organic phase was washed with a saturated sodium chloride solution, dried with anhydrous sodium sulfate, and concentrated under reduced pressure after filtration. The residue was purified by silica gel column chromatography to obtain compound 1d. MS-ESI calculated value $[M+H]^+$ 378, actually measured value 378.

Step 3

At 0° C., to a solution of compound 1d (8 g, 20.3 mmol) in dichloromethane (100 mL) was added chloroperoxybenzoic acid (6.48 g, 30.4 mmol, purity: 81%) in batch, stirred for 2 hours at 25° C. After the reaction was completed, the reaction mixture was quenched with saturated sodium bicarbonate solution (100 mL), extracted with dichloromethane (60 mL×3), and the organic phase was dried by anhydrous sodium sulfate, then filtered, concentrated under reduced pressure to obtain compound 1e. MS-ESI calculated value $[M+H]^+$ 394, actually measured value 394.

Step 4

Compound 1e (11.1 g, 28.2 mmol) was dissolved in acetic anhydride (109 g, 1.07 mol), and after stirred for 2 hours at 130° C., acetic anhydride was removed by concentration. Tetrahydrofuran (100 mL) and 30% aqueous sodium hydroxide solution (150 mL) were added, stirred for 30 minutes at 25° C. After removal of tetrahydrofuran by concentration under reduced pressure, a 6 M hydrochloric acid solution was added dropwise to the system to adjust the pH of the reaction solution to 7, extracted with ethyl acetate (50 mL×3), and the combined organic phase dried with anhydrous sodium sulfate, filtered, and concentrated under reduced pressure. The residue was purified by silica gel column chromatography to obtain intermediate 1. $^1H$ NMR (400 MHz, DMSO-$d_6$) δ=8.52 (d, J=7.8 Hz, 1H), 8.21 (dd, J=7.8, 1.3 Hz, 1H), 7.64 (t, J=7.8 Hz, 1H), 7.37 (d, J=7.8 Hz, 1H), 7.23 (d, J=7.6 Hz, 1H), 3.91 (d, J=5.4 Hz, 1H), 3.20-3.28 (m, 3H), 3.03 (dd, J=9.8, 5.0 Hz, 1H), 1.92-2.05 (m, 1H), 1.68-1.77 (m, 1H), 1.34 (s, 9H). MS-ESI calculated value $[M+Na]^+$ 416, actually measured value 416.

Intermediate 2

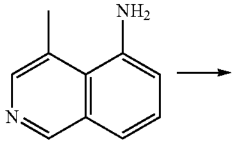

2a

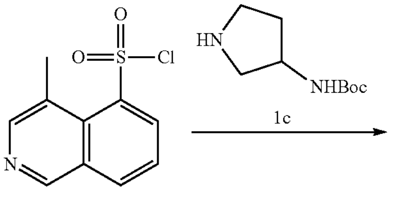

2b

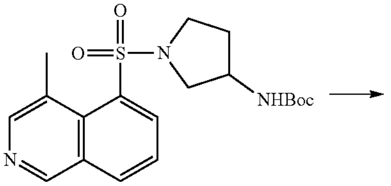

2c

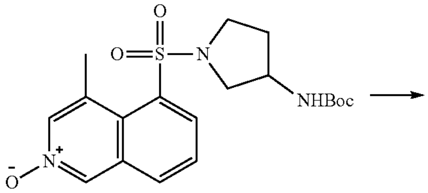

2d

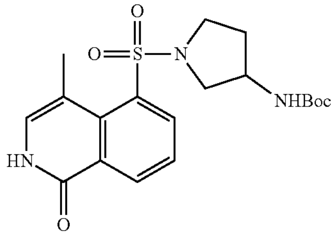

2

Step 1

To a solution of compound 2a (5.0 g, 36.7 mmol) in concentrated hydrochloric acid (50 mL, 12 M) was added slowly the solution of sodium nitrite (2.29 g, 33.2 mmol) in water (8 mL) at −5° C., stirred for 1 hour at −5° C. To a solution of cuprous chloride (156 mg, 1.58 mmol) and cupric chloride (2.34 g, 17.4 mmol) in glacial acetic acid (80 mL) was introduced sulphur dioxide until saturation, and then the previous reaction solution was slowly added dropwise to the solution containing sulfur dioxide at −5° C., stirred for 1 hour at 20° C. After the reaction was completed, water (150 mL) was added to the reaction solution, extracted with dichloromethane (150 mL×4). The combined organic phase was washed with saturated brine (500 mL×1), dried with anhydrous sodium sulfate, filtered, the filtrate was concentrated under reduced pressure to obtain a residue, and the residue crude 2b was directly used for the next step without purification. MS-ESI calculated value $[M+H]^+$ 242, actually measured value 242.

Step 2

Compound 2c was obtained referring to step 2 of intermediate 1.

Step 3

Compound 2d was obtained referring to step 3 of intermediate 1.

Step 4

Intermediate 2 was obtained referring to step 4 of intermediate 1. MS-ESI calculated value $[M+H]^+$ 408, actually measured value 408.

Intermediate 3

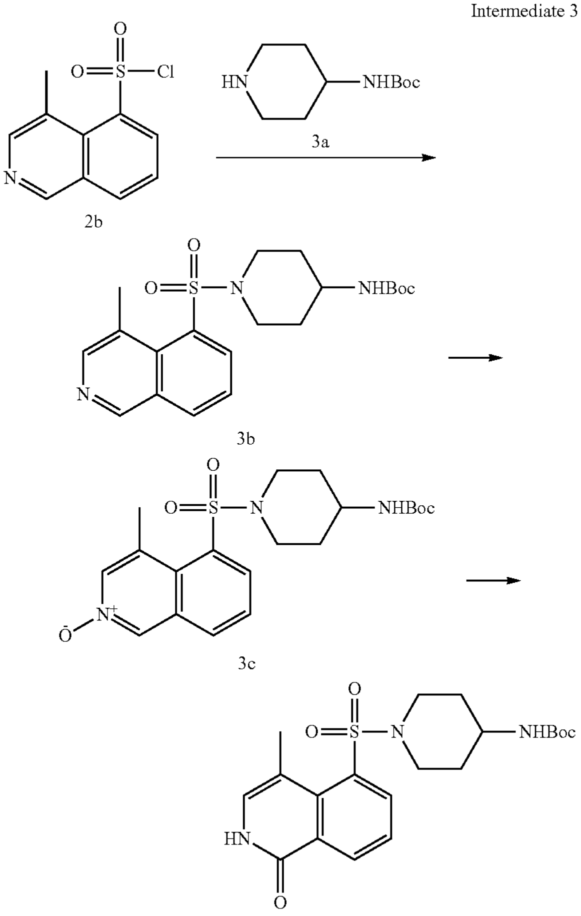

2b

3b

3c

3

Step 1

Compound 3b was obtained referring to step 2 of intermediate 1. MS-ESI calculated value $[M+H]^+$ 406, actually measured value 406.

Step 2

Compound 3c was obtained referring to step 3 of intermediate 1. MS-ESI calculated value $[M+H]^+$ 422, actually measured value 422.

Step 3

Intermediate 3 was obtained referring to step 4 of intermediate 1. MS-ESI calculated value $[M+H]^+$ 422, actually measured value 422.

Intermediate 4

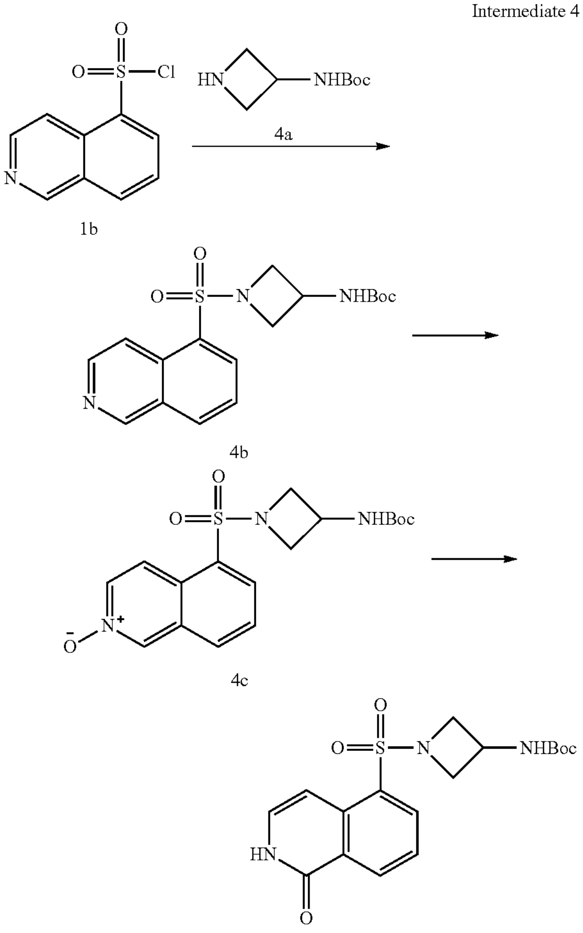

1b

4b

4c

4

Step 1

Compound 4b was obtained referring to step 2 of intermediate 1. MS-ESI calculated value $[M+H]^+$ 364, actually measured value 364.

Step 2

Compound 4c was obtained referring to step 3 of intermediate 1. MS-ESI calculated value $[M+H]^+$ 380, actually measured value 380.

Step 3

Intermediate 4 was obtained referring to step 4 of intermediate 1. MS-ESI calculated value $[M+Na]^+$ 402, actually measured value 402.

Intermediate 5

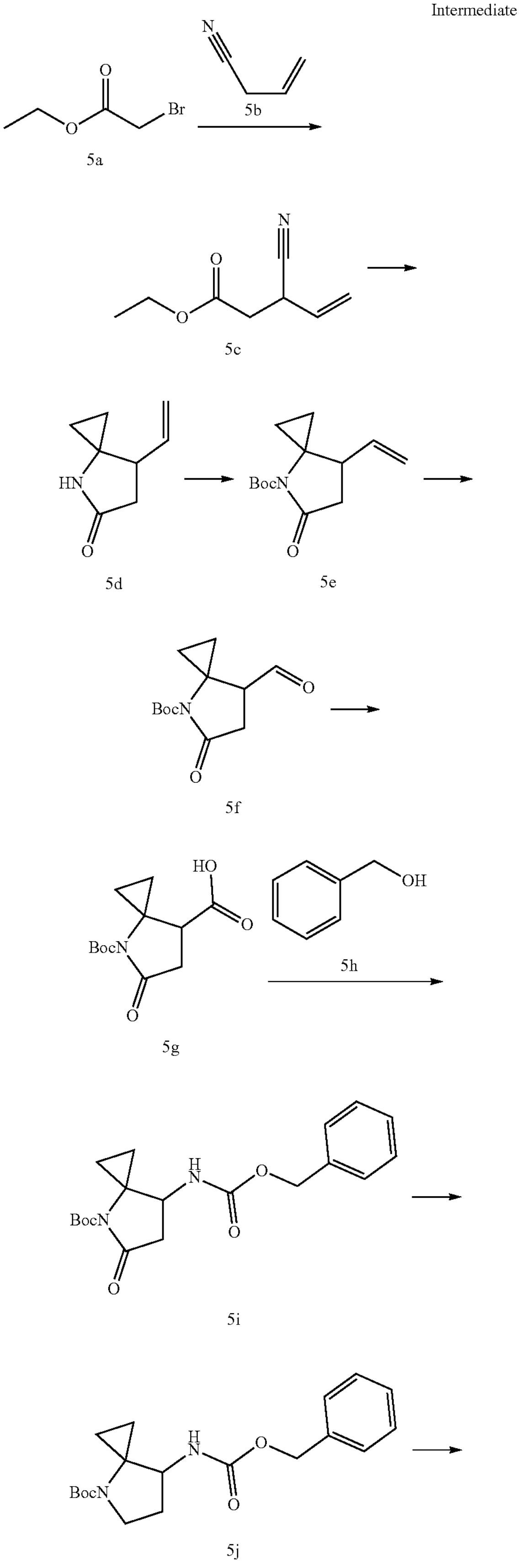

-continued

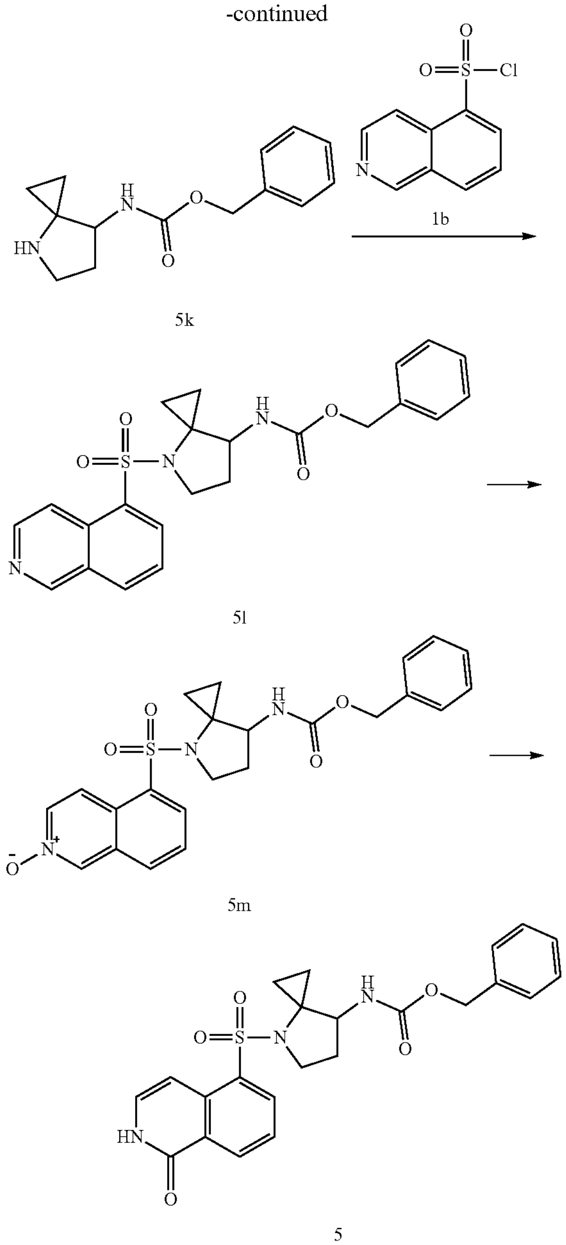

Step 1

To a solution of diisopropylamine (36.4 g, 359 mmol) in tetrahydrofuran (1.5 mL) was added dropwise n-butyl lithium (2.5 M, 131.2 mL) at −78° C. under the nitrogen atmosphere; after stirred for 1 hour at −78° C., compound 5b (20.1 g, 299 mmol) was added dropwise to the reaction solution at −78° C. under the nitrogen atmosphere; after stirred for 1 hour at −78° C., compound 5a (50 g, 299 mmol) was added dropwise to the reaction solution at −78° C. under the nitrogen atmosphere, stirred for 1 hour at −78° C. under the nitrogen atmosphere. After the reaction was completed, quenched with saturated aqueous ammonium chloride solution (2 L) and extracted with ethyl acetate (500 mL×3). The combined organic phase was washed with saturated brine (1 L×1) and dried with anhydrous sodium sulfate, filtered, the filtrate was concentrated under reduced pressure, and the crude product was separated and purified by silica gel column chromatography (petroleum ether/ethyl acetate) to obtain compound 5c. $^1H$ NMR (400 MHz, $CDCl_3$) δ=5.83-5.70 (m, 1H), 5.50 (dd, J=1.5, 16.9 Hz, 1H), 5.36-5.30 (m, 1H), 4.22-4.17 (m, 2H), 3.77-3.70 (m, 1H), 2.81-2.71 (m, 1H), 2.68-2.59 (m, 1H), 1.29-1.26 (m, 3H).

Step 2

To a solution of compound 5c (60.7 g, 396 mmol) in tetrahydrofuran (1.2 L) was added tetraisopropyltitanate (113 g, 396 mmol) under the nitrogen atmosphere, and added dropwise ethyl magnesium bromide (89.8 g, 674 mmol) at 20° C. under the nitrogen atmosphere, stirred for 3 hours at 20° C. After the reaction was completed, quenched with water (300 mL) and filtered, the filtrate was concentrated under reduced pressure, and the crude product was separated and purified by silica gel column chromatography (petroleum ether/ethyl acetate) to obtain compound 5d. MS-ESI calculated value $[M+H]^+$138, actually measured value 138.

Step 3

To a solution of compounds 5d (81.0 g, 590.5 mmol) in acetonitrile (500 mL) was added 4-dimethylaminopyridine (7.21 g, 59.1 mmol) and di-tert-butyl dicarbonate (155 g, 709 mmol) successively, stirred for 3 hours at 20° C. After the reaction was completed, quenched with water (1 L) and extracted with ethyl acetate (500 mL×3). The combined organic phase was washed with saturated brine (500 mL×1) and dried with anhydrous sodium sulfate, filtered, the filtrate was concentrated under reduced pressure, and the crude product was separated and purified by silica gel column chromatography (petroleum ether/ethyl acetate) to obtain compound 5e. MS-ESI calculated value $[M+H]^+$ 238, actually measured value 238.

Step 4

To a solution of compound 5e (10.8 g, 45.5 mmol) in methanol (48 mL) and water (72 mL) was added sodium periodate (29.2 g, 136.4 mmol) and osmium tetraoxide (173 mg, 682 μmol) at 20° C., stirred for 2 hours at 20° C. After the reaction was completed, water (100 mL) was added to the reaction solution and the reaction solution was extracted with ethyl acetate (100 mL×3). The combined organic phase was washed with saturated brine (100 mL×1) and dried with anhydrous sodium sulfate, filtered, the filtrate was concentrated under reduced pressure, and the crude product was separated and purified by silica gel column chromatography (petroleum ether/ethyl acetate) to obtain compound 5f.

Step 5

To a solution of compound 5f (4.00 g, 16.7 mmol) in tert-butanol (50 mL) and tetrahydrofuran (50 mL) was added isopentene (14.6 g, 208 mmol), sodium hypochlorite (1.66 g, 18.4 mmol), sodium phosphate monobasic monohydrate (4.61 g, 33.4 mmol) and water (35 mL) successively at 0° C., stirred for 12 hours at 20° C. After the reaction was completed, the pH of the reaction solution was adjusted to 4 with 1N aqueous hydrochloric acid solution and the reaction solution was extracted with ethyl acetate (50 mL×3). The combined organic phase was washed with saturated brine (100 mL×1) and dried with anhydrous sodium sulfate, and filtered, the filtrate was concentrated under reduced pressure to obtain a residual. Water (50 mL) was added to the residue, aqueous $Na_2CO_3$ solution was used to adjust the pH to 10, and ethyl acetate (50 mL×1) was used for extraction to collect aqueous phase. The pH of the aqueous phase was adjusted to 4 with the 1N aqueous hydrochloric acid solution and the aqueous phase was extracted with ethyl acetate (50 mL×3). The combined organic phase was washed with saturated brine (100 mL×1), dried with anhydrous sodium sulfate and filtered, and the filtrate was concentrated under reduced pressure to obtain compound 5g.

Step 6

To a solution of compound 5g (3.10 g, 12.1 mmol) in toluene (30 mL) was added N,N-diisopropylethylamine (2.04 g, 15.8 mmol), diphenylphosphorylazide (4.34 g, 15.8 mmol, 3.42 ml) and a 4 A molecular sieve (2.00 g) at 0° C., stirred for 0.5 hours at 20° C., and stirred for another 0.5 hour at 90° C., then cooled to 20° C. Compound 5h (1.44 g, 13.4 mmol) was added to the reaction solution at 20° C., stirred the reaction solution for 12 hours at 20° C. After the reaction was completed, the reaction solution was filtered, water (30 mL) was added to the filtrate and extracted with ethyl acetate (30 mL×2). The combined organic phase was washed with saturated brine (50 mL×1) and dried with anhydrous sodium sulfate, filtered, the filtrate was concentrated under reduced pressure, and the crude product was separated and purified by silica gel column chromatography (petroleum ether/ethyl acetate) to obtain compound 5i.

Step 7

To a solution of compound 5i (500 mg, 1.39 mmol) in tetrahydrofuran (5 mL) was added borane-tetrahydrofuran (1 M, 13.9 mL) at 0° C. under the nitrogen atmosphere, stirred for 1 hour at 25° C. After the reaction was completed, quenched with saturated aqueous ammonium chloride solution (20 mL), and extracted with ethyl acetate (20 mL×3). The combined organic phase was washed with saturated brine (20 mL×1) and dried with anhydrous sodium sulfate, filtered, the filtrate was concentrated under reduced pressure, and the crude product was separated and purified by preparative thin layer chromatography (petroleum ether/ethyl acetate) to obtain compound 5j.

Step 8

To a solution of Compound 5j (295 mg, 852 μmol) in ethyl acetate (3 mL) was added ethyl acetate hydrochloride (4 M, 5 mL), stirred for 0.5 hour at 25° C. After the reaction was completed, the reaction solution was concentrated under reduced pressure to obtain compound 5k.

Step 9

To a solution of compound 5k (420 mg, 1.59 mmol) in dichloromethane (10 mL) was added compound 1b (268 mg, 948 μmol) and N,N-diisopropylethylamine (489.98 mg, 3.79 mmol) at 0° C. under the nitrogen atmosphere, stirred the reaction mixture for 12 hours at 25° C. After the reaction was completed, dichloromethane (10 mL) and water (15 mL) were added to the reaction solution, extracted with dichloromethane (10 mL×2); and the combined organic phase was washed with saturated brine (20 mL×1), dried with anhydrous sodium sulfate, filtered and concentrated under reduced pressure. The crude product was separated and purified by silica gel plate chromatography (petroleum ether/ethyl acetate) to obtain compound 5l. MS-ESI calculated value $[M+H]^+$ 438, actually measured value 438.

Step 10

Compound 5m was obtained referring to step 3 of intermediate 1. MS-ESI calculated value $[M+H]^+$ 454, actually measured value 454.

Step 11

Intermediate 5 was obtained referring to step 4 of intermediate 1. MS-ESI calculated value $[M+H]^+$ 454, actually measured value 454.

Intermediate 6

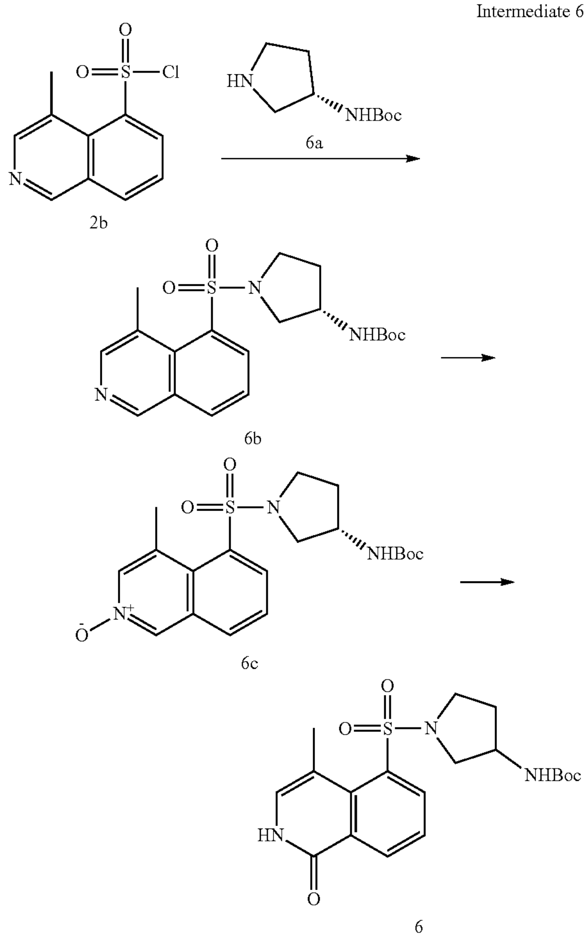

2b

6a

6b

6c

6

Step 1

Compound 6b was obtained referring to step 2 of intermediate 1.

Step 2

Compound 6c was obtained referring to step 3 of intermediate 1.

Step 3

Intermediate 6 was obtained referring to step 4 of intermediate 1. MS-ESI calculated value $[M+H]^+$ 408, actually measured value 408.

Example 1: Compound 7

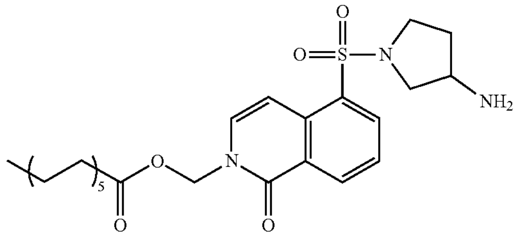

Synthesis Route:

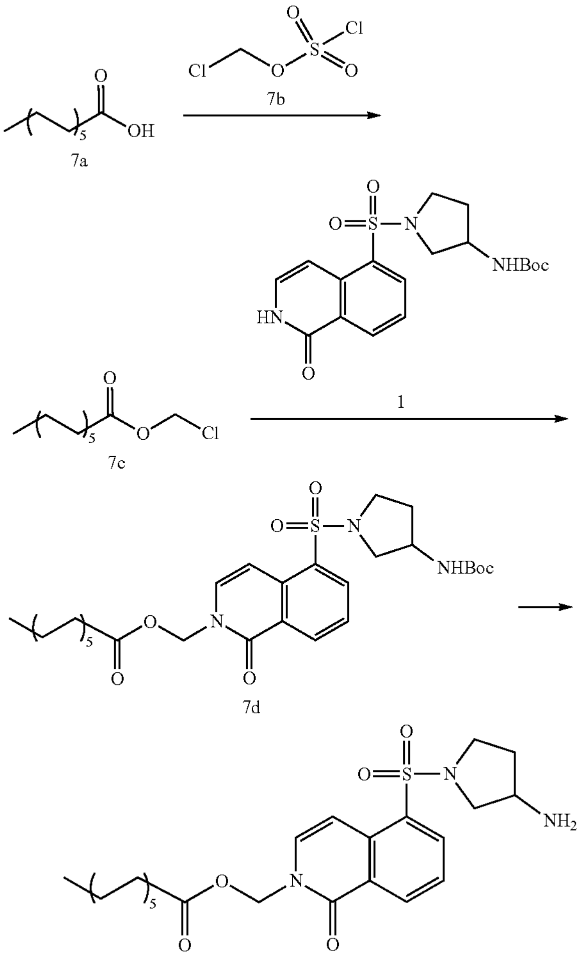

7a

7c

7d

7

Step 1

To a solution of compound 7a (1 g, 4.99 mmol) in dichloromethane (30 mL) and water (30 mL) was added sodium bicarbonate (1.68 g, 12.0 mmol) and tetrabutylammonium fluoride (1 M, 499 μL), then a solution of compound 7b (824 mg, 4.99 mmol) in dichloromethane (10 mL) was added to the reaction system under the condition of stirring at 0° C., stirred for 16 hours at 30° C. The organic phase was separated, dried with anhydrous magnesium sulfate and filtered, concentrated under reduced pressure to obtain compound 7c.

Step 2

At 0° C., to a solution of intermediate 1 (150 mg, 324 μmol) in N,N-dimethylformamide (6 mL) was added sodium hydride (15.6 mg, 389 μmol, purity: 60%) under nitrogen atmosphere, then added compound 7c (113 mg, 454 μmol) after stirred for 0.5 hour, warmed to 25° C. stirred for 2 hours. Ice water (30 mL) was slowly added to the reaction solution, extracted with ethyl acetate (20 mL×3), and the organic phase was dried with anhydrous sodium sulfate, filtered, concentrated under reduced pressure. The residue was purified by silica gel plate to obtain compound 7d. MS-ESI calculated value $[M+Na]^+$ 628, actually measured value 628.

Step 3

To a solution of compound 7d (96.0 mg, 154 μmol) in dichloromethane (20 mL) was added trimethylsllytrifluoromethanesulphonate (68.6 mg, 309 μmol), then stirred for 1 hour at 0-5° C. 2,6-dimethylpyridine (49.6 mg, 462 μmol) was added dropwise, stirred for another 1 hour at 0-5° C. Water (30 mL) was added to the reaction solution, extracted with dichloromethane (20 mL×3), and the organic phase was dried with anhydrous sodium sulfate, filtered, concentrated under reduced pressure. The residue was purified by preparative high performance liquid (formic acid condition) to obtain a formate of compound 7. $^1H$ NMR (400 MHz, $CD_3OD$) δ=8.70 (d, J=7.8 Hz, 1H), 8.52 (s, 1H), 8.39 (dd, J=7.8, 1.3 Hz, 1H), 7.74 (t, J=7.8 Hz, 1H), 7.67 (d, J=7.8 Hz, 1H), 7.51 (d, J=7.8 Hz, 1H), 6.00 (s, 2H), 3.81-3.90 (m, 1H), 3.57-3.66 (m, 1H), 3.49-3.56 (m, 1H), 3.42 (dd, J=10.8, 4.1 Hz, 1H), 3.30 (d, J=6.2 Hz, 1H), 2.39 (t, J=7.4 Hz, 2H), 2.26-2.36 (m, 1H), 1.92-2.03 (m, 1H), 1.55-1.69 (m, 1H), 1.55-1.69 (m, 2H), 1.20-1.34 (m, 16H), 0.91 (t, J=6.8 Hz, 3H). MS-ESI calculated value $[M+H]^+$ 506, actually measured value 506.

The formate of compound 7 can be adjusted the pH of the reaction solution to 8-9 by adding a saturated aqueous sodium carbonate solution to the system, and then, after the extraction with ethyl acetate, the reaction solution was concentrated to obtain compound 7.

Example 2: Compound 8

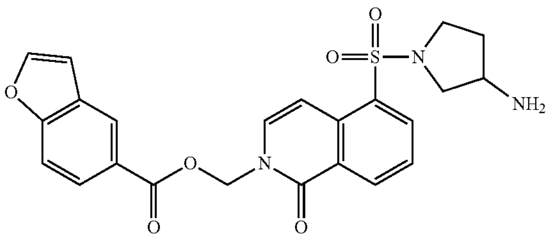 [SMILES: NC1CCN(S(=O)(=O)c2cccc3c(=O)n(COC(=O)c4ccc5occc5c4)ccc23)C1]

Synthesis Route:

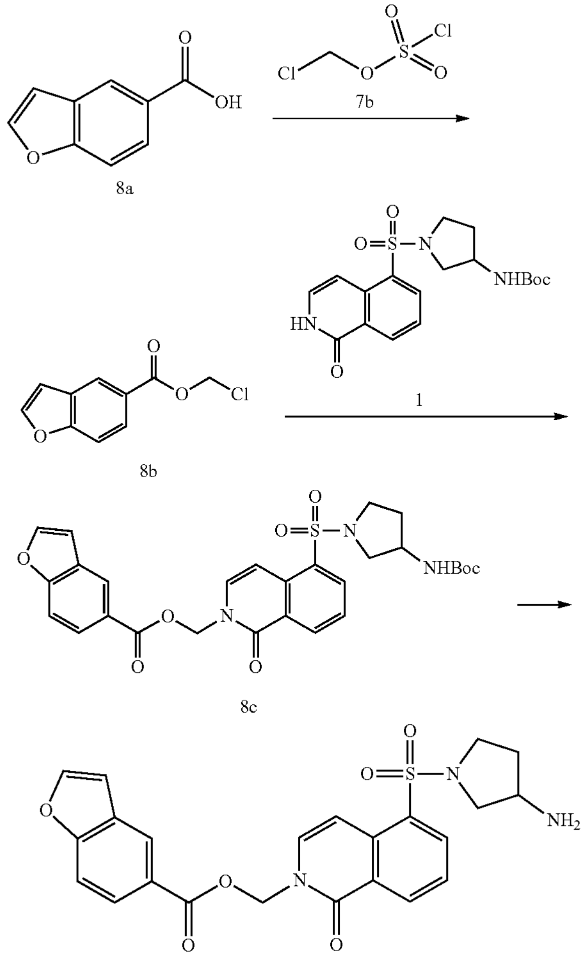

8

Step 1

Compound 8b was obtained referring to step 1 of Example 1. $^1H$ NMR (400 MHz, $CDCl_3$) δ=8.27 (d, J=1.6 Hz, 1H), 7.94 (dd, J=8.8, 1.7 Hz, 1H), 7.60 (d, J=2.4 Hz, 1H), 7.44 (d, J=8.8 Hz, 1H), 6.74 (dd, J=2.2, 0.7 Hz, 1H), 5.89 (s, 2H).

Step 2

Compound 8c was obtained referring to step 2 of Example 1. MS-ESI calculated value $[M+Na]^+$ 590, actually measured value 590.

Step 3

A formate of compound 8 was obtained referring to step 3 of Example 1. $^1H$ NMR (400 MHz, $CD_3OD$) δ=8.72 (d, J=7.8 Hz, 1H), 8.48 (s, 1H), 8.37-8.42 (m, 2H), 8.04 (dd, J=8.8, 1.7 Hz, 1H), 7.88 (d, J=2.2 Hz, 1H), 7.82 (d, J=7.8 Hz, 1H), 7.73 (t, J=7.8 Hz, 1H), 7.58 (dd, J=19.8, 8.4 Hz, 2H), 6.97 (dd, J=2.2, 0.7 Hz, 1H), 6.27 (s, 2H), 3.72-3.83 (m, 1H), 3.49-3.63 (m, 2H), 3.35 (d, J=1.4 Hz, 1H), 2.20-2.33 (m, 1H), 1.85-1.97 (m, 1H). MS-ESI calculated value $[M+H]^+$ 468, actually measured value 468.

The formate of compound 8 can be adjusted the pH of the reaction solution to 8-9 by adding a saturated aqueous sodium carbonate solution to the system, and then, after the extraction with ethyl acetate, the reaction solution was concentrated to obtain compound 8.

Example 3: Compound 9

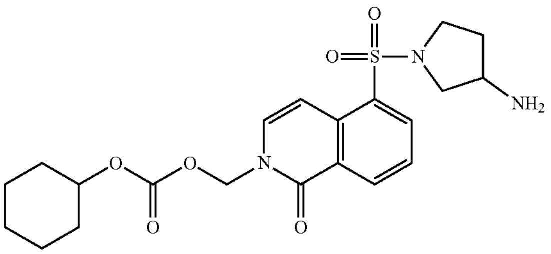 [SMILES: NC1CCN(S(=O)(=O)c2cccc3c(=O)n(COC(=O)OC4CCCCC4)ccc23)C1]

Synthesis Route:

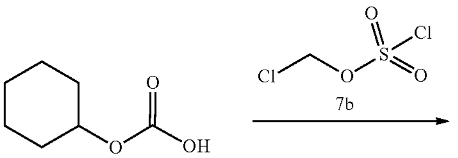

9a

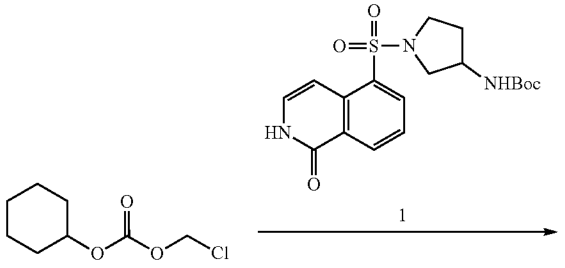

9b

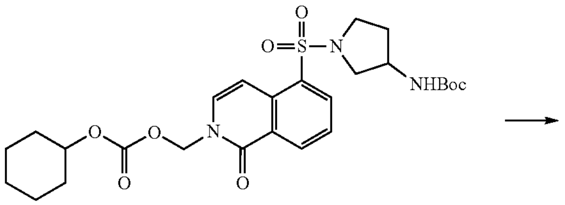

9c

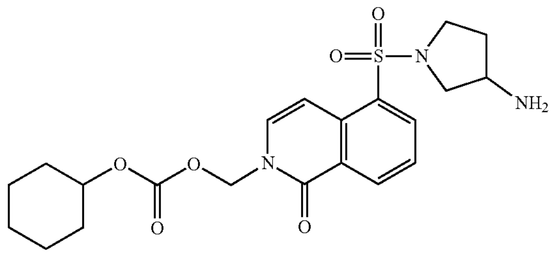

9

Step 1

Compound 9b was obtained referring to step 1 of Example 1. $^{1}$H NMR (400 MHz, $CDCl_3$) δ=5.72 (s, 2H), 4.63-4.77 (m, 1H), 1.93 (dd, J=12.5, 3.9 Hz, 2H), 1.75 (dd, J=9.2, 3.9 Hz, 2H), 1.45-1.58 (m, 3H), 1.23-1.42 (m, 3H).

Step 2

Compound 9c was obtained referring to step 2 of Example 1. MS-ESI calculated value $[M+Na]^+$ 572, actually measured value 572.

Step 3

A formate of compound 9 was obtained referring to step 3 of Example 1. $^{1}$H NMR (400 MHz, $CD_3OD$) δ=8.68 (d, J=8.0 Hz, 1H), 8.46 (s, 1H), 8.39 (dd, J=7.8, 1.2 Hz, 1H), 7.73 (t, J=7.8 Hz, 1H), 7.67 (d, J=7.8 Hz, 1H), 7.51 (d, J=7.8 Hz, 1H), 6.00 (s, 2H), 4.62-4.71 (m, 1H), 3.77-3.87 (m, 1H), 3.50-3.64 (m, 2H), 3.34-3.40 (m, 2H), 2.24-2.36 (m, 1H), 1.86-2.03 (m, 3H), 1.75 (dt, J=6.4, 3.1 Hz, 2H), 1.24-1.61 (m, 6H). MS-ESI calculated value $[M+H]^+$ 450, actually measured value 450.

The formate of compound 9 can be adjusted the pH of the reaction solution to 8-9 by adding saturated aqueous sodium carbonate solution to the system, and then, after the extraction with ethyl acetate, the reaction solution was concentrated to obtain compound 9.

Example 4: Compound 10

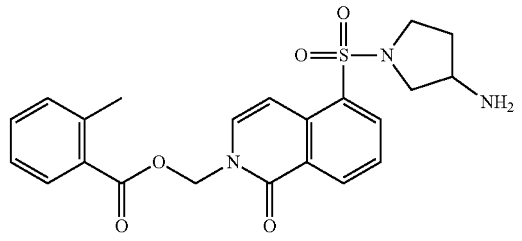 [SMILES: Cc1ccccc1C(=O)OCn1ccc2c(S(=O)(=O)N3CCC(N)C3)cccc2c1=O]

Synthesis Route:

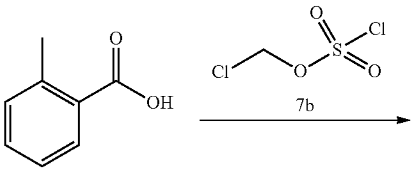

10a

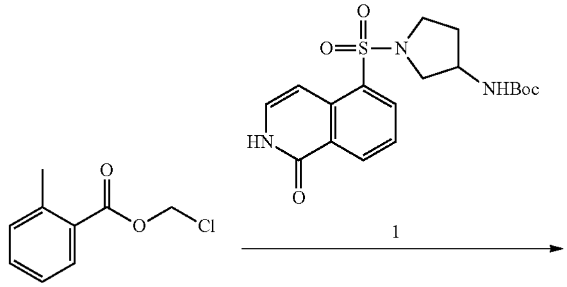

10b

-continued

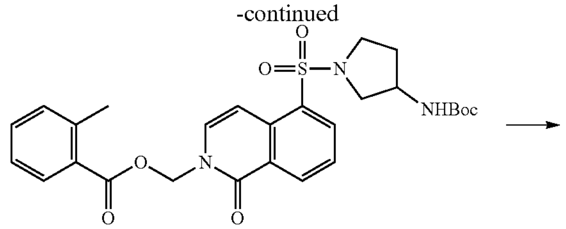

10c

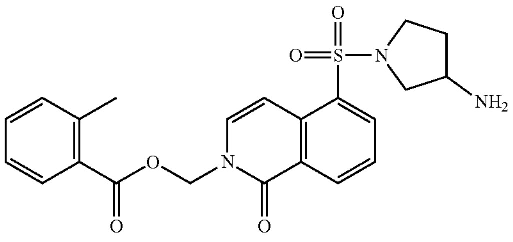

10

Step 1

Compound 10b was obtained referring to step 1 of Example 1. $^1$H NMR (400 MHz, $CDCl_3$) δ=7.99 (dd, J=8.2, 1.3 Hz, 1H), 7.47 (td, J=7.4, 1.4 Hz, 1H), 7.25-7.32 (m, 2H), 5.96 (s, 2H), 2.65 (s, 3H).

Step 2

Compound 10c was obtained referring to step 2 of Example 1. MS-ESI calculated value $[M+Na]^+$ 564, actually measured value 564.

Step 3

A formate of compound 10 was obtained referring to step 3 of Example 1. $^1$H NMR (400 MHz, $CD_3OD$) δ=8.69 (d, J=7.8 Hz, 1H), 8.37 (dd, J=7.6, 1.2 Hz, 1H), 7.91 (d, J=7.8 Hz, 1H), 7.79 (d, J=7.8 Hz, 1H), 7.69-7.76 (m, 1H), 7.53 (d, J=7.8 Hz, 1H), 7.45 (td, J=7.4, 1.2 Hz, 1H), 7.22-7.33 (m, 2H), 6.21 (s, 2H), 3.81-3.92 (m, 1H), 3.51-3.64 (m, 2H), 3.41 (dd, J=10.8, 4.2 Hz, 1H), 3.32-3.33 (m, 1H), 2.57 (s, 3H), 2.24-2.40 (m, 1H), 1.90-2.04 (m, 1H). MS-ESI calculated value $[M+H]^+$ 442, actually measured value 442.

The formate of compound 10 can be adjusted the pH of the reaction solution to 8-9 by adding a saturated aqueous sodium carbonate solution to the system, and then, after the extraction with ethyl acetate, the reaction solution was concentrated to obtain compound 10.

Example 5: Compound 11

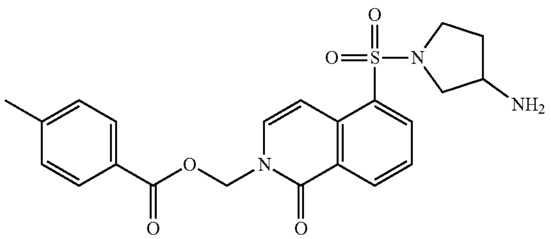

Synthesis Route:

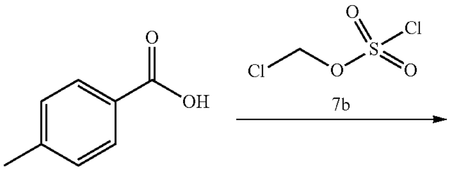

11a

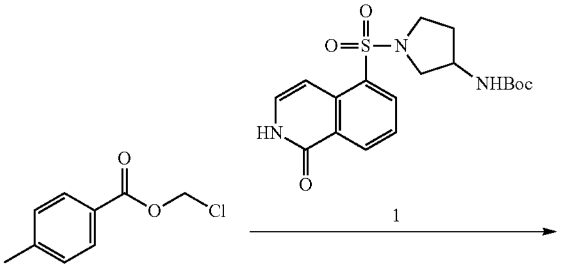

11b

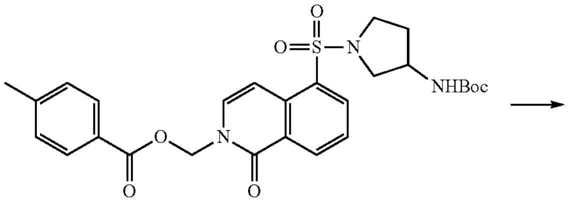

11c

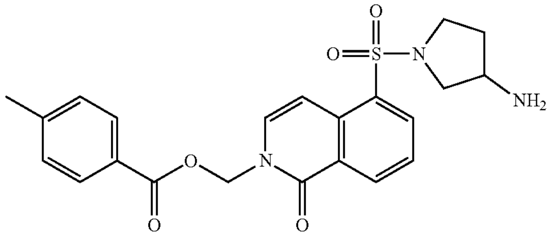 [SMILES: Cc1ccc(C(=O)OCn2ccc3c(S(=O)(=O)N4CCC(N)C4)cccc3c2=O)cc1]

11

Step 1

Compound 11b was obtained referring to step 1 of Example 1. $^1$H NMR (400 MHz, $CDCl_3$) δ=7.94-7.98 (m, 2H), 7.25 (d, J=8.4 Hz, 2H), 5.93 (s, 2H), 2.40 (s, 3H).

Step 2

Compound 11c was obtained referring to step 2 of Example 1. MS-ESI calculated value $[M+Na]^+$ 564, actually measured value 564.

Step 3

A formate of compound 11 was obtained referring to step 3 of Example 1. $^1$H NMR (400 MHz, $CD_3OD$) δ=8.72 (d, J=8.6 Hz, 1H), 8.39 (d, J=7.6 Hz, 1H), 7.94 (d, J=8.0 Hz, 2H), 7.68-7.84 (m, 2H), 7.54 (d, J=7.8 Hz, 1H), 7.31 (d, J=7.8 Hz, 2H), 6.23 (s, 2H), 3.84 (s, 1H), 3.49-3.64 (m, 2H), 3.39 (d, J=15.2 Hz, 2H), 2.42 (s, 3H), 2.30 (s, 1H), 1.97 (s, 1H). MS-ESI calculated value $[M+H]^+$ 442, actually measured value 442.

The formate of compound 11 can be adjusted the pH of the reaction solution to 8-9 by adding a saturated aqueous sodium carbonate solution to the system, and then, after the extraction with ethyl acetate, the reaction solution was concentrated to obtain compound 11.

Example 6: Compound 12

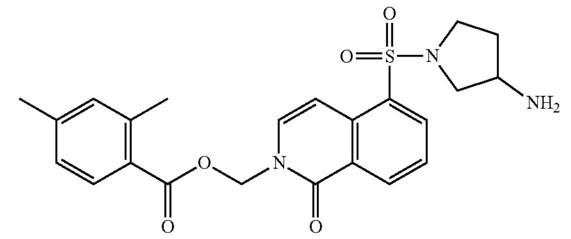 [SMILES: Cc1ccc(C(=O)OCn2ccc3c(S(=O)(=O)N4CCC(N)C4)cccc3c2=O)c(C)c1]

Synthesis Route:

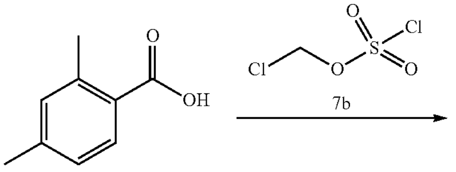

12a

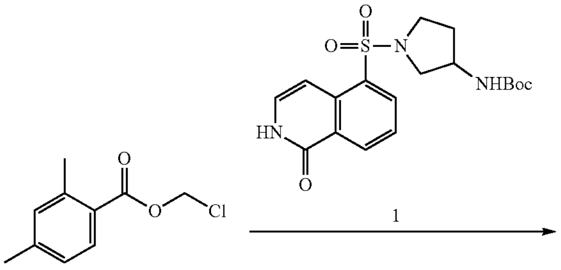

12b

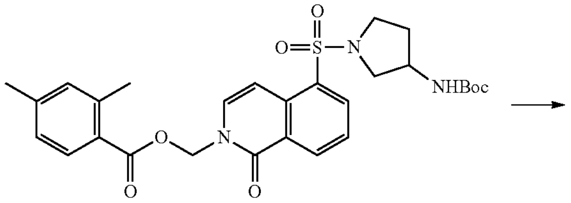

12c

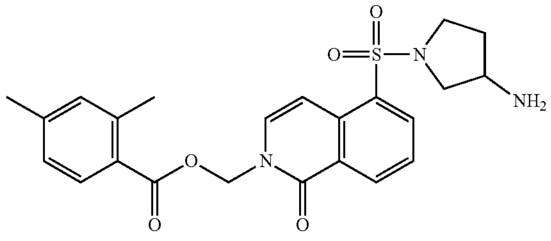

12

Step 1

Compound 12b was obtained referring to step 1 of Example 1. $^1$H NMR (400 MHz, $CDCl_3$) δ=7.92 (d, J=7.8 Hz, 1H), 7.05-7.15 (m, 2H), 5.95 (s, 2H), 2.63 (s, 3H), 2.39 (s, 3H).

Step 2

Compound 12c was obtained referring to step 2 of Example 1. MS-ESI calculated value $[M+Na]^+$ 578, actually measured value 578.

Step 3

Compound 12 was obtained referring to step 3 of Example 1. $^1$H NMR (400 MHz, $CD_3OD$) δ=8.73 (d, J=7.8 Hz, 1H), 8.40 (dd, J=7.8, 1.3 Hz, 1H), 7.83 (dd, J=18.2, 8.0 Hz, 2H), 7.74 (t, J=7.8 Hz, 1H), 7.55 (d, J=7.8 Hz, 1H), 7.14 (s, 1H), 7.09 (d, J=8.4 Hz, 1H), 6.20 (s, 2H), 3.79-3.89 (m, 1H), 3.50-3.65 (m, 2H), 3.35-3.45 (m, 2H), 2.56 (s, 3H), 2.35 (s, 3H), 2.24-2.34 (m, 1H), 1.90-2.03 (m, 1H). MS-ESI calculated value $[M+H]^+$ 456, actually measured value 456.

Example 7: Compound 13

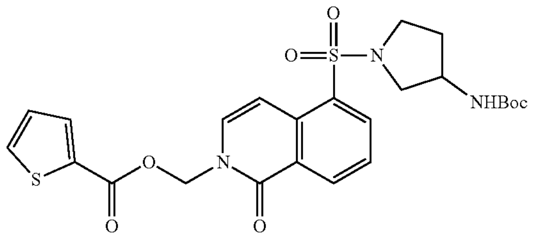 [SMILES: CC(C)(C)OC(=O)NC1CCN(S(=O)(=O)c2cccc3c(=O)n(COC(=O)c4cccs4)ccc23)C1]

Synthesis Route:

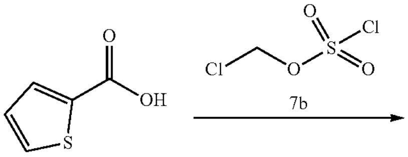

13a

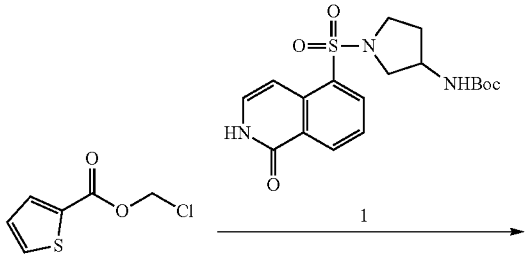

13b

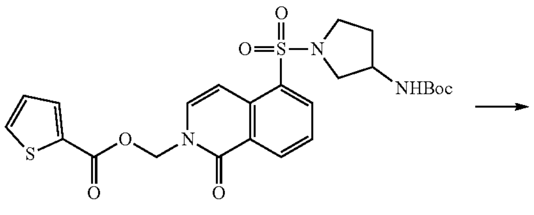

13c

-continued

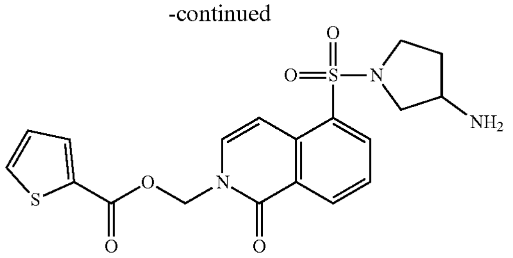

13

Step 1

Compound 13b was obtained referring to step 1 of Example 1. $^1$H NMR (400 MHz, $CDCl_3$) δ=7.79-7.85 (m, 1H), 7.59 (dd, J=4.8, 1.2 Hz, 1H), 7.04-7.10 (m, 1H), 5.79-5.90 (m, 2H)

Step 2

Compound 13c was obtained referring to step 2 of Example 1. MS-ESI calculated value $[M+Na]^+$ 556, actually measured value 556.

Step 3

A formate of compound 13 was obtained referring to step 3 of Example 1. $^1$H NMR (400 MHz, $CD_3OD$) δ=8.71 (d, J=7.8 Hz, 1H), 8.40 (s, 1H), 8.39 (dd, J=7.8, 1.3 Hz, 1H), 7.89 (dd, J=3.8, 1.2 Hz, 1H), 7.83 (dd, J=5.0, 1.2 Hz, 1H), 7.69-7.79 (m, 2H), 7.54 (d, J=7.8 Hz, 1H), 7.19 (dd, J=5.0, 3.9 Hz, 1H), 6.21 (s, 2H), 3.70-3.83 (m, 1H), 3.48-3.65 (m, 2H), 3.33-3.35 (m, 2H), 2.21-2.35 (m, 1H), 1.84-1.99 (m, 1H). MS-ESI calculated value $[M+H]^+$ 434, actually measured value 434.

The formate of compound 13 can be adjusted the pH of the reaction solution to 8-9 by adding a saturated aqueous sodium carbonate solution to the system, and then, after the extraction with ethyl acetate, the reaction solution was concentrated to obtain compound 13.

Example 8: Compound 14

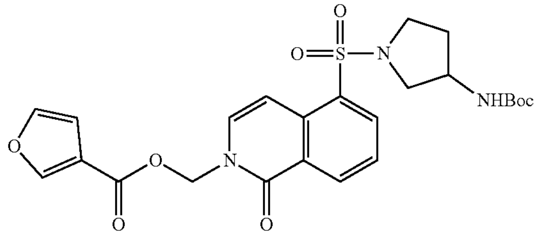 [SMILES: CC(C)(C)OC(=O)NC1CCN(S(=O)(=O)c2cccc3c(=O)n(COC(=O)c4ccoc4)ccc23)C1]

Synthesis Route:

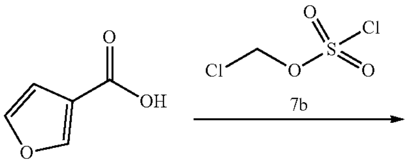

14a

7b

-continued

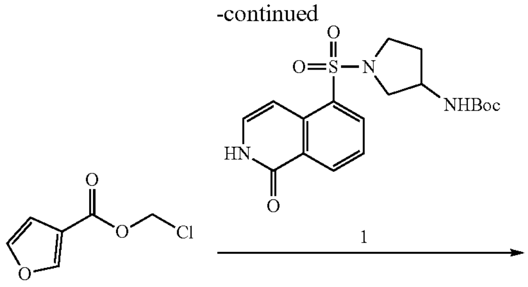

14b

1

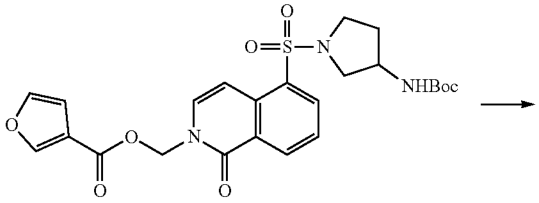

14c

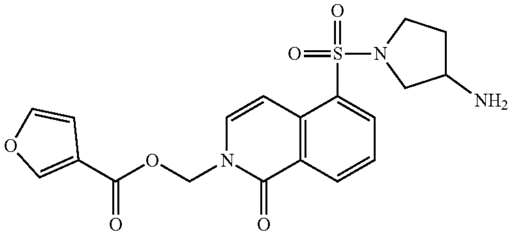

14

Step 1

Compound 14b was obtained referring to step 1 of Example 1. $^1$H NMR (400 MHz, $CDCl_3$) δ=7.98-8.05 (m, 1H), 7.37-7.42 (m, 1H), 6.71 (dd, J=1.8, 0.7 Hz, 1H), 5.81 (s, 2H).

Step 2

Compound 14c was obtained referring to step 2 of Example 1. MS-ESI calculated value $[M+Na]^+$ 540, actually measured value 540.

Step 3

A formate of compound 14 was obtained referring to step 3 of Example 1. $^1$H NMR (400 MHz, $CD_3OD$) δ=8.70 (d, J=7.8 Hz, 1H), 8.49 (s, 1H), 8.39 (dd, J=7.8, 1.3 Hz, 1H), 8.23-8.26 (m, 1H), 7.69-7.78 (m, 2H), 7.62 (t, J=1.8 Hz, 1H), 7.53 (d, J=7.8 Hz, 1H), 6.80 (dd, J=1.8, 0.7 Hz, 1H), 6.17 (s, 2H), 3.74-3.83 (m, 1H), 3.50-3.62 (m, 2H), 3.34-3.38 (m, 1H), 3.29-3.32 (m, 1H), 2.20-2.34 (m, 1H), 1.85-1.99 (m, 1H). MS-ESI calculated value $[M+H]^+$ 418, actually measured value 418.

The formate of compound 14 can be adjusted the pH of the reaction solution to 8-9 by adding a saturated aqueous sodium carbonate solution to the system, and then, after the extraction with ethyl acetate, the reaction solution was concentrated to obtain compound 14.

Example 9: Compound 15

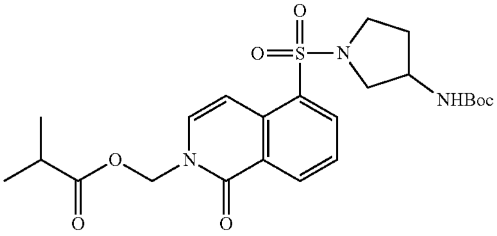 [SMILES: CC(C)C(=O)OCn1ccc2c(S(=O)(=O)N3CCC(NC(=O)OC(C)(C)C)C3)cccc2c1=O]

Synthesis Route:

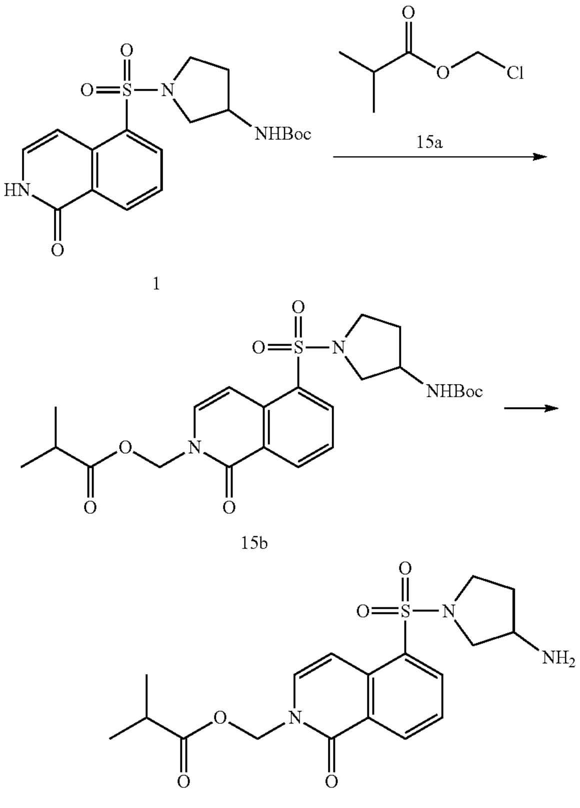

1

15a

15b

15

Step 1

Compound 15b was obtained referring to step 2 of Example 1. MS-ESI calculated value $[M+Na]^+$ 516, actually measured value 516.

Step 2

A formate of compound 15 was obtained referring to step 3 of Example 1. $^1H$ NMR (400 MHz, $CD_3OD$) δ=8.67 (d, J=7.8 Hz, 1H), 8.39 (s, 1H), 8.37 (dd, J=7.8, 1.3 Hz, 1H), 7.72 (t, J=7.8 Hz, 1H), 7.66 (d, J=7.8 Hz, 1H), 7.50 (d, J=7.8 Hz, 1H), 5.99 (s, 2H), 3.76-3.89 (m, 1H), 3.50-3.65 (m, 2H), 3.33 (d, J=1.6 Hz, 2H), 2.62 (spt, J=7.0 Hz, 1H), 2.22-2.37 (m, 1H), 1.90-2.02 (m, 1H), 1.17 (d, J=7.0 Hz, 6H), 0.00-0.00 (m, 1H). MS-ESI calculated value $[M+H]^+$ 394, actually measured value 394.

The formate of compound 15 can be adjusted the pH of the reaction solution to 8-9 by adding a saturated aqueous sodium carbonate solution to the system, and then, after the extraction with ethyl acetate, the reaction solution was concentrated to obtain compound 15.

Example 10: Compound 16

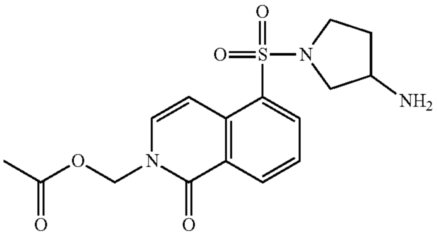 [SMILES: CC(=O)OCn1ccc2c(S(=O)(=O)N3CCC(N)C3)cccc2c1=O]

Synthesis Route:

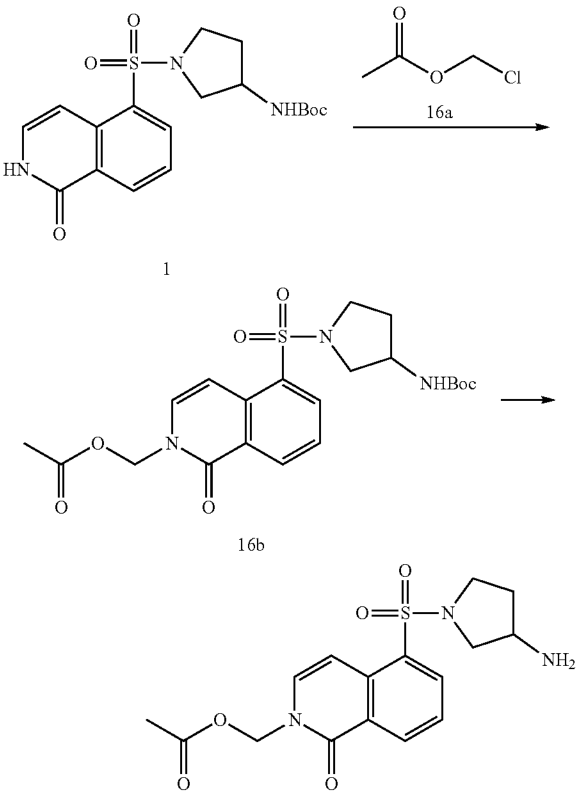

1

16a

16b

16

Step 1

Compound 16b was obtained referring to step 2 of Example 1. $^1H$ NMR (400 MHz, $CDCl_3$) δ=8.72 (dd, J=8.0, 1.2 Hz, 1H), 8.32 (dd, J=7.8, 1.2 Hz, 1H), 7.59 (t, J=8.0 Hz, 1H), 7.34-7.48 (m, 2H), 5.95 (s, 2H), 4.66 (s, 1H), 4.18 (s, 1H), 3.37-3.61 (m, 2H), 3.27 (s, 2H), 2.09-2.18 (m, 4H), 1.84 (d, J=5.6 Hz, 1H), 1.42 (s, 9H).

Step 2

A formate of compound 16 was obtained referring to step 3 of Example 1. $^1$H NMR (400 MHz, $CD_3OD$) δ=8.68 (d, J=7.6 Hz, 1H), 8.44 (s, 1H), 8.37 (dd, J=7.6, 1.3 Hz, 1H), 7.72 (t, J=8.0 Hz, 1H), 7.65 (d, J=8.0 Hz, 1H), 7.50 (d, J=8.0 Hz, 1H), 5.97 (s, 2H), 3.75-3.88 (m, 1H), 3.46-3.63 (m, 2H), 3.32-3.43 (m, 2H), 2.21-2.36 (m, 1H), 2.09 (s, 3H), 1.86-2.01 (m, 1H). MS-ESI calculated value $[M+H]^+$ 366, actually measured value 366.

The formate of compound 16 can be adjusted the pH of the reaction solution to 8-9 by adding a saturated aqueous sodium carbonate solution to the system, and then, after the extraction with ethyl acetate, the reaction solution was concentrated to obtain compound 16.

Example 11: Compound 17

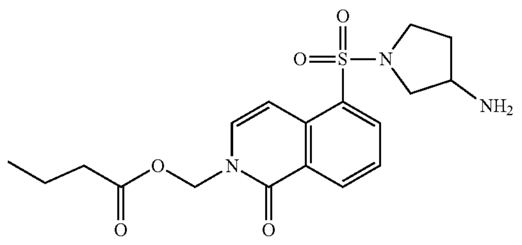 [SMILES: CCCC(=O)OCn1ccc2c(S(=O)(=O)N3CCC(N)C3)cccc2c1=O]

Synthesis Route:

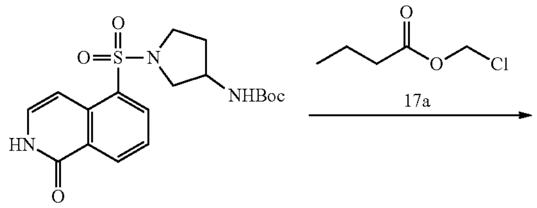

1

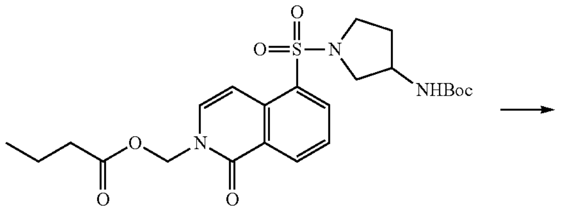

17b

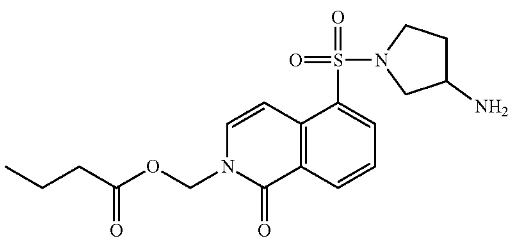

17

Step 1

Compound 17b was obtained referring to step 2 of Example 1. $^1$H NMR (400 MHz, $CDCl_3$) δ=8.66-8.78 (m, 1H), 8.31 (dd, J=7.8, 1.4 Hz, 1H), 7.59 (t, J=7.8 Hz, 1H), 7.36-7.48 (m, 2H), 5.96 (s, 2H), 4.68 (s, 1H), 4.14-4.30 (m, 1H), 3.36-3.64 (m, 2H), 3.27 (s, 2H), 2.36 (t, J=7.4 Hz, 2H), 2.14 (td, J=13.8, 6.8 Hz, 1H), 1.78-1.88 (m, 1H), 1.63-1.70 (m, 2H), 1.42 (s, 9H), 0.94 (t, J=7.4 Hz, 3H).

Step 2

A formate of compound 17 was obtained referring to step 3 of Example 1. $^1$H NMR (400 MHz, $CD_3OD$) δ=8.67 (d, J=7.8 Hz, 1H), 8.48 (s, 1H), 8.37 (dd, J=7.8, 1.2 Hz, 1H), 7.71 (t, J=7.8 Hz, 1H), 7.65 (d, J=7.8 Hz, 1H), 7.49 (d, J=7.8 Hz, 1H), 5.98 (s, 2H), 3.73-3.89 (m, 1H), 3.46-3.64 (m, 2H), 3.32-3.41 (m, 2H), 2.36 (t, J=7.3 Hz, 2H), 2.18-2.30 (m, 1H), 1.84-1.98 (m, 1H), 1.64 (sxt, J=7.4 Hz, 2H), 0.93 (t, J=7.4 Hz, 3H). MS-ESI calculated value $[M+H]^+$ 394, actually measured value 394.

The formate of compound 17 can be adjusted the pH of the reaction solution to 8-9 by adding a saturated aqueous sodium carbonate solution to the system, and then, after the extraction with ethyl acetate, the reaction solution was concentrated to obtain compound 17.

Example 12: Compound 18

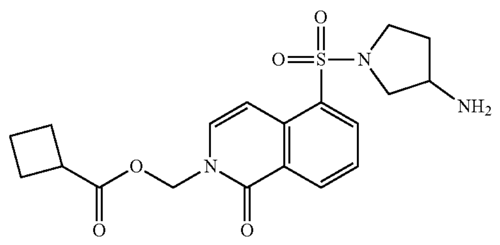 [SMILES: NC1CCN(S(=O)(=O)c2cccc3c(=O)n(COC(=O)C4CCC4)ccc23)C1]

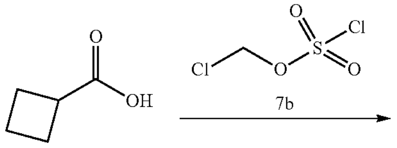

18a

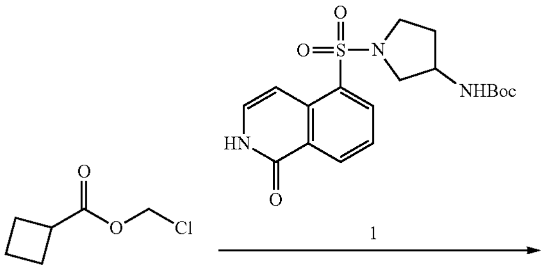

18b

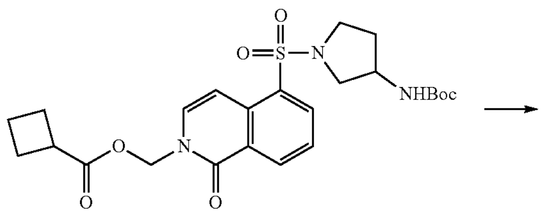

18c

-continued

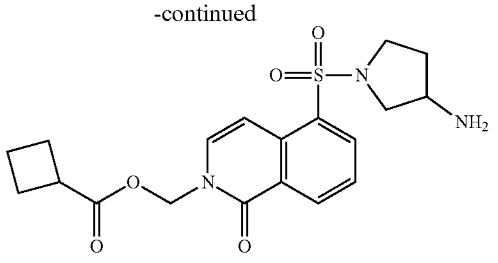

18

Step 1

Compound 18b was obtained referring to step 1 of Example 1.

Step 2

Compound 18c was obtained referring to step 2 of Example 1. $^1$H NMR (400 MHz, $CDCl_3$) δ=8.72 (d, J=7.8 Hz, 1H), 8.28-8.35 (m, 1H), 7.59 (t, J=7.8 Hz, 1H), 7.37-7.48 (m, 2H), 5.90-6.03 (m, 1H), 5.96 (s, 1H), 4.64 (s, 1H), 4.17 (d, J=9.4 Hz, 1H), 3.38-3.60 (m, 2H), 3.15-3.36 (m, 3H), 2.13-2.37 (m, 5H), 1.81-2.02 (m, 3H), 1.43 (s, 9H).

Step 3

A formate of compound 18 was obtained referring to step 3 of Example 1. $^1$H NMR (400 MHz, $CD_3OD$) δ=8.67 (d, J=7.8 Hz, 1H), 8.38 (s, 1H), 8.37 (dd, J=7.8, 1.2 Hz, 1H), 7.71 (t, J=7.8 Hz, 1H), 7.65 (d, J=8.0 Hz, 1H), 7.49 (d, J=8.0 Hz, 1H), 5.98 (s, 2H), 3.74-3.87 (m, 1H), 3.45-3.64 (m, 2H), 3.32-3.38 (m, 2H), 3.14-3.27 (m, 1H), 2.14-2.36 (m, 5H), 1.83-2.07 (m, 3H). MS-ESI calculated value $[M+H]^+$ 406, actually measured value 406.

The formate of compound 18 can be adjusted the pH of the reaction solution to 8-9 by adding a saturated aqueous sodium carbonate solution to the system, and then, after the extraction with ethyl acetate, the reaction solution was concentrated to obtain compound 18.

Example 13: Compound 19

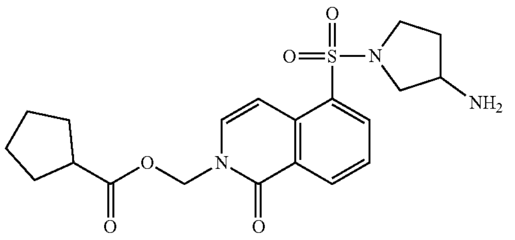 [SMILES: NC1CCN(S(=O)(=O)c2cccc3c(=O)n(COC(=O)C4CCCC4)ccc23)C1]

Synthesis Route:

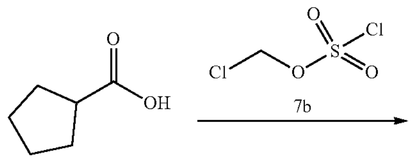

19a

-continued

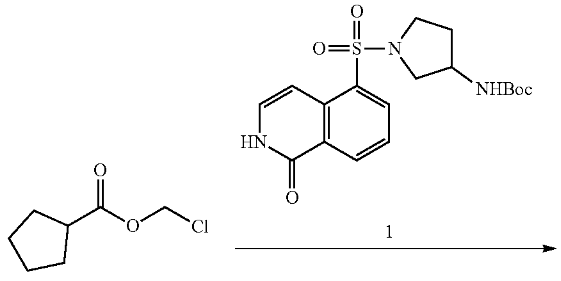

19b

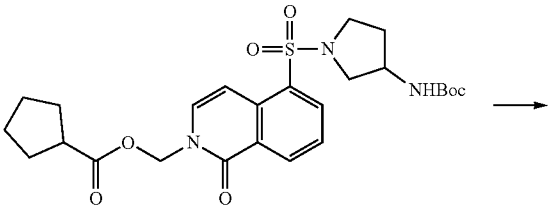

19c

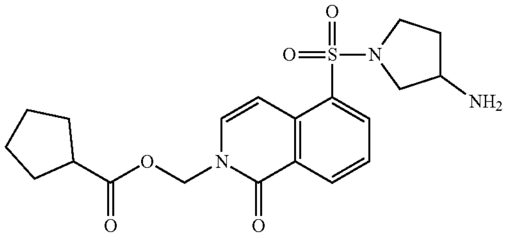

19

Step 1

Compound 19b was obtained referring to step 1 of Example 1.

Step 2

Compound 19c was obtained referring to step 2 of Example 1. MS-ESI calculated value $[M+Na]^+$ 542, actually measured value 542.

Step 3

A formate of compound 19 was obtained referring to step 3 of Example 1. $^1$H NMR (400 MHz, $CD_3OD$) δ=8.68 (d, J=7.6 Hz, 1H), 8.37 (dd, J=7.6, 1.4 Hz, 2H), 7.72 (t, J=8.0 Hz, 1H), 7.65 (d, J=7.8 Hz, 1H), 7.49 (d, J=8.4 Hz, 1H), 5.97 (s, 2H), 4.62 (s, 1H), 3.78-3.87 (m, 1H), 3.55-3.65 (m, 1H), 3.51 (dd, J=10.8, 6.4 Hz, 1H), 3.38 (dd, J=10.8, 4.0 Hz, 1H), 2.76-2.86 (m, 1H), 2.19-2.35 (m, 1H), 1.84-2.01 (m, 3H), 1.73-1.83 (m, 2H), 1.53-1.72 (m, 4H). MS-ESI calculated value $[M+H]^+$ 420, actually measured value 420.

The formate of compound 19 can be adjusted the pH of the reaction solution to 8-9 by adding a saturated aqueous sodium carbonate solution to the system, and then, after the extraction with ethyl acetate, the reaction solution was concentrated to obtain compound 19.

Example 14: Compound 20

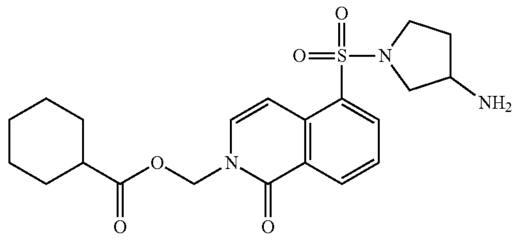

Synthesis Route:

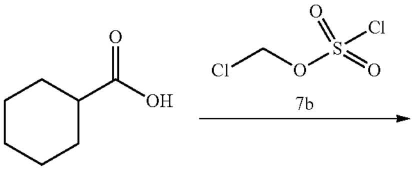

20a

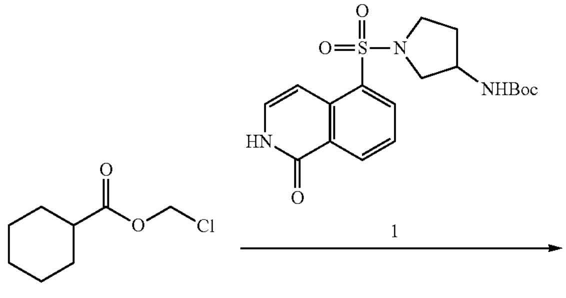

20b

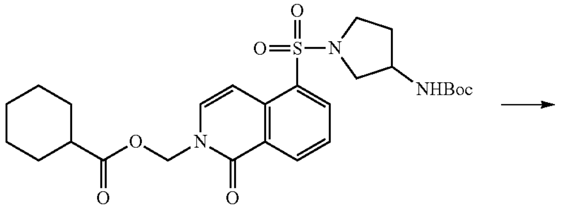

20c

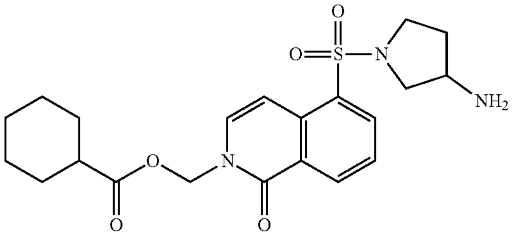 [SMILES: NC1CCN(S(=O)(=O)c2cccc3c(=O)n(COC(=O)C4CCCCC4)ccc23)C1]

20

Step 1

Compound 20b was obtained referring to step 1 of Example 1.

Step 2

Compound 20c was obtained referring to step 2 of Example 1.

Step 3

A formate of compound 20 was obtained referring to step 3 of Example 1. $^1$H NMR (400 MHz, $CD_3OD$) δ=8.69 (d, J=7.8 Hz, 1H), 8.40 (s, 1H), 8.39 (dd, J=7.8, 1.2 Hz, 1H), 7.73 (t, J=7.8 Hz, 1H), 7.66 (d, J=8.0 Hz, 1H), 7.51 (d, J=8.0 Hz, 1H), 5.99 (s, 2H), 4.58 (s, 2H), 3.71-3.83 (m, 1H), 3.46-3.65 (m, 2H), 2.40 (tt, J=11.0, 3.6 Hz, 1H), 2.21-2.33 (m, 1H), 1.85-2.00 (m, 3H), 1.71-1.82 (m, 2H), 1.65 (d, J=8.8 Hz, 1H), 1.22-1.50 (m, 5H). MS-ESI calculated value $[M+H]^+$ 434, actually measured value 434.

The formate of compound 20 can be adjusted the pH of the reaction solution to 8-9 by adding a saturated aqueous sodium carbonate solution to the system, and then, after the extraction with ethyl acetate, the reaction solution was concentrated to obtain compound 20.

Example 15: Compound 21

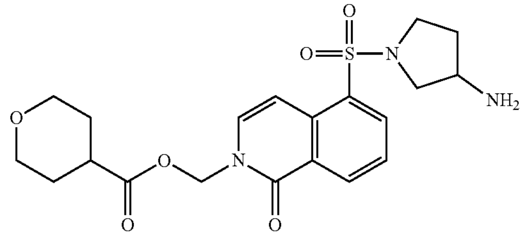

Synthesis Route:

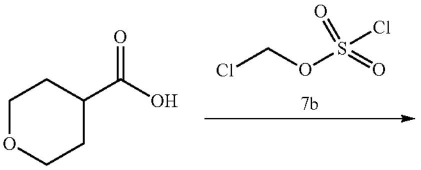

21a

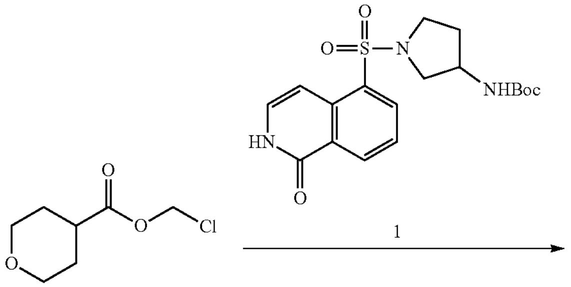

21b

-continued

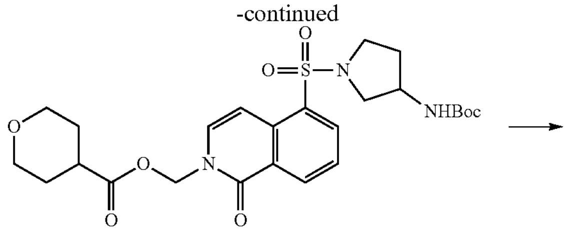

21c

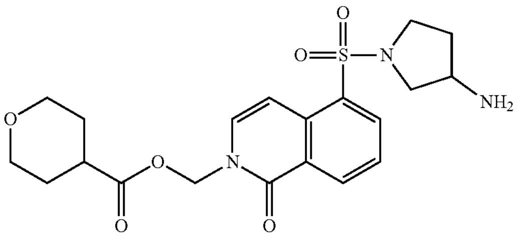 [SMILES: NC1CCN(S(=O)(=O)c2cccc3c(=O)n(COC(=O)C4CCOCC4)ccc23)C1]

21

Step 1

Compound 21b was obtained referring to step 1 of Example 1.

Step 2

Compound 21c was obtained referring to step 2 of Example 1. $^1$H NMR (400 MHz, $CDCl_3$) δ=8.70 (dd, J=8.0, 1.1 Hz, 1H), 8.26-8.35 (m, 1H), 7.59 (t, J=7.8 Hz, 1H), 7.34-7.45 (m, 2H), 5.97 (s, 2H), 4.59-4.83 (m, 1H), 4.06-4.29 (m, 1H), 3.94 (dt, J=11.4, 3.5 Hz, 2H), 3.48-3.54 (m, 1H), 3.34-3.42 (m, 2H), 3.16-3.33 (m, 2H), 2.56-2.69 (m, 1H), 2.08-2.20 (m, 1H), 1.74-1.84 (m, 6H), 1.34-1.43 (m, 9H).

Step 3

A formate of compound 21 was obtained referring to step 3 of Example 1. $^1$H NMR (400 MHz, $CD_3OD$) δ=8.67 (d, J=8.2 Hz, 1H), 8.45 (s, 1H), 8.37 (d, J=7.8 Hz, 1H), 7.71 (t, J=8.0 Hz, 1H), 7.65 (d, J=7.8 Hz, 1H), 7.49 (d, J=8.0 Hz, 1H), 7.45-7.53 (m, 1H), 6.00 (s, 2H), 3.89 (dt, J=11.7, 3.5 Hz, 2H), 3.72-3.82 (m, 1H), 3.48-3.63 (m, 2H), 3.43 (td, J=11.4, 2.4 Hz, 2H), 3.35 (d, J=3.6 Hz, 1H), 2.59-2.73 (m, 1H), 2.18-2.33 (m, 1H), 1.92 (td, J=13.5, 5.8 Hz, 1H), 1.61-1.87 (m, 5H). MS-ESI calculated value $[M+H]^+$ 436, actually measured value 436.

The formate of compound 21 can be adjusted the pH of the reaction solution to 8-9 by adding a saturated aqueous sodium carbonate solution to the system, and then, after the extraction with ethyl acetate, the reaction solution was concentrated to obtain compound 21.

Example 16: Compound 22

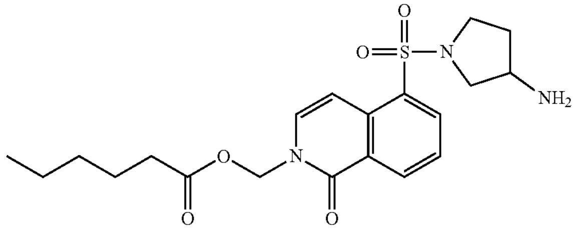 [SMILES: CCCCCC(=O)OCn1ccc2c(S(=O)(=O)N3CCC(N)C3)cccc2c1=O]

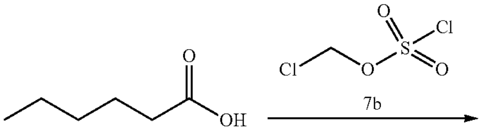

22a

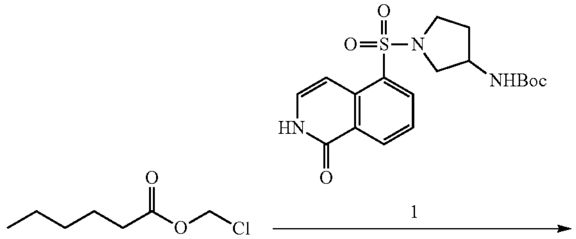

22b

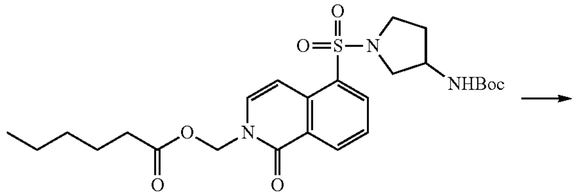

22c

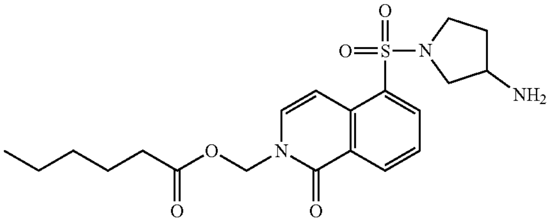

22

Step 1

Compound 22b was obtained referring to step 1 of Example 1.

Step 2

Compound 22c was obtained referring to step 2 of Example 1. $^1$H NMR (400 MHz, $CDCl_3$) δ=8.72 (dd, J=8.0, 0.8 Hz, 1H), 8.32 (dd, J=7.8, 1.4 Hz, 1H), 7.59 (t, J=7.8 Hz, 1H), 7.34-7.48 (m, 2H), 5.96 (s, 2H), 4.67 (s, 1H), 4.18 (s, 1H), 3.36-3.64 (m, 2H), 3.27 (s, 2H), 2.37 (t, J=7.6 Hz, 2H), 2.14 (dq, J=14.4, 6.6 Hz, 1H), 1.75-1.91 (m, 1H), 1.65-1.68 (m, 1H), 1.59-1.62 (m, 1H), 1.42 (s, 9H), 1.27-1.33 (m, 4H), 0.78-0.89 (m, 3H).

Step 3

A formate of compound 22 was obtained referring to step 3 of Example 1. $^1H$ NMR (400 MHz, $CD_3OD$) δ=8.67 (d, J=8.0 Hz, 1H), 8.48 (s, 1H), 8.37 (d, J=7.4 Hz, 1H), 7.71 (t, J=7.8 Hz, 1H), 7.64 (d, J=8.0 Hz, 1H), 7.49 (d, J=7.8 Hz, 1H), 5.98 (s, 2H), 4.57 (s, 1H), 3.71-3.74 (m, 1H), 3.46-3.64 (m, 2H), 2.37 (t, J=7.6 Hz, 2H), 2.23-2.24 (m, 1H), 1.88-1.89 (m, 1H), 1.53-1.71 (m, 2H), 1.27-1.30 (m, 5H), 0.85 (t, J=6.8 Hz, 3H). MS-ESI calculated value $[M+H]^+$ 422, actually measured value 422.

The formate of compound 22 can be adjusted the pH of the reaction solution to 8-9 by adding a saturated aqueous sodium carbonate solution to the system, and then, after the extraction with ethyl acetate, the reaction solution was concentrated to obtain compound 22.

Example 17: Compound 23

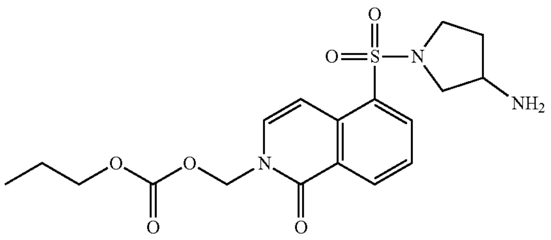 [SMILES: CCCOC(=O)OCn1ccc2c(S(=O)(=O)N3CCC(N)C3)cccc2c1=O]

Synthesis Route:

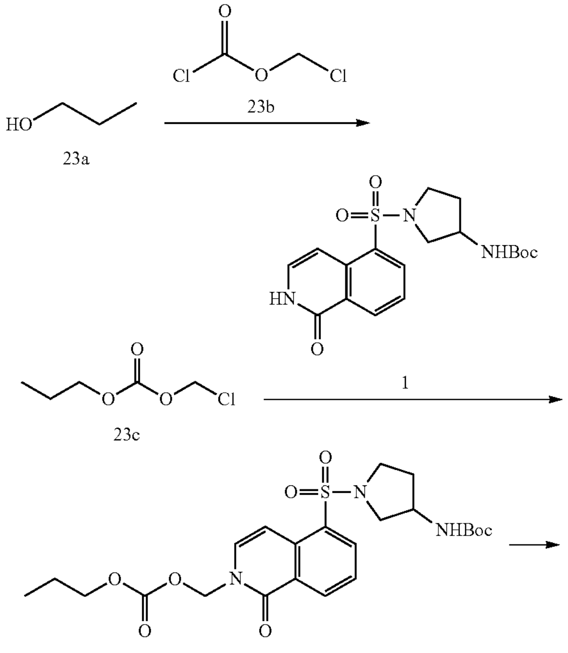

23d

-continued

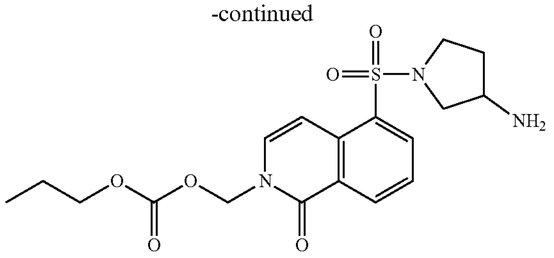

23

Step 1

To a solution of compound 23b (1.0 g, 7.76 mmol) and pyridine (920 mg, 11.6 mmol) in dichloromethane (10 mL) was added compound 23a (466 mg, 7.76 mmol) dropwise at 0° C., stirred for 16 hours at 30° C. Hydrochloric acid (1M, 10 mL) was added to the reaction solution, stirred for 5 minutes; the organic phase was separated, washed with water (10 mL), dried with anhydrous magnesium sulfate, filtered and concentrated to obtain compound 23c. $^1H$ NMR (400 MHz, $CDCl_3$) δ=5.73 (s, 2H), 4.19 (t, J=6.6 Hz, 2H), 1.73 (sxt, J=7.2 Hz, 2H), 0.97 (t, J=7.2 Hz, 3H).

Step 2

Compound 23d was obtained referring to step 2 of Example 1. MS-ESI calculated value $[M+Na]^+$ 532, actually measured value 532.

Step 3

A formate of compound 23 was obtained referring to step 3 of Example 1. $^1H$ NMR (400 MHz, $CD_3OD$) δ=8.67 (d, J=8.0 Hz, 1H), 8.38 (s, 1H), 8.37 (d, J=7.8 Hz, 1H), 7.71 (t, J=7.8 Hz, 1H), 7.65 (d, J=8.0 Hz, 1H), 7.50 (d, J=8.0 Hz, 1H), 5.99 (s, 2H), 4.58 (s, 1H), 4.13 (t, J=6.6 Hz, 2H), 3.76-3.88 (m, 1H), 3.46-3.64 (m, 2H), 3.34-3.40 (m, 1H), 2.20-2.34 (m, 1H), 1.94 (td, J=13.6, 5.8 Hz, 1H), 1.68 (sxt, J=7.2 Hz, 2H), 0.94 (t, J=7.6 Hz, 3H). MS-ESI calculated value $[M+H]^+$ 410, actually measured value 410.

The formate of compound 23 can be adjusted the pH of the reaction solution to 8-9 by adding a saturated aqueous sodium carbonate solution to the system, and then, after the extraction with ethyl acetate, the reaction solution was concentrated to obtain compound 23.

Example 18: Compound 24

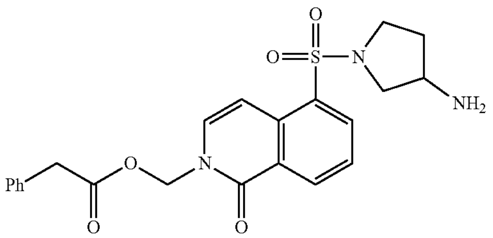 [SMILES: NC1CCN(S(=O)(=O)c2cccc3c(=O)n(COC(=O)Cc4ccccc4)ccc23)C1]

Synthesis Route:

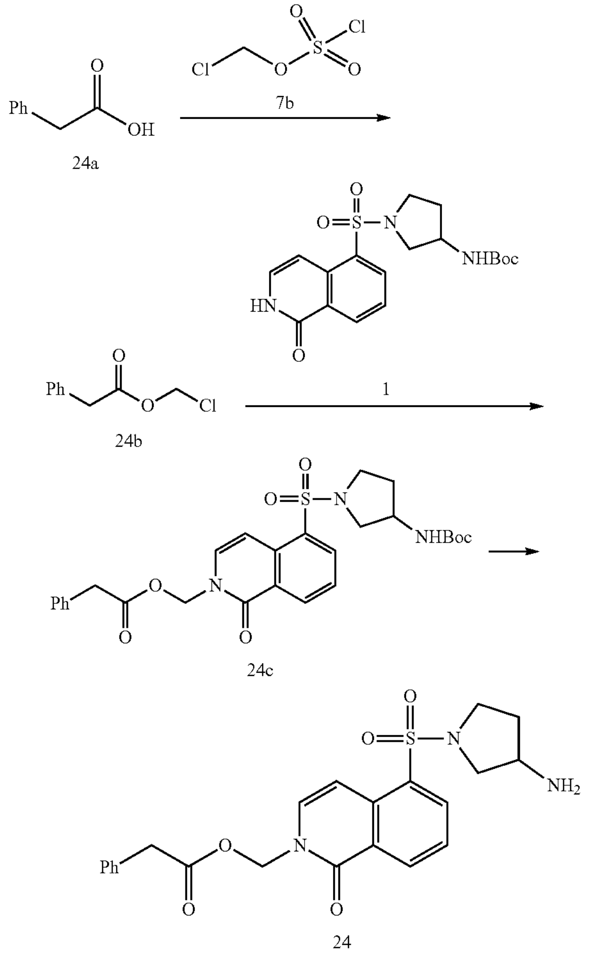

24a, 24b, 24c, 24

Step 1

Compound 24b was obtained referring to step 1 of Example 1.

Step 2

Compound 24c was obtained referring to step 2 of Example 1. $^1$H NMR (400 MHz, $CDCl_3$) δ ppm 8.72 (d, J=7.2 Hz, 1H), 8.32 (dd, J=7.8, 1.4 Hz, 1H), 7.60 (t, J=7.8 Hz, 1H), 7.33-7.43 (m, 3H), 7.27-7.32 (m, 4H), 5.97 (s, 2H), 4.53-4.75 (m, 1H), 4.18 (s, 1H), 3.70 (s, 2H), 3.37-3.60 (m, 2H), 3.25 (s, 2H), 2.08-2.24 (m, 1H), 1.77-1.91 (m, 1H), 1.43 (s, 9H).

Step 3

A formate of compound 24 was obtained referring to step 3 of Example 1. $^1$H NMR (400 MHz, $CD_3OD$) δ=8.66 (d, J=7.8 Hz, 1H), 8.45 (s, 1H), 8.37 (dd, J=7.8, 1.2 Hz, 1H), 7.71 (t, J=8.0 Hz, 1H), 7.60 (d, J=8.0 Hz, 1H), 7.46 (d, J=7.8 Hz, 1H), 7.16-7.32 (m, 4H), 6.00 (s, 2H), 3.74-3.85 (m, 1H), 3.70 (s, 2H), 3.46-3.61 (m, 2H), 3.33-3.38 (m, 1H), 3.25-3.30 (m, 1H), 2.18-2.33 (m, 1H), 1.83-2.02 (m, 1H). MS-ESI calculated value $[M+Na]^+$ 464, actually measured value 464.

The formate of compound 24 can be adjusted the pH of the reaction solution to 8-9 by adding a saturated aqueous sodium carbonate solution to the system, and then, after the extraction with ethyl acetate, the reaction solution was concentrated to obtain compound 24.

Example 19: Compound 25

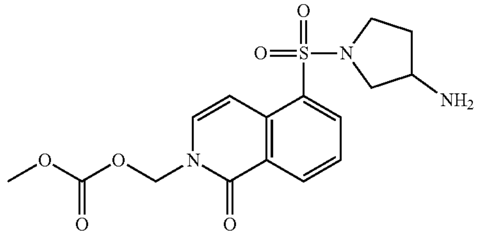 [SMILES: COC(=O)OCn1ccc2c(S(=O)(=O)N3CCC(N)C3)cccc2c1=O]

Synthesis Route:

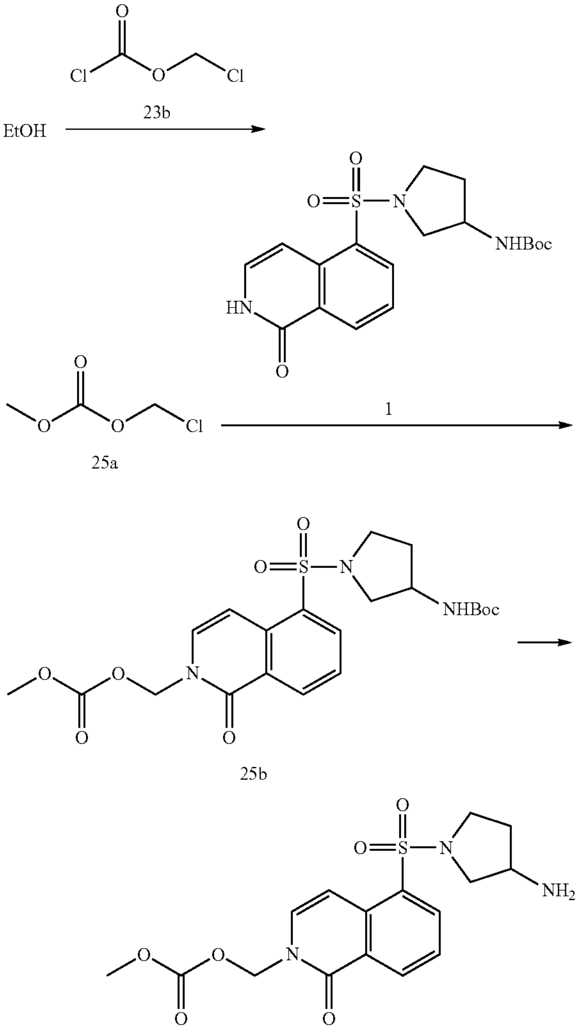

25a, 25b, 25

Step 1

Compound 25a was obtained referring to step 1 of Example 17.

Step 2

Compound 25b was obtained referring to step 2 of Example 1. MS-ESI calculated value $[M+Na]^+$ 504, actually measured value 504.

Step 3

A formate of compound 25 was obtained referring to step 3 of Example 1. $^1H$ NMR (400 MHz, $CD_3OD$) δ=8.68 (d, J=7.8 Hz, 1H), 8.38 (dd, J=7.8, 1.2 Hz, 1H), 7.72 (t, J=8.0 Hz, 1H), 7.65 (d, J=7.8 Hz, 1H), 7.50 (d, J=8.0 Hz, 1H), 5.99 (s, 2H), 3.83-3.90 (m, 1H), 3.80 (s, 3H), 3.59-3.68 (m, 1H), 3.44-3.59 (m, 2H), 3.37-3.42 (m, 1H), 2.23-2.37 (m, 1H), 1.97 (td, J=13.6, 6.0 Hz, 1H). MS-ESI calculated value $[M+H]^+$ 382, actually measured value 382.

The formate of compound 25 can be adjusted the pH of the reaction solution to 8-9 by adding a saturated aqueous sodium carbonate solution to the system, and then, after the extraction with ethyl acetate, the reaction solution was concentrated to obtain compound 25.

Example 20: Compound 26

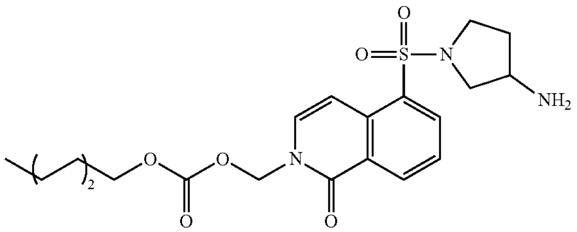

Synthesis Route:

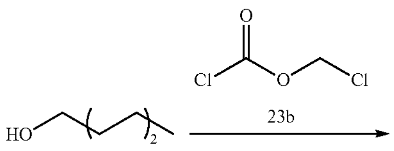

26a

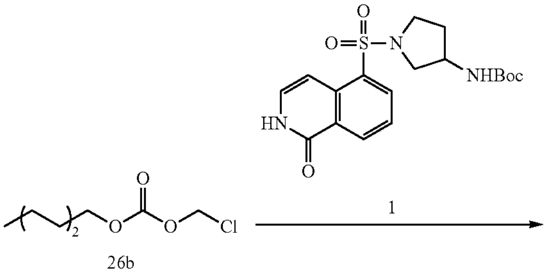

26b

-continued

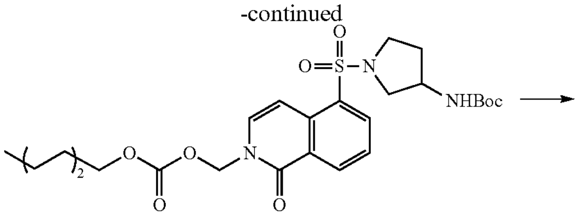

26c

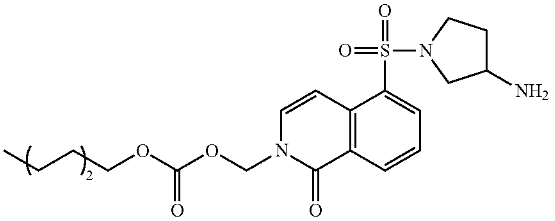

26

Step 1

Compound 26b was obtained referring to step 1 of Example 17.

Step 2

Compound 26c was obtained referring to step 2 of Example 1. $^1H$ NMR (400 MHz, $CDCl_3$) δ=8.72 (d, J=8.0 Hz, 1H), 8.32 (d, J=7.8 Hz, 1H), 7.59 (t, J=8.0 Hz, 1H), 7.43 (s, 2H), 5.98 (s, 2H), 4.65 (s, 1H), 4.18 (t, J=6.8 Hz, 2H), 3.46 (d, J=18.0 Hz, 2H), 3.28 (s, 2H), 2.14 (dq, J=13.6, 7.2 Hz, 1H), 1.84 (s, 1H), 1.64-1.72 (m, 2H), 1.43 (s, 9H), 1.27-1.37 (m, 6H), 0.88 (t, J=6.8 Hz, 3H).

Step 3

A formate of compound 26 was obtained referring to step 3 of Example 1. $^1H$ NMR (400 MHz, $CD_3OD$) δ=8.67 (d, J=8.0 Hz, 1H), 8.45 (s, 1H), 8.37 (dd, J=7.8, 1.2 Hz, 1H), 7.71 (t, J=8.0 Hz, 1H), 7.65 (d, J=7.8 Hz, 1H), 7.50 (d, J=8.0 Hz, 1H), 5.99 (s, 2H), 4.17 (t, J=6.6 Hz, 2H), 3.76-3.85 (m, 1H), 3.48-3.63 (m, 2H), 3.32-3.40 (m, 2H), 2.22-2.39 (m, 1H), 1.89-1.99 (m, 1H), 1.60-1.72 (m, 2H), 1.30-1.40 (m, 6H), 0.83-0.94 (m, 3H). MS-ESI calculated value $[M+H]^+$ 452, actually measured value 452.

The formate of compound 26 can be adjusted the pH of the reaction solution to 8-9 by adding a saturated aqueous sodium carbonate solution to the system, and then, after the extraction with ethyl acetate, the reaction solution was concentrated to obtain compound 26.

Example 21: Compound 27

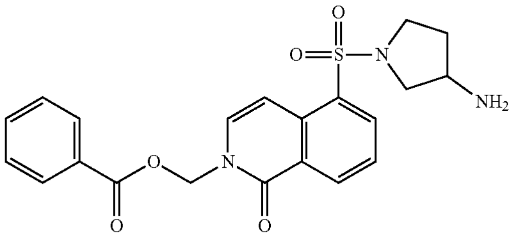 [SMILES: NC1CCN(S(=O)(=O)c2cccc3c(=O)n(COC(=O)c4ccccc4)ccc23)C1]

Synthesis Route:

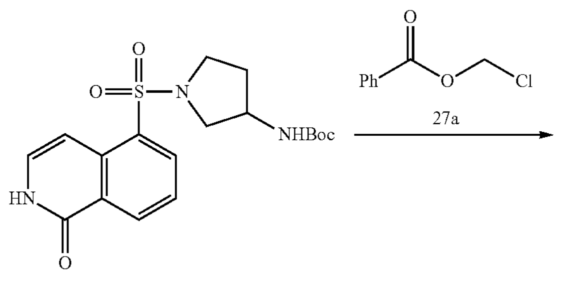

27a

1

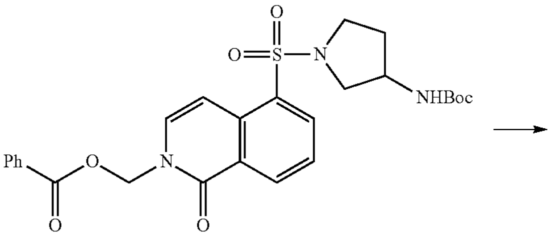

27b

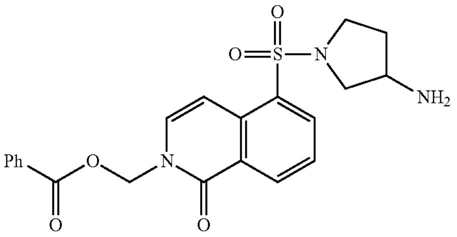

27

Step 1

Compound 27b was obtained referring to step 2 of Example 1. MS-ESI calculated value $[M+Na]^+$ 550, actually measured value 550.

Step 2

A formate of compound 27 was obtained referring to step 3 of Example 1. $^1H$ NMR (400 MHz, $CDCl_3$) δ=8.73 (d, J=8.0 Hz, 1H), 8.35 (d, J=7.8 Hz, 1H), 8.09 (d, J=7.4 Hz, 2H), 7.54-7.64 (m, 3H), 7.45 (dt, J=7.8, 3.8 Hz, 3H), 6.22 (s, 2H), 3.62 (s, 1H), 3.46-3.55 (m, 2H), 3.31-3.42 (m, 1H), 3.10 (dd, J=9.9, 4.1 Hz, 1H), 2.03-2.22 (m, 2H). MS-ESI calculated value $[M+H]^+$ 428, actually measured value 428.

The formate of compound 27 can be adjusted the pH of the reaction solution to 8-9 by adding a saturated aqueous sodium carbonate solution to the system, and then, after the extraction with ethyl acetate, the reaction solution was concentrated to obtain compound 27.

Example 22: Compound 28

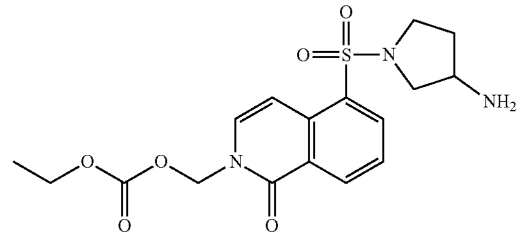 [SMILES: CCOC(=O)OCn1ccc2c(S(=O)(=O)N3CCC(N)C3)cccc2c1=O]

Synthesis Route:

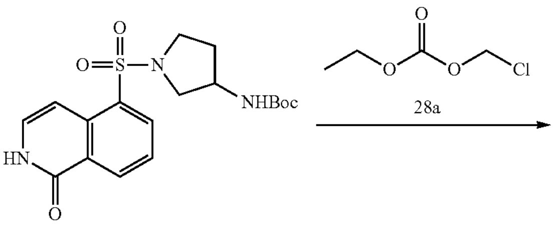

28a

1

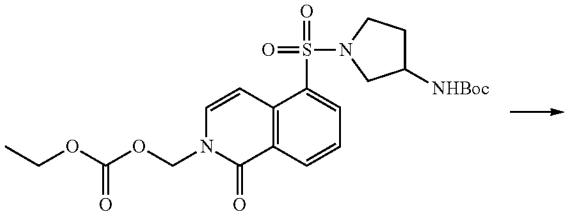

28b

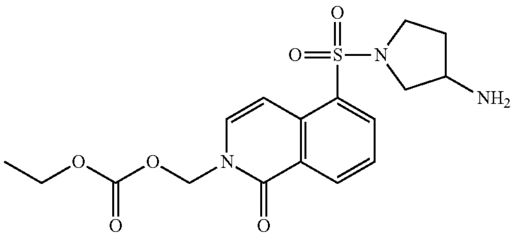

28

Step 1

Compound 28b was obtained referring to step 2 of Example 1. MS-ESI calculated value $[M+Na]^+$ 518, actually measured value 518.

Step 2

A formate of compound 28 was obtained referring to step 3 of Example 1. $^1H$ NMR (400 MHz, deuterated acetone) 6 ppm 8.63 (d, J=7.4 Hz, 1H), 8.43 (dd, J=7.8, 1.4 Hz, 1H), 8.12 (s, 1H), 7.64-7.74 (m, 2H), 7.49 (d, J=8.0 Hz, 1H), 6.03 (d, J=1.0 Hz, 2H), 4.22 (q, J=7.0 Hz, 2H), 4.16 (t, J=4.6 Hz, 1H), 3.59 (dd, J=9.8, 5.8 Hz, 1H), 3.45-3.52 (m, 2H), 3.22 (dd, J=9.8, 3.9 Hz, 1H), 2.11-2.16 (m, 1H), 1.76 (td, J=12.4, 5.2 Hz, 1H), 1.27 (t, J=7.0 Hz, 3H). MS-ESI calculated value $[M+H]^+$ 396, actually measured value 396.

The formate of compound 28 can be adjusted the pH of the reaction solution to 8-9 by adding a saturated aqueous sodium carbonate solution to the system, and then, after the extraction with ethyl acetate, the reaction solution was concentrated to obtain compound 28.

Example 23: Compound 29

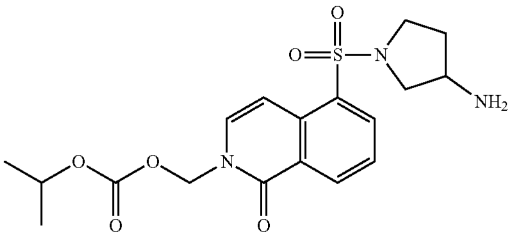 [SMILES: CC(C)OC(=O)OCn1ccc2c(S(=O)(=O)N3CCC(N)C3)cccc2c1=O]

Synthesis Route:

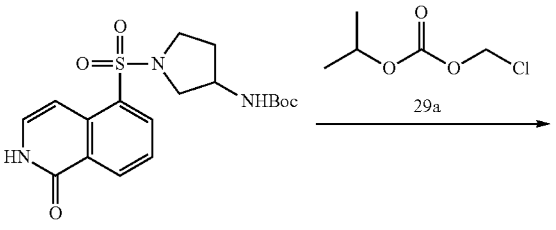

1

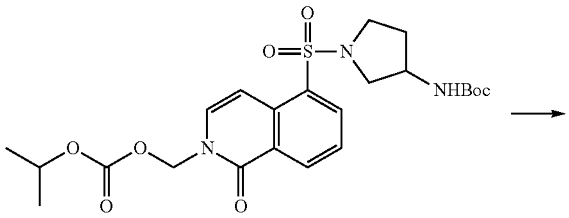

29b

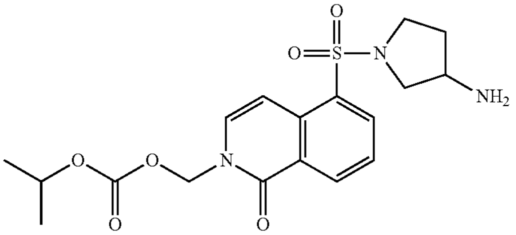

29

Step 1

Compound 29b was obtained referring to step 2 of Example 1. MS-ESI calculated value $[M+Na]^+$ 532, actually measured value 532.

Step 2

A formate of compound 29 was obtained referring to step 3 of Example 1. $^1H$ NMR (400 MHz, $CD_3OD$) δ=8.69 (d, J=7.8 Hz, 1H), 8.49 (s, 1H), 8.39 (dd, J=7.8, 1.3 Hz, 1H), 7.73 (t, J=7.8 Hz, 1H), 7.67 (d, J=7.8 Hz, 1H), 7.51 (d, J=7.8 Hz, 1H), 5.99 (s, 2H), 3.76-3.88 (m, 1H), 3.49-3.66 (m, 2H), 3.28-3.40 (m, 3H), 2.22-2.38 (m, 1H), 1.87-2.01 (m, 1H), 1.30 (d, J=6.4 Hz, 7H). MS-ESI calculated value $[M+H]^+$ 410, actually measured value 410.

The formate of compound 29 can be adjusted the pH of the reaction solution to 8-9 by adding a saturated aqueous sodium carbonate solution to the system, and then, after the extraction with ethyl acetate, the reaction solution was concentrated to obtain compound 29.

Example 24: Compound 30

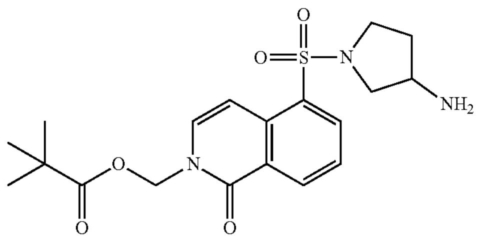 [SMILES: CC(C)(C)C(=O)OCn1ccc2c(S(=O)(=O)N3CCC(N)C3)cccc2c1=O]

Synthesis Route:

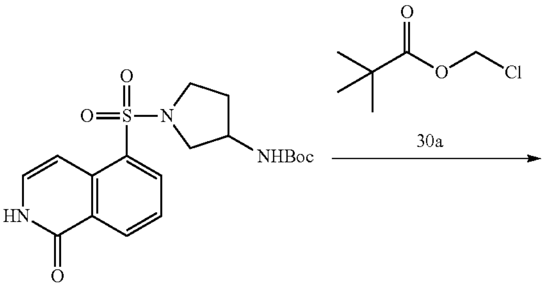

1

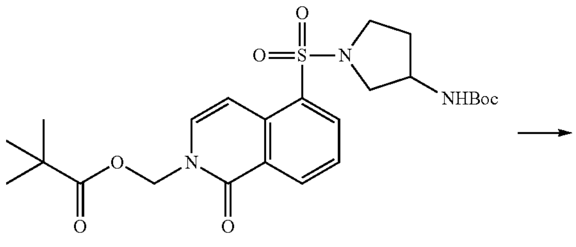

30b

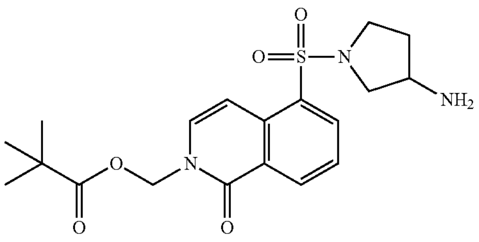

30

Step 1

Compound 30b was obtained referring to step 2 of Example 1. MS-ESI calculated value $[M+Na]^+$ 530, actually measured value 530.

Step 2

A formate of compound 30 was obtained referring to step 3 of Example 1. $^1H$ NMR (400 MHz, $CDCl_3$) δ ppm 8.63 (d, J=7.8 Hz, 1H), 8.25 (d, J=7.6 Hz, 1H), 8.21 (s, 1H), 7.51 (t, J=7.8 Hz, 1H), 7.34-7.40 (m, 1H), 7.29-7.34 (m, 1H), 5.87 (s, 2H), 3.69 (s, 1H), 3.50 (s, 1H), 3.42 (s, 1H), 3.26 (s, 2H), 2.10 (s, 1H), 1.85 (s, 1H), 1.13 (s, 9H). MS-ESI calculated value $[M+H]^+$ 408, actually measured value 408.

The formate of compound 30 can be adjusted the pH of the reaction solution to 8-9 by adding a saturated aqueous sodium carbonate solution to the system, and then, after the extraction with ethyl acetate, the reaction solution was concentrated to obtain compound 30.

Example 25: Compound 31

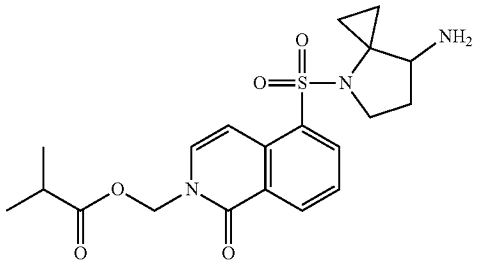 [SMILES: CC(C)C(=O)OCn1ccc2c(S(=O)(=O)N3CCC(N)C34CC4)cccc2c1=O]

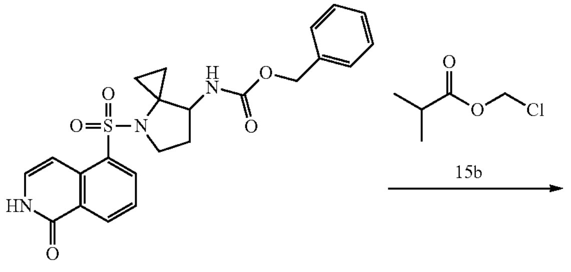

5

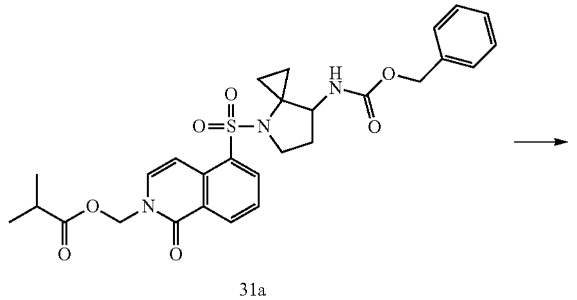

31a

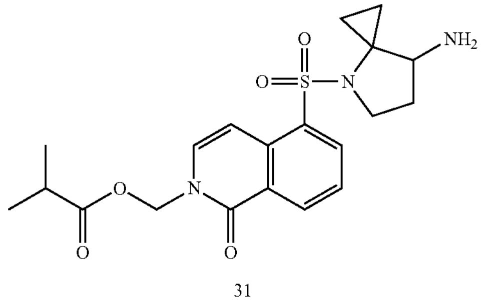

31

Step 1

Compound 31a was obtained referring to step 2 of Example 1. MS-ESI calculated value $[M+H]^+$ 554, actually measured value 554.

Step 2

Trifluoroacetic acid (1.0 mL) was added to a microwave tube and compound 31a (79 mg, 143 μmol) was added to the microwave tube, microwaving for 1 hour at 60° C. The solvent was removed by concentration under reduced pressure, and the crude product was purified by high performance liquid chromatography (acid, formic acid system) to obtain a formate of compound 31. $^1H$ NMR (400 MHz, $CD_3OD$) δ=8.66 (d, J=8.1 Hz, 1H), 8.50 (s, 1H), 8.45-8.39 (m, 1H), 7.73-7.63 (m, 2H), 7.17 (d, J=7.9 Hz, 1H), 5.97 (s, 2H), 4.12-4.01 (m, 1H), 3.66-3.55 (m, 1H), 3.41 (br d, J=4.5 Hz, 1H), 2.65-2.57 (m, 1H), 2.56-2.46 (m, 1H), 2.13-2.02 (m, 1H), 1.23-1.17 (m, 1H), 1.15 (d, J=7.0 Hz, 7H), 0.80 (t, J=8.9 Hz, 2H). MS-ESI calculated value $[M+H]^+$ 420, actually measured value 420.

The formate of compound 31 can be adjusted the pH of the reaction solution to 8-9 by adding a saturated aqueous sodium carbonate solution to the system, and then, after the extraction with ethyl acetate, the reaction solution was concentrated to obtain compound 31.

Example 26: Compound 32

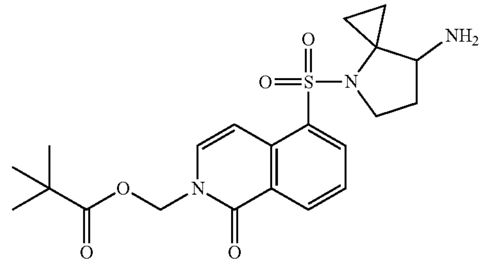 [SMILES: CC(C)(C)C(=O)OCn1ccc2c(S(=O)(=O)N3CCC(N)C34CC4)cccc2c1=O]

Synthesis Route:

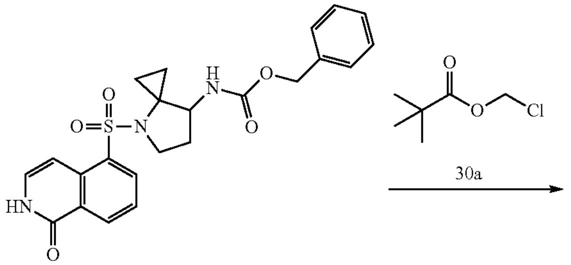

5

-continued

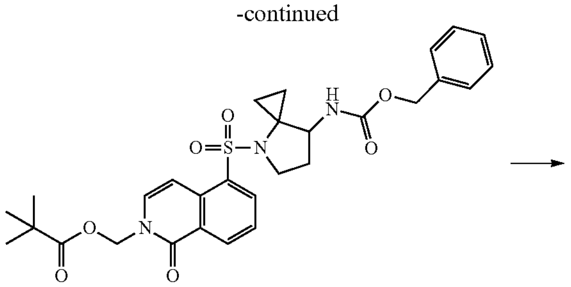

32a

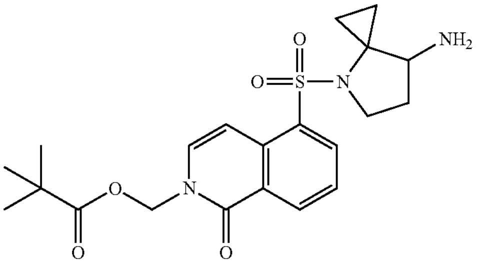

32

Step 1

Compound 32a was obtained referring to step 2 of Example 1. MS-ESI calculated value $[M+Na]^+$ 590, actually measured value 590.

Step 2

A formate of compound 32 was obtained referring to step 2 of Example 25. $^1H$ NMR (400 MHz, $CD_3OD$) δ=8.67 (d, J=7.6 Hz, 1H), 8.47 (s, 1H), 8.45-8.41 (m, 1H), 7.74-7.61 (m, 2H), 7.19 (d, J=7.8 Hz, 1H), 5.97 (s, 2H), 4.12-3.99 (m, 1H), 3.68-3.54 (m, 1H), 3.36-3.33 (m, 1H), 2.59-2.42 (m, 1H), 2.08-1.94 (m, 1H), 1.19 (s, 9H), 1.18-1.06 (m, 2H), 0.88-0.74 (m, 2H). MS-ESI calculated value [M+H]+ 434, actually measured value 434.

The formate of compound 32 can be adjusted the pH of the reaction solution to 8-9 by adding a saturated aqueous sodium carbonate solution to the system, and then, after the extraction with ethyl acetate, the reaction solution was concentrated to obtain compound 32.

Example 27: Compound 33

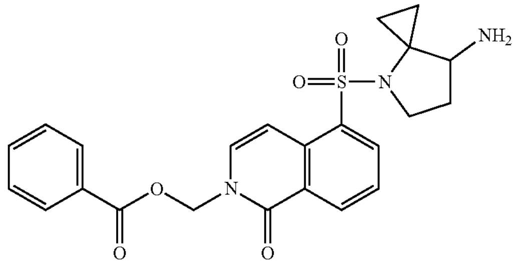 [SMILES: NC1CCN(S(=O)(=O)c2cccc3c(=O)n(COC(=O)c4ccccc4)ccc23)C12CC2]

Synthesis Route:

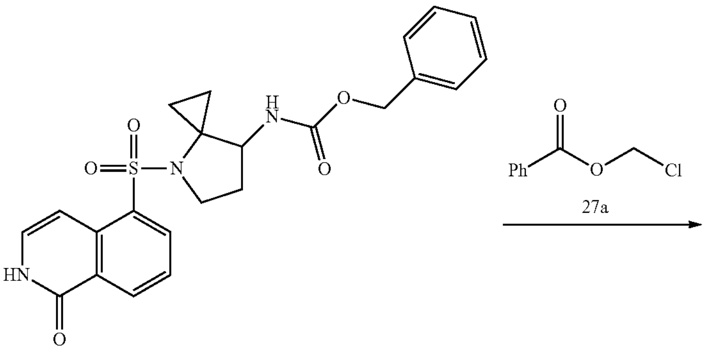

5

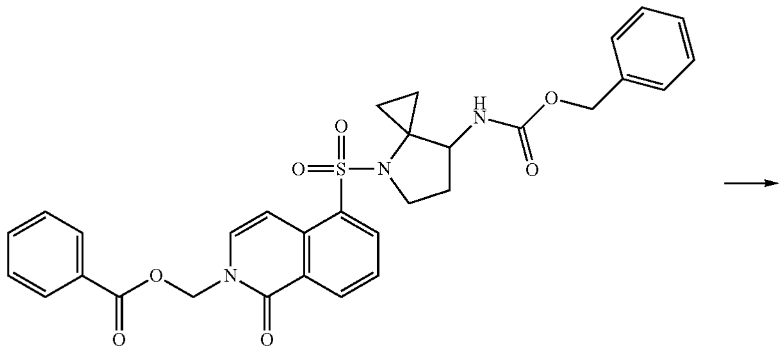

33a

-continued

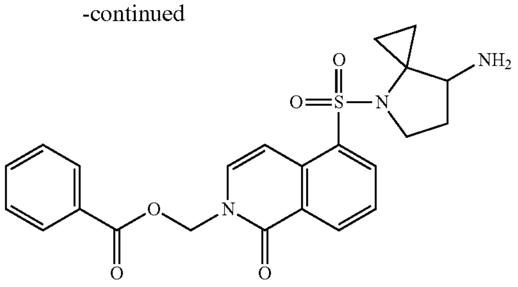

33

Step 1

Compound 33a was obtained referring to step 2 of Example 1. MS-ESI calculated value $[M+H]^+$ 588, actually measured value 588.

Step 2

A formate of compound 33 was obtained referring to step 2 of Example 25. $^1H$ NMR (400 MHz, $CD_3OD$) δ=8.66 (d, J=7.9 Hz, 1H), 8.48 (s, 1H), 8.43-8.37 (m, 1H), 8.05-7.99 (m, 2H), 7.78 (d, J=7.9 Hz, 1H), 7.68 (t, J=7.9 Hz, 1H), 7.64-7.57 (m, 1H), 7.50-7.43 (m, 2H), 7.19 (d, J=7.8 Hz, 1H), 6.22 (s, 2H), 4.12-4.00 (m, 1H), 3.65-3.55 (m, 1H), 3.47-3.39 (m, 1H), 2.59-2.44 (m, 1H), 2.15-2.03 (m, 1H), 1.26-1.10 (m, 2H), 0.83-0.74 (m, 2H). MS-ESI calculated value $[M+H]^+$ 454, actually measured value 454.

The formate of compound 33 can be adjusted the pH of the reaction solution to 8-9 by adding a saturated aqueous sodium carbonate solution to the system, and then, after the extraction with ethyl acetate, the reaction solution was concentrated to obtain compound 33.

Example 28: Compound 34

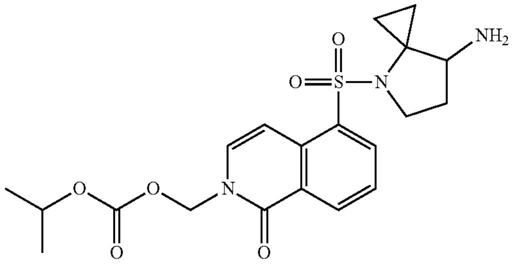 [SMILES: CC(C)OC(=O)OCn1ccc2c(S(=O)(=O)N3CCC(N)C34CC4)cccc2c1=O]

Synthesis Route:

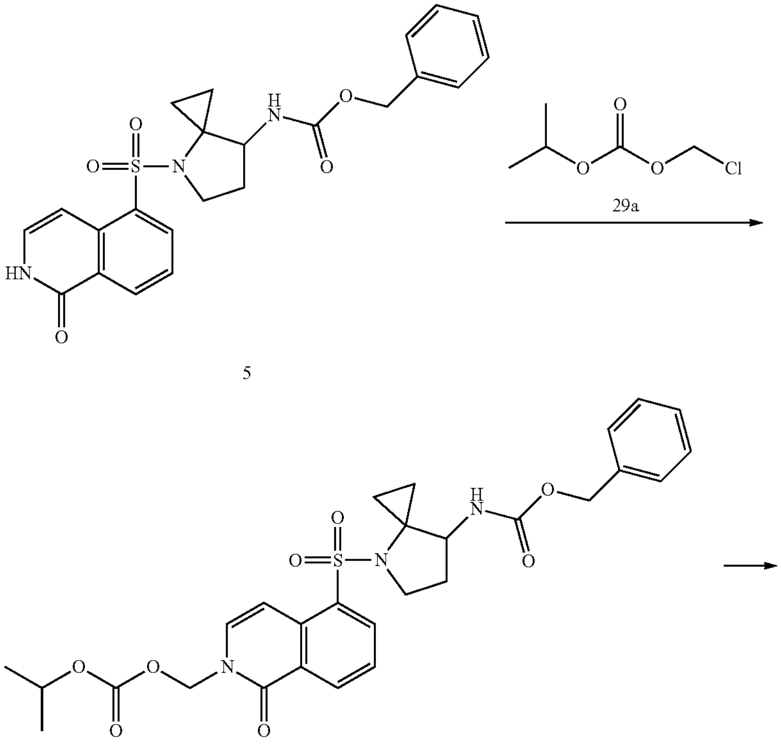

5

29a

34a

-continued

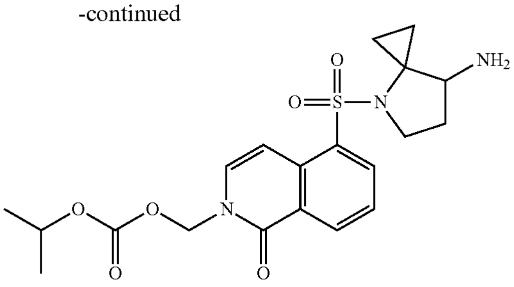

34

Step 1

Compound 34a was obtained referring to step 2 of Example 1. MS-ESI calculated value $[M+Na]^+$ 592, actually measured value 592.

Step 2

A formate of compound 34 was obtained referring to step 2 of Example 25. $^1H$ NMR (400 MHz, $CD_3OD$) δ=8.66 (d, J=8.1 Hz, 1H), 8.50 (br s, 1H), 8.46-8.40 (m, 1H), 7.72-7.63 (m, 2H), 7.23 (d, J=7.8 Hz, 1H), 5.97 (s, 2H), 4.92-4.90 (m, 1H), 4.02-3.92 (m, 1H), 3.66-3.55 (m, 1H), 3.29-3.20 (m, 1H), 2.51-2.36 (m, 1H), 2.00-1.88 (m, 1H), 1.28 (d, J=6.4 Hz, 6H), 1.18-1.02 (m, 2H), 0.95-0.87 (m, 1H), 0.79-0.72 (m, 1H). MS-ESI calculated value $[M+H]^+$ 436, actually measured value 436.

The formate of compound 34 can be adjusted the pH of the reaction solution to 8-9 by adding a saturated aqueous sodium carbonate solution to the system, and then, after the extraction with ethyl acetate, the reaction solution was concentrated to obtain compound 34.

Example 29: Compound 35

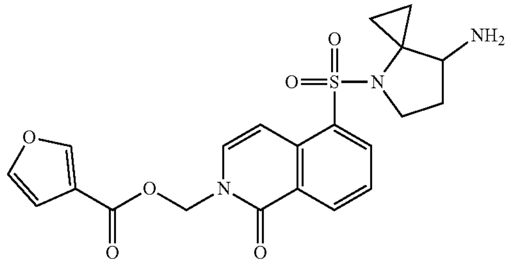 [SMILES: NC1CCN(S(=O)(=O)c2cccc3c(=O)n(COC(=O)c4ccoc4)ccc23)C12CC2]

Synthesis Route:

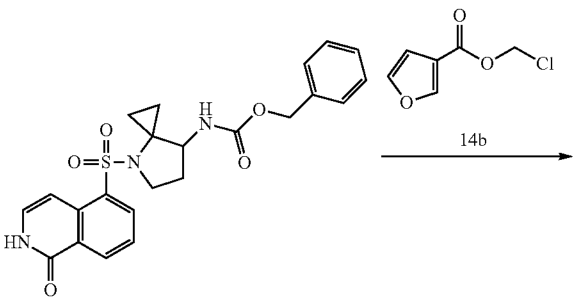

5

-continued

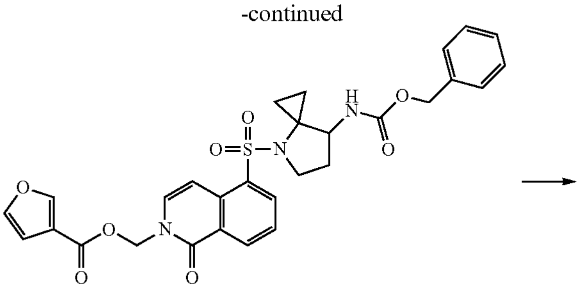

35a

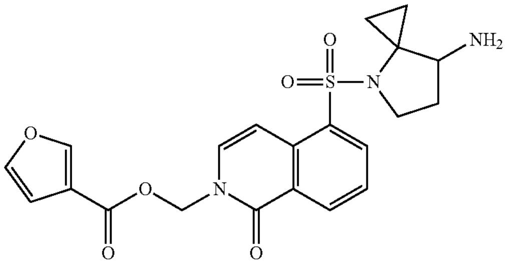

35

Step 1

Compound 35a was obtained referring to step 2 of Example 1. MS-ESI calculated value $[M+Na]^+$ 600, actually measured value 600.

Step 2

A formate of compound 35 was obtained referring to step 2 of Example 25. $^1H$ NMR (400 MHz, $CD_3OD$) δ=8.68 (d, J=7.9 Hz, 1H), 8.46 (br s, 1H), 8.44-8.41 (m, 1H), 8.23 (s, 1H), 7.78-7.67 (m, 2H), 7.60 (t, J=1.7 Hz, 1H), 7.20 (d, J=7.8 Hz, 1H), 6.79 (d, J=1.2 Hz, 1H), 6.15 (s, 2H), 4.12-4.02 (m, 1H), 3.65-3.55 (m, 1H), 3.43-3.35 (m, 1H), 2.59-2.45 (m, 1H), 2.11-2.00 (m, 1H), 1.26-1.08 (m, 2H), 0.87-0.74 (m, 2H). MS-ESI calculated value $[M+H]^+$ 444, actually measured value 444.

The formate of compound 35 can be adjusted the pH of the reaction solution to 8-9 by adding a saturated aqueous sodium carbonate solution to the system, and then, after the extraction with ethyl acetate, the reaction solution was concentrated to obtain compound 35.

Example 30: Compound 36

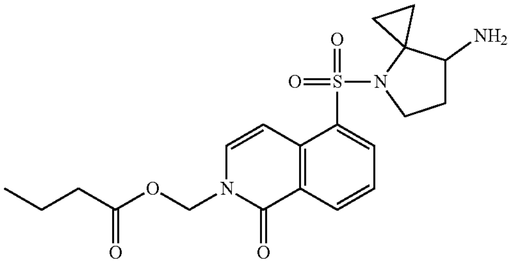

Synthesis Route:

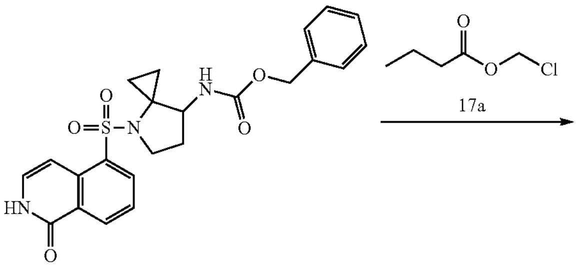

5

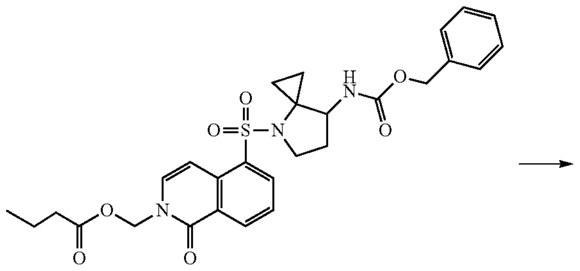

36a

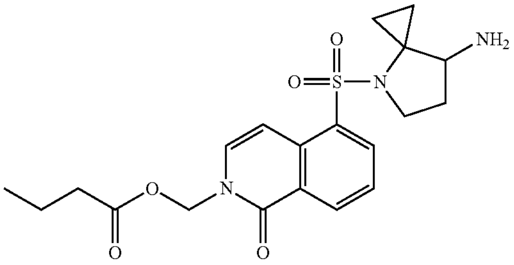

36

Step 1

Compound 36a was obtained referring to step 2 of Example 1. MS-ESI calculated value $[M+H]^+$ 554, actually measured value 554.

Step 2

A formate of compound 36 was obtained referring to step 2 of Example 25. $^1H$ NMR (400 MHz, $CD_3OD$) δ=8.67 (d, J=7.8 Hz, 1H), 8.53 (br s, 1H), 8.49-8.43 (m, 1H), 7.74-7.63 (m, 2H), 7.25 (d, J=7.9 Hz, 1H), 5.99 (s, 2H), 4.02-3.89 (m, 1H), 3.68-3.57 (m, 1H), 3.27-3.19 (m, 1H), 2.48-2.40 (m, 1H), 2.38 (t, J=7.3 Hz, 2H), 1.99-1.88 (m, 1H), 1.72-1.60 (m, 2H), 1.17-1.02 (m, 2H), 0.99-0.91 (m, 4H), 0.80-0.72 (m, 1H). MS-ESI calculated value $[M+H]^+$ 420, actually measured value 420.

The formate of compound 36 can be adjusted the pH of the reaction solution to 8-9 by adding saturated aqueous sodium carbonate solution to the system, and then, after the extraction with ethyl acetate, the reaction solution was concentrated to obtain compound 36.

Example 31: Compound 37

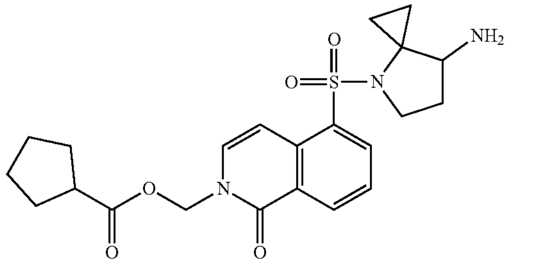 [SMILES: NC1CCN(S(=O)(=O)c2cccc3c(=O)n(COC(=O)C4CCCC4)ccc23)C12CC2]

Synthesis Route:

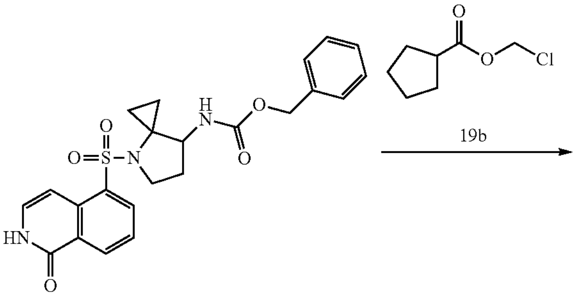

5

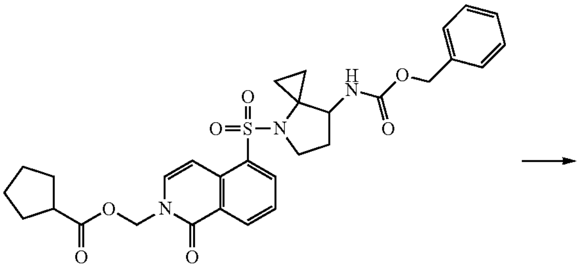

37a

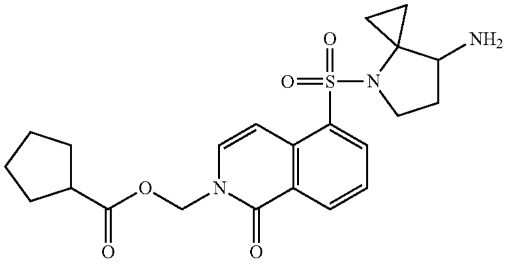

37

Step 1

Compound 37a was obtained referring to step 2 of Example 1. MS-ESI calculated value $[M+H]^+$ 580, actually measured value 580.

Step 2

A formate of compound 37 was obtained referring to step 2 of Example 25. $^1H$ NMR (400 MHz, $CD_3OD$) δ=8.66 (d, J=8.0 Hz, 1H), 8.46 (br s, 1H), 8.43-8.40 (m, 1H), 7.74-7.62 (m, 2H), 7.16 (d, J=7.8 Hz, 1H), 5.97 (s, 2H), 4.14-4.04 (m, 1H), 3.64-3.55 (m, 1H), 3.48-3.41 (m, 1H), 2.86-2.76 (m, 1H), 2.61-2.47 (m, 1H), 2.16-2.05 (m, 1H), 1.94-1.84 (m, 2H), 1.83-1.73 (m, 2H), 1.72-1.53 (m, 4H), 1.25-1.11 (m, 2H), 0.85-0.73 (m, 2H). MS-ESI calculated value $[M+H]^+$ 446, actually measured value 446.

The formate of compound 37 can be adjusted the pH of the reaction solution to 8-9 by adding a saturated aqueous sodium carbonate solution to the system, and then, after the extraction with ethyl acetate, the reaction solution was concentrated to obtain compound 37.

Example 32: Compound 38

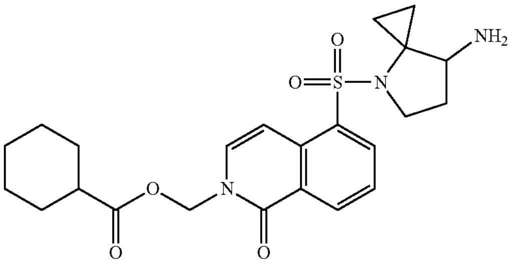 [SMILES: NC1CCN(S(=O)(=O)c2cccc3c(=O)n(COC(=O)C4CCCCC4)ccc23)C12CC2]

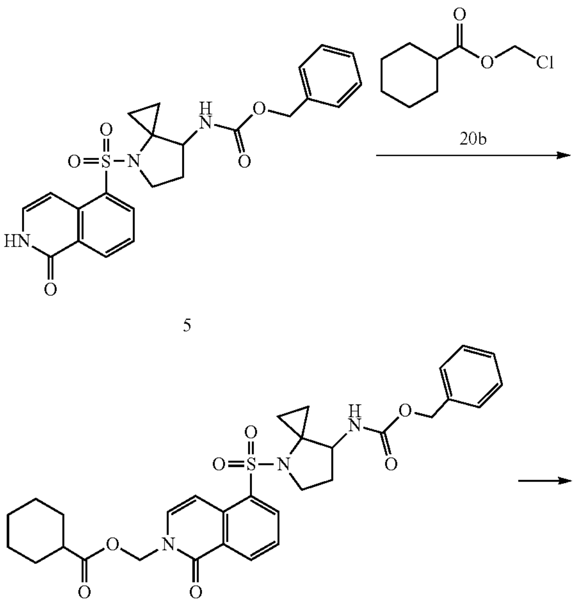

5

38a

-continued

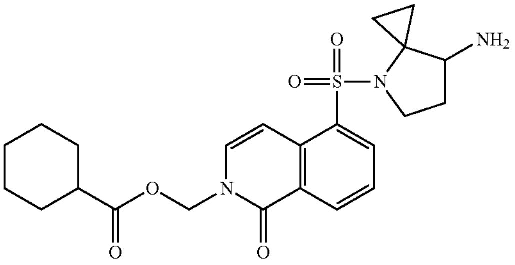

38a

Step 1

Compound 38a was obtained referring to step 2 of Example 1. MS-ESI calculated value $[M+H]^+$ 594, actually measured value 594.

Step 2

A formate of compound 38 was obtained referring to step 3 of Example 25. $^1H$ NMR (400 MHz, $CD_3OD$) δ=8.64 (d, J=8.0 Hz, 1H), 8.47-8.40 (m, 1H), 7.74-7.59 (m, 2H), 7.29 (d, J=7.9 Hz, 1H), 5.97 (s, 2H), 3.88-3.77 (m, 1H), 3.67-3.56 (m, 1H), 3.08-3.02 (m, 1H), 2.44-2.26 (m, 2H), 1.88 (d, J=13.4 Hz, 2H), 1.82-1.68 (m, 3H), 1.63 (br d, J=9.5 Hz, 1H), 1.49-1.38 (m, 2H), 1.34-1.27 (m, 3H), 1.09-0.94 (m, 3H), 0.75-0.67 (m, 1H). MS-ESI calculated value $[M+H]^+$ 460, actually measured value 460.

The formate of compound 38 can be adjusted the pH of the reaction solution to 8-9 by adding a saturated aqueous sodium carbonate solution to the system, and then, after the extraction with ethyl acetate, the reaction solution was concentrated to obtain compound 38.

Example 33: Compound 39

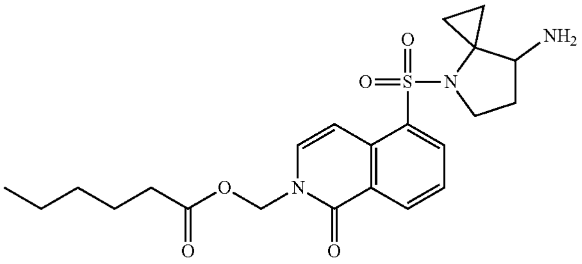 [SMILES: CCCCCC(=O)OCn1ccc2c(S(=O)(=O)N3CCC(N)C34CC4)cccc2c1=O]

Synthesis Route:

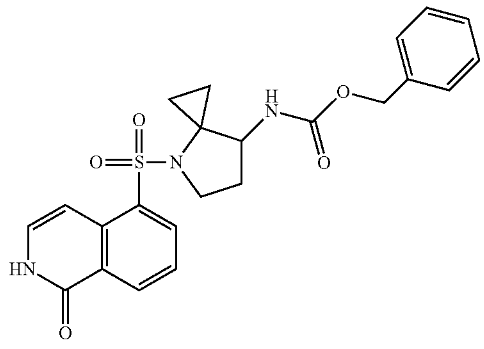

5

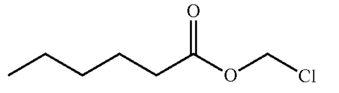

22b

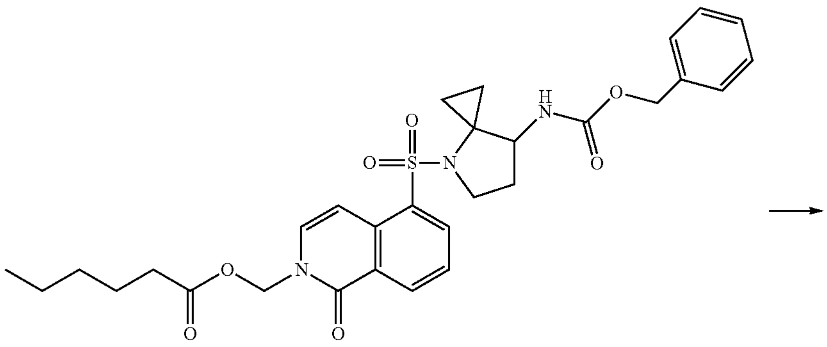

39a

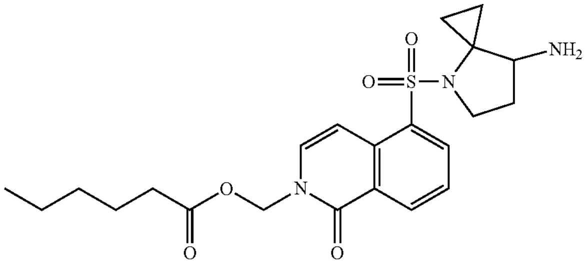

39

Step 1

Compound 39a was obtained referring to step 2 of Example 1. MS-ESI calculated value $[M+H]^+$ 582, actually measured value 582.

Step 2

Compound 39 was obtained referring to step 2 of Example 25. $^1H$ NMR (400 MHz, $CD_3OD$) δ=8.66-8.59 (m, 1H), 8.47-8.39 (m, 1H), 7.72-7.60 (m, 2H), 7.37-7.28 (m, 1H), 5.97 (s, 2H), 3.83-3.57 (m, 2H), 3.01-2.93 (m, 1H), 2.37 (t, J=7.4 Hz, 2H), 2.32-2.21 (m, 1H), 1.80-1.67 (m, 1H), 1.65-1.56 (m, 2H), 1.27 (dd, J=3.6, 7.3 Hz, 4H), 1.16-1.06 (m, 1H), 1.03-0.95 (m, 1H), 0.95-0.89 (m, 1H), 0.84 (t, J=7.0 Hz, 3H), 0.73-0.63 (m, 1H). MS-ESI calculated value $[M+H]^+$ 448, actually measured value 448.

The formate of compound 39 can be adjusted the pH of the reaction solution to 8-9 by adding a saturated aqueous sodium carbonate solution to the system, and then, after the extraction with ethyl acetate, the reaction solution was concentrated to obtain compound 39.

Example 34: Compound 40

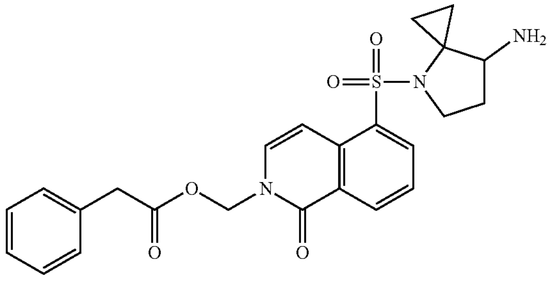 [SMILES: NC1CCN(S(=O)(=O)c2cccc3c(=O)n(COC(=O)Cc4ccccc4)ccc23)C12CC2]

Synthesis Route:

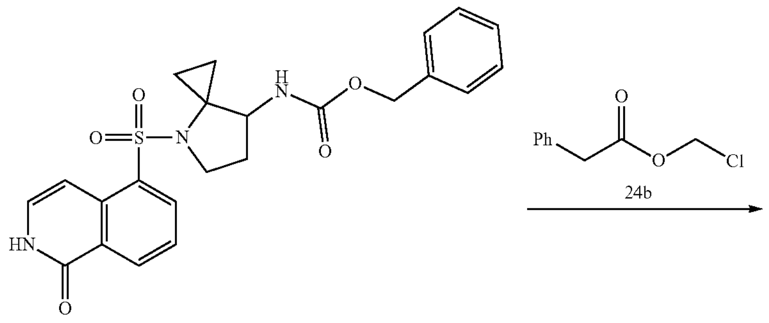

5

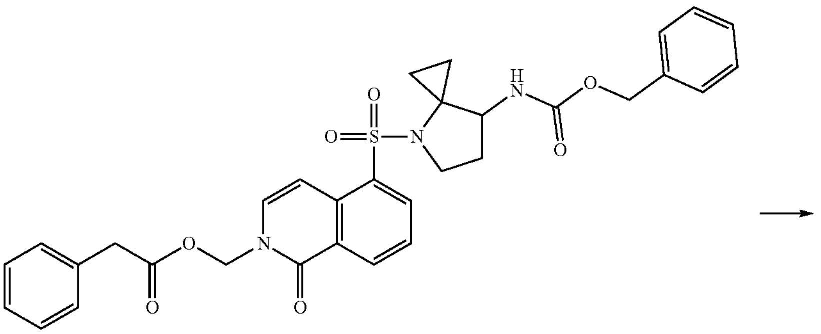

40a

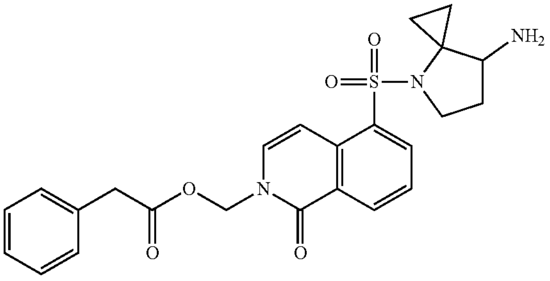

40

Step 1

Compound 40a was obtained referring to step 2 of Example 1. MS-ESI calculated value $[M+H]^+$ 602, actually measured value 602.

Step 2

A formate of compound 40 was obtained referring to step 2 of Example 25. $^1H$ NMR (400 MHz, $CD_3OD$) δ=8.64 (d, J=7.8 Hz, 1H), 8.48 (br s, 1H), 8.44-8.39 (m, 1H), 7.69 (t, J=7.9 Hz, 1H), 7.60 (d, J=7.9 Hz, 1H), 7.29-7.17 (m, 4H), 7.13 (d, J=7.9 Hz, 1H), 5.99 (s, 2H), 4.12-4.00 (m, 1H), 3.70 (s, 2H), 3.64-3.52 (m, 1H), 3.44-3.36 (m, 1H), 2.57-2.45 (m, 1H), 2.16-1.99 (m, 1H), 1.21-1.09 (m, 2H), 0.83-0.73 (m, 2H). MS-ESI calculated value $[M+H]^+$ 468, actually measured value 468.

The formate of compound 40 can be adjusted the pH of the reaction solution to 8-9 by adding a saturated aqueous sodium carbonate solution to the system, and then, after the extraction with ethyl acetate, the reaction solution was concentrated to obtain compound 40.

Example 35: Compound 41

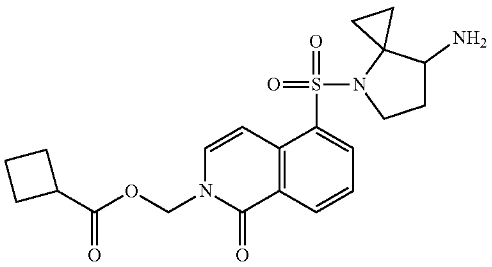

Synthesis Route:

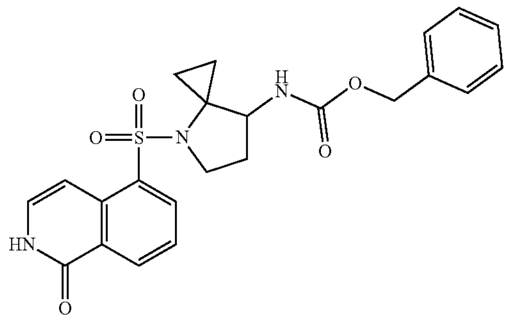

5

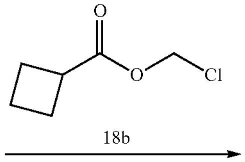

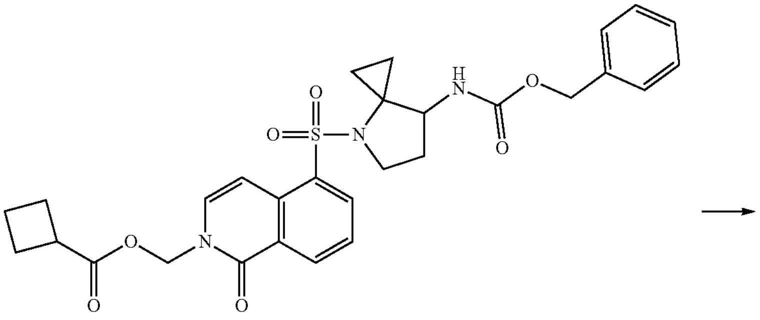

41a

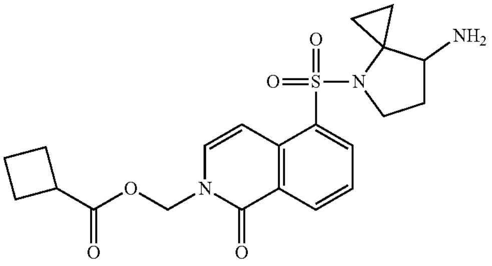 [SMILES: NC1CCN(S(=O)(=O)c2cccc3c(=O)n(COC(=O)C4CCC4)ccc23)C12CC2]

41

Step 1

Compound 41a was obtained referring to step 2 of Example 1. MS-ESI calculated value $[M+H]^+$ 566, actually measured value 566.

Step 2

A formate of compound 41 was obtained referring to step 2 of Example 25. $^1H$ NMR (400 MHz, $CD_3OD$) δ=8.66 (d, J=7.9 Hz, 1H), 8.50 (br s, 1H), 8.45-8.39 (m, 1H), 7.73-7.63 (m, 2H), 7.18 (d, J=7.9 Hz, 1H), 5.97 (s, 2H), 4.10-3.99 (m, 1H), 3.67-3.55 (m, 1H), 3.39-3.33 (m, 1H), 3.27-3.18 (m, 1H), 2.57-2.44 (m, 1H), 2.33-2.14 (m, 4H), 2.09-1.95 (m, 2H), 1.94-1.81 (m, 1H), 1.24-1.07 (m, 2H), 0.90-0.71 (m, 2H). MS-ESI calculated value $[M+H]^+$ 432, actually measured value 432.

The formate of compound 41 can be adjusted the pH of the reaction solution to 8-9 by adding a saturated aqueous sodium carbonate solution to the system, and then, after the extraction with ethyl acetate, the reaction solution was concentrated to obtain compound 41.

Example 36: Compound 42

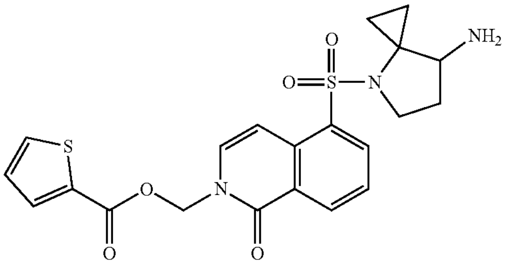

Synthesis Route:

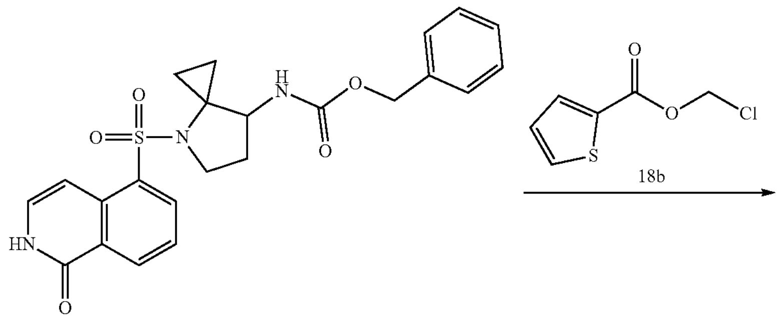
18b

5

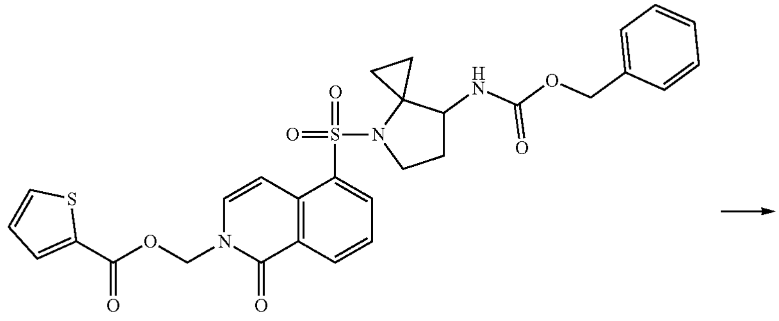

42a

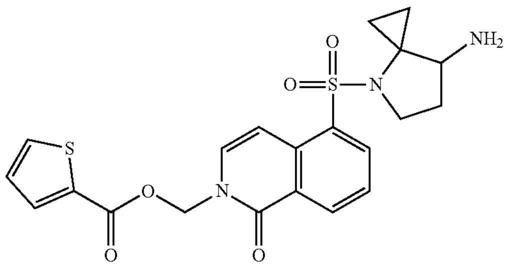 [SMILES: NC1CCN(S(=O)(=O)c2cccc3c(=O)n(COC(=O)c4cccs4)ccc23)C12CC2]

42

Step 1

Compound 42a was obtained referring to step 2 of Example 1. MS-ESI calculated value $[M+H]^+$ 594, actually measured value 594.

Step 2

A formate of compound 42 was obtained referring to step 2 of Example 25. $^1H$ NMR (400 MHz, $CD_3OD$) δ=8.68 (d, J=7.6 Hz, 1H), 8.46 (s, 1H), 8.44-8.41 (m, 1H), 7.90-7.86 (m, 1H), 7.83-7.79 (m, 1H), 7.76 (d, J=8.1 Hz, 1H), 7.70 (t, J=7.9 Hz, 1H), 7.23-7.14 (m, 2H), 6.18 (s, 2H), 4.11-4.01 (m, 1H), 3.65-3.56 (m, 1H), 3.40-3.36 (m, 1H), 2.59-2.45 (m, 1H), 2.12-1.98 (m, 1H), 1.27-1.06 (m, 2H), 0.88-0.72 (m, 2H). MS-ESI calculated value $[M+H]^+$ 460, actually measured value 460.

The formate of compound 42 can be adjusted the pH of the reaction solution to 8-9 by adding a saturated aqueous sodium carbonate solution to the system, and then, after the extraction with ethyl acetate, the reaction solution was concentrated to obtain compound 42.

Example 37: Compound 43

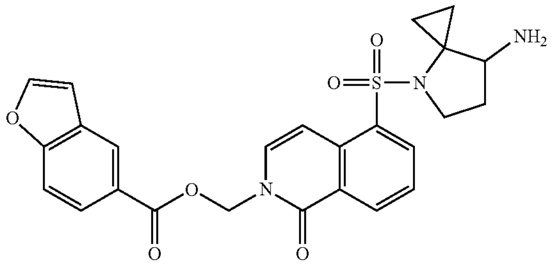 [SMILES: NC1CCN(S(=O)(=O)c2cccc3c(=O)n(COC(=O)c4ccc5occc5c4)ccc23)C12CC2]

Synthesis Route:

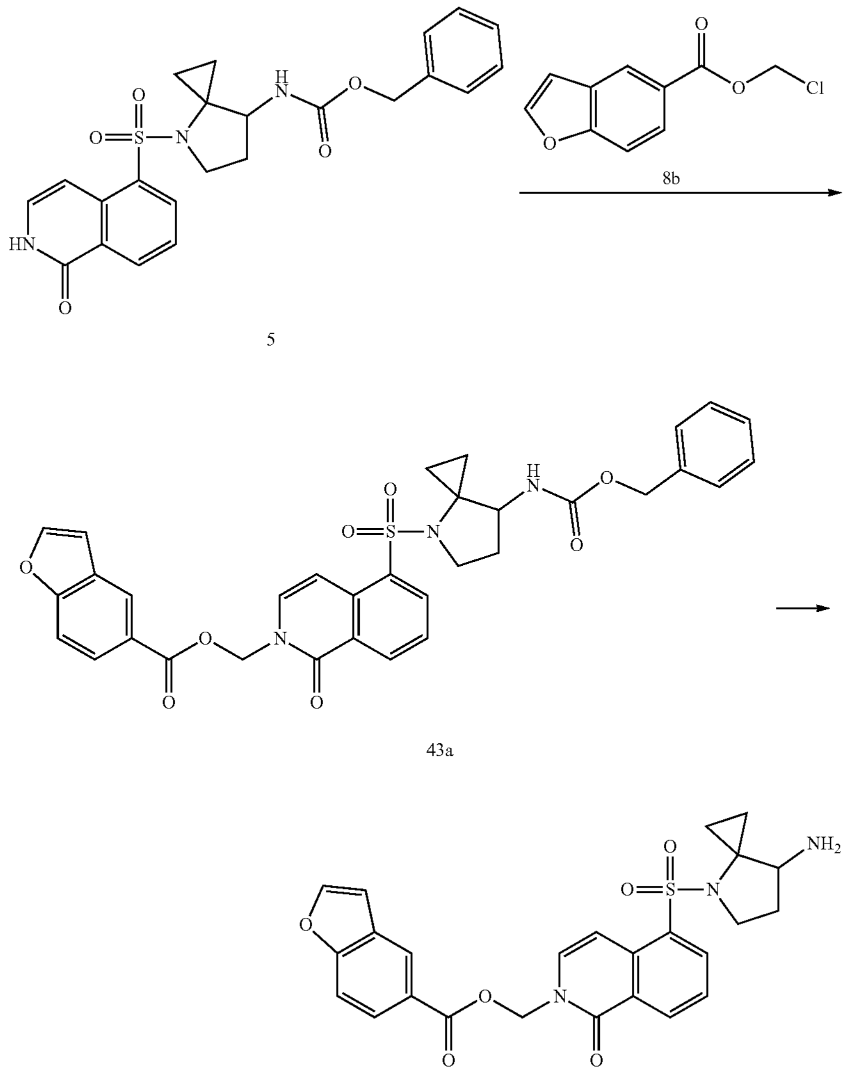

5

8b

43a

43

Step 1

Compound 43a was obtained referring to step 2 of Example 1. MS-ESI calculated value $[M+H]^+$ 628, actually measured value 628.

Step 2

A formate of compound 43 was obtained referring to step 2 of Example 25. $^1H$ NMR (400 MHz, $CD_3OD$) δ=8.69 (d, J=7.9 Hz, 1H), 8.49 (s, 1H), 8.45-8.41 (m, 1H), 8.38 (d, J=1.6 Hz, 1H), 8.05-8.00 (m, 1H), 7.86 (d, J=2.3 Hz, 1H), 7.81 (d, J=7.9 Hz, 1H), 7.70 (t, J=7.9 Hz, 1H), 7.58 (d, J=8.8 Hz, 1H), 7.23 (d, J=7.9 Hz, 1H), 6.95 (d, J=1.5 Hz, 1H), 6.24 (s, 2H), 4.10-3.96 (m, 1H), 3.68-3.54 (m, 1H), 3.36-3.32 (m, 1H), 2.55-2.42 (m, 1H), 2.08-1.94 (m, 1H), 1.26-1.04 (m, 2H), 0.89-0.72 (m, 2H). MS-ESI calculated value $[M+H]^+$ 494, actually measured value 494.

The formate of compound 43 can be adjusted the pH of the reaction solution to 8-9 by adding a saturated aqueous sodium carbonate solution to the system, and then, after the extraction with ethyl acetate, the reaction solution was concentrated to obtain compound 43.

Example 38: Compound 44

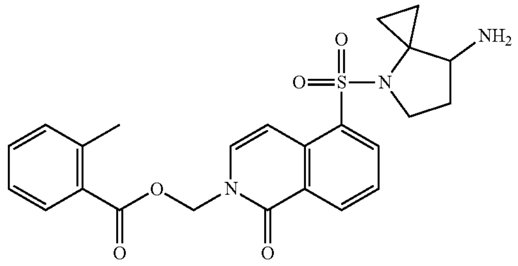 [SMILES: Cc1ccccc1C(=O)OCn1ccc2c(S(=O)(=O)N3CCC(N)C34CC4)cccc2c1=O]

Synthesis Route:

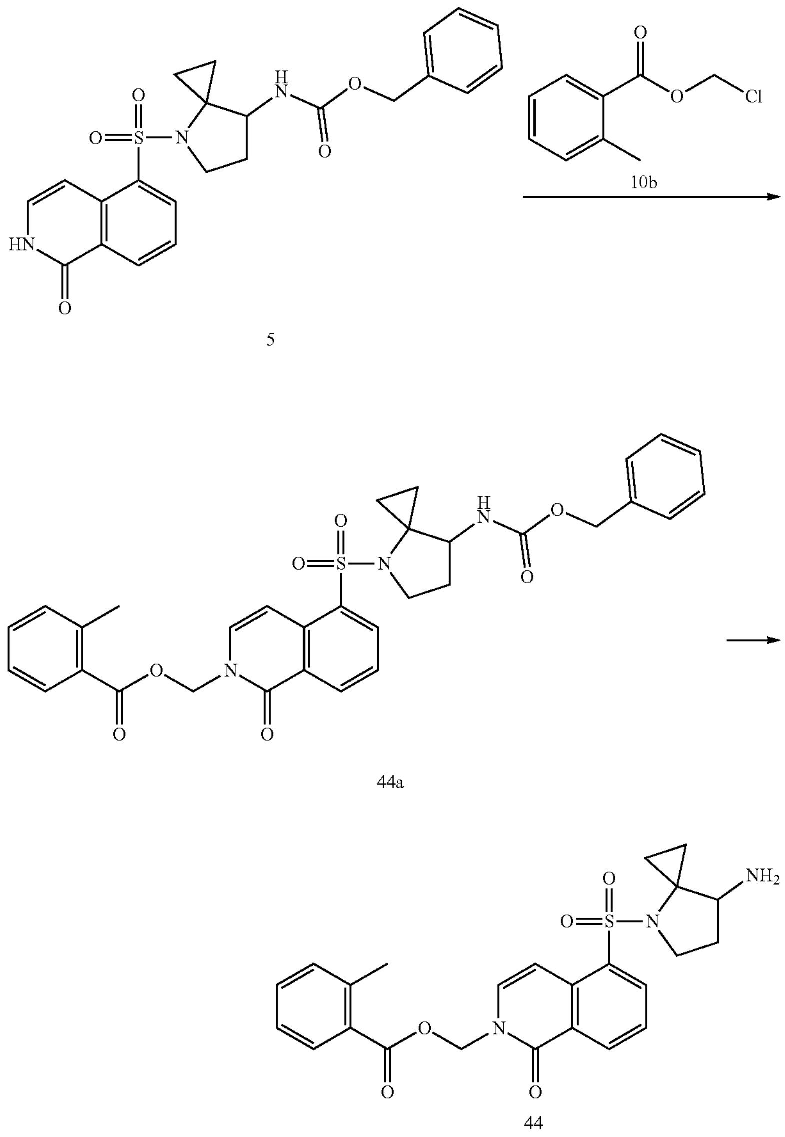

5

44a

44

Step 1

Compound 44a was obtained referring to step 2 of Example 1. MS-ESI calculated value $[M+H]^+$ 602, actually measured value 602.

Step 2

A formate of compound 44 was obtained referring to step 2 of Example 25. $^1H$ NMR (400 MHz, $CD_3OD$) δ=8.69 (d, J=8.0 Hz, 1H), 8.50 (s, 1H), 8.46-8.40 (m, 1H), 7.91 (d, J=7.9 Hz, 1H), 7.80 (d, J=7.9 Hz, 1H), 7.74-7.67 (m, 1H), 7.49-7.41 (m, 1H), 7.32-7.19 (m, 3H), 6.20 (s, 2H), 4.15-4.05 (m, 1H), 3.67-3.57 (m, 1H), 3.49-3.43 (m, 1H), 2.60-2.50 (m, 4H), 2.17-2.05 (m, 1H), 1.28-1.13 (m, 2H), 0.86-0.75 (m, 2H). MS-ESI calculated value $[M+H]^+$ 468, actually measured value 468.

The formate of compound 44 can be adjusted the pH of the reaction solution to 8-9 by adding a saturated aqueous sodium carbonate solution to the system, and then, after the extraction with ethyl acetate, the reaction solution was concentrated to obtain compound 44.

Example 39: Compound 45

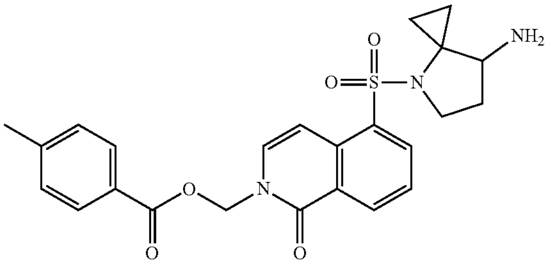 [SMILES: Cc1ccc(C(=O)OCn2ccc3c(S(=O)(=O)N4CCC(N)C45CC5)cccc3c2=O)cc1]

Synthesis Route:

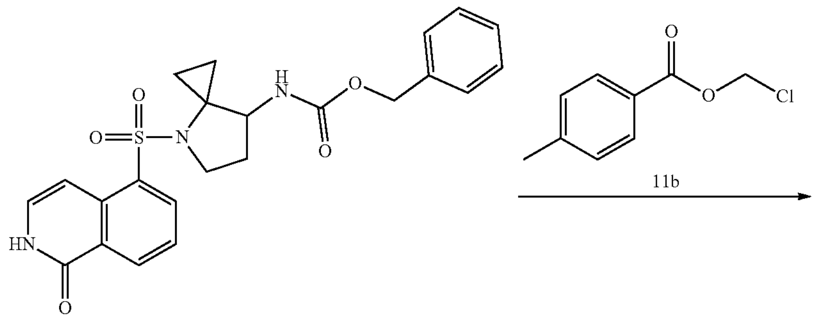

5

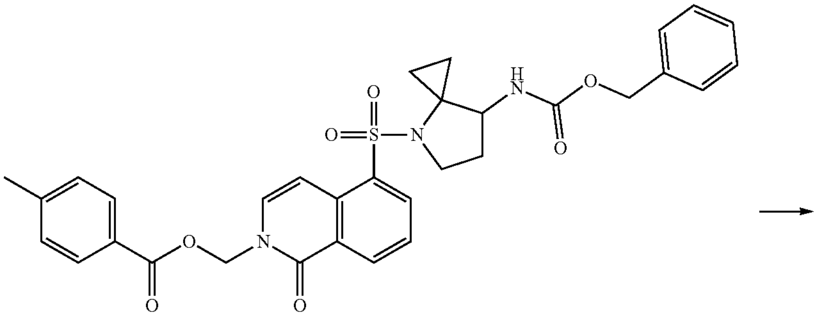

45a

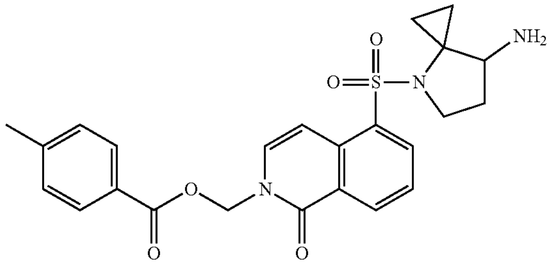

45

Step 1

Compound 45a was obtained referring to step 2 of Example 1. MS-ESI calculated value $[M+H]^+$ 602, actually measured value 602.

Step 2

A formate of compound 45 was obtained referring to step 2 of Example 25. $^1H$ NMR (400 MHz, $CD_3OD$) δ=8.69 (d, J=8.0 Hz, 1H), 8.46 (s, 1H), 8.44-8.40 (m, 1H), 7.92 (d, J=8.3 Hz, 2H), 7.78 (d, J=8.0 Hz, 1H), 7.70 (t, J=7.9 Hz, 1H), 7.29 (d, J=8.2 Hz, 2H), 7.20 (d, J=8.0 Hz, 1H), 6.20 (s, 2H), 4.12-4.01 (m, 1H), 3.65-3.54 (m, 1H), 3.43-3.36 (m, 1H), 2.58-2.46 (m, 1H), 2.39 (s, 3H), 2.11-1.99 (m, 1H), 1.26-1.08 (m, 2H), 0.86-0.74 (m, 2H). MS-ESI calculated value $[M+H]^+$ 468, actually measured value 468.

The formate of compound 45 can be adjusted the pH of the reaction solution to 8-9 by adding a saturated aqueous sodium carbonate solution to the system, and then, after the extraction with ethyl acetate, the reaction solution was concentrated to obtain compound 45.

Example 40: Compound 46

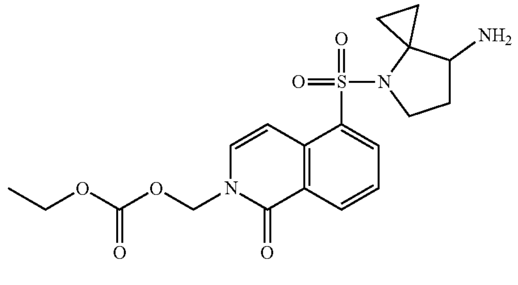

Synthesis Route:

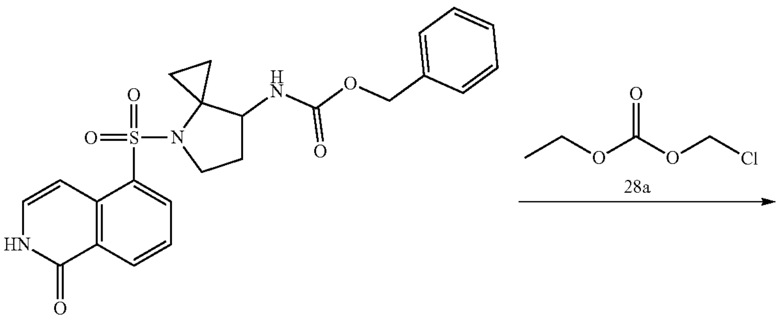

5

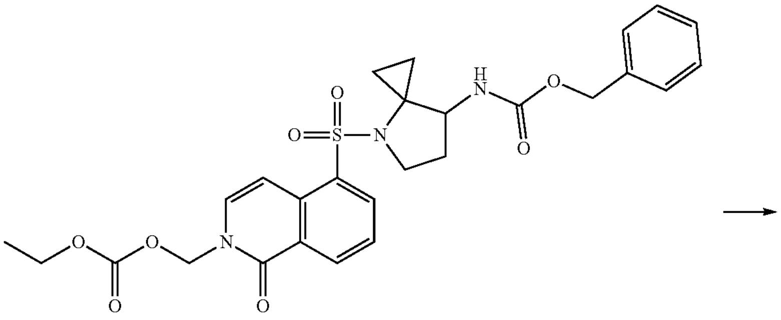

46a

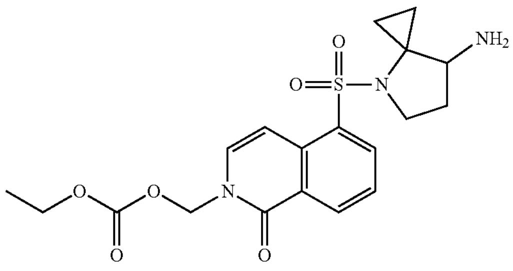 [SMILES: CCOC(=O)OCn1ccc2c(S(=O)(=O)N3CCC(N)C34CC4)cccc2c1=O]

46

Step 1

Compound 46a was obtained referring to step 2 of Example 1. MS-ESI calculated value $[M+H]^+$ 556, actually measured value 556.

Step 2

A formate of compound 46 was obtained referring to step 2 of Example 25. $^1H$ NMR (400 MHz, $CD_3OD$) δ=8.66 (d, J=7.9 Hz, 1H), 8.52 (s, 1H), 8.46-8.40 (m, 1H), 7.74-7.65 (m, 2H), 7.18 (d, J=7.9 Hz, 1H), 5.99 (s, 2H), 4.27-4.19 (m, 2H), 4.11-4.02 (m, 1H), 3.67-3.56 (m, 1H), 3.45-3.39 (m, 1H), 2.59-2.47 (m, 1H), 2.14-2.02 (m, 1H), 1.29 (t, J=7.1 Hz, 3H), 1.24-1.11 (m, 2H), 0.88-0.76 (m, 2H). MS-ESI calculated value $[M+H]^+$ 422, actually measured value 422.

The formate of compound 46 can be adjusted the pH of the reaction solution to 8-9 by adding a saturated aqueous sodium carbonate solution to the system, and then, after the extraction with ethyl acetate, the reaction solution was concentrated to obtain compound 46.

Example 41: Compound 47

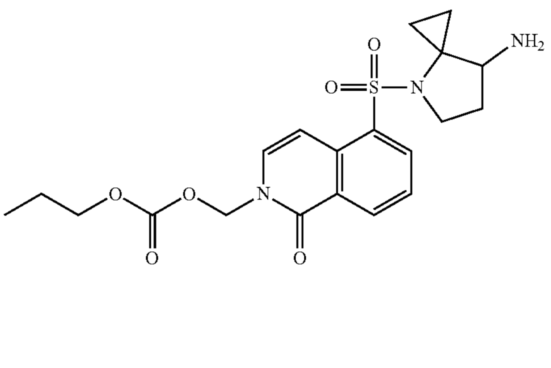

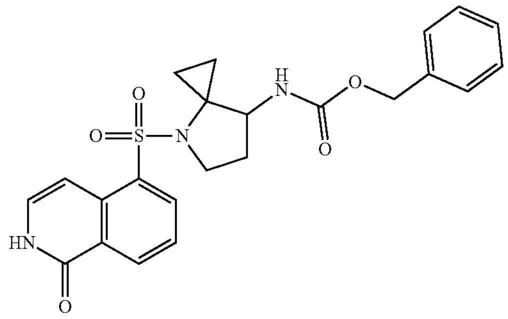

5

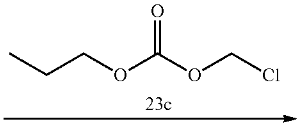

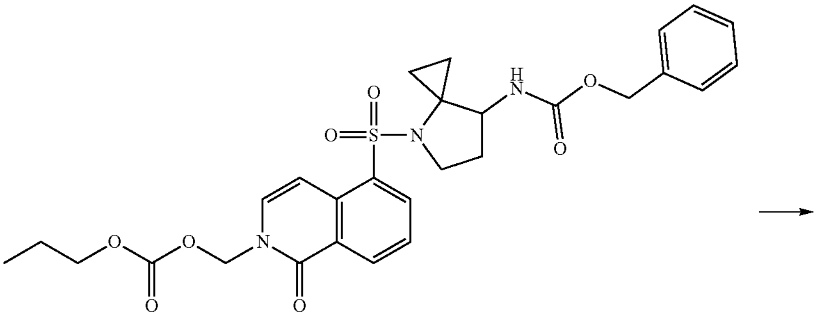

47a

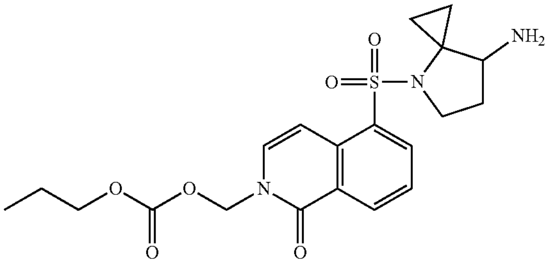 [SMILES: CCCOC(=O)OCn1ccc2c(S(=O)(=O)N3CCC(N)C34CC4)cccc2c1=O]

47

Step 1

Compound 47a was obtained referring to step 2 of Example 1. MS-ESI calculated value $[M+H]^+$ 570, actually measured value 570.

Step 2

A formate of compound 47 was obtained referring to step 2 of Example 25. $^1$H NMR (400 MHz, $CD_3OD$) δ=8.66 (d, J=7.9 Hz, 1H), 8.49 (s, 1H), 8.44-8.38 (m, 1H), 7.74-7.63 (m, 2H), 7.17 (d, J=7.8 Hz, 1H), 6.01-5.94 (m, 2H), 4.13 (t, J=6.6 Hz, 2H), 4.10-4.02 (m, 1H), 3.65-3.56 (m, 1H), 3.45-3.39 (m, 1H), 2.58-2.47 (m, 1H), 2.13-2.03 (m, 1H), 1.73-1.63 (m, 2H), 1.24-1.10 (m, 2H), 0.94 (t, J=7.5 Hz, 3H), 0.80 (t, J=9.0 Hz, 2H). MS-ESI calculated value $[M+H]^+$ 436, actually measured value 436.

The formate of compound 47 can be adjusted the pH of the reaction solution to 8-9 by adding a saturated aqueous sodium carbonate solution to the system, and then, after the extraction with ethyl acetate, the reaction solution was concentrated to obtain compound 47.

Example 42: Compound 48

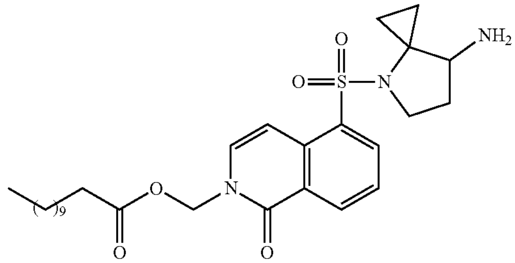

Synthesis Route:

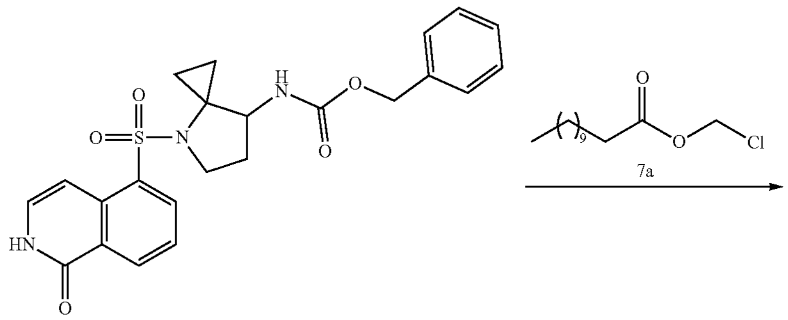

7a

5

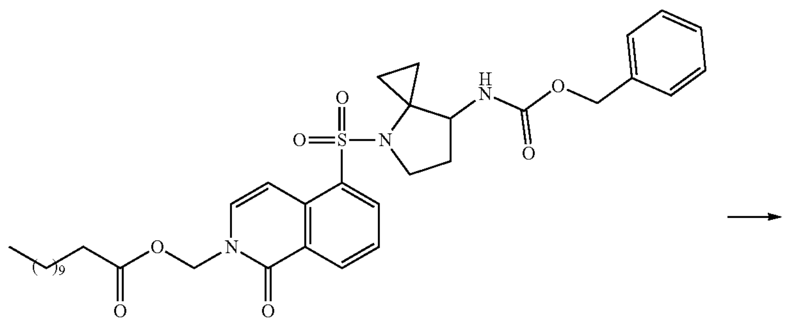

48a

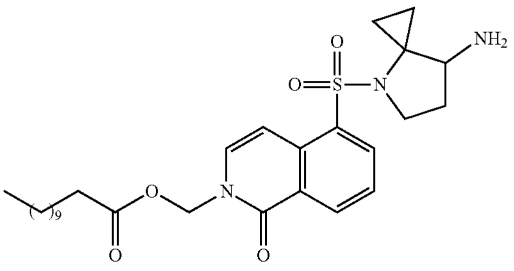

48

Step 1

Compound 48a was obtained referring to step 2 of Example 1. MS-ESI calculated value $[M+H]^+$ 666, actually measured value 666.

Step 2

A formate of compound 48 was obtained referring to step 2 of Example 25. $^1H$ NMR (400 MHz, $CD_3OD$) δ=8.65 (d, J=7.6 Hz, 1H), 8.48 (s, 1H), 8.43-8.39 (m, 1H), 7.74-7.60 (m, 2H), 7.16 (d, J=7.9 Hz, 1H), 5.97 (s, 2H), 4.14-4.02 (m, 1H), 3.65-3.54 (m, 1H), 3.47-3.38 (m, 1H), 2.61-2.47 (m, 1H), 2.37 (t, J=7.3 Hz, 2H), 2.14-2.03 (m, 1H), 1.66-1.54 (m, 2H), 1.30-1.15 (m, 18H), 0.89 (t, J=7.0 Hz, 3H), 0.83-0.73 (m, 2H). MS-ESI calculated value $[M+H]^+$ 532, actually measured value 532.

The formate of compound 48 can be adjusted the pH of the reaction solution to 8-9 by adding a saturated aqueous sodium carbonate solution to the system, and then, after the extraction with ethyl acetate, the reaction solution was concentrated to obtain compound 48.

Example 43: Compound 49

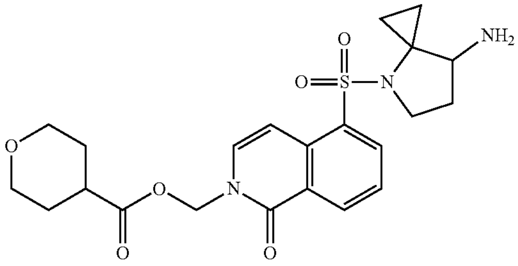

Synthesis Route:

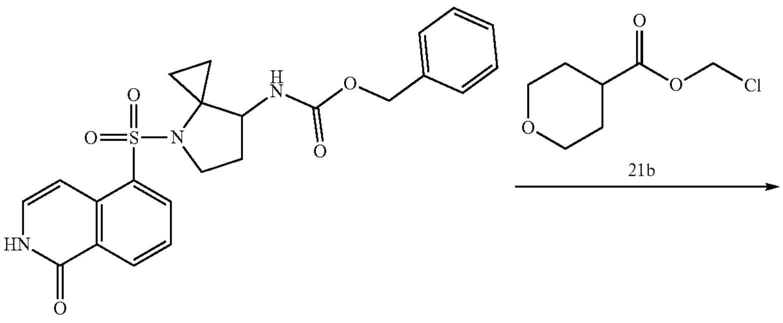

5

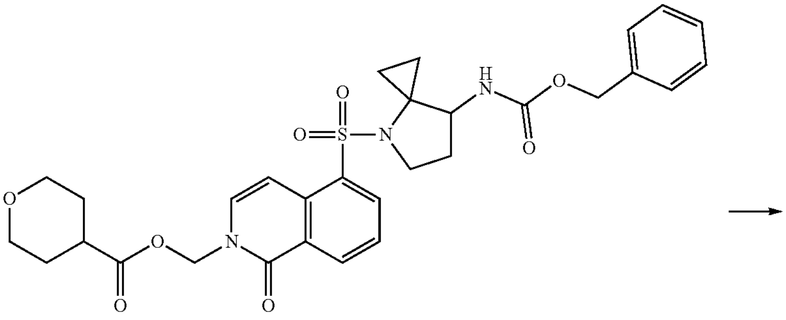

49a

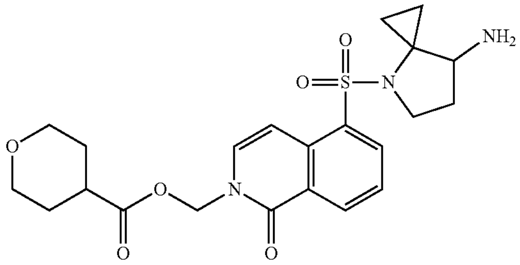 [SMILES: NC1CCN(S(=O)(=O)c2cccc3c(=O)n(COC(=O)C4CCOCC4)ccc23)C12CC2]

49

Step 1

Compound 49a was obtained referring to step 2 of Example 1. MS-ESI calculated value $[M+H]^+$ 596, actually measured value 596.

Step 2

A formate of compound 49 was obtained referring to step 2 of Example 25. $^1H$ NMR (400 MHz, $CD_3OD$) δ=8.65 (d, J=7.6 Hz, 1H), 8.49 (s, 1H), 8.43-8.40 (m, 1H), 7.75-7.61 (m, 2H), 7.16 (d, J=7.8 Hz, 1H), 5.99 (s, 2H), 4.12-4.02 (m, 1H), 3.92-3.83 (m, 2H), 3.66-3.54 (m, 1H), 3.47-3.37 (m, 3H), 2.73-2.62 (m, 1H), 2.59-2.45 (m, 1H), 2.15-2.01 (m, 1H), 1.88-1.78 (m, 2H), 1.75-1.61 (m, 2H), 1.24-1.10 (m, 2H), 0.85-0.75 (m, 2H). MS-ESI calculated value $[M+H]^+$ 462, actually measured value 462.

The formate of compound 49 can be adjusted the pH of the reaction solution to 8-9 by adding a saturated aqueous sodium carbonate solution to the system, and then, after the extraction with ethyl acetate, the reaction solution was concentrated to obtain compound 49.

Example 44: Compound 50

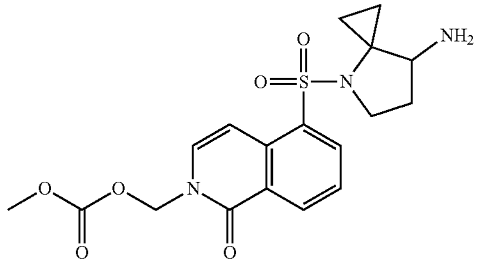 [SMILES: COC(=O)OCn1ccc2c(S(=O)(=O)N3CCC(N)C34CC4)cccc2c1=O]

Synthesis Route:

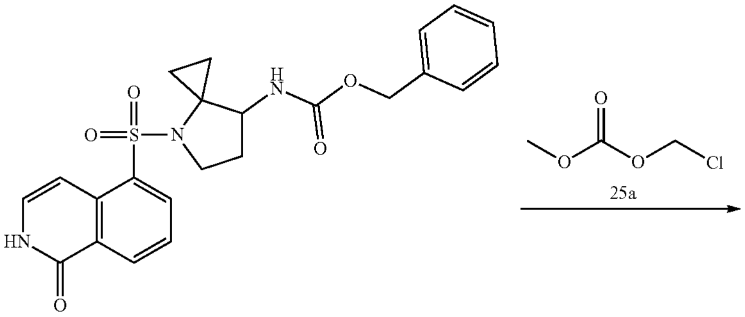

5

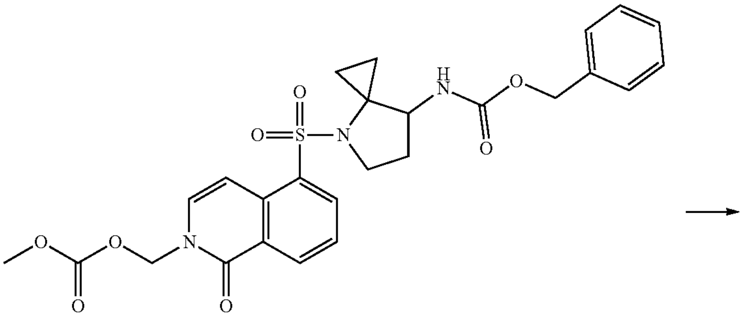

50a

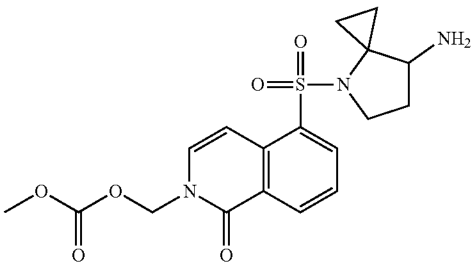

50

Step 1

Compound 50a was obtained referring to step 2 of Example 1. MS-ESI calculated value $[M+H]^+$ 542, actually measured value 542.

Step 2

A formate of compound 50 was obtained referring to step 2 of Example 25. $^1H$ NMR (400 MHz, $CD_3OD$) δ=8.64 (d, J=7.9 Hz, 1H), 8.44 (s, 1H), 8.42-8.38 (m, 1H), 7.72-7.64 (m, 2H), 7.14 (d, J=7.8 Hz, 1H), 5.98 (s, 2H), 4.14-4.05 (m, 1H), 3.80 (s, 3H), 3.64-3.56 (m, 1H), 3.48 (d, J=5.1 Hz, 1H), 2.61-2.50 (m, 1H), 2.18-2.07 (m, 1H), 1.26-1.14 (m, 2H), 0.85-0.73 (m, 2H). MS-ESI calculated value [M+H]+408, actually measured value 408.

The formate of compound 50 can be adjusted the pH of the reaction solution to 8-9 by adding a saturated aqueous sodium carbonate solution to the system, and then, after the extraction with ethyl acetate, the reaction solution was concentrated to obtain compound 50.

Example 45: Compound 51

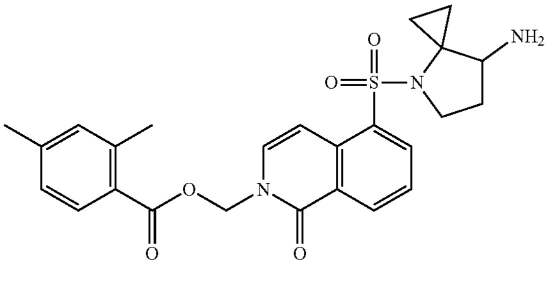 [SMILES: Cc1ccc(C(=O)OCn2ccc3c(S(=O)(=O)N4CCC(N)C45CC5)cccc3c2=O)c(C)c1]

Synthesis Route:

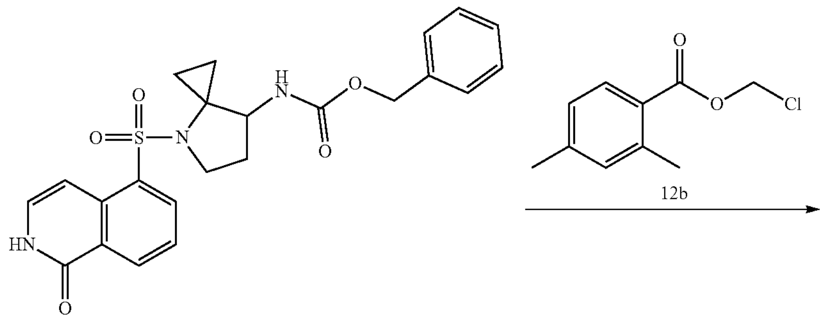

5

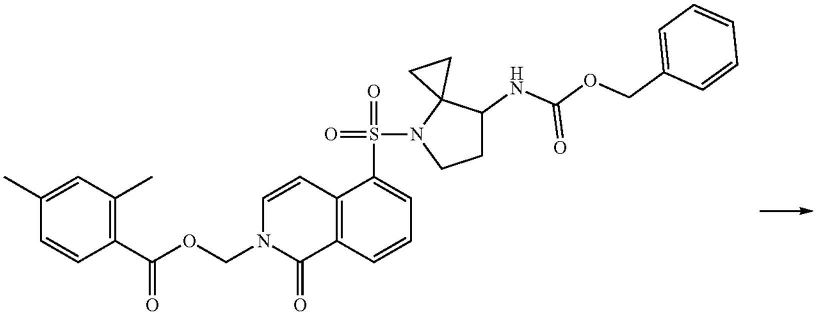

51a

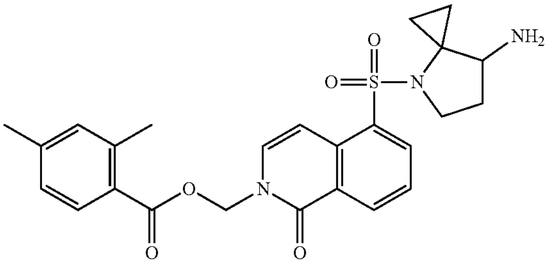

51

Step 1

Compound 51a was obtained referring to step 2 of Example 1. MS-ESI calculated value $[M+H]^+$ 616, actually measured value 616.

Step 2

A formate of compound 51 was obtained referring to step 2 of Example 25. $^1H$ NMR (400 MHz, $CD_3OD$) δ=8.64 (d, J=7.9 Hz, 1H), 8.49 (br s, 1H), 8.42-8.35 (m, 1H), 7.77 (t, J=8.1 Hz, 2H), 7.70-7.62 (m, 1H), 7.18 (d, J=7.8 Hz, 1H), 7.09-6.98 (m, 2H), 6.15 (s, 2H), 4.10-3.98 (m, 1H), 3.63-3.53 (m, 1H), 3.45-3.37 (m, 1H), 2.57-2.44 (m, 4H), 2.30 (s, 3H), 2.14-2.01 (m, 1H), 1.26-1.08 (m, 2H), 0.79 (t, J=9.0 Hz, 2H). MS-ESI calculated value $[M+H]^+$ 482, actually measured value 482.

The formate of compound 51 can be adjusted the pH of the reaction solution to 8-9 by adding a saturated aqueous sodium carbonate solution to the system, and then, after the extraction with ethyl acetate, the reaction solution was concentrated to obtain compound 51.

Example 46: Compound 52

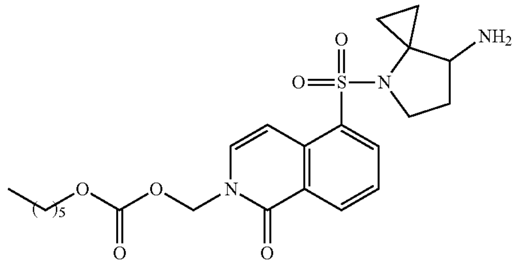

Synthesis Route:

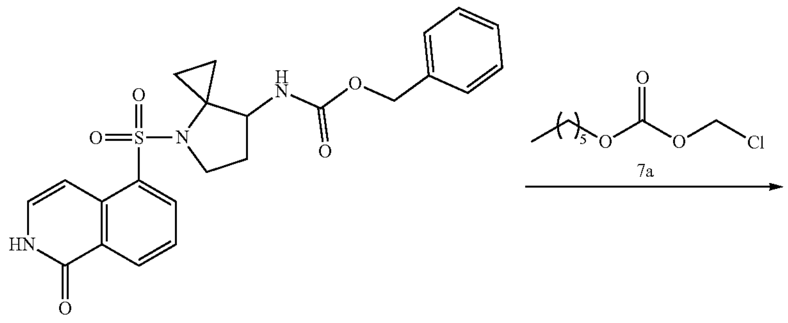

5

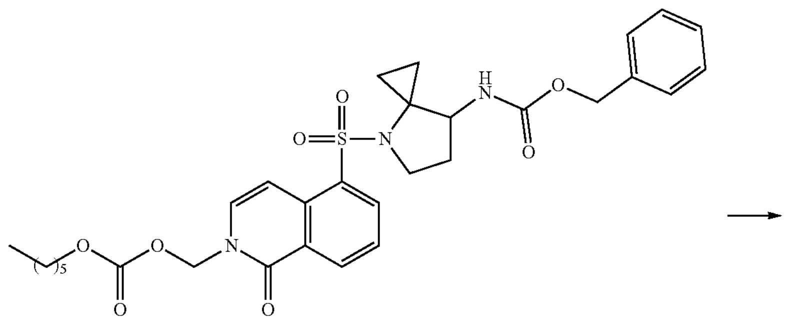

52a

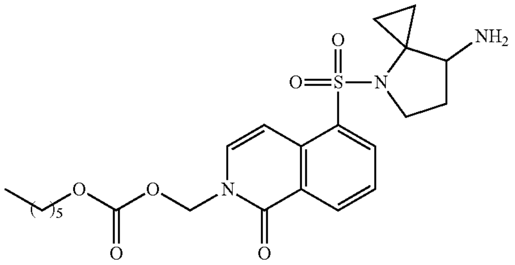

52

Step 1

Compound 52a was obtained referring to step 2 of Example 1. MS-ESI calculated value $[M+Na]^+$ 634, actually measured value 634.

Step 2

A formate of compound 52 was obtained referring to step 2 of Example 25. $^1H$ NMR (400 MHz, $CD_3OD$) δ=8.66 (d, J=7.8 Hz, 1H), 8.61 (s, 1H), 8.42 (d, J=7.8 Hz, 1H), 7.74-7.64 (m, 2H), 7.14 (d, J=7.8 Hz, 1H), 6.03-5.92 (m, 2H), 4.22-4.05 (m, 3H), 3.59-3.61 (m, 1H), 3.50 (d, J=4.8 Hz, 1H), 2.54-2.57 (m, 1H), 2.20-2.08 (m, 1H), 1.71-1.59 (m, 2H), 1.41-1.12 (m, 8H), 0.87 (t, J=6.8 Hz, 3H), 0.84-0.67 (m, 2H). MS-ESI calculated value $[M+H]^+$ 478, actually measured value 478.

The formate of compound 52 can be adjusted the pH of the reaction solution to 8-9 by adding a saturated aqueous sodium carbonate solution to the system, and then, after the extraction with ethyl acetate, the reaction solution was concentrated to obtain compound 52.

Example 47: Compound 53

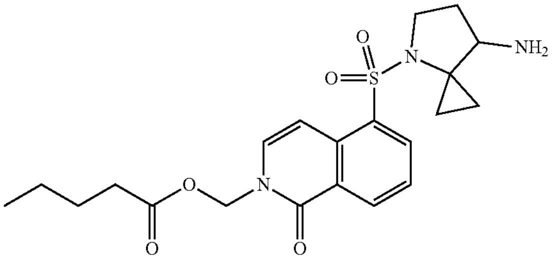 [SMILES: CCCCC(=O)OCn1ccc2c(S(=O)(=O)N3CCC(N)C34CC4)cccc2c1=O]

Synthesis Route:

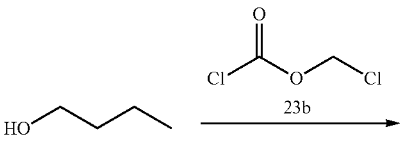

53a

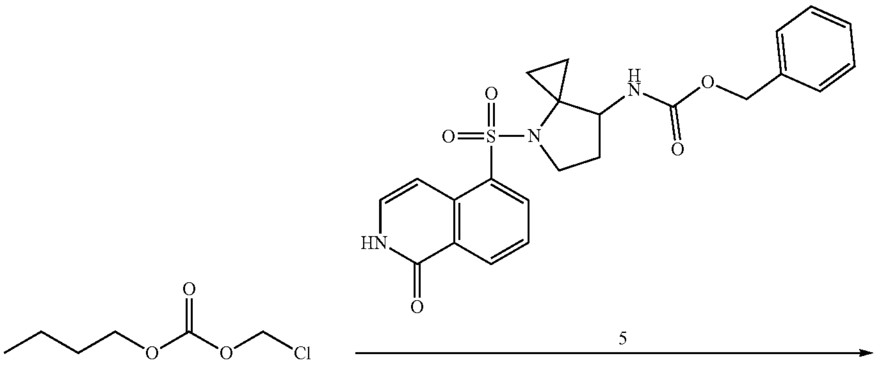

53b

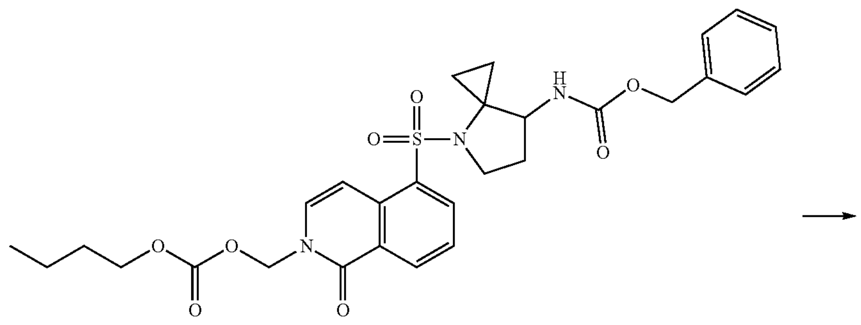

53c

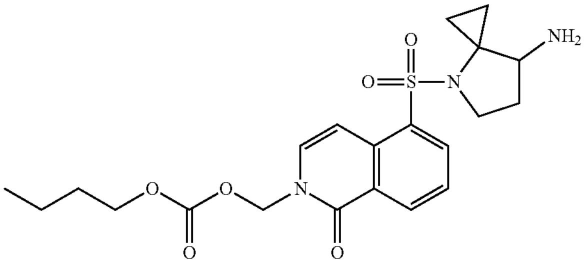

53

Step 1

Compound 53b was obtained referring to step 1 of Example 17.

Step 2

Compound 53c was obtained referring to step 2 of Example 1. MS-ESI calculated value $[M+Na]^+$ 606, actually measured value 606.

Step 3

A formate of compound 53 was obtained referring to step 2 of Example 25. $^1H$ NMR (400 MHz, $CD_3OD$) δ=8.66 (d, J=8.0 Hz, 1H), 8.48 (s, 1H), 8.42 (dd, J=1.1, 7.8 Hz, 1H), 7.75-7.62 (m, 2H), 7.17 (d, J=7.8 Hz, 1H), 6.04-5.91 (m, 2H), 4.17 (t, J=6.6 Hz, 2H), 4.05-4.07 (m, 1H), 3.65-3.53 (m, 1H), 3.41 (dd, J=3.2, 7.6 Hz, 1H), 2.51-2.53 (m, 1H), 2.13-1.99 (m, 1H), 1.69-1.56 (m, 2H), 1.35-1.40 (m, 2H), 1.25-1.08 (m, 2H), 0.92 (t, J=7.4 Hz, 3H), 0.85-0.75 (m, 2H). MS-ESI calculated value $[M+H]^+$ 450, actually measured value 450.

The formate of compound 53 can be adjusted the pH of the reaction solution to 8-9 by adding a saturated aqueous sodium carbonate solution to the system, and then, after the extraction with ethyl acetate, the reaction solution was concentrated to obtain compound 53.

Example 48: Compound 54

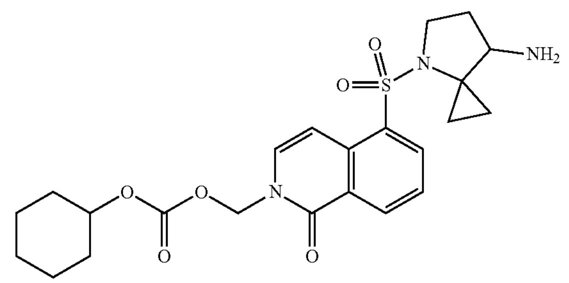 [SMILES: NC1CCN(S(=O)(=O)c2cccc3c(=O)n(COC(=O)OC4CCCCC4)ccc23)C12CC2]

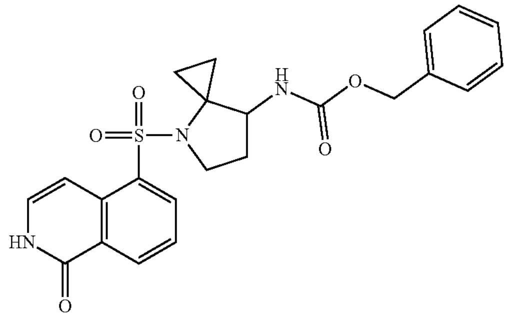

5

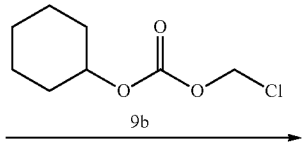

9b

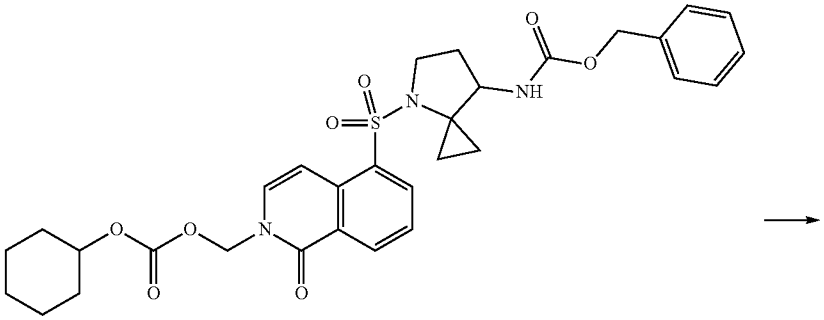

54a

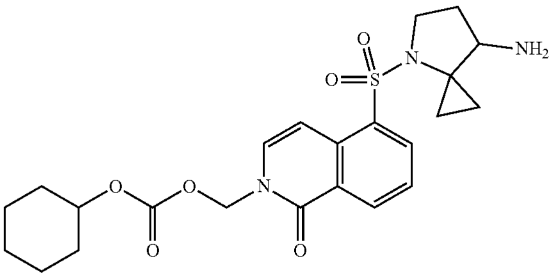

54

Step 1

Compound 54a was obtained referring to step 2 of Example 1. MS-ESI calculated value $[M+Na]^+$ 610, actually measured value 610.

Step 2

A formate of compound 54 was obtained referring to step 2 of Example 25. $^1H$ NMR (400 MHz, $CD_3OD$) δ=8.66-8.64 (d, J=7.8 Hz, 1H), 8.50 (s, 1H), 8.43-8.41 (d, J=7.8 Hz, 1H), 8.34 (m, 1H), 7.76-7.63 (m, 2H), 7.14 (d, J=7.8 Hz, 1H), 5.96-5.93 (m, 2H), 4.66-4.61 (m, 1H), 3.94-3.59 (m, J=6.4, 9.0, 11.8 Hz, 1H), 3.58-3.56 (m, J=4.8 Hz, 1H), 3.56-3.24 (m, J=4.8 Hz, 1H), 3.24-3.22 (m, J=4.8 Hz, 1H), 2.41-1.89 (dt, J=8.4, 14.0 Hz, 2H), 1.87-1.72 (m, 2H), 1.71-1.36 (m, 7H), 1.36-1.39 (m, 2H), 1.14-1.12 (m, J=6.8 Hz, 1H), 0.90-0.75 (m, 1H). MS-ESI calculated value $[M+H]^+$ 476, actually measured value 476.

The formate of compound 54 can be adjusted the pH of the reaction solution to 8-9 by adding a saturated aqueous sodium carbonate solution to the system, and then, after the extraction with ethyl acetate, the reaction solution was concentrated to obtain compound 54.

Example 49: Compound 55

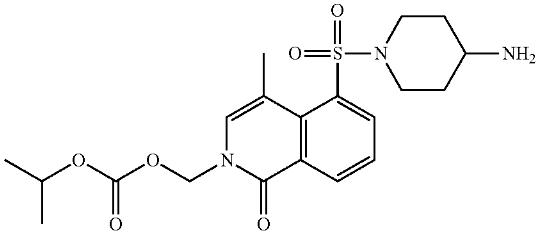

Synthesis Route:

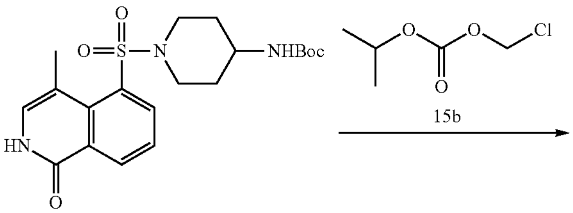

3

15b

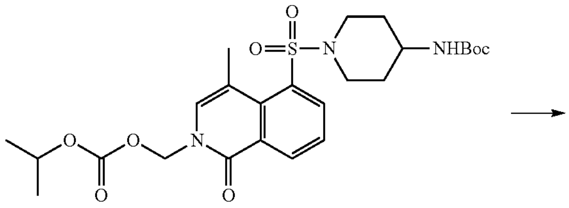

55a

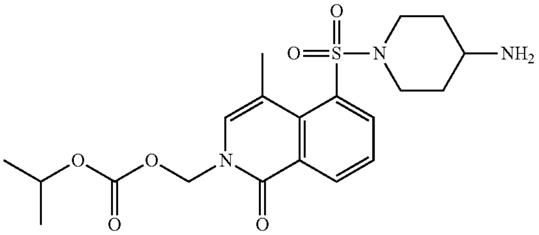 [SMILES: Cc1cn(COC(=O)OC(C)C)c(=O)c2cccc(S(=O)(=O)N3CCC(N)CC3)c12]

55

Step 1

Compound 3 (150 mg, 231 μmol) and potassium carbonate (63.8 mg, 462 μmol) were dissolved in anhydrous tetrahydrofuran (5 mL), stirred for 1 hour at 60° C. Then compound 15b (70.4 mg, 462 μmol) was added to the reaction system at 60° C., stirred for 12 hours at 60° C. The solvent was removed by concentration under reduced pressure, and the crude product was purified by silica gel plate chromatography (ethyl acetate:ethanol) and concentrated under reduced pressure to obtain compound 55a. MS-ESI calculated value $[M+H]^+$ 538, actually measured value 538.

Step 2

Compound 55 was obtained referring to step 3 of Example 1 (purified by neutral preparative high performance liquid chromatography). $^1H$ NMR (400 MHz, $CD_3OD$) δ=8.68 (dd, J=1.4, 8.1 Hz, 1H), 8.07 (dd, J=1.5, 7.8 Hz, 1H), 7.63 (t, J=7.9 Hz, 1H), 7.42 (d, J=0.9 Hz, 1H), 5.93 (s, 2H), 4.93-4.89 (m, 1H), 3.84 (d, J=12.9 Hz, 2H), 3.18-3.09 (m, 2H), 2.99-2.87 (m, 1H), 2.68 (d, J=0.8 Hz, 3H), 2.01-1.90 (m, 2H), 1.55-1.42 (m, 2H), 1.28 (d, J=6.3 Hz, 6H). MS-ESI calculated value $[M+H]^+$ 438, actually measured value 438.

Example 50: Compound 56

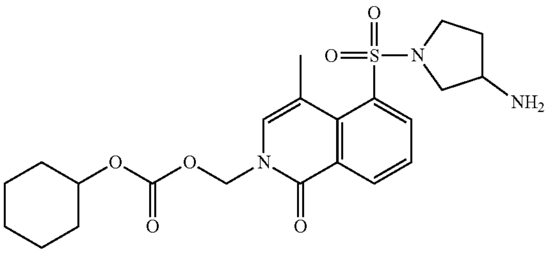 [SMILES: Cc1cn(COC(=O)OC2CCCCC2)c(=O)c2cccc(S(=O)(=O)N3CCC(N)C3)c12]

Synthesis Route:

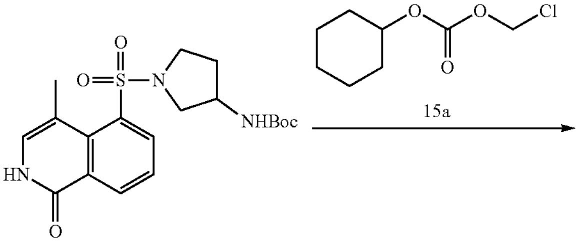

2

15a

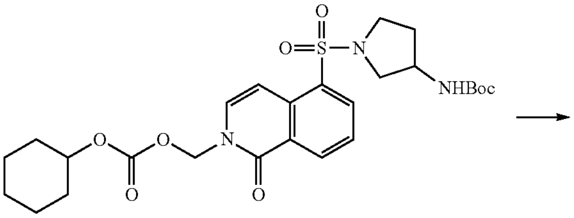

56a

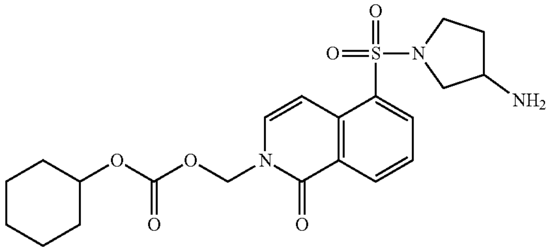

56

Step 1

To a solution of compound 2 (435 mg, 1.07 mmol) in N,N-dimethylformamide (10 mL) was added potassium tert-butoxide (359 mg, 3.20 mmol) at 0° C., stirred for 1 hour at 0° C. Compound 15a (226 mg, 1.17 mmol) was added to the reaction solution at 0° C., stirred for 13 hours at 25° C. Water (4 mL) was added to the reaction solution which was extracted with ethyl acetate (3 mL×3), the combined organic phase was washed with saturated brine (5 mL×3), dried with anhydrous sodium sulfate, filtered, concentrated under reduced pressure, and the crude product was separated and purified by silica gel column chromatography (petroleum ether/ethyl acetate) to obtain compound 56a.

Step 2

To a solution of compound 56a (150 mg, 0.266 mmol) in anhydrous ethyl acetate (2 mL) added ethyl acetate hydrochloride (4M, 16.0 mmol), stirred for 3 hours at 20° C. The solvent was removed by concentration under reduced pressure, and the crude product was prepared by high performance liquid chromatography (hydrochloride system) to obtain a hydrochloride of compound 56. $^1$H NMR (400 MHz, $CD_3OD$) δ8.68 (d, J=8.0 Hz, 1H), 8.46 (s, 1H), 8.39 (dd, J=7.8, 1.2 Hz, 1H), 7.73 (t, J=7.8 Hz, 1H), 7.67 (d, J=7.8 Hz, 1H), 7.51 (d, J=7.8 Hz, 1H), 6.00 (s, 2H), 4.62-4.71 (m, 1H), 3.77-3.87 (m, 1H), 3.50-3.64 (m, 2H), 3.34-3.40 (m, 2H), 2.24-2.36 (m, 1H), 1.86-2.03 (m, 3H), 1.75 (dt, J=6.4, 3.1 Hz, 2H), 1.24-1.61 (m, 6H). MS-ESI calculated value $[M+H]^+$ 450, actually measured value 450.

The hydrochloride of compound 56 can be adjusted the pH of the reaction solution to 8-9 by adding a saturated aqueous sodium carbonate solution to the system, and then, after the extraction with ethyl acetate, the reaction solution was concentrated to obtain compound 56.

Example 51: Compound 57

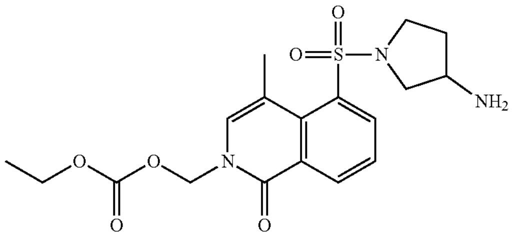

Synthesis Route:

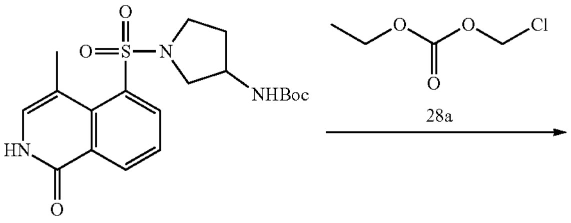

28a

2

-continued

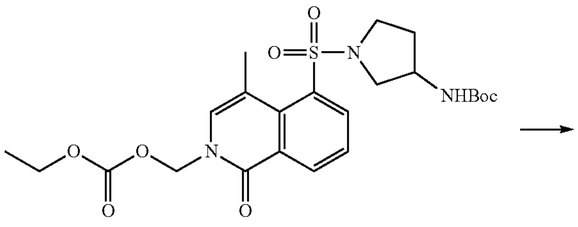

57a

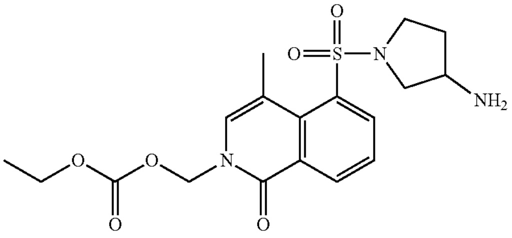 [SMILES: CCOC(=O)OCn1cc(C)c2c(S(=O)(=O)N3CCC(N)C3)cccc2c1=O]

57

Step 1

Compound 57a was obtained referring to step 1 of Example 50. MS-ESI calculated value $[M+H]^+$ 510, actually measured value 510.

Step 2

A formate of compound 57 was obtained from crude product by high performance liquid chromatography (formic acid system) referring to step 3 of Example 1. $^1$H NMR (400 MHz, $CDCl_3$) δ 8.69-8.63 (m, 1H), 8.25-8.20 (m, 1H), 7.64-7.61 (m, 1H), 7.59-7.40 (m, 1H), 5.96-5.74 (m, 2H), 4.24-4.20 (m, 2H), 3.70-3.66 (m, 3H), 3.54 (s, 1H), 3.20-3.18 (m, 1H), 2.68-2.66 (m, 3H), 2.28-2.27 (m, 1H), 1.92-1.91 (m, 1H), 1.31-1.26 (m, 3H). MS-ESI calculated value $[M+H]^+$ 410, actually measured value 410.

The formate of compound 57 can be adjusted the pH of the reaction solution to 8-9 by adding a saturated aqueous sodium carbonate solution to the system, and then, after the extraction with ethyl acetate, the reaction solution was concentrated to obtain compound 57.

Example 52: Compound 58

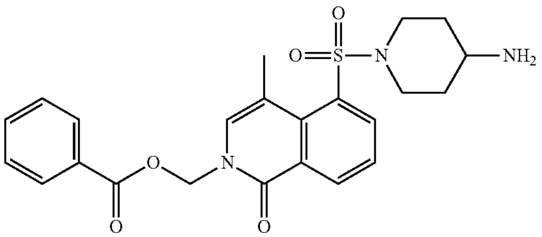 [SMILES: Cc1cn(COC(=O)c2ccccc2)c(=O)c2cccc(S(=O)(=O)N3CCC(N)CC3)c12]

Synthesis Route:

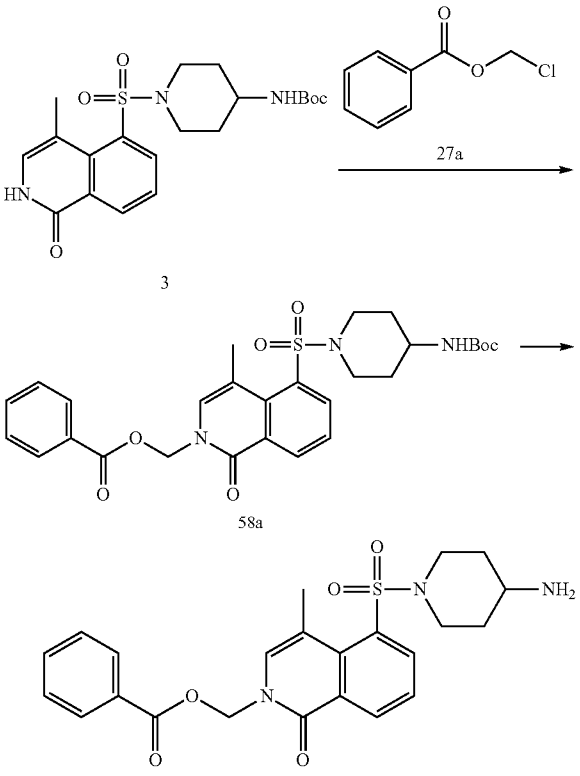

3

58a

58

Step 1

Compound 58a was obtained referring to step 2 of Example 1. MS-ESI calculated value $[M+H]^+$ 556, actually measured value 556.

Step 2

Compound 58 was obtained from crude product by high performance liquid chromatography (neutral system) referring to step 3 of Example 1. $^1H$ NMR (400 MHz, $CD_3OD$) δ=8.72 (d, J=8.1 Hz, 1H), 8.10 (d, J=7.7 Hz, 1H), 8.04 (d, J=8.1 Hz, 2H), 7.68-7.59 (m, 2H), 7.56 (s, 1H), 7.51-7.45 (m, 2H), 6.20 (s, 2H), 3.85 (d, J=13.0 Hz, 2H), 3.14 (t, J=11.2 Hz, 2H), 2.99-2.89 (m, 1H), 2.72 (s, 3H), 1.95 (d, J=10.9 Hz, 2H), 1.55-1.42 (m, 2H). MS-ESI calculated value $[M+H]^+$ 456, actually measured value 456.

Example 53: Compound 59

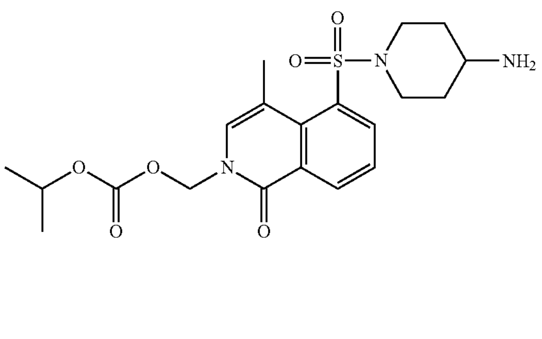 [SMILES: Cc1cn(COC(=O)OC(C)C)c(=O)c2cccc(S(=O)(=O)N3CCC(N)CC3)c12]

Synthesis Route:

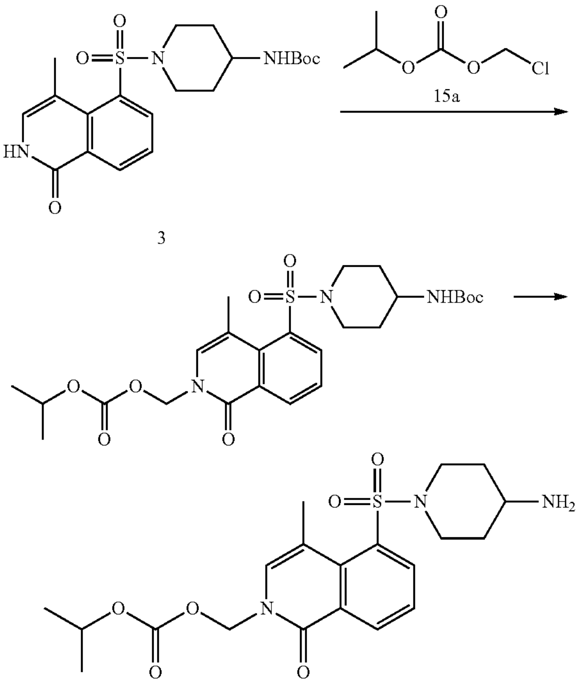

3

59

Step 1

Compound 59a was obtained referring to step 1 of Example 49. MS-ESI calculated value $[M+H]^+$ 538, actually measured value 538.

Step 2

A formate of compound 59 was obtained referring to step 3 of Example 1. $^1H$ NMR (400 MHz, $CD_3OD$) δ=8.73 (d, J=7.7 Hz, 1H), 8.55 (s, 1H), 8.10 (d, J=7.6 Hz, 1H), 7.66 (t, J=7.8 Hz, 1H), 7.47 (s, 1H), 5.96 (s, 2H), 4.59 (m, 1H), 3.99 (d, J=12.8 Hz, 2H), 3.46-3.37 (m, 1H), 3.23 (t, J=12.3 Hz, 2H), 2.70 (s, 3H), 2.14 (d, J=11.2 Hz, 2H), 1.85-1.61 (m, 2H), 1.30 (d, J=6.1 Hz, 6H). MS-ESI calculated value $[M+H]^+$ 438, actually measured value 438.

The formate of compound 59 can be adjusted the pH of the reaction solution to 8-9 by adding a saturated aqueous sodium carbonate solution to the system, and then, after the extraction with ethyl acetate, the reaction solution was concentrated to obtain compound 59.

Example 54: Compound 60

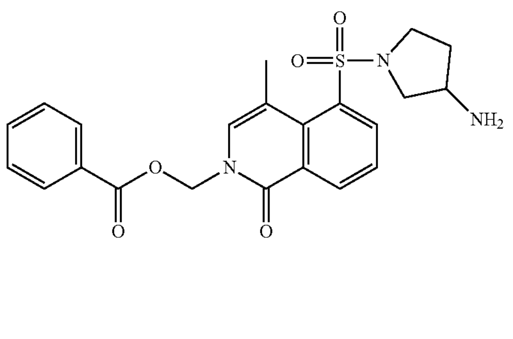 [SMILES: Cc1cn(COC(=O)c2ccccc2)c(=O)c2cccc(S(=O)(=O)N3CCC(N)C3)c12]

Synthesis Route:

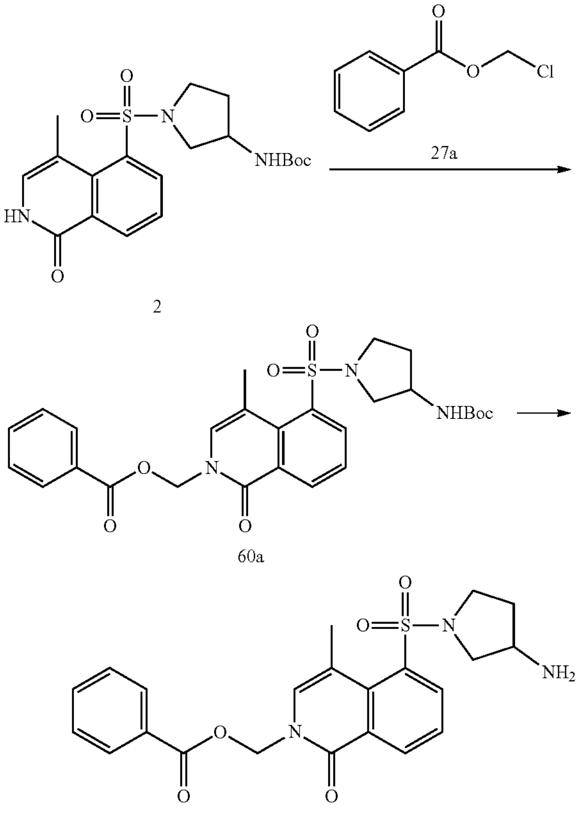

Step 1

Compound 60a was obtained referring to step 1 of Example 49. MS-ESI calculated value $[M+H]^+$ 542, actually measured value 542.

Step 2

Compound 60 was obtained from crude product by high performance liquid chromatography (neutral system) referring to step 3 of Example 1. MS-ESI calculated value $[M+H]^+$ 442, actually measured value 442. $^1H$ NMR (400 MHz, $CD_3OD$) δ=8.72 (dd, J=1.41, 8.01 Hz, 1H), 8.25 (dd, J=1.47, 7.70 Hz, 1H), 7.98-8.11 (m, 2H), 7.58-7.71 (m, 2H), 7.56 (d, J=0.86 Hz, 1H), 7.43-7.52 (m, 2H), 6.21 (s, 2H), 3.63-3.76 (m, 3H), 3.51-3.60 (m, 1H), 3.21 (dd, J=4.65, 9.17 Hz, 1H), 2.72 (d, J=0.86 Hz, 3H), 2.24-2.35 (m, 1H), 1.92 (dd, J=6.97, 13.33 Hz, 1H).

Example 55: Compound 61

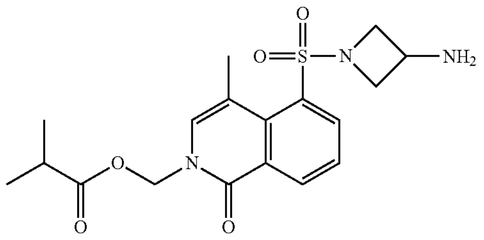 [SMILES: Cc1cn(COC(=O)C(C)C)c(=O)c2cccc(S(=O)(=O)N3CC(N)C3)c12]

Synthesis Route:

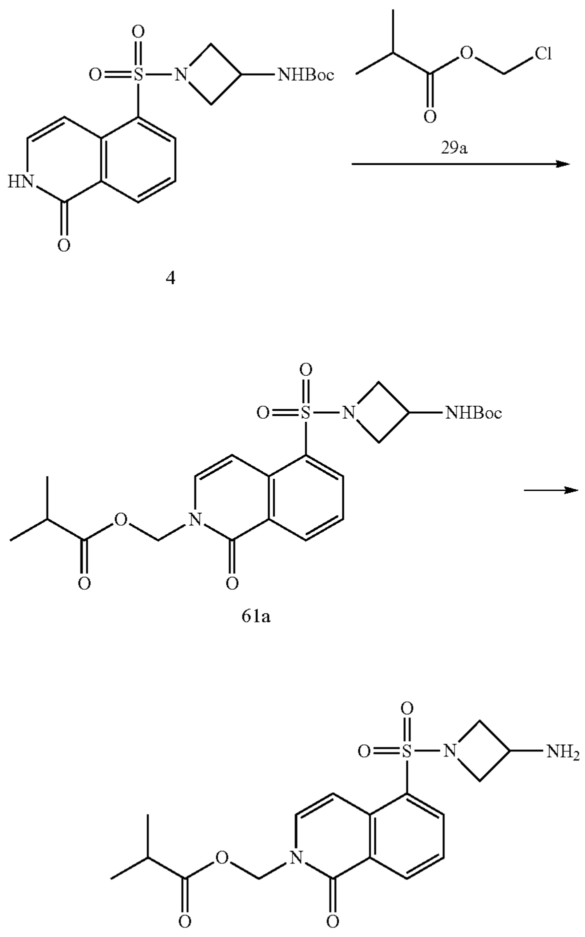

61

Step 1

Compound 61a was obtained referring to step 1 of Example 49. MS-ESI calculated value $[M+Na]^+$ 502, actually measured value 502.

Step 2

A formate of compound 61 was obtained referring to step 3 of Example 1. MS-ESI calculated value $[M+Na]^+$ 402, actually measured value 402. $^1H$ NMR (400 MHz, $CDCl_3$) δ=8.84-8.56 (m, 1H), 8.30 (d, J=6.5 Hz, 1H), 8.13 (s, 1H), 7.56 (s, 1H), 7.45 (d, J=7.5 Hz, 1H), 7.28-7.23 (m, 1H), 5.94 (s, 2H), 4.10-3.96 (m, 2H), 3.85 (s, 2H), 3.79 (s, 2H), 3.72-3.37 (m, 1H), 2.74-2.46 (m, 1H), 1.25-1.04 (m, 6H).

The formate of compound 61 can be adjusted the pH of the reaction solution to 8-9 by adding a saturated aqueous sodium carbonate solution to the system, and then, after the extraction with ethyl acetate, the reaction solution was concentrated to obtain compound 61.

Example 56: Compound 62

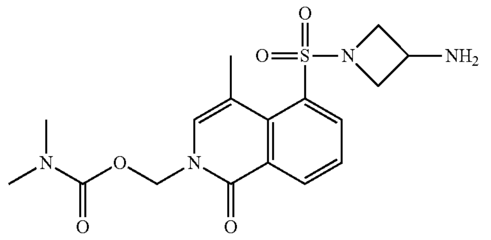 [SMILES: Cc1cn(COC(=O)N(C)C)c(=O)c2cccc(S(=O)(=O)N3CC(N)C3)c12]

Synthesis Route:

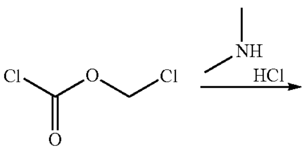

23b

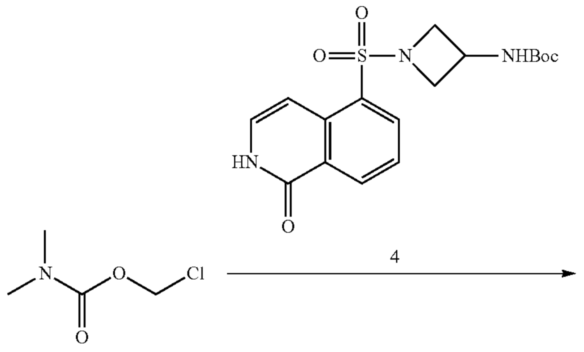

62a

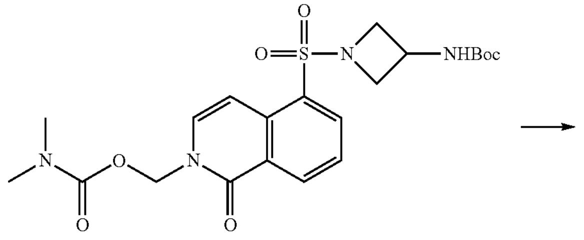

62b

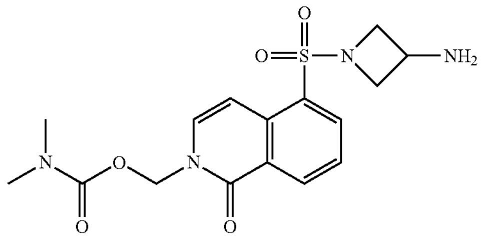

62

Step 1

To a solution of dimethylamine hydrochloride (332 mg, 4.07 mmol) and potassium carbonate (1.23 g, 8.92 mmol) in anhydrous dichloromethane (5 mL) was added dropwise chloromethylchloroformate 23b (500 mg, 3.88 mmol) at −78° C., stirred for 3 hours at −78° C. The reaction solution was filtered when being cold, and concentrated to obtain the crude product compound 62a which was directly used for the next step of the reaction without purification. $^1$H NMR (400 MHz, $CDCl_3$) δ=5.71 (s, 2H), 2.89 (d, J=8.8 Hz, 6H).

Step 2

Compound 62b was obtained referring to step 1 of Example 49. MS-ESI calculated value $[M+H]^+$ 481, actually measured value 481.

Step 3

A formate of compound 62 was obtained referring to step 3 of Example 1. MS-ESI calculated value $[M+H]^+$ 381, actually measured value 381. $^1$H NMR (400 MHz, $CD_3OD$) δ=8.66 (d, J=7.6 Hz, 1H), 8.37 (s, 1H), 8.36 (dd, J=1.3, 7.7 Hz, 1H), 7.74-7.61 (m, 2H), 7.32 (d, J=7.9 Hz, 1H), 5.96 (s, 2H), 4.13-4.06 (m, 2H), 3.99-3.87 (m, 1H), 3.87-3.77 (m, 2H), 2.91 (d, J=2.7 Hz, 6H).

The formate of compound 62 can be adjusted the pH of the reaction solution to 8-9 by adding a saturated aqueous sodium carbonate solution to the system, and then, after the extraction with ethyl acetate, the reaction solution was concentrated to obtain compound 62.

Example 57: Compound 63

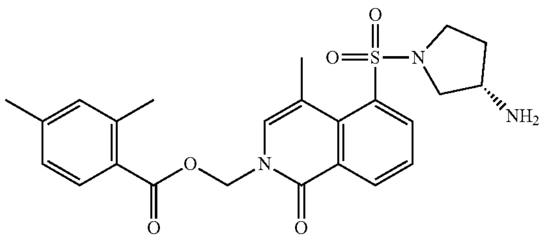 [SMILES: Cc1ccc(C(=O)OCn2cc(C)c3c(S(=O)(=O)N4CC[C@H](N)C4)cccc3c2=O)c(C)c1]

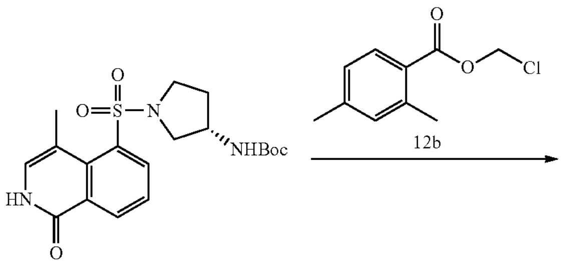

6

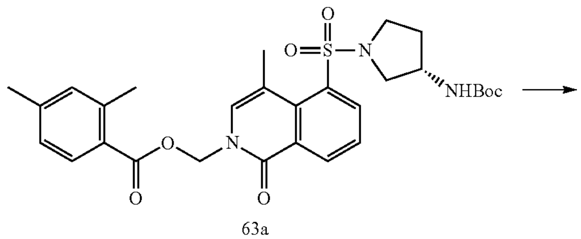

63a

-continued

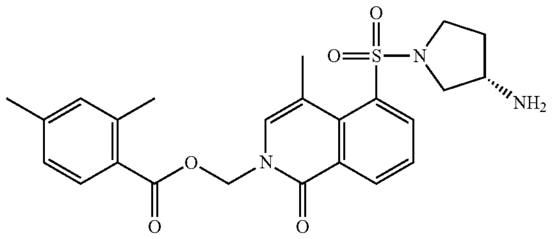

63

Step 1

Compound 63a was obtained referring to step 1 of Example 49. MS-ESI calculated value $[M+H]^+$ 570, actually measured value 570.

Step 2

Compound 63 was obtained from crude product by high performance liquid chromatography (neutral system) referring to step 3 of Example 50. MS-ESI calculated value $[M+H]^+$ 470, actually measured value 470. $^1H$ NMR (400 MHz, $CD_3OD$) δ=8.71 (dd, J=1.4, 8.0 Hz, 1H), 8.24 (dd, J=1.5, 7.8 Hz, 1H), 7.81 (d, J=7.9 Hz, 1H), 7.64 (t, J=7.9 Hz, 1H), 7.54 (d, J=0.9 Hz, 1H), 7.09 (s, 1H), 7.05 (d, J=7.9 Hz, 1H), 6.14 (s, 2H), 3.77-3.62 (m, 3H), 3.59-3.50 (m, 1H), 3.20 (dd, J=4.9, 9.5 Hz, 1H), 2.70 (d, J=0.9 Hz, 3H), 2.53 (s, 3H), 2.32 (s, 3H), 2.30-2.23 (m, 1H), 1.96-1.86 (m, 1H).

Example 58: Compound 64

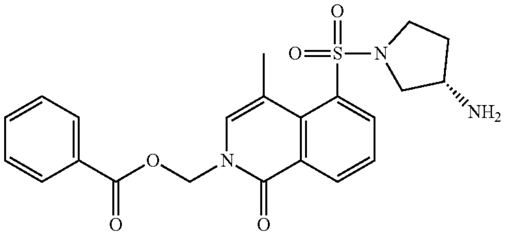 [SMILES: Cc1cn(COC(=O)c2ccccc2)c(=O)c2cccc(S(=O)(=O)N3CC[C@H](N)C3)c12]

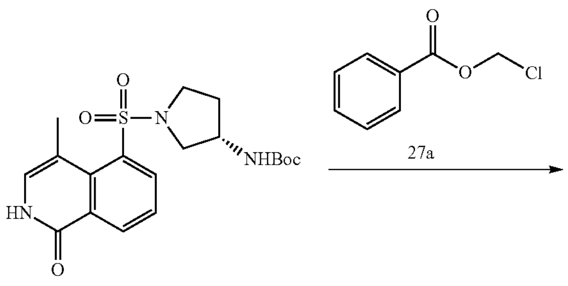

6

27a

-continued

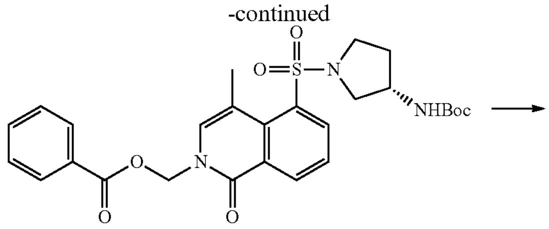

64a

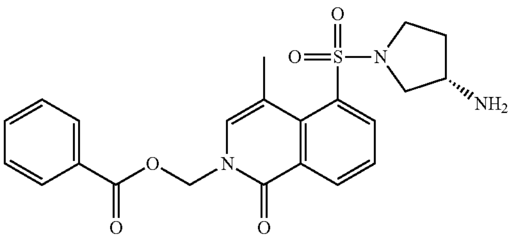

64

Step 1

Compound 64a was obtained referring to step 1 of Example 49. MS-ESI calculated value $[M+H]^+$ 542, actually measured value 542.

Step 2

Compound 64 was obtained from crude product by high performance liquid chromatography (neutral system) referring to step 3 of Example 1. MS-ESI calculated value $[M+H]^+$ 442, actually measured value 442. $^1H$ NMR (400 MHz, $CD_3OD$) δ=8.69-8.63 (m, 1H), 8.23-8.16 (m, 1H), 8.04-7.96 (m, 2H), 7.64-7.54 (m, 2H), 7.51 (s, 1H), 7.46-7.39 (m, 2H), 6.17 (s, 2H), 3.75-3.59 (m, 3H), 3.57-3.48 (m, 1H), 3.23-3.13 (m, 1H), 2.67 (s, 3H), 2.33-2.20 (m, 1H), 1.96-1.81 (m, 1H).

Example 59: Control Compound 1

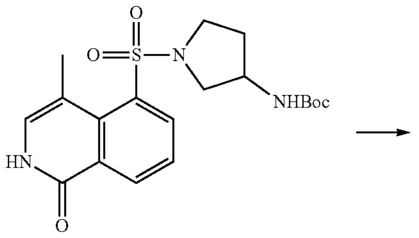

2

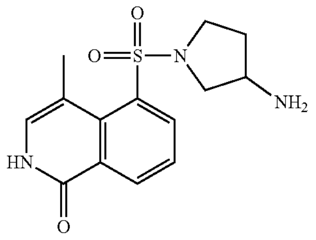

Control compound 1

Step 1

To a solution of intermediate 2 (360 mg, 0.82 mmol) in ethyl acetate (5 mL) was added dropwise an ethyl acetate hydrochloride solution (1.86 mL, 4M). After the reaction was completed, the precipitated solid was filtered, then washed with ethyl acetate (5 mL×3), and dried to obtain a hydrochloride of control compound 1. MS-ESI calculated value $[M+H]^+$ 308, actually measured value 308.

The hydrochloride of control compound 1 can be adjusted the pH of the reaction solution to 8-9 by adding a saturated aqueous sodium carbonate solution to the system, and then, after the extraction with ethyl acetate, the reaction solution was concentrated to obtain control compound 1.

Example 60: Control Compound 2

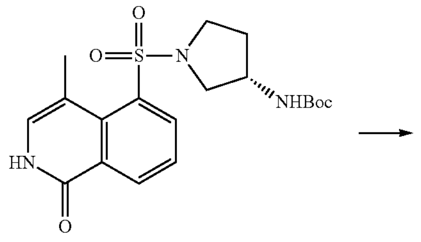

6

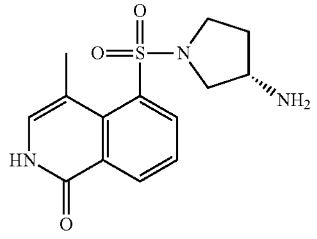

Control compound 2

Step 1

To a solution of intermediate 6 (4 g, 9.57 mmol) in tetrahydrofuran (40 mL) was added concentrated sulfuric acid (1.88 g, 19.15 mmol) dropwise at 0° C. After the reaction was completed, the precipitated solid was filtered, and then control compound 2 was prepared by high performance liquid chromatography (neutral system). MS-ESI calculated value $[M+H]^+$ 308, actually measured value 308. $^1H$ NMR (400 MHz, $CD_3OD$) δ 8.68 (d, 1H), 8.24-8.26 (m, 1H), 7.61-7.65 (m, 1H), 7.13 (s, 1H), 3.67-3.73 (m, 3H), 3.57-3.66 (m, 1H), 3.19-3.22 (m, 1H), 2.69 (s, 3H), 2.27-2.30 (m, 1H), 1.91-1.95 (m, 1H).

BIOASSAY EXPERIMENTS

Experimental Example 1. Pharmacokinetic Test in Aqueous Humor

Experiment Objective:

The compounds are prodrug molecules containing ester functional groups, which can be hydrolyzed into active drug molecules (technical concentrate) by the action of abundant ester hydrolases in the ocular tissue during eye-drop administration. In this experiment, the production rate of the active drug ingredients and the exposure amount of the active drug ingredients were detected.

Experiment Materials:

Male New Zealand rabbits, aged 3-6 months, weighted 2.0-5.0 kg, purchased from PizhouDongfang Breeding Co. Ltd.

Preparation of Eye-Drop Sample:

Solvents used were 1.2% hydroxypropyl methyl cellulose E5/20.5% Poloxamer P407/1.6% Poloxamer P188.

Experiment Operations:

The dose of eye-drop administration was 0.5 mg/eye and eye-drop administration was performed on both eyes. Aqueous humor was collected 0.25 h. 0.5 h, 2 h, 4 h, 8 h, and 24 h after administration to prepare the aqueous humor sample. All samples were quantitatively detected for the content of the administered compound in aqueous humor of the experiment animals by liquid chromatography-coupled mass spectrometry (LC-MS) and mass spectrometry (MS) technology. The detected concentration values were subject to WinNonlin non-compartment model. According to the aqueous humor concentration-time data, parameters of the half-life period, peak concentration of the drug in the aqueous humor, peak time of the drug in the aqueous humor, unit exposure and the like were calculated.

TABLE 1

Pharmacokinetic test results in aqueous humor of New Zealand rabbits

| Test sample (compounds obtained in various examples) | Peak concentration of drug in aqueous humor (nM) | Half-life period (h) | Peak time of drug in aqueous humor (h) | Unit exposure (nM · h) |
|---|---|---|---|---|
| Formate of compound 30 | 1222 | 3.39 | 2.00 | 8322 |
| Formate of compound 31 | 3505 | 2.39 | 0.5 | 15911 |
| Formate of compound 42 | 3810 | 1.91 | 2.0 | 14826 |
| Hydrochloride of compound 56 | 3345 | 2.47 | 2.00 | 14124 |
| Compound 60 | 2600 | 2.83 | 0.5 | 14332 |
| Compound 63 | 7470 | 2.72 | 2.0 | 36581 |
| Hydrochloride of control compound 1 | 425 | 3.9 | 0.5 | 2508 |
| Control compound 2 | 868 | — | 2.0 | 3555 |

"—": not detected.

Conclusion: Experiment results showed that the test sample compounds (prodrug molecules) were not detected in the aqueous humor, and what were mainly detected were their active metabolites (technical concentrate molecules) after the ester hydrolysis. Compared with control compound 1 and control compound 2, the compounds of the present disclosure significantly increase the exposure amount of the active drugs and meanwhile significantly increase the peak blood concentration and the action duration.

Experimental Example 2. Intraocular Pressure Reduction Experiment in New Zealand Rabbits with Normal Intraocular Pressure Experiment Objective:

Rabbits with normal intraocular pressure were adopted to screen intraocular pressure reduction actions of the potential compounds by eye-drop administration.

Experiment Materials:

Male New Zealand rabbits, aged 97-127 days, weighted 2.65-3.5 kg, purchased from PizhouDongfang Breeding Co. Ltd.

Experiment Operations:

The male New Zealand rabbits were randomly divided into 8 rabbits/per group using a computer-generated randomization method Animals in each group were eye-dropped with different test samples in the right eye, and normal saline or solvent in the left eye, and the volume of the administration was both 50 μL/eye. The intraocular pressure of the animals was measured before administration and in 1, 2, 4, 6, 8 and 10 hours after the administration, respectively. Experimental results are shown in Table 2:

TABLE 2

Change results of the intraocular pressure of both eyes (Mean +/− SEM) of the New Zealand rabbits before and after administration of different test samples

| Measured intraocular pressure | | Time point of measurement: Before administration | 1 hour after administration | 2 hours after administration | 4 hours after administration | 6 hours after administration | 8 hours after administration | 10 hours after administration |
|---|---|---|---|---|---|---|---|---|
| K-115 20 mg/mL | Intraocular pressure in the left eye (mmHg) | 12.29 | 11.42 | 11.67 | 12.08 | 12.38 | 12.83 | 15.25 |
| | Intraocular pressure in the right eye (mmHg) | 12.92 | 7.54 | 8.63 | 10.83 | 11.83 | 12.63 | 14.92 |
| | Reduction magnitude of intraocular pressure (mmHg) | −0.63 | 3.88 | 3.04 | 1.25 | 0.55 | 0.2 | 0.33 |
| Compound 60 20 mg/mL | Intraocular pressure in the left eye (mmHg) | 12.63 | 12.42 | 12.96 | 13.17 | 12.54 | 13.17 | 13.71 |
| | Intraocular pressure in the right eye (mmHg) | 12.42 | 10.21 | 7.17 | 7.92 | 7.63 | 8.83 | 10.83 |
| | Reduction magnitude of intraocular pressure (mmHg) | 0.21 | 2.21 | 5.79 | 5.25 | 4.91 | 4.34 | 2.88 |
| Compound 64 20 mg/mL | Intraocular pressure in the left eye (mmHg) | 11.29 | 11.96 | 9.79 | 11.50 | 11.54 | 11.75 | 11.88 |
| | Intraocular pressure in the right eye (mmHg) | 12.04 | 11.54 | 7.42 | 7.13 | 7.38 | 7.63 | 9.71 |
| | Reduction magnitude of intraocular pressure (mmHg) | −0.75 | 0.42 | 2.37 | 4.37 | 4.16 | 4.12 | 2.17 |
| Compound 60 2.5 mg/mL | Intraocular pressure in the left eye (mmHg) | 12.13 | 11.63 | 11.58 | 12.83 | 12.38 | 12.29 | 14.33 |
| | Intraocular pressure in the right eye (mmHg) | 12.38 | 8.38 | 7.58 | 9.04 | 9.88 | 11.33 | 13.71 |
| | Reduction magnitude of intraocular pressure (mmHg) | −0.25 | 3.25 | 4 | 3.79 | 2.5 | 0.96 | 0.62 |

TABLE 2-continued

Change results of the intraocular pressure of both eyes (Mean +/− SEM) of the New Zealand rabbits before and after administration of different test samples

| Measured intraocular pressure | | Time point of measurement: Before administration | 1 hour after administration | 2 hours after administration | 4 hours after administration | 6 hours after administration | 8 hours after administration | 10 hours after administration |
|---|---|---|---|---|---|---|---|---|
| Compound 60 5.0 mg/mL | Intraocular pressure in the left eye (mmHg) | 11.79 | 11.33 | 11.42 | 12.63 | 12.75 | 13.29 | 14.08 |
| | Intraocular pressure in the right eye (mmHg) | 11.75 | 7.83 | 7.00 | 7.79 | 8.54 | 10.13 | 12.54 |
| | Reduction magnitude of intraocular pressure (mmHg) | 0.04 | 3.5 | 4.42 | 4.84 | 4.21 | 3.16 | 1.54 |
| Compound 60 10.0 mg/mL | Intraocular pressure in the left eye (mmHg) | 11.96 | 12.08 | 12.08 | 12.96 | 12.38 | 13.04 | 13.38 |
| | Intraocular pressure in the right eye (mmHg) | 11.33 | 7.96 | 6.42 | 7.13 | 8.00 | 9.42 | 10.96 |
| | Reduction magnitude of intraocular pressure (mmHg) | 0.63 | 4.12 | 5.66 | 5.83 | 4.38 | 3.62 | 2.42 |

Conclusion: Compared with K-115, the compound of the present disclosure exhibited a larger reduction magnitude of intraocular pressure and a longer intraocular pressure reduction action duration. Moreover, compound 60 witnessed a remarkably significant reduction of intraocular pressure at the concentrations of 2.5, 5 and 10 mg/mL.

Experimental Example 3. Intraocular Pressure Reduction Experiment in New Zealand Rabbits with Acute Ocular Hypertension Experiment Objective:

Acute ocular hypertension of rabbits were induced by anterior chamber injection of a viscoelastic agent and the intraocular pressure reduction action of compound 60 and compound 63 at different concentrations were explored by eye-drop administration.

Experiment Materials:

Male New Zealand rabbits, aged 97-127 days, weighted 2.5-3.4 kg, purchased from PizhouDongfang Breeding Co. Ltd.

Experiment Operation 1

Male New Zealand rabbits were randomly divided into 8 rabbits/per group according to body weight using a computer-generated randomization method. The animals in each group were injected with medical sodium hyaluronate gel in the anterior chamber of right eye in a single dose, 100 μL/eye, to induce ocular hypertension. In 5-15 minutes, 3 hours and 6 hours after right eye modeling, both eyes were dropped with a solvent, K-115 or test samples (compound 60 at different concentrations) at a volume of 50 μL/eye and intraocular pressure of the animals was measured before administration and in 1, 2, 4, 6, 8 and 10 hours after administration, respectively. Experimental results are shown in Table 3:

TABLE 3

Change results of the intraocular pressure of both eyes (Mean +/− SEM) of animals in each group before and after modeling and administration

| Measured Intraocular pressure | | Time point of measurement: Before administration | 1 hour after administration | 2 hours after administration | 4 hours after administration | 6 hours after administration | 8 hours after administration | 10 hours after administration |
|---|---|---|---|---|---|---|---|---|
| Negative control | Intraocular pressure | 12.46 | 5.21 | 6.25 | 9.04 | 11.63 | 12.63 | 12.46 |

TABLE 3-continued

Change results of the intraocular pressure of both eyes (Mean +/− SEM) of animals in each group before and after modeling and administration

| Measured Intraocular pressure | | Time point of measurement Before administration | 1 hour after administration | 2 hours after administration | 4 hours after administration | 6 hours after administration | 8 hours after administration | 10 hours after administration |
|---|---|---|---|---|---|---|---|---|
| | in the left eye (mmHg) | | | | | | | |
| | Intraocular pressure in the right eye (mmHg) | 12.00 | 31.14 | 25.05 | 26.33 | 24.38 | 23.14 | 12.00 |
| K-115 10 mg/mL | Intraocular pressure in the left eye (mmHg) | 11.79 | 5.88 | 5.96 | 8.29 | 10.54 | 11.88 | 11.79 |
| | Intraocular pressure in the right eye (mmHg) | 11.92 | 28.79 | 22.67 | 26.08 | 23.25 | 23.25 | 11.92 |
| Compound 60 2.5 mg/mL | Intraocular pressure in the left eye (mmHg) | 12.00 | 5.00 | 6.63 | 8.29 | 10.71 | 12.17 | 12.00 |
| | Intraocular pressure in the right eye (mmHg) | 12.54 | 22.33 | 19.75 | 20.29 | 17.00 | 14.54 | 12.54 |
| Compound 60 5.0 mg/mL | Intraocular pressure in the left eye (mmHg) | 11.75 | 4.96 | 5.96 | 8.29 | 11.21 | 11.46 | 11.75 |
| | Intraocular pressure in the right eye (mmHg) | 11.25 | 21.00 | 16.29 | 16.75 | 14.88 | 13.08 | 11.25 |
| Compound 60 10.0 mg/mL | Intraocular pressure in the left eye (mmHg) | 12.13 | 4.63 | 5.50 | 9.25 | 10.79 | 11.75 | 12.13 |
| | Intraocular pressure in the right eye (mmHg) | 12.08 | 19.83 | 17.46 | 15.00 | 12.33 | 11.25 | 12.08 |

Experiment Operation 2

50 male New Zealand rabbits were randomly divided into 5 groups according to body weight, with 10 rabbits/per group Animals in 1-5 groups were injected with medical sodium hyaluronate gel in the anterior chamber of right eye in a single dose, 100 μL/eye, to induce ocular hypertension. In 5-15 minutes after modeling, the right eye was respectively dropped with a solvent, K-115 and test samples (compound 63 at different concentrations), the left eye was dropped with a solvent, the volume of the administration was all 50 μL/eye, and intraocular pressure in both eyes of the animals was measured before administration and in 2, 4, 6, 8 and 10 hours after administration, respectively. Experimental results are shown in Table 4:

TABLE 4

Change results of the intraocular pressure of both eyes (Mean +/− SEM) of animals in each group before and after modeling and administration

| Measured Intraocular pressure | | Time point of measurement: Before administration | 2 hours after administration | 4 hours after administration | 6 hours after administration | 8 hours after administration | 10 hours after administration |
|---|---|---|---|---|---|---|---|
| Negative control | Intraocular pressure in the left eye (mmHg) | 9.93 | 6.40 | 6.97 | 9.83 | 12.03 | 13.63 |
| | Intraocular pressure in the right eye (mmHg) | 10.57 | 8.57 | 14.00 | 17.67 | 16.30 | 15.87 |
| K-115 4 mg/mL | Intraocular pressure in the left eye (mmHg) | 11.80 | 6.50 | 8.54 | 11.40 | 13.20 | 13.37 |
| | Intraocular pressure in the right eye (mmHg) | 11.77 | 8.20 | 11.27 | 15.07 | 15.57 | 16.47 |
| Compound 63 0.25 mg/mL | Intraocular pressure in the left eye (mmHg) | 10.53 | 6.07 | 6.60 | 9.10 | 11.50 | 12.43 |
| | Intraocular pressure in the right eye (mmHg) | 11.43 | 8.47 | 8.60 | 11.20 | 13.37 | 13.10 |
| Compound 63 2.0 mg/mL | Intraocular pressure in the left eye (mmHg) | 11.27 | 6.60 | 7.04 | 11.23 | 12.84 | 13.10 |
| | Intraocular pressure in the right eye (mmHg) | 11.23 | 8.52 | 11.56 | 13.81 | 12.96 | 11.96 |
| Compound 63 8.0 mg/mL | Intraocular pressure in the left eye (mmHg) | 11.20 | 5.93 | 6.43 | 10.10 | 11.87 | 13.19 |
| | Intraocular pressure in the | 11.53 | 7.40 | 7.97 | 8.84 | 8.60 | 8.78 |

TABLE 4-continued

Change results of the intraocular pressure of both eyes (Mean +/− SEM) of animals in each group before and after modeling and administration

| Measured Intraocular pressure | Time point of measurement: Before administration | 2 hours after administration | 4 hours after administration | 6 hours after administration | 8 hours after administration | 10 hours after administration |
|---|---|---|---|---|---|---|
| right eye (mmHg) | | | | | | |

Conclusion: In the model of acute ocular hypertension, the compounds of the present disclosure all exhibited good hypotensive effects at different test doses, showed certain dose correlation, and the hypotensive amplitude and the action duration were both superior to K-115.

Experimental example 4. Experiment on reduction of intraocular pressure and ocular toxicity of New Zealand rabbits with normal intraocular pressure by repeated eye-drop administration for 14 days Experiment Objective:

The intraocular pressure reduction action and the potential ocular toxicity of compound 63 were explored by 14 days of repeated eye-drop administration in rabbits with normal intraocular pressure.

Experiment Materials:

Male New Zealand rabbits, aged 97-127 days, weighted 2.6-3.5 kg, purchased from PizhouDongfang Breeding Co. Ltd.

Experiment Operation 1

The male New Zealand rabbits were randomly divided into 7 groups, with 6 rabbits per group. Animals were randomly divided according to body weight Animals in 1-7 groups were eye-dropped with solvent/control sample/test sample in both eyes, the volume of the administration was all 50 μL/eye, once per day for 14 consecutive days, and the day of the administration was recorded as Day 1. On Day 1, intraocular pressure of the animals was measured before the administration and in 1, 2, 4, 6, 8 and 10 hours after the administration, respectively; on Days 2-14, intraocular pressure of the animals was measured in 1 hour after daily administration for the group administered with K-115, and intraocular pressure of the animal was measured in 4 hours after daily administration for the other groups. Experiment results are shown in Tables 5, 6 and 7:

TABLE 5

Changes of the intraocular pressure of both eyes (Mean +/− +/− SEM) of animals in each group before and after Day 1 administration

| Measured intraocular pressure | | Time point of measurement: Before administration | 1 hour after administration | 2 hours after administration | 4 hours after administration | 6 hours after administration | 8 hours after administration | 10 hours after administration |
|---|---|---|---|---|---|---|---|---|
| Negative control | Mean intraocular pressure of both eyes (mmHg) | 9.89 | 10.31 | 10.97 | 11.31 | 11.94 | 12.97 | 14.42 |
| K-115 4 mg/mL | Mean intraocular pressure of both eyes (mmHg) | 10.83 | 7.72 | 9.00 | 9.67 | 10.56 | 10.28 | 12.81 |
| | Change of intraocular pressure (mmHg) | −0.94 | 2.59 | 1.97 | 1.64 | 1.38 | 2.69 | 1.61 |
| Compound 63 0.5 mg/mL | Mean intraocular pressure of both eyes (mmHg) | 10.11 | 8.83 | 7.56 | 7.11 | 9.61 | 9.06 | 9.97 |
| | Change of intraocular pressure (mmHg) | −0.22 | 1.48 | 3.41 | 4.2 | 2.33 | 3.91 | 4.45 |
| Compound 63 1.0 mg/mL | Mean intraocular pressure of both eyes (mmHg) | 9.94 | 7.08 | 6.67 | 6.44 | 8.00 | 9.22 | 10.56 |

TABLE 5-continued

Changes of the intraocular pressure of both eyes (Mean +/− +/− SEM) of animals in each group before and after Day 1 administration

| Measured intraocular pressure | | Time point of measurement: Before administration | 1 hour after administration | 2 hours after administration | 4 hours after administration | 6 hours after administration | 8 hours after administration | 10 hours after administration |
|---|---|---|---|---|---|---|---|---|
| | Change of intraocular pressure (mmHg) | −0.05 | 3.23 | 4.3 | 4.87 | 3.94 | 3.75 | 3.86 |
| Compound 63 2.0 mg/mL | Mean intraocular pressure of both eyes (mmHg) | 9.67 | 8.56 | 7.47 | 7.47 | 7.25 | 8.44 | 9.67 |
| | Change of intraocular pressure (mmHg) | 0.22 | 1.75 | 3.5 | 3.84 | 4.69 | 4.53 | 4.75 |
| Compound 63 4.0 mg/mL | Mean intraocular pressure of both eyes (mmHg) | 9.67 | 10.44 | 7.81 | 6.47 | 6.22 | 7.33 | 8.64 |
| | Change of intraocular pressure (mmHg) | 0.22 | −0.13 | 3.16 | 4.84 | 5.72 | 5.64 | 5.78 |
| Compound 63 8.0 mg/mL | Mean intraocular pressure of both eyes (mmHg) | 10.17 | 7.69 | 6.39 | 7.06 | 7.11 | 7.22 | 7.97 |
| | Change of intraocular pressure (mmHg) | −0.28 | 2.62 | 4.58 | 4.25 | 4.83 | 5.75 | 6.45 |

TABLE 6

Changes of the intraocular pressure of both eyes (Mean +/− SEM) of animals in each group before and after Days 2-7 repeated administration

| Measured intraocular pressure | | Time point of measurement: Day 2 | Day 3 | Day 4 | Day 5 | Day 6 | Day 7 |
|---|---|---|---|---|---|---|---|
| Negative control | Mean intraocular pressure of both eyes (mmHg) | 11.08 | 10.39 | 10.61 | 10.97 | 9.31 | 10.06 |
| K-115 4 mg/mL | Mean intraocular pressure of both eyes (mmHg) | 6.83 | 6.81 | 6.92 | 6.67 | 6.75 | 7.39 |
| | Change of intraocular pressure (mmHg) | 4.25 | 3.58 | 3.69 | 4.3 | 2.56 | 2.67 |
| Compound 63 0.5 mg/mL | Mean intraocular pressure of both eyes (mmHg) | 7.94 | 7.31 | 7.78 | 7.19 | 6.61 | 6.00 |
| | Change of intraocular pressure (mmHg) | 3.14 | 3.08 | 2.83 | 3.78 | 2.7 | 4.06 |

TABLE 6-continued

Changes of the intraocular pressure of both eyes (Mean +/− SEM) of animals in each group before and after Days 2-7 repeated administration

| Measured intraocular pressure | | Time point of measurement | | | | | |
|---|---|---|---|---|---|---|---|
| | | Day 2 | Day 3 | Day 4 | Day 5 | Day 6 | Day 7 |
| Compound 63 1.0 mg/mL | Mean intraocular pressure of both eyes (mmHg) | 7.64 | 7.50 | 7.33 | 7.44 | 6.92 | 7.00 |
| | Change of intraocular pressure (mmHg) | 3.44 | 2.89 | 3.28 | 3.53 | 2.39 | 3.06 |
| Compound 63 2.0 mg/mL | Mean intraocular pressure of both eyes (mmHg) | 7.03 | 7.25 | 6.86 | 6.47 | 5.92 | 5.78 |
| | Change of intraocular pressure (mmHg) | 4.05 | 3.14 | 3.75 | 4.5 | 3.39 | 4.28 |
| Compound 63 4.0 mg/mL | Mean intraocular pressure of both eyes (mmHg) | 6.53 | 5.58 | 5.53 | 6.61 | 5.47 | 5.56 |
| | Change of intraocular pressure (mmHg) | 4.55 | 4.81 | 5.08 | 4.36 | 3.84 | 4.5 |
| Compound 63 8.0 mg/mL | Mean intraocular pressure of both eyes (mmHg) | 6.33 | 5.78 | 5.97 | 6.42 | 5.56 | 5.28 |
| | Change of intraocular pressure (mmHg) | 4.75 | 4.61 | 4.64 | 4.55 | 3.75 | 4.78 |

TABLE 7

Changes of the intraocular pressure of both eyes (Mean +/− SEM) of animals in each group before and after Days 8-14 repeated administration

| Measured intraocular pressure | | Time point of measurement | | | | | | |
|---|---|---|---|---|---|---|---|---|
| | | Day 8 | Day 9 | Day 10 | Day 11 | Day 12 | Day 13 | Day 14 |
| Negative control | Mean intraocular pressure of both eyes (mmHg) | 11.31 | 9.44 | 9.75 | 9.69 | 9.53 | 11.39 | 10.97 |
| K-115 4 mg/mL | Mean intraocular pressure of both eyes (mmHg) | 7.53 | 7.78 | 7.94 | 7.94 | 7.89 | 8.25 | 8.50 |
| | Change of intraocular pressure (mmHg) | 3.78 | 1.66 | 1.81 | 1.75 | 1.64 | 3.14 | 2.47 |
| Compound 63 0.5 mg/mL | Mean intraocular pressure of both eyes (mmHg) | 7.11 | 6.19 | 6.75 | 6.44 | 6.25 | 8.08 | 7.25 |

TABLE 7-continued

Changes of the intraocular pressure of both eyes (Mean +/− SEM) of animals in each group before and after Days 8-14 repeated administration

| Measured intraocular pressure | | Day 8 | Day 9 | Day 10 | Day 11 | Day 12 | Day 13 | Day 14 |
|---|---|---|---|---|---|---|---|---|
| | Change of intraocular pressure (mmHg) | 4.2 | 3.25 | 3 | 3.25 | 3.28 | 3.31 | 3.72 |
| Compound 63 1.0 mg/mL | Mean intraocular pressure of both eyes (mmHg) | 7.28 | 6.94 | 7.31 | 7.50 | 6.89 | 8.06 | 7.44 |
| | Change of intraocular pressure (mmHg) | 4.03 | 2.5 | 2.44 | 2.19 | 2.64 | 3.33 | 3.53 |
| Compound 63 2.0 mg/mL | Mean intraocular pressure of both eyes (mmHg) | 6.78 | 5.72 | 5.94 | 6.03 | 6.03 | 7.11 | 7.06 |
| | Change of intraocular pressure (mmHg) | 4.53 | 3.72 | 3.81 | 3.66 | 3.5 | 4.28 | 3.91 |
| Compound 63 4.0 mg/mL | Mean intraocular pressure of both eyes (mmHg) | 6.78 | 5.47 | 5.08 | 5.83 | 5.89 | 7.03 | 6.33 |
| | Change of intraocular pressure (mmHg) | 4.53 | 3.97 | 4.67 | 3.86 | 3.64 | 4.36 | 4.64 |
| Compound 63 8.0 mg/mL | Mean intraocular pressure of both eyes (mmHg) | 5.72 | 5.19 | 5.56 | 5.53 | 5.56 | 6.67 | 6.94 |
| | Change of intraocular pressure (mmHg) | 5.59 | 4.25 | 4.19 | 4.16 | 3.97 | 4.72 | 4.03 |

(Column header "Time point of measurement" spans Day 8 to Day 14.)

Conclusion: A single dose of compound 63 exhibited superior efficacy (highest hypotensive effect and action duration) at all test doses (0.5-8.0 mg/mL), significantly superior to K-115. After 14 days of continuous administration, compound 63 can maintain a significant hypotensive effect at the dose of 0.5 mg/mL and is still significantly superior to K-115 in evaluation of peak hypotensive effect (Cmax).

Experiment Operation 2

42 male New Zealand rabbits were randomly divided into 7 groups, with 6 rabbits per group. Animals were randomly divided according to body weight Animals in 1-7 groups were eye-dropped with normal saline in the left eye and with solvent/control sample/test sample in the right eye respectively by a volume of 50 μL/eye, once per day for 14 consecutive days, and the day of administration was recorded as Day 1. The intraocular pressure of the animals was measured before Day 1 administration and in 1, 2, 4, 6, 8 and 10 hours after Day 1 administration, respectively (Table 8).

Before the experiment (Day 2/Day 1), before daily administration during the administration (Days 1-14), and in 1, 2, 4, 24, 48 and 72 hours after the last administration (Day 14), the eyes of animals were examined for ocular stimulation response and fluorescein sodium by a hand-held slit lamp (scoring by referring to the scoring criteria).

TABLE 8

Changes of the intraocular pressure of both eyes (Mean +/− SEM) of animals in each group before and after Day 1 administration

| Measured intraocular pressure | | Before administration | 1 hour after administration | 2 hours after administration | 4 hours after administration | 6 hours after administration | 8 hours after administration | 10 hours after administration |
|---|---|---|---|---|---|---|---|---|
| | | Time point of measurement | | | | | | |
| Negative control | 9.89 intraocular pressure of both eyes (mmHg) | 9.33 | 8.89 | 9.56 | 9.89 | 10.78 | 10.39 | 12.17 |
| K-115 4 mg/mL | Mean intraocular pressure of both eyes (mmHg) | 10.17 | 5.50 | 7.06 | 9.00 | 9.17 | 10.61 | 12.33 |
| | Change of intraocular pressure (mmHg) | 0.83 | −3.39 | −2.50 | −0.89 | −1.61 | 0.23 | 0.17 |
| Compound 63 0.25 mg/mL | Mean intraocular pressure of both eyes (mmHg) | 9.84 | 6.22 | 6.17 | 6.67 | 8.06 | 9.72 | 10.95 |
| | Change of intraocular pressure (mmHg) | 0.50 | −2.67 | −3.39 | −3.22 | −2.72 | −0.66 | −1.22 |
| Compound 63 0.5 mg/mL | Mean intraocular pressure of both eyes (mmHg) | 9.22 | 5.39 | 5.50 | 6.95 | 8.94 | 9.89 | 11.56 |
| | Change of intraocular pressure (mmHg) | −0.11 | −3.50 | −4.05 | −2.94 | −1.84 | −0.50 | −0.61 |
| Compound 63 1.0 mg/mL | Mean intraocular pressure of both eyes (mmHg) | 9.17 | 5.56 | 5.39 | 6.67 | 7.33 | 10.50 | 10.89 |
| | Change of intraocular pressure (mmHg) | −0.17 | −3.33 | −4.17 | −3.22 | −3.45 | 0.11 | −1.28 |
| Compound 63 2.0 mg/mL | Mean intraocular pressure of both eyes (mmHg) | 9.72 | 8.11 | 5.84 | 6.06 | 7.11 | 9.00 | 10.05 |
| | Change of intraocular pressure (mmHg) | 0.39 | −0.78 | −3.72 | −3.83 | −3.67 | −1.39 | −2.11 |
| Compound 63 4.0 mg/mL | Mean intraocular pressure of both eyes (mmHg) | 10.00 | 6.61 | 5.84 | 5.72 | 6.61 | 8.39 | 10.67 |
| | Change of intraocular pressure (mmHg) | 0.67 | −2.28 | −3.72 | −4.17 | −4.17 | −2.00 | −1.50 |

Conclusion: A single dose of compound 63 exhibited superior efficacy (highest hypotensive effect and action duration) at all test doses (0.25-4.0 mg/mL), significantly superior to K-115.

Before the experiment (Day 2/Day 1), before the first daily administration (Days 1-14) during the administration, and in 1, 2, 4, 24, 48 and 72 hours after the last administration, the eyes of animals were examined for ocular stimulation response by a hand-held slit lamp. The scoring criteria were as follows.

| Ocular stimulation response | Score |
|---|---|
| Cornea | |
| No turbidity | 0 |
| Scattered or diffuse turbidity, clear and visible iris | 1 |
| Semi-transparent region easy to be recognized, obscure iris | 2 |
| Gray semi-transparent region, details of the iris being obscure, marginally visible pupils | 3 |
| Opaque cornea, iris beyond recognition | 4 |
| Iris | |
| Normal | 0 |
| Remarkably deepened, congested and swollen crease, slight congestion around cornea, pupils still responsive to light | 1 |
| Bleeding/visible necrosis/not responsive to light (or at least one of them) | 2 |
| Conjunctiva | |
| Congestion (palpebral conjunctiva and bulbar conjunctiva) | |
| Normal blood vessels | 0 |
| Congested and bright red blood vessels | 1 |
| Congested and dark red blood vessels, beyond recognition | 2 |
| Diffuse congestion and being magenta | 3 |
| Edema | |
| No edema | 0 |
| Slight edema (eyelid included) | 1 |
| Obvious edema accompanied by partial eyelid ectropion | 2 |
| Edema to near eyelid semi-closure | 3 |
| Edema to beyond eyelid semi-closure | 4 |
| Secretion | |
| No secretion | 0 |
| A small amount of secretion | 1 |
| Secretion making eyelids and eyelashes moist or adhered | 2 |
| Secretion making the entire eye region moist or adhered | 3 |
| Maximum total score | 16 |

Evaluation of ocular stimulation response: adding the maximum score of cornea, iris, conjunctiva, edema, and secretion to obtain the total score of ocular stimulation symptoms for each animal eye at each time point. For the score of ocular stimulation symptom, calculate the integral mean value of each group of animals at each observation time point, and determine the degree of ocular stimulation of each group of animals at each time point according to the following table.

Evaluation Standard of Ocular Stimulation

| Score | Evaluation |
|---|---|
| 0-3 | No stimulation |
| 4-8 | Slight stimulation |
| 9-12 | Mild stimulation |
| 13-16 | Severe stimulation |

Fluorescein sodium examination: after each ocular stimulation response examination, a hand-held slit lamp was used for fluorescein sodium examination, and the scoring criteria were as follows:

| Fluorescent staining | |
|---|---|
| Fluorescein was used to aid the diagnosis of corneal epithelial injury. Fluorescent staining areas can be divided into grades 0-4 according to the degree of corneal opacity: | |
| No fluorescent staining. | 0 |
| Local small-area slight fluorescent staining. Observed under diffuse light, clear and visible eye structures under cornea (clear pupil edge, observation not affected by fluorescent staining). | 1 |
| Local small-area mild fluorescent staining Observed under diffuse light, although some details of the eye under the cornea missed, structure being clear and visible. | 2 |
| Large obvious fluorescent staining in the staning area Observed under diffuse light, eye structures under cornea marginally recognizable. | 3 |
| Serious fluorescent staining Observed under diffuse light, eye structures under cornea beyond recognition. | 4 |

The results of the experiment were as follows:

According to the evaluation criteria of ocular stimulation, the total score of ocular stimulation response of each group at each time point was less than 3, and all were classified as no stimulation according to the standard.

During the experiment, the scores of fluorescein sodium examination on eyes (with left eyes treated with normal saline, and right eyes treated with the solvent, K-115 and compound 63) were all lower than 1. Corneal fluorescence staining score of 1 was observed in each group of animals at each treatment and individual time point, and biological staining was considered. There was no corneal epithelial injury in each group at each time point.

Conclusion: Under the conditions of this experiment, K-115 was eye-dropped at the concentration of 4 mg/mL for 14 consecutive days by 50 μL/eye/day, showing no stimulation. Compound 63 was eye-dropped in the concentration range of 0.25-4 mg/mL for 14 consecutive days by 50 μL/eye/day, showing no stimulation.

Experimental Example 5. Toxicokinetics Experiment

Experiment Objective:

The production rate of active drug ingredients and the exposure amount of active drug ingredients of the compound in plasma were detected after 14 days of continuous administration.

Experiment Materials:

Male New Zealand rabbits, aged 3-6 months, weighted 2.0-5.0 kg, purchased from PizhouDongfang Breeding Co. Ltd.

Experiment Operations:

After 14 days of continuous administration, blood samples from the group administrated with compound 63 (8.0 mg/mL) were collected at 0 hour (before administration) and in 0.5, 1, 2, 4, 8, and 24 hours after administration on Days 14-15. About 0.8 mL of whole blood was collected from the auricular artery or the saphenous vein of the hind limb (or other appropriate sites) of toxicokinetics experiment animals, and was placed in labeled collection tubes using ethylenediaminetetraacetic acid dipotassium ($K_2EDTA$) as an anticoagulant. Plasma was obtained by centrifugation for 10 minutes at 3000 rpm and under the condition of 2° C. to 8° C. in 60 minutes after blood collection. All samples were quantitatively detected for the content of the administered compounds in plasma of the experimental animals by liquid chromatography-coupled mass spectrometry (LC-MS) and mass spectrometry (MS) technology.

TABLE 9

Test results of active compounds in plasma of New Zealand rabbits after 14 days of continuous administration

| Compound No. | Time (hour) | Concentration (ng/mL) Group 1 | Group 2 |
| --- | --- | --- | --- |
| Compound 63 | 0.00 | BQL | BQL |
| | 0.50 | 3.63 | 3.44 |
| | 1.00 | 2.87 | 2.20 |
| | 2.00 | 1.80 | 1.66 |
| | 4.00 | 0.934 | 0.818 |
| | 8.00 | BQL | BQL |
| | 24.0 | BQL | BQL |

Note:
BQL indicates below the detection limit.

Conclusion: The metabolite concentration of compound 63 was 0.934 ng/mL in 4 hours after high administration dose of 8 mg/mL; in 8 hours after administration, the concentration of metabolite of the compound was below the detection limit, indicating high system safety.

What is claimed is:

1. A compound of formula (I), an isomer thereof or a pharmaceutically acceptable salt thereof, (I)

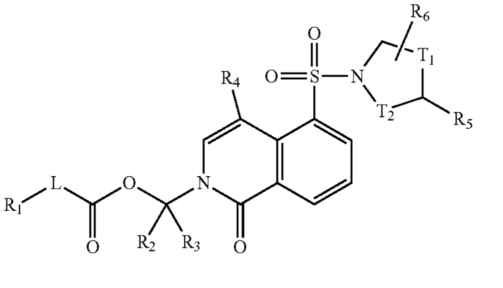

wherein, $T_1$ is $-(CH_2)_n-$;

$T_2$ is selected from a group consisting of $-(CH_2)_m-$ and $-C(R_7)(R_8)-$;

$R_1$ is selected from a group consisting of $C_{1-16}$ alkyl, phenyl, $C_{3-7}$ cycloalkyl, 3-8 membered heterocycloalkyl and 5-10 membered heteroaryl, each of $C_{1-16}$ alkyl, phenyl, $C_{3-7}$ cycloalkyl, 3-8 membered heterocycloalkyl and 5-10 membered heteroaryl is optionally substituted by 1, 2 or 3 $R_a$;

each of $R_2$ and $R_3$ is independently selected from a group consisting of H, F, Cl, Br, I, OH, $NH_2$, CN and $C_{1-3}$ alkyl;

$R_4$ is selected from a group consisting of H, F, Cl, Br, I, OH, $NH_2$, CN, and $C_{1-3}$ alkyl which is optionally substituted by 1, 2 or 3 $R_b$;

$R_5$ is $NR_9R_{10}$;

$R_6$ is selected from a group consisting of H, F, Cl, Br, I, OH, $NH_2$, CN and $C_{1-3}$ alkyl;

each of $R_7$ and $R_8$ is independently selected from a group consisting of H, F, Cl, Br, I, OH, $NH_2$, CN, and $C_{1-3}$ alkyl which is optionally substituted by 1, 2 or 3 $R_c$; or, $R_7$ and $R_8$ together with the atom that they attached to form a $C_{3-5}$ cycloalkyl which is optionally substituted by 1, 2 or 3 $R_d$;

each of $R_9$ and $R_{10}$ is independently selected from a group consisting of H, and $C_{1-3}$ alkyl which is optionally substituted by 1, 2 or 3 $R_e$;

L is selected from a group consisting of a single bond, —O— and $-NR_{11}-$;

$R_{11}$ is selected from a group consisting of H and $C_{1-3}$ alkyl;

n is selected from a group consisting of 0, 1 and 2;

m is selected from a group consisting of 0, 1, 2 and 3;

$R_a$ is selected from a group consisting of F, Cl, Br, I, OH, $NH_2$, CN, $C_{1-3}$ alkyl and $C_{1-3}$ alkoxy, wherein each of $C_{1-3}$ alkyl and $C_{1-3}$ alkoxy is optionally substituted by 1, 2 or 3 R;

each of $R_b$, $R_c$, $R_d$ and $R_e$ is independently selected from a group consisting of H, F, Cl, Br, I, OH, $NH_2$, CN and $C_{1-3}$ alkyl;

R is selected from a group consisting of F, Cl, Br, I, OH, $NH_2$, CN and $CH_3$;

wherein, each of the 3-8 membered heterocycloalkyl and 5-10 membered heteroaryl independently includes 1, 2, 3 or 4 heteroatom(s) or heteroatom group(s) which is/are independently selected from a group consisting of —NH—, —O—, —S— and N.

2. The compound, the isomer thereof or the pharmaceutically acceptable salt thereof according to claim 1, wherein, $R_a$ is selected from a group consisting of F, Cl, Br, I, OH, $NH_2$, CN, $CH_3$, $CF_3$, $CH_2F$, $CHF_2$, $CH_2CH_3$ and $OCH_3$.

3. The compound, the isomer thereof or the pharmaceutically acceptable salt thereof according to claim 1, wherein, $R_1$ is selected from a group consisting of $C_{1-12}$ alkyl, phenyl, cyclobutyl, cyclopentyl, cyclohexyl, tetrahydrofuranyl, tetrahydropyranyl, piperidinyl, thienyl, furyl, pyrrolyl and benzofuryl, wherein, each of $C_{1-12}$ alkyl, phenyl, cyclobutyl, cyclopentyl, cyclohexyl, tetrahydrofuranyl, tetrahydropyranyl, piperidinyl, thienyl, furyl, pyrrolyl and benzofuryl is optionally substituted by 1, 2 or 3 $R_a$.

4. The compound, the isomer thereof or the pharmaceutically acceptable salt thereof according to claim 3, wherein, $R_1$ is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$,

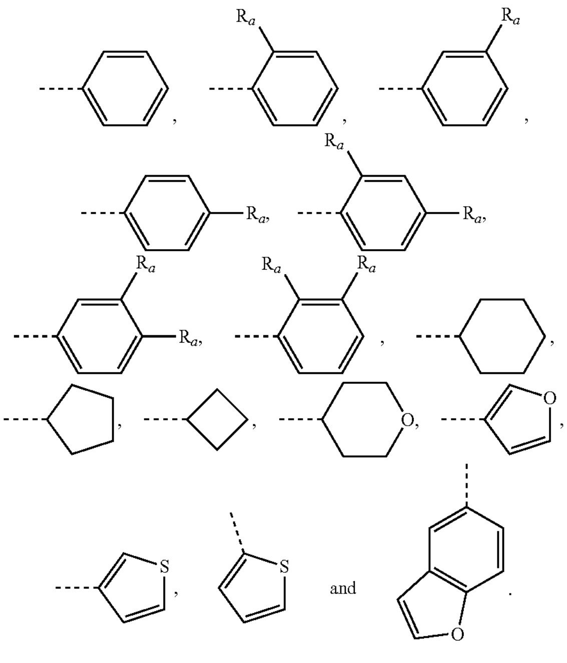

and

5. The compound, the isomer thereof or the pharmaceutically acceptable salt thereof according to claim 4, wherein, $R_1$ is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$,

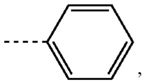, 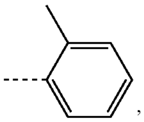, 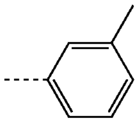, 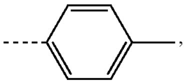, 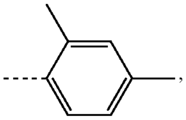, 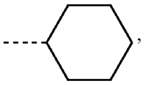, 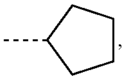, 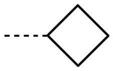, 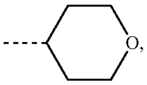, 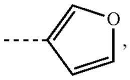, 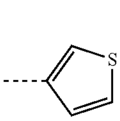, 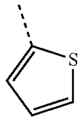 and 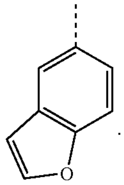.

6. The compound, the isomer thereof or the pharmaceutically acceptable salt thereof according to claim 1, wherein, each of $R_2$ and $R_3$ is independently selected from a group consisting of H, F, Cl, Br, I, OH and $NH_2$.

7. The compound, the isomer thereof or the pharmaceutically acceptable salt thereof according to claim 1, wherein, $R_4$ is selected from a group consisting of H, F, Cl, Br, I, OH, $NH_2$, CN, $CH_3$ and $CH_2CH_3$.

8. The compound, the isomer thereof or the pharmaceutically acceptable salt thereof according to claim 1, wherein, each of $R_9$ and $R_{10}$ is independently selected from a group consisting of H, $CH_3$ and $CH_2CH_3$.

9. The compound, the isomer thereof or the pharmaceutically acceptable salt thereof according to claim 1, wherein, $R_5$ is selected from a group consisting of $NH_2$, $NH(CH_3)$ and $N(CH_3)_2$.

10. The compound, the isomer thereof or the pharmaceutically acceptable salt thereof according to claim 1, wherein, $R_6$ is selected from a group consisting of H, F, Cl, Br, I, OH, $NH_2$, CN and $CH_3$.

11. The compound, the isomer thereof or the pharmaceutically acceptable salt thereof according to claim 1, wherein, each of $R_7$ and $R_8$ is independently selected from a group consisting of H, F, Cl, Br, I, OH, $NH_2$, CN and $CH_3$.

12. The compound, the isomer thereof or the pharmaceutically acceptable salt thereof according to claim 1, wherein, $R_7$ and $R_8$ together with the atom that they attached to form a cyclopropyl which is optionally substituted by 1, 2 or 3 $R_d$.

13. The compound, the isomer thereof or the pharmaceutically acceptable salt thereof according to claim 12, wherein, $R_7$ and $R_8$ together with the atom that they attached to form a cyclopropyl.

14. The compound, the isomer thereof or the pharmaceutically acceptable salt thereof according to claim 1, wherein, L is selected from a group consisting of a single bond, —O—, —NH— and —N($CH_3$)—.

15. The compound, the isomer thereof or the pharmaceutically acceptable salt thereof according to claim 1, wherein, $T_2$ is selected from a group consisting of —$CH_2$—, —$(CH_2)_2$ — and

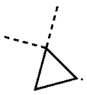.

16. The compound, the isomer thereof or the pharmaceutically acceptable salt thereof according to claim 1, wherein, the structure unit

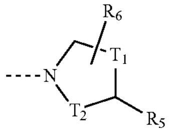

is selected from a group consisting of

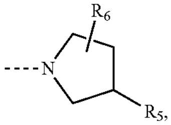 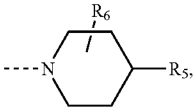 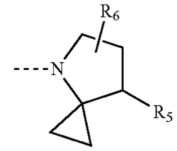

and 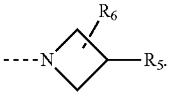

17. The compound, the isomer thereof or the pharmaceutically acceptable salt thereof according to claim 16, wherein, the structure unit

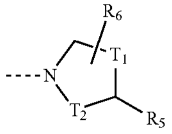

is selected from a group consisting of

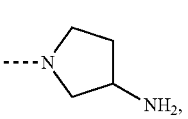 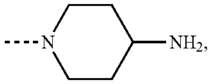

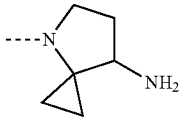 and 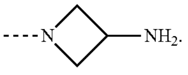

18. The compound, the isomer thereof or the pharmaceutically acceptable salt thereof according to claim 1, wherein, the structure unit

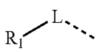

is selected from a group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_{10}CH_3$, $CH(CH_3)_2$, $C(CH_3)_3$, $OCH_3$, $OCH_2CH_3$, $O(CH_2)_2CH_3$, $O(CH_2)_3CH_3$, $O(CH_2)_4CH_3$, $O(CH_2)_5CH_3$, $O(CH_2)_6CH_3$, $OCH(CH_3)_2$, $OC(CH_3)_3$, $N(CH_3)_2$,

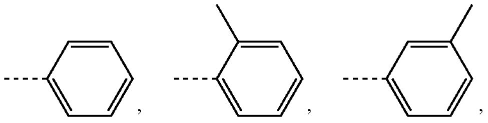

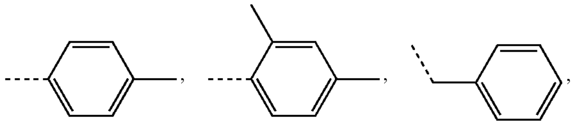

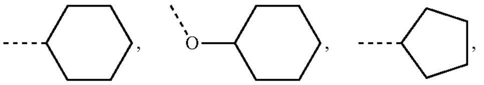

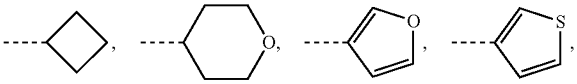

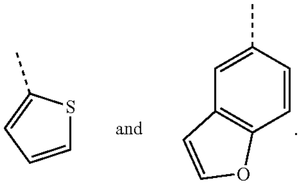

19. The compound, the isomer thereof or the pharmaceutically acceptable salt thereof according to claim 1, which is selected from a group consisting of:

(I-1)

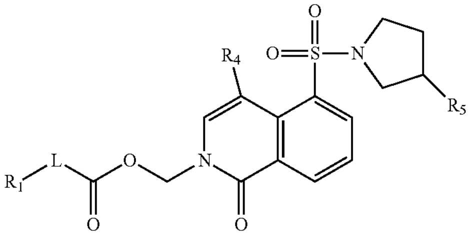

(I-2)

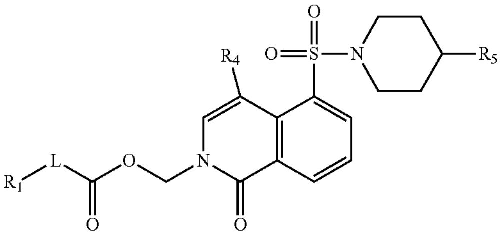

(I-3)

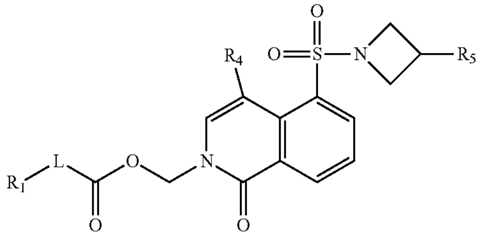

-continued (I-4)

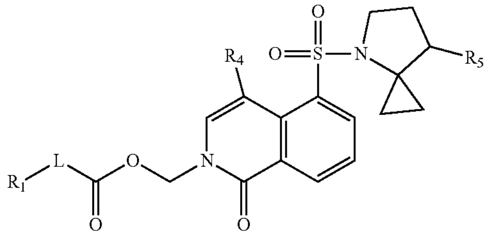

wherein, $R_1$ is s as defined in claim 1;

$R_4$ is as defined in claim 1;

$R_5$ is as defined in claim 1; and

L is as defined in claim 1.

20. The compound, the isomer thereof or the pharmaceutically acceptable salt thereof according to claim 19, which is selected from a group consisting of:

(I-1a)

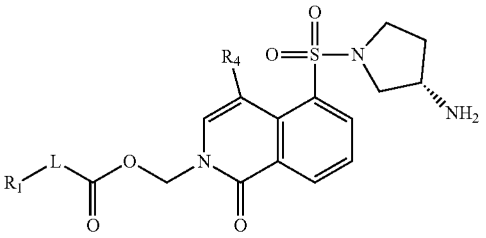

(I-1b)

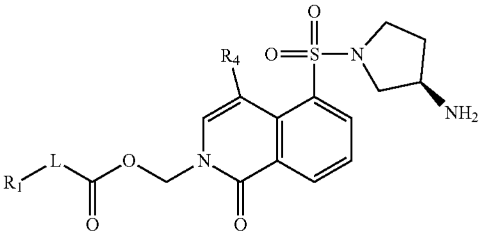

(I-2)

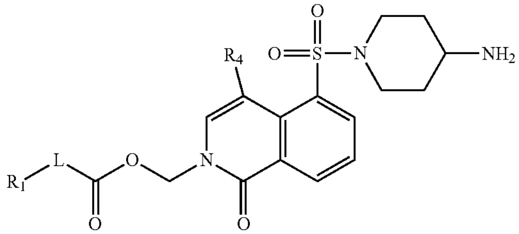

-continued
(I-3)
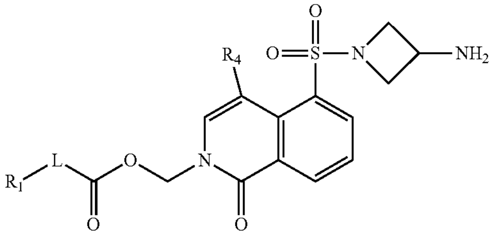
(I-4a)
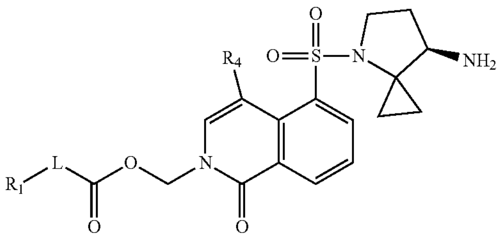
-continued
(I-4b)
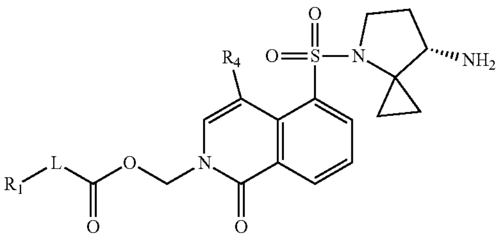
wherein,
$R_1$, $R_4$ and L are as defined in claim 19.
21. The compound, the isomer thereof or the pharmaceutically acceptable salt thereof according to claim 1, which is selected from a group consisting of:
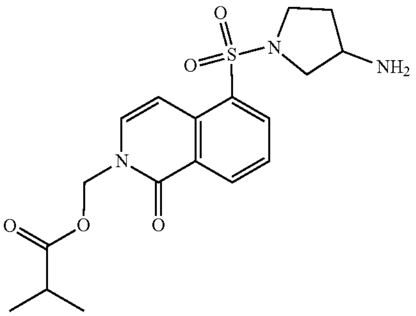
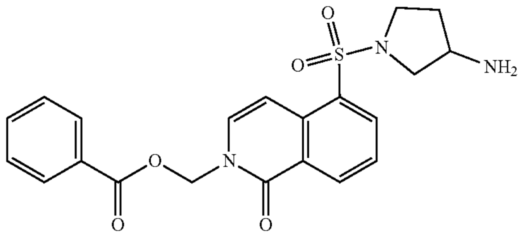
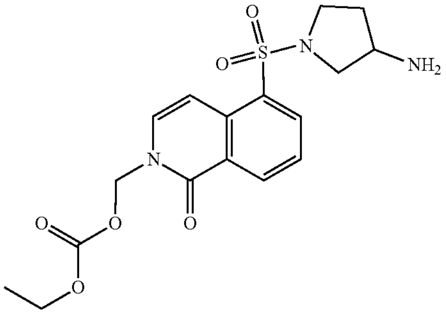
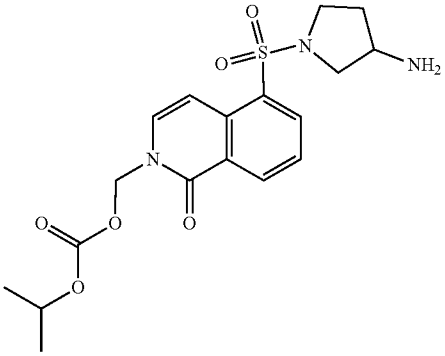
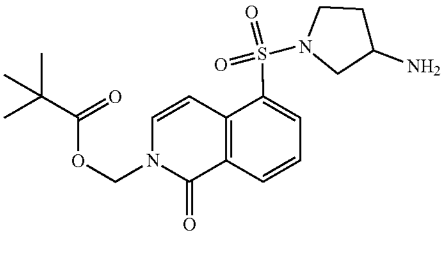
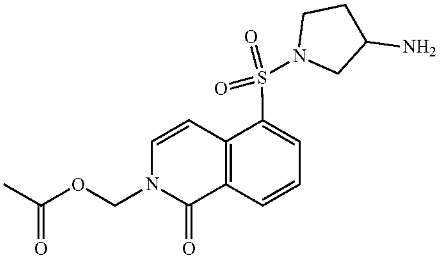

-continued
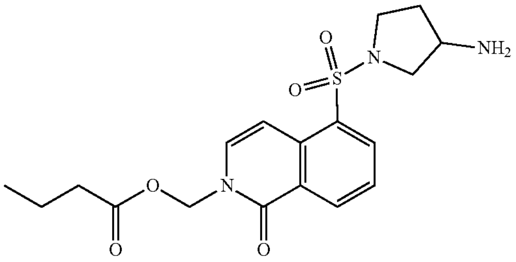
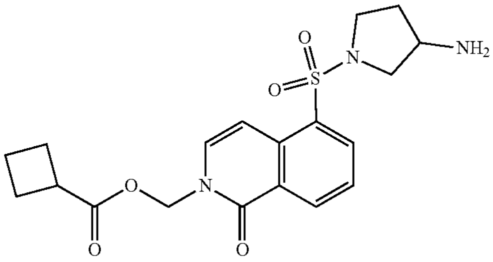
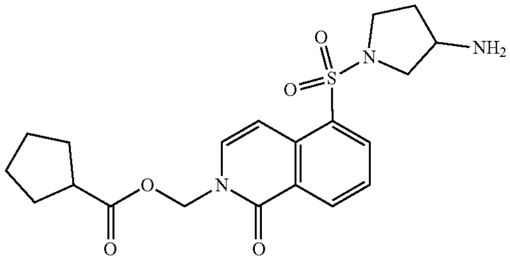
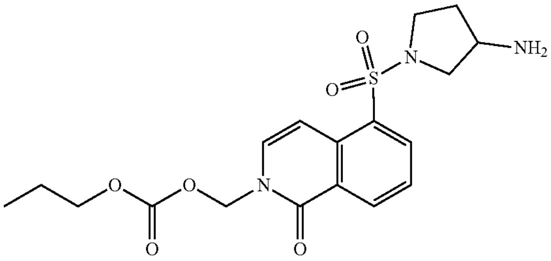
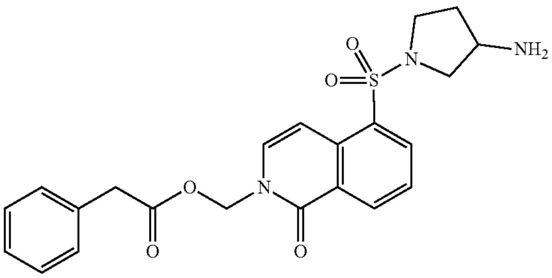
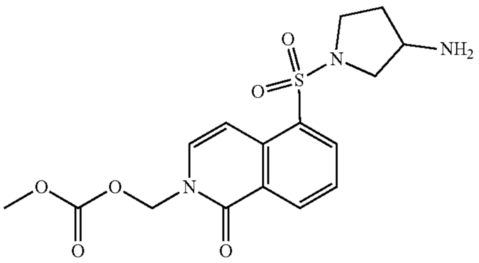
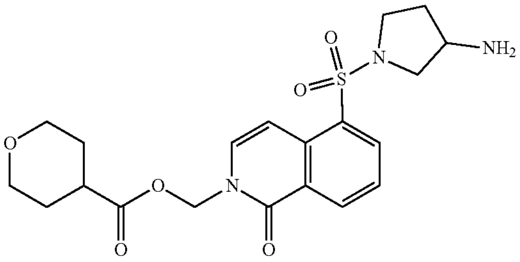
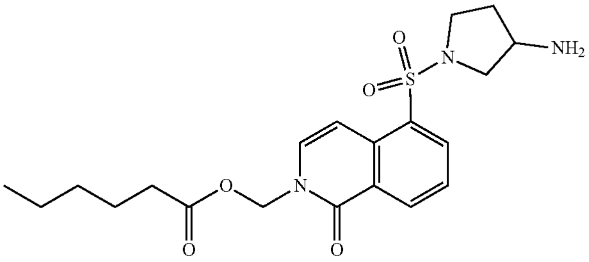
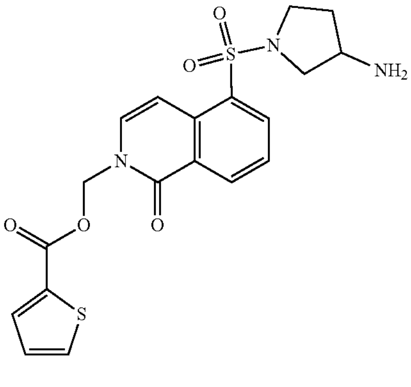
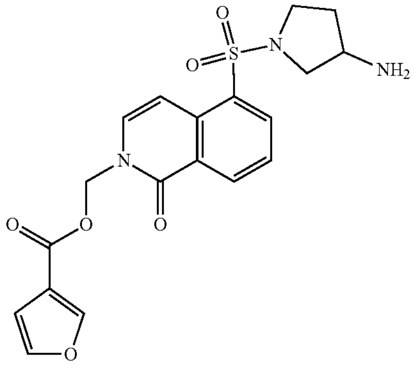

-continued
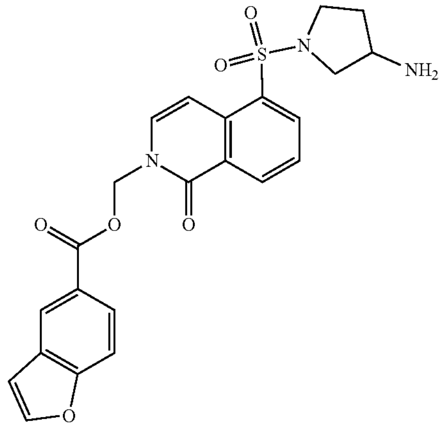
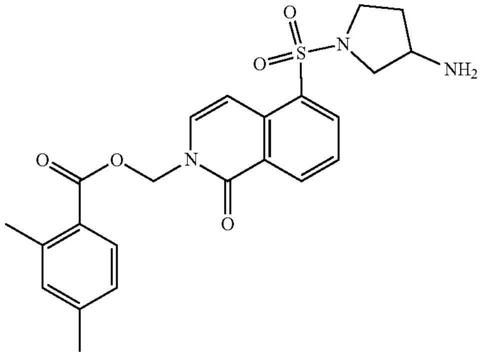
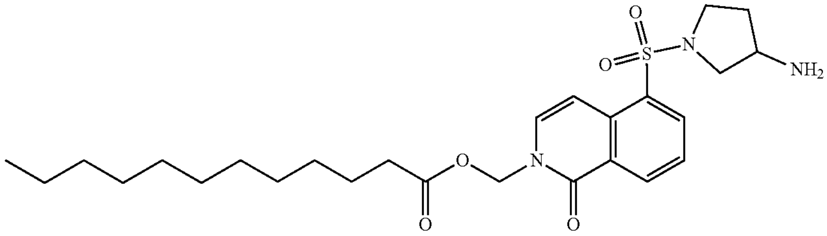
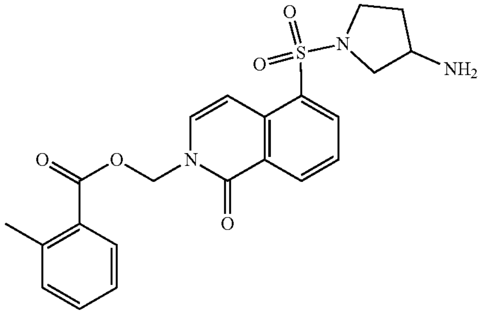
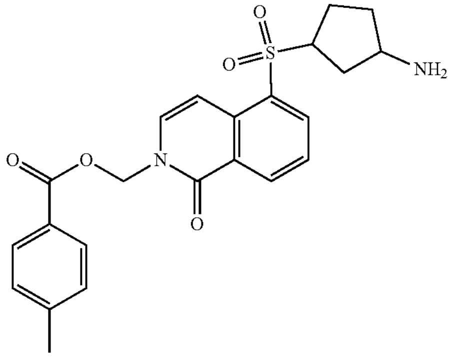
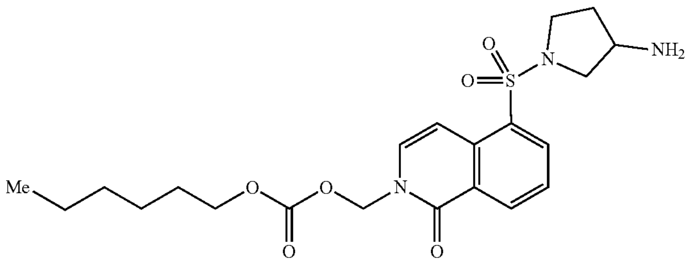
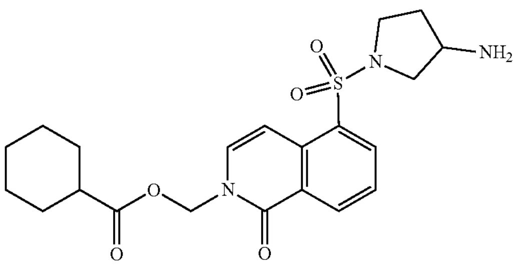
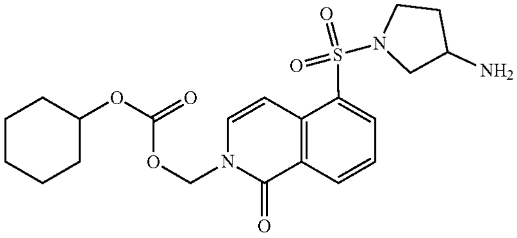

-continued
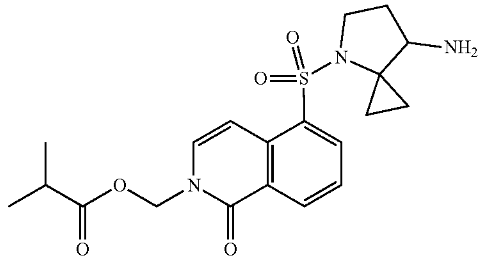
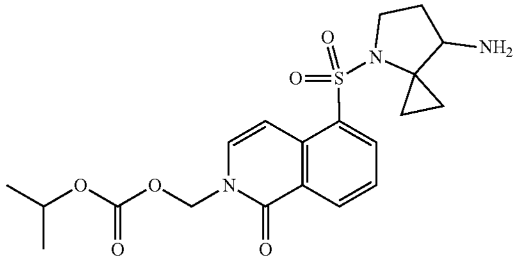
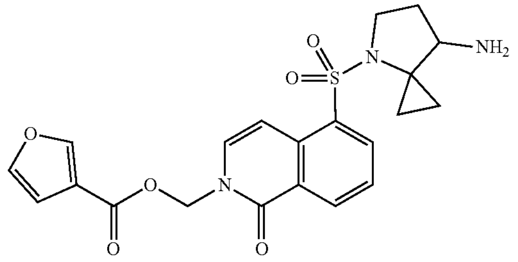
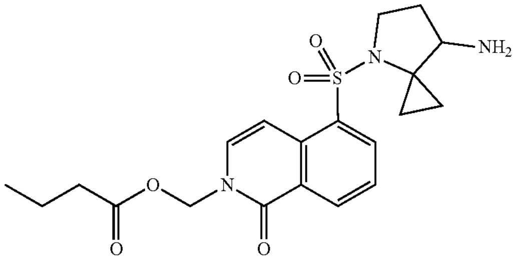
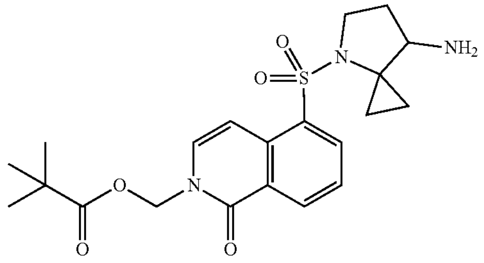
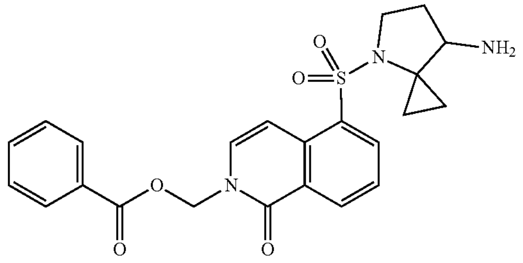
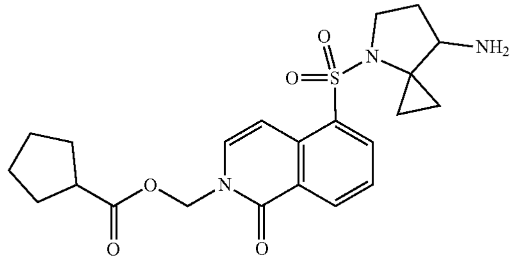
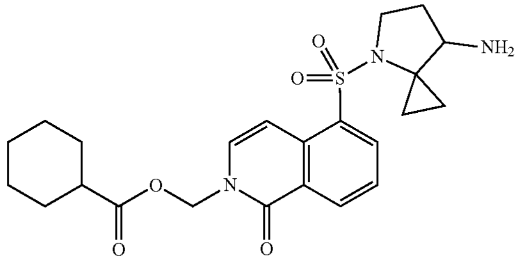
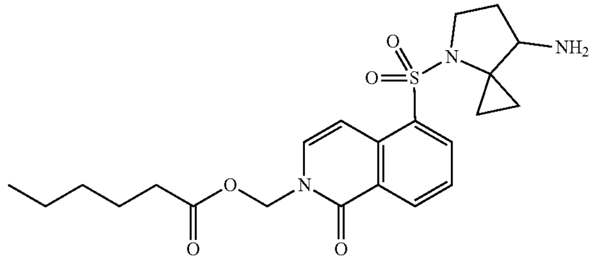
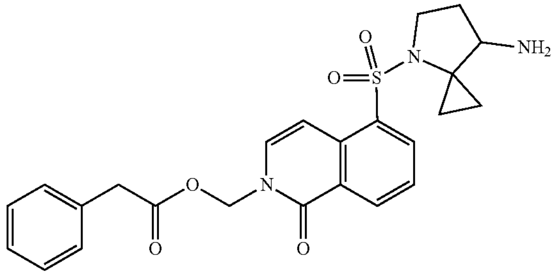
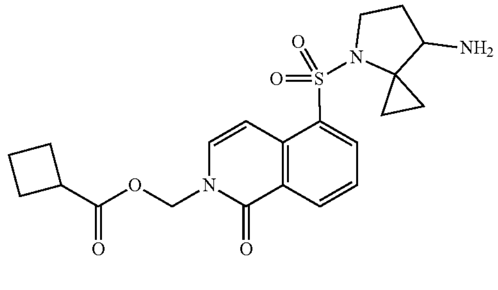
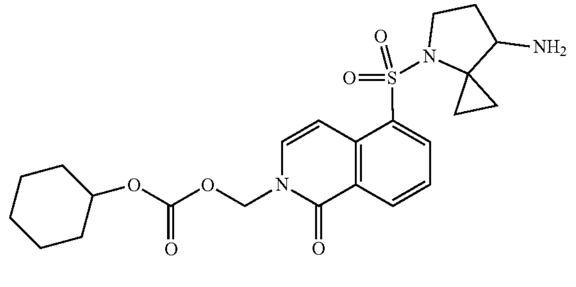

-continued
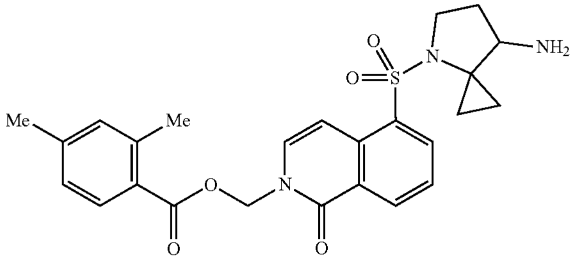
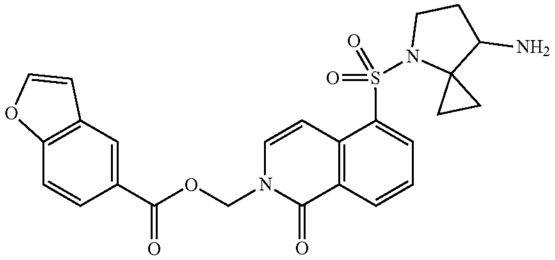
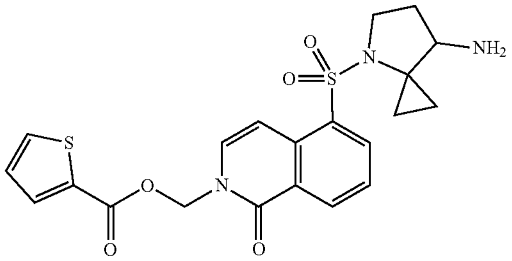
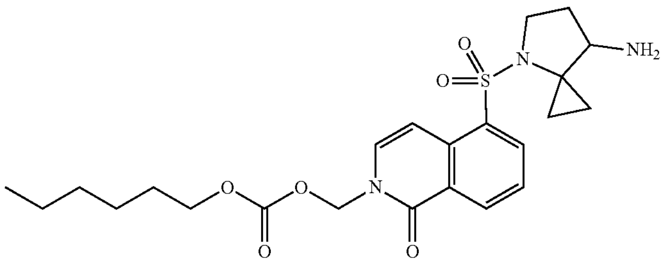
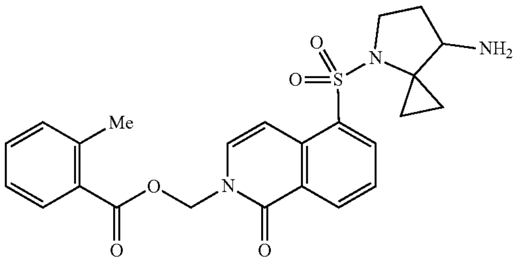
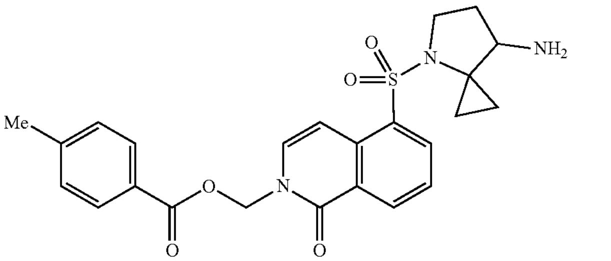
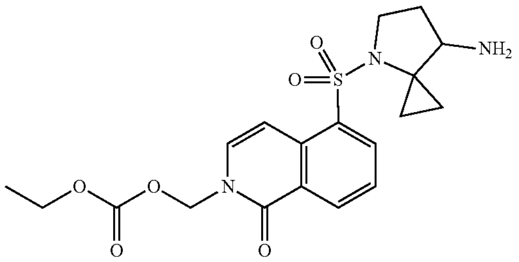
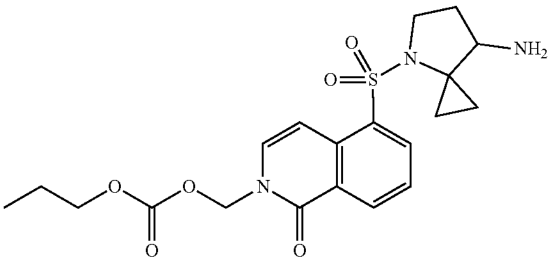
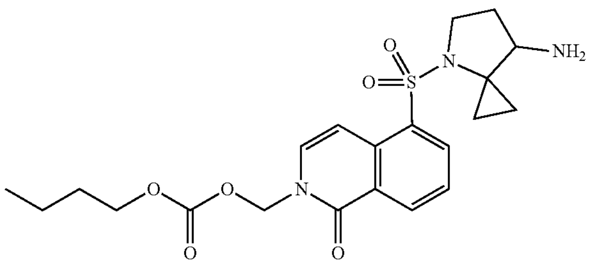

-continued
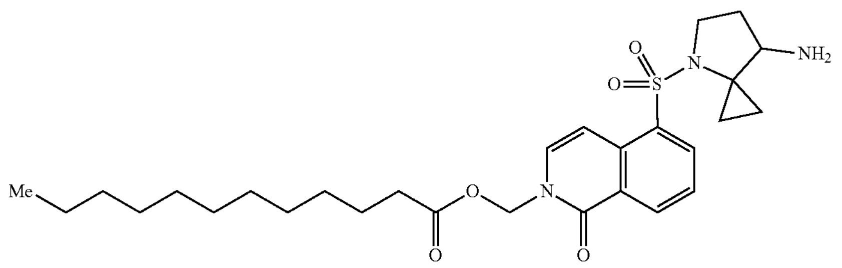
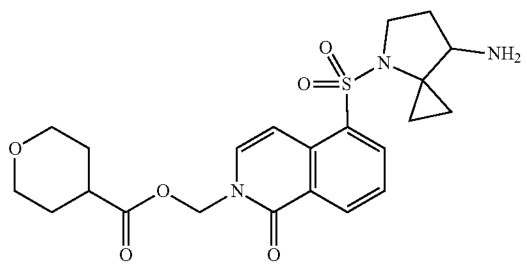
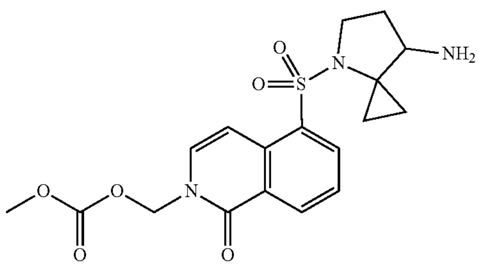
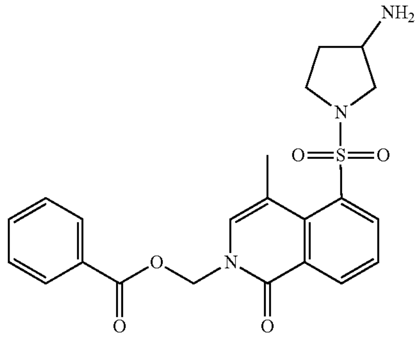
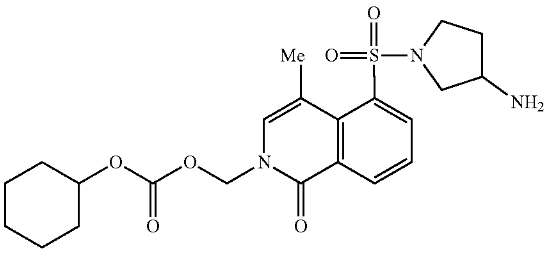
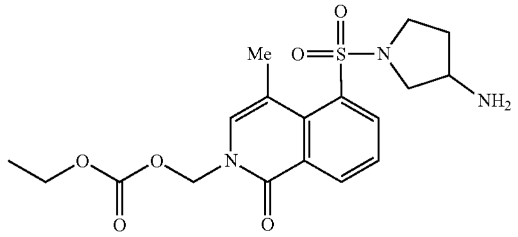
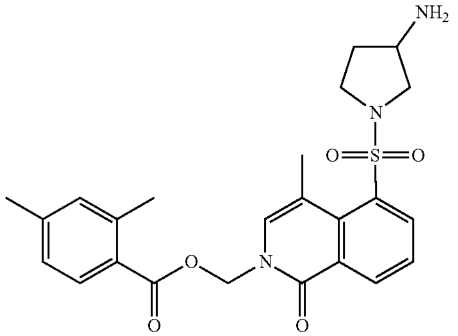
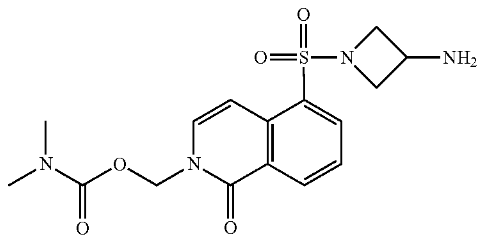
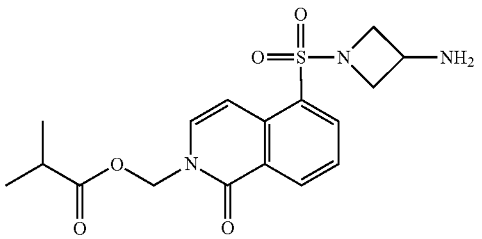

-continued
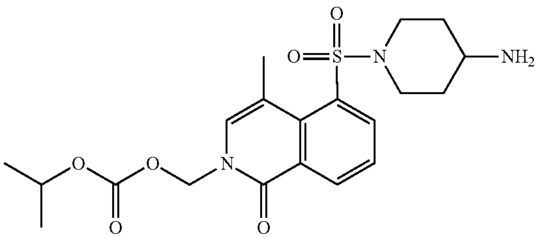
and
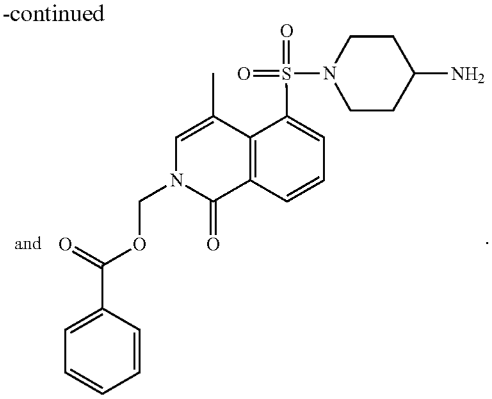
.
22. The compound, the isomer thereof or the pharmaceutically acceptable salt thereof according to claim 21, which is selected from a group consisting of:
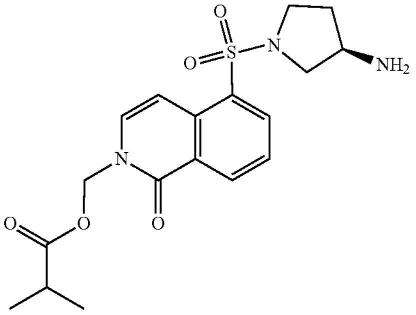
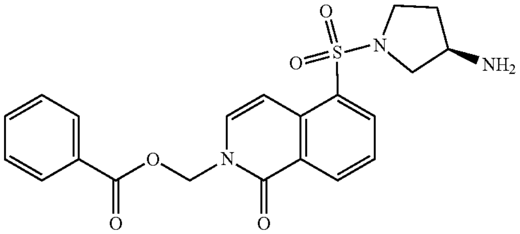
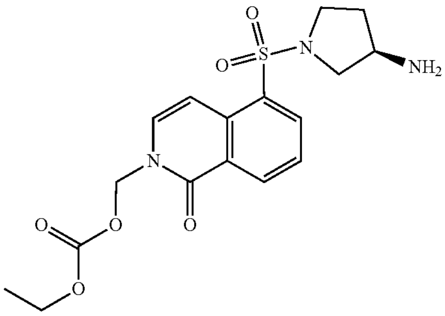
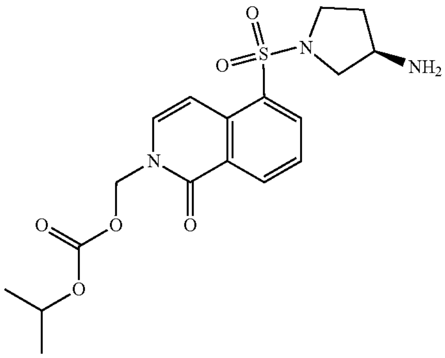
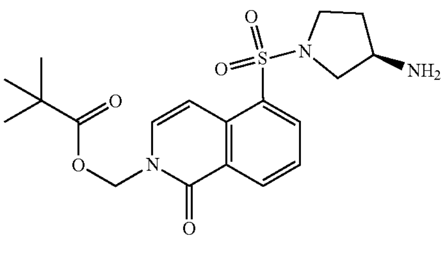
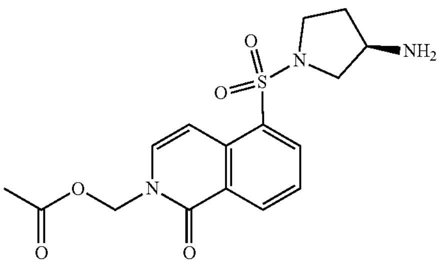

-continued
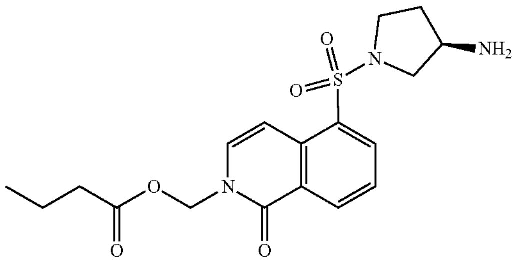
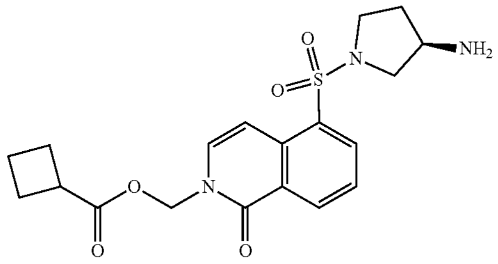
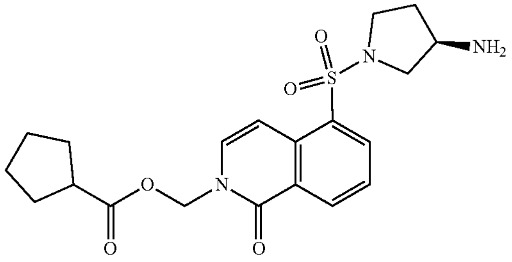
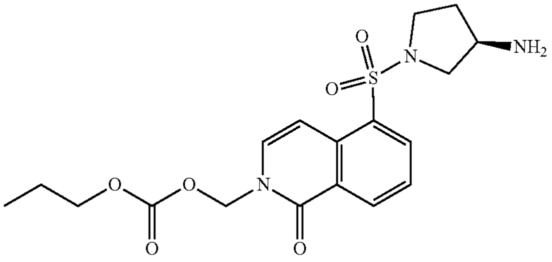
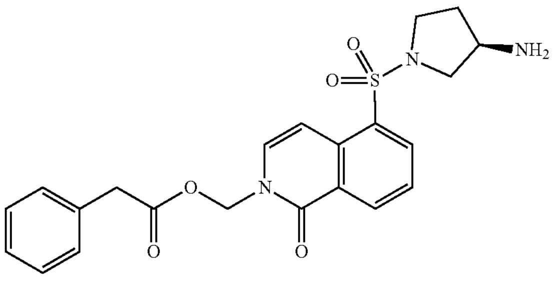
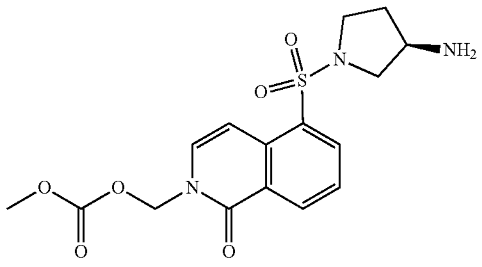
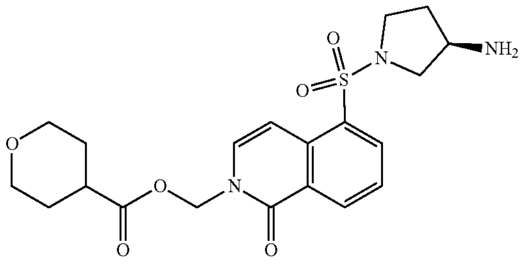
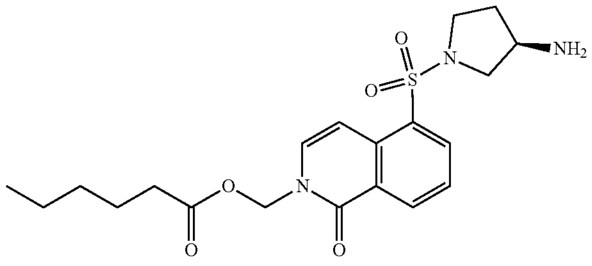
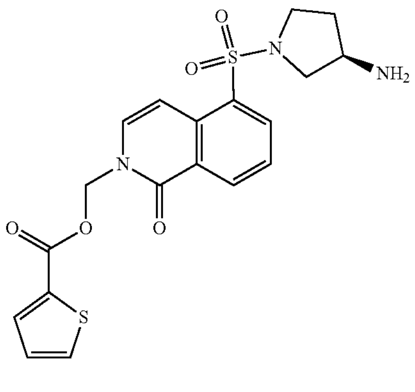
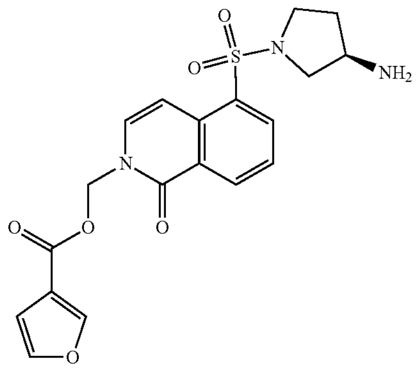

-continued
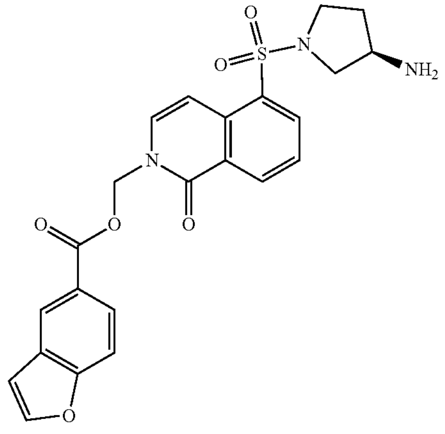
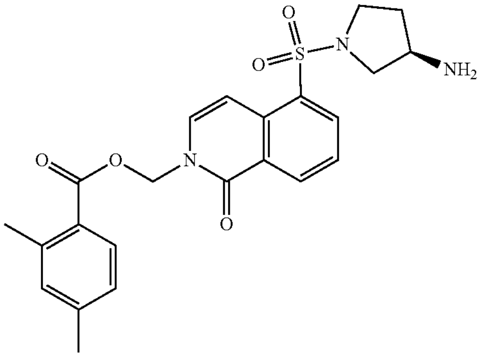
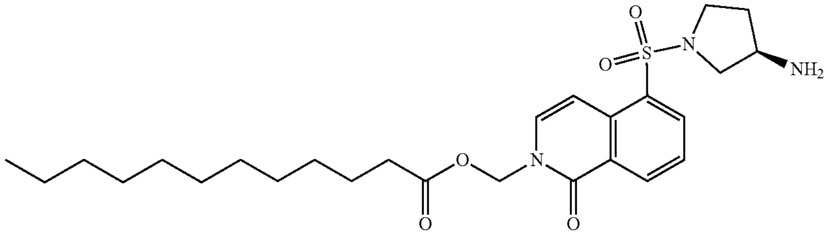
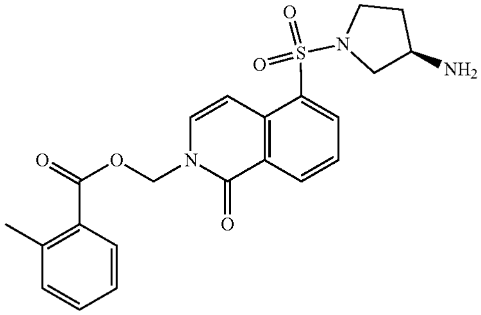
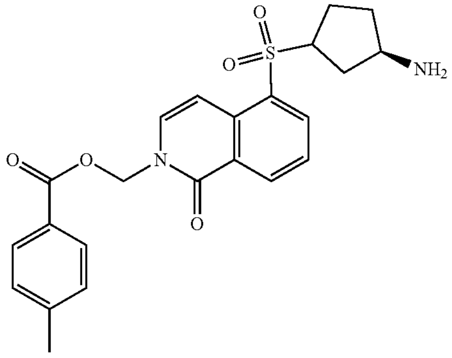
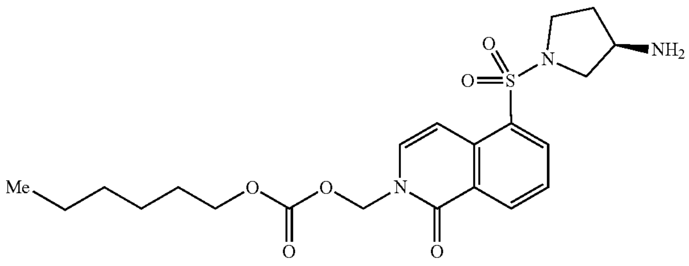
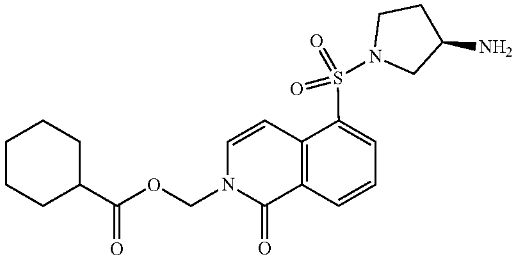
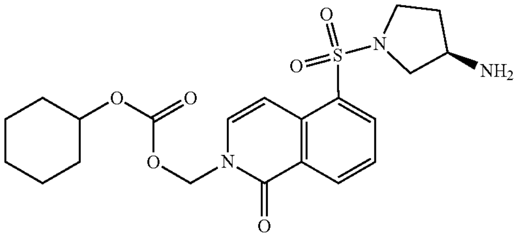

-continued
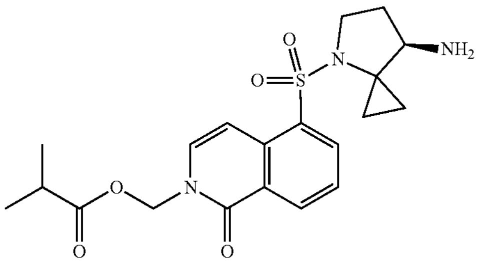
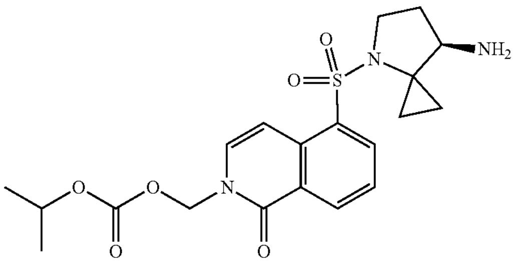
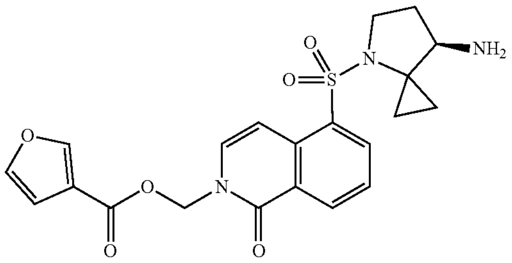
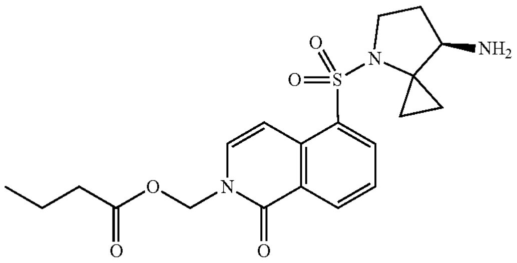
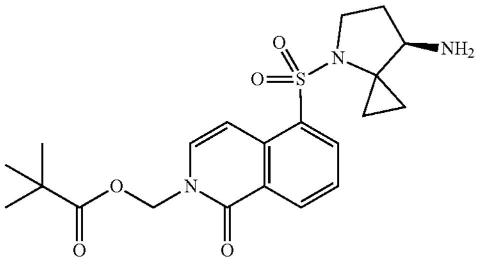
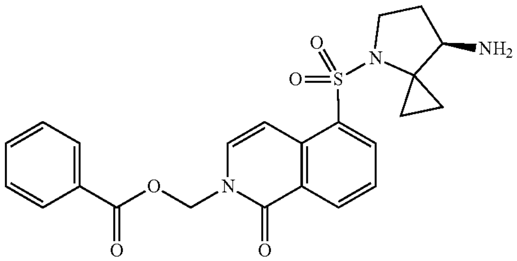
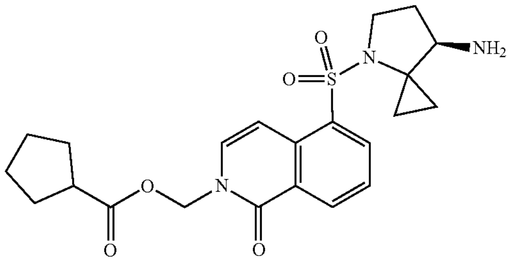
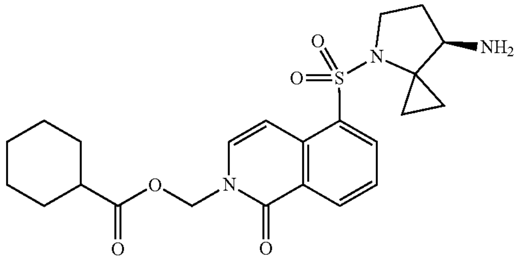
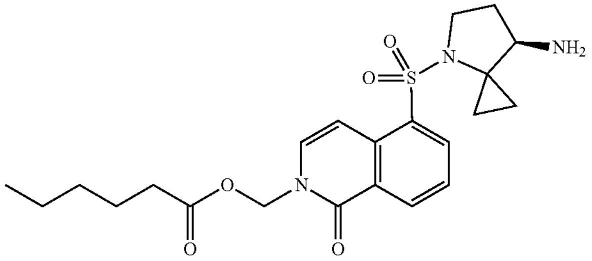
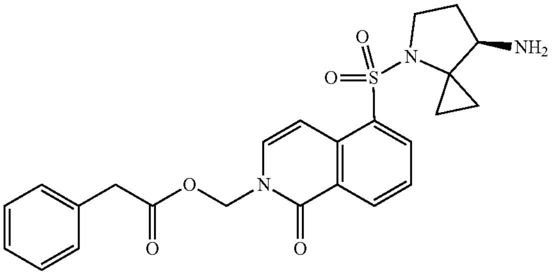
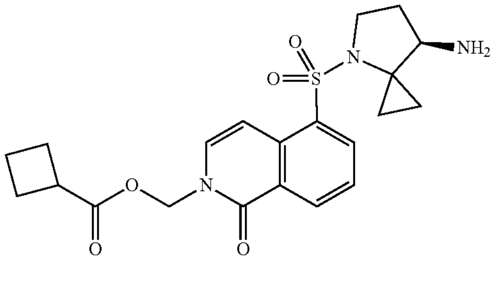
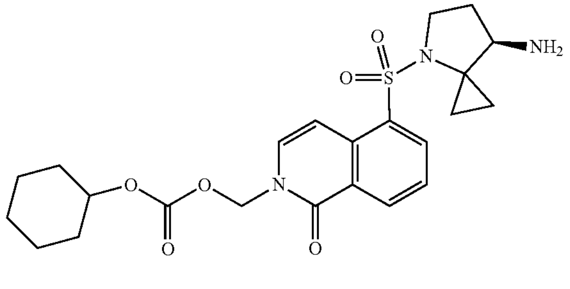

-continued
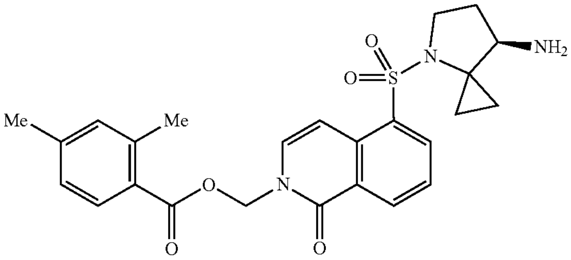
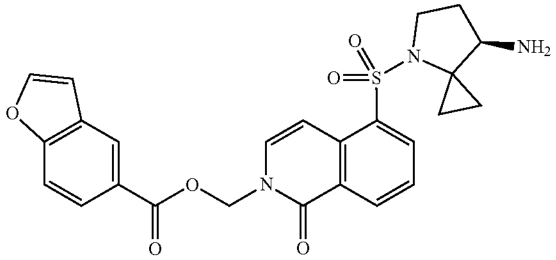
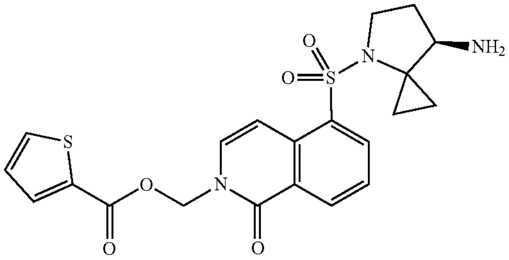
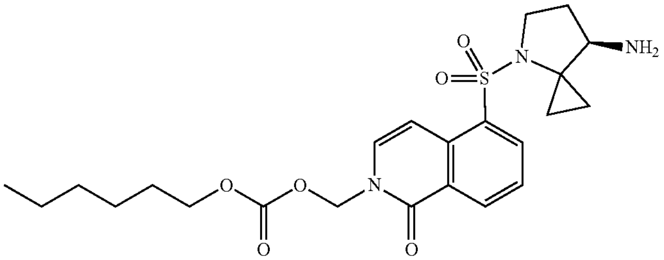
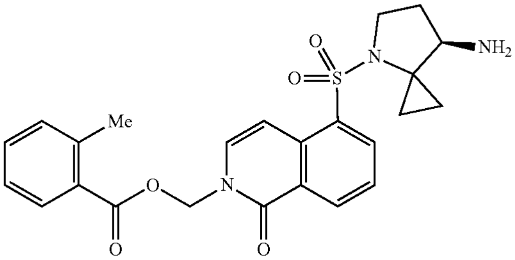
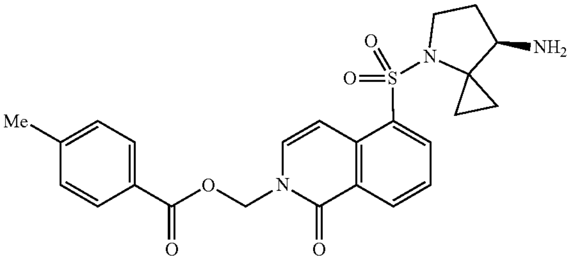
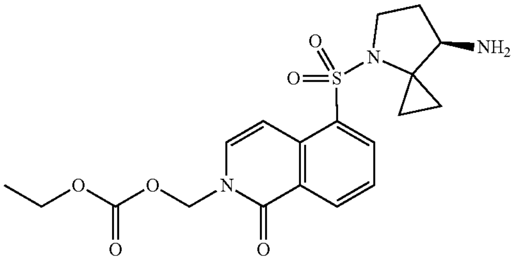
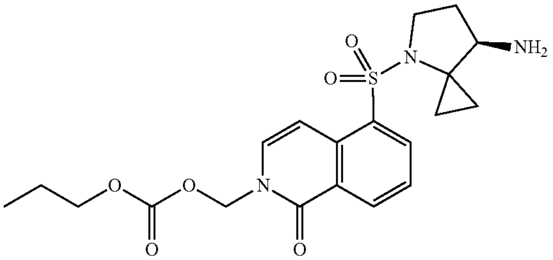
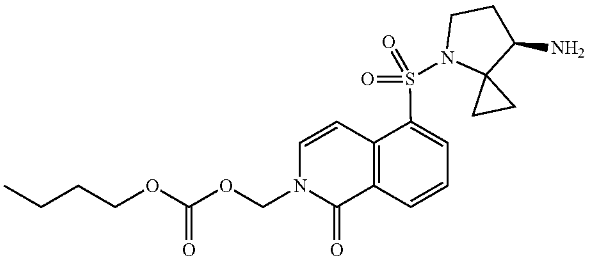

-continued
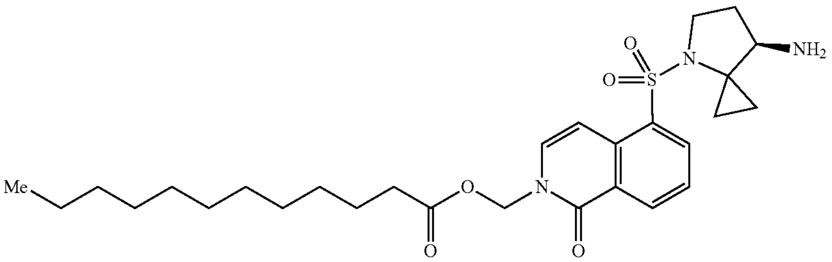
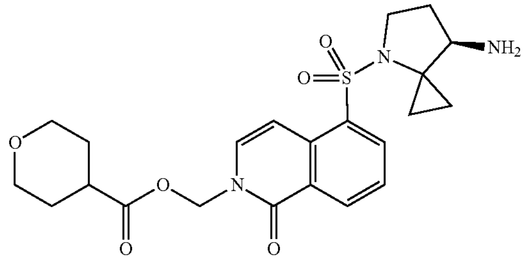
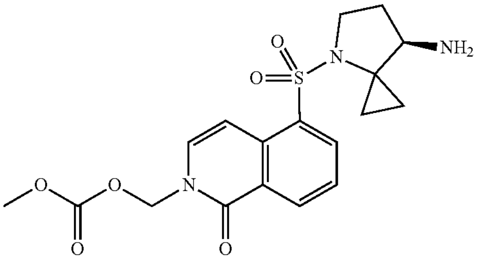
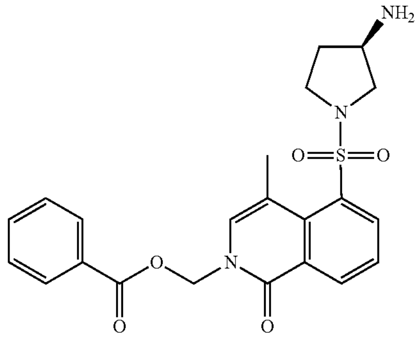
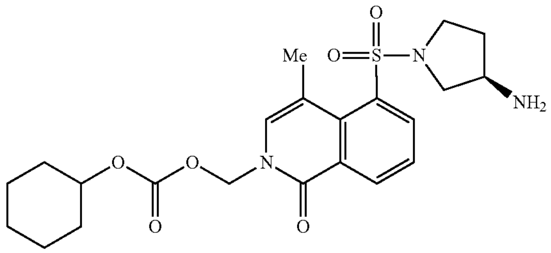
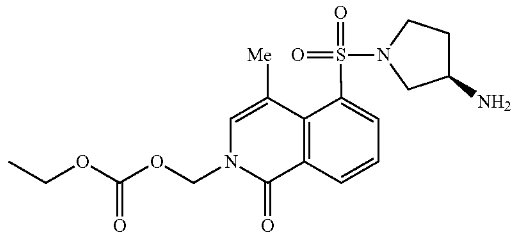
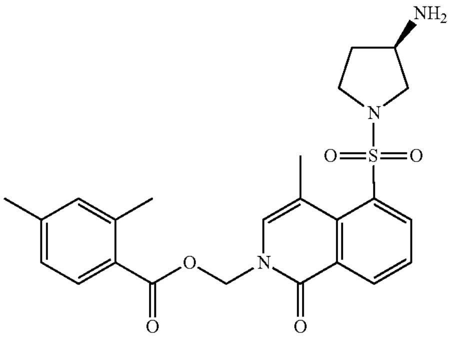
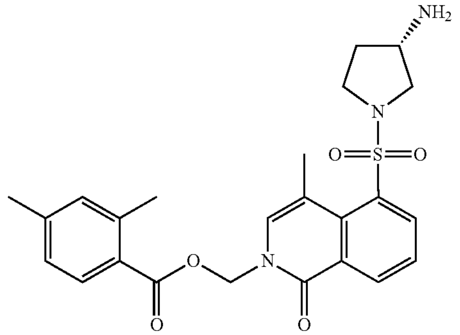
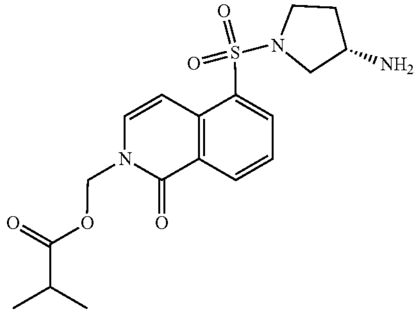

-continued
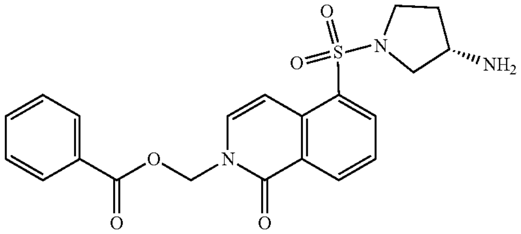
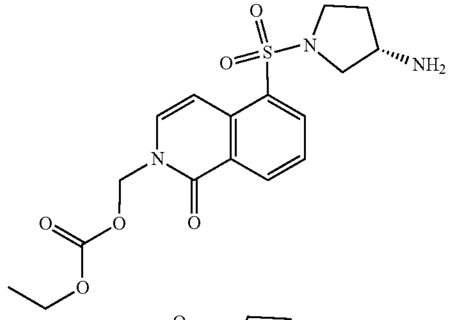
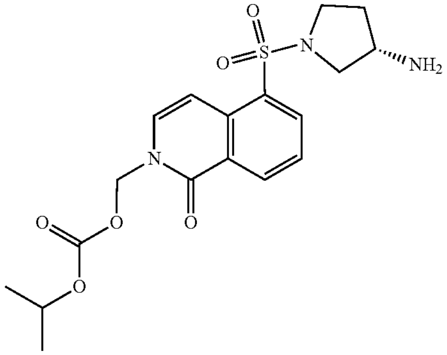
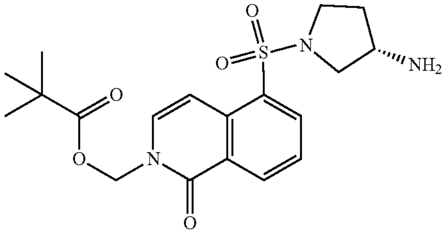
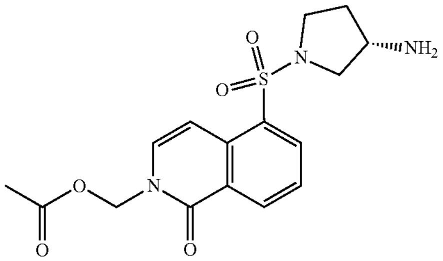
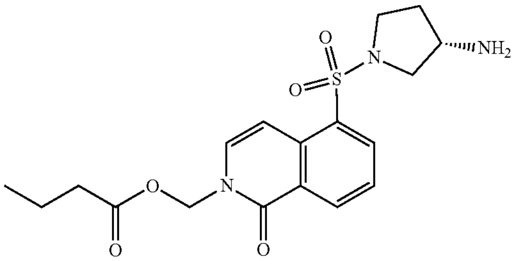
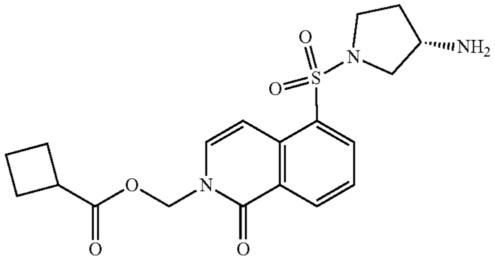
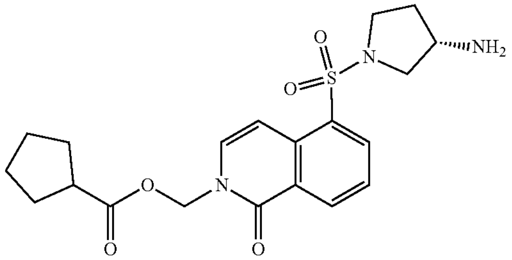
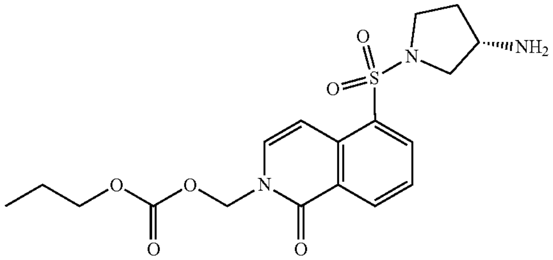
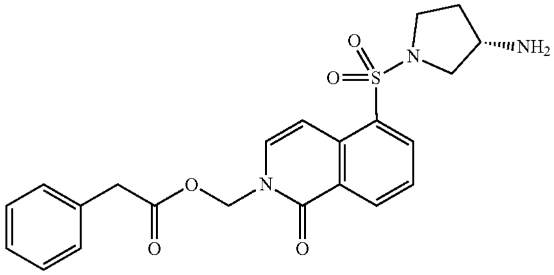
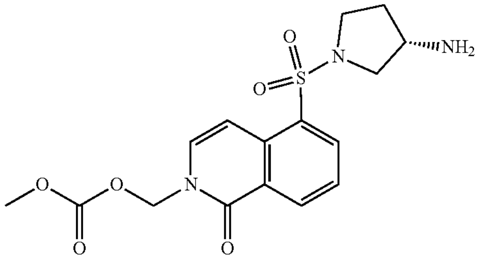
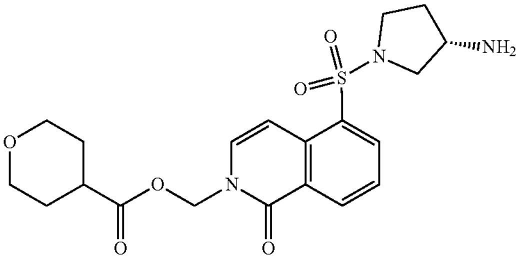

-continued
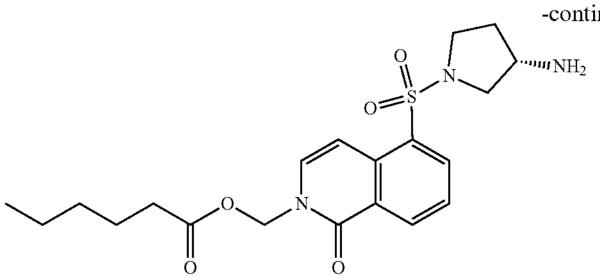
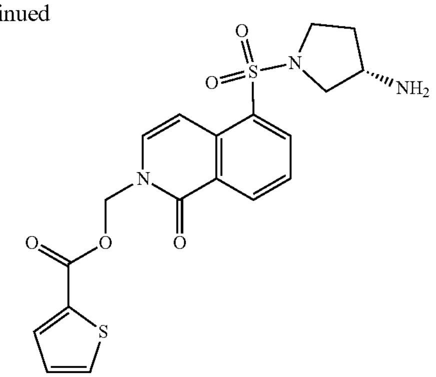
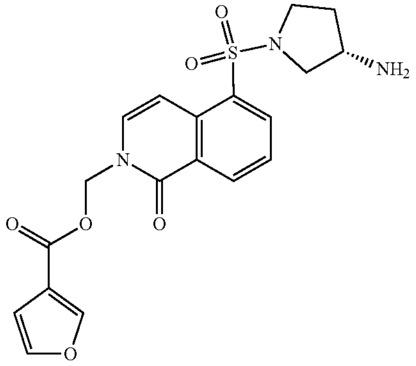
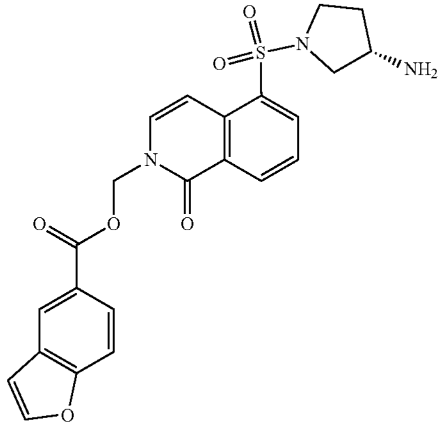
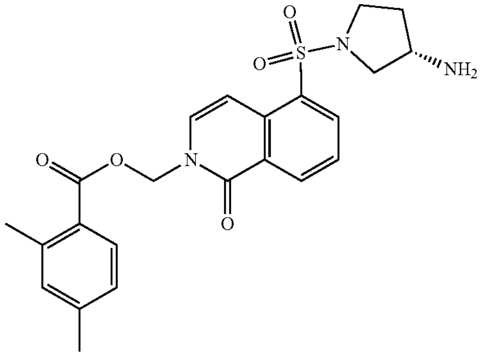
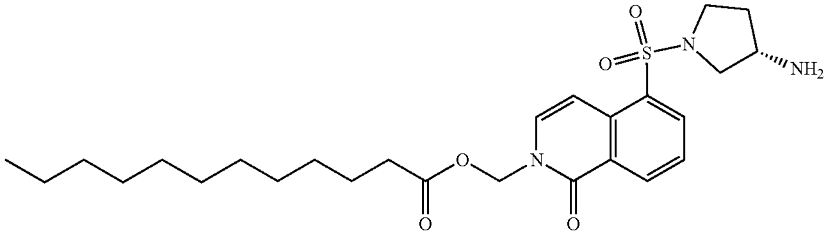
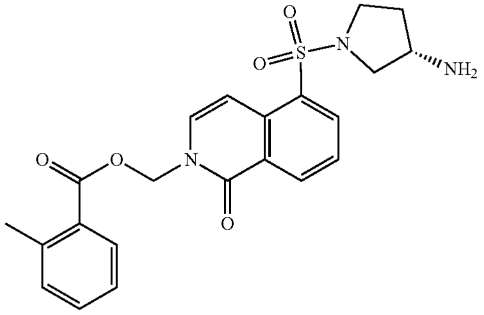
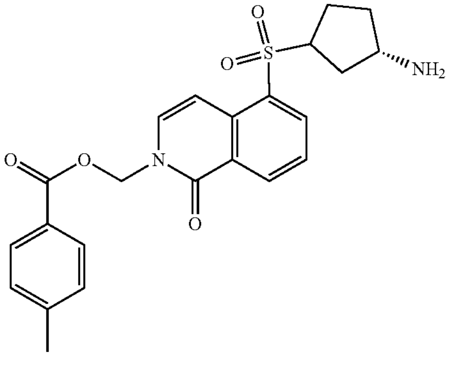

-continued
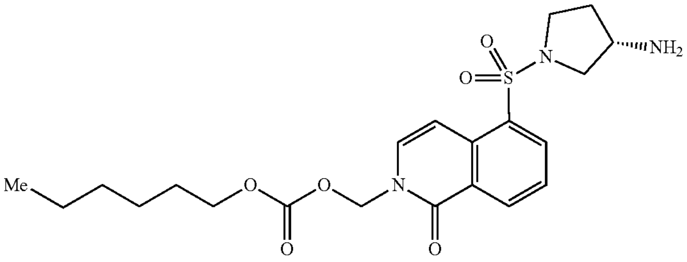
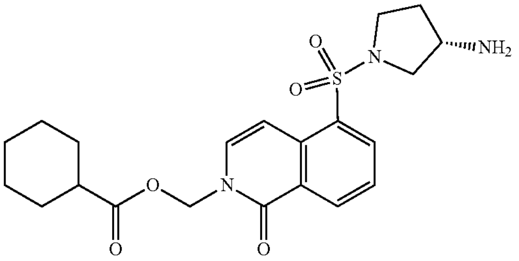
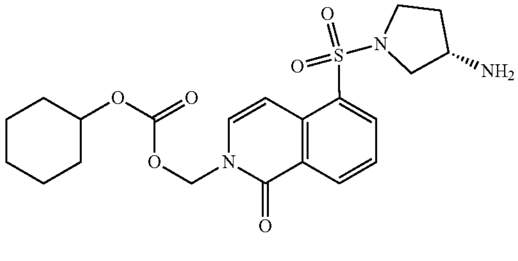
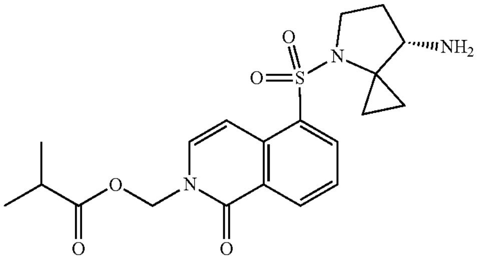
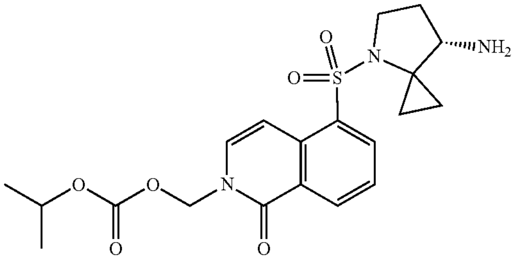
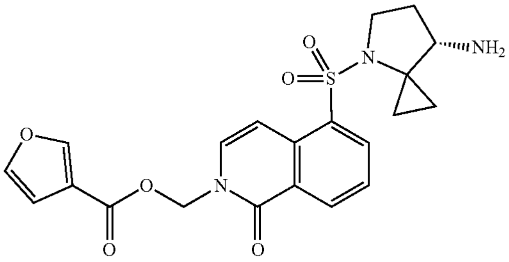
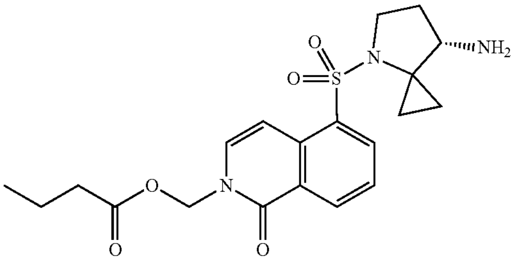
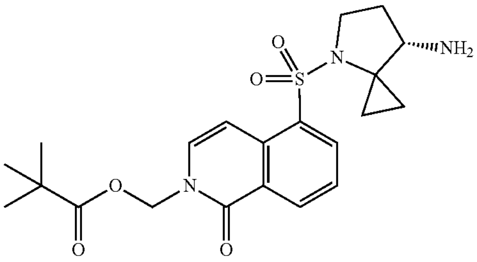
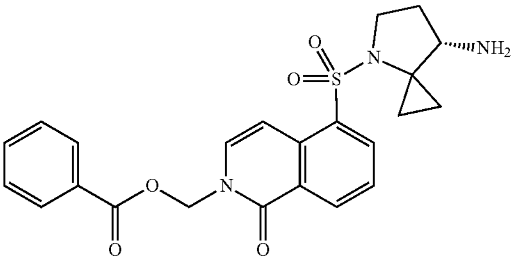
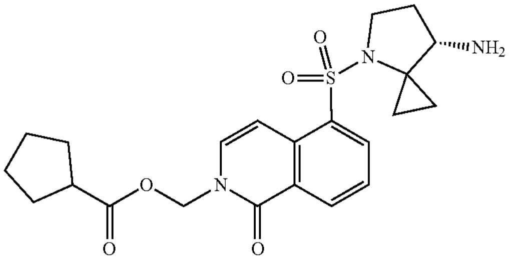
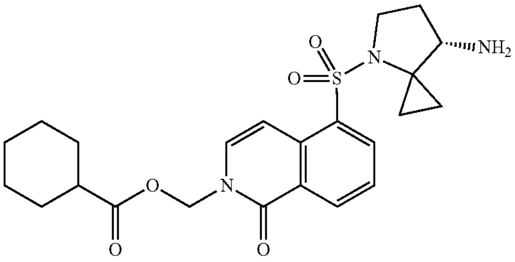

-continued
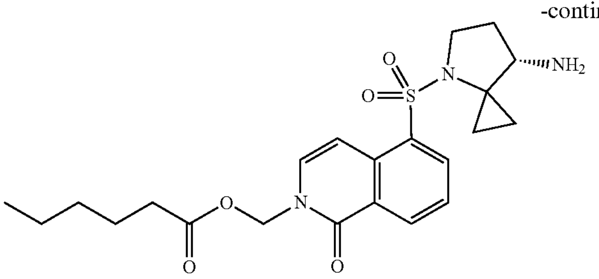
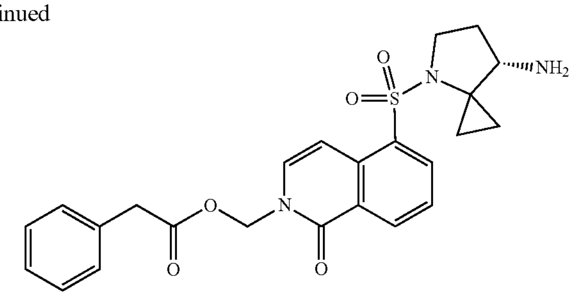
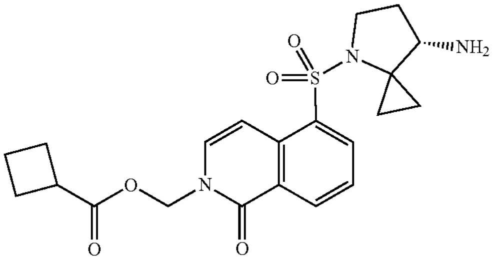
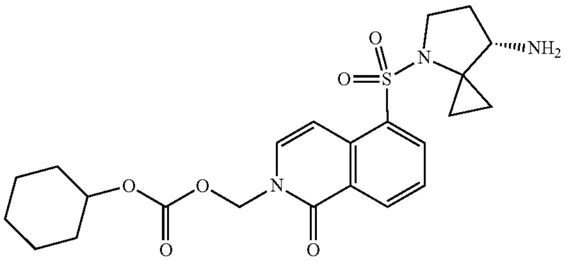
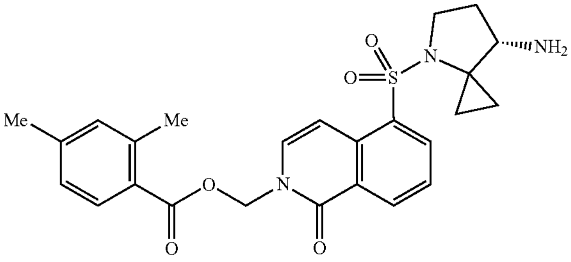
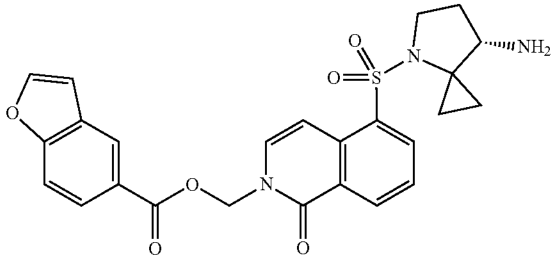
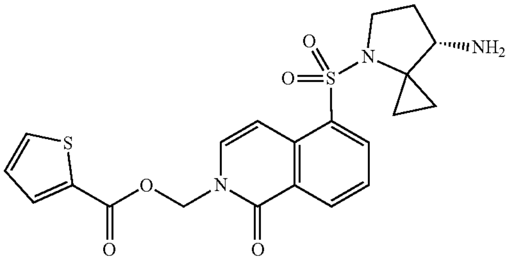
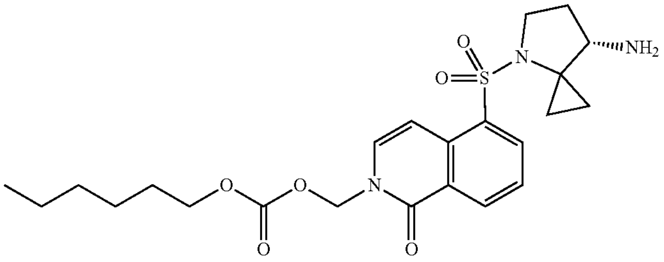
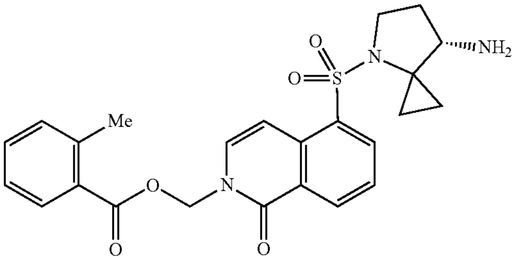
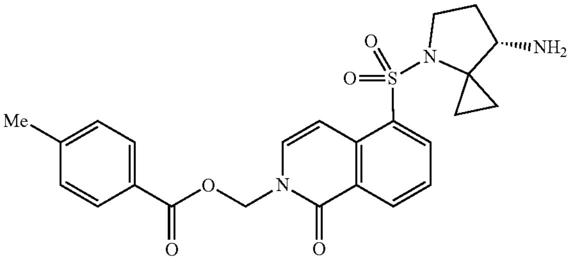

-continued
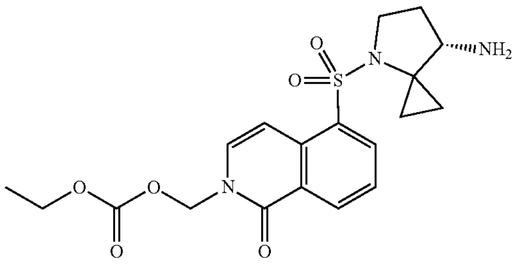
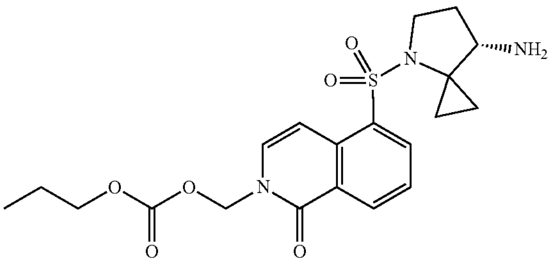
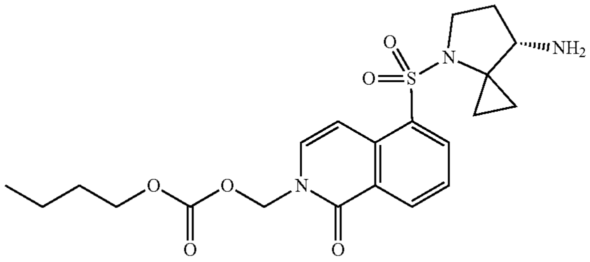
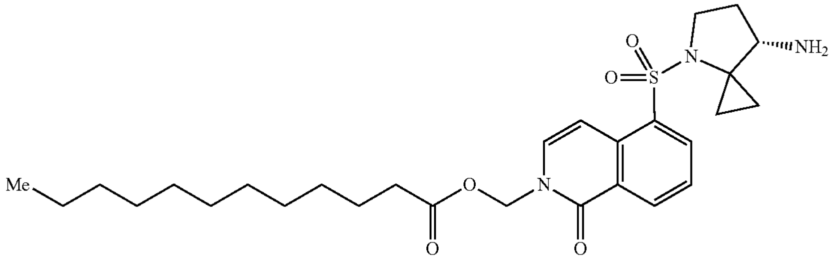
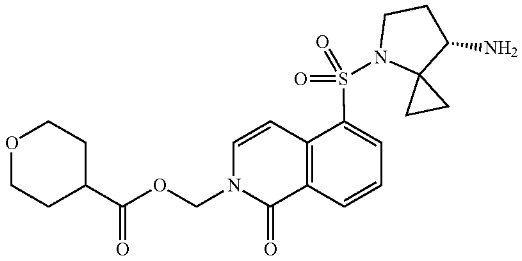
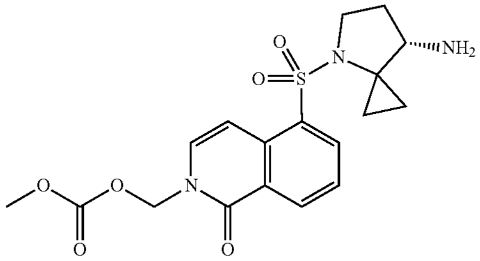
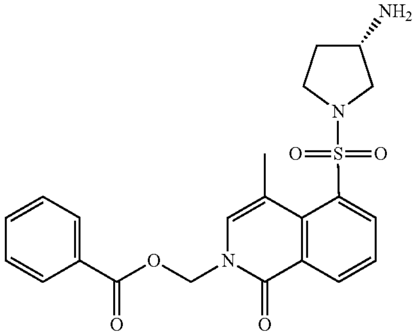
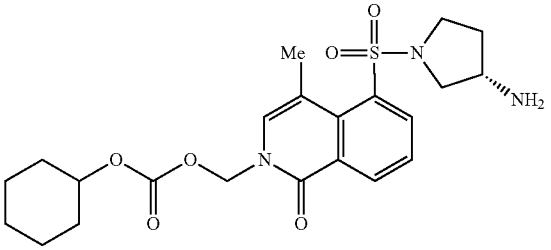
and
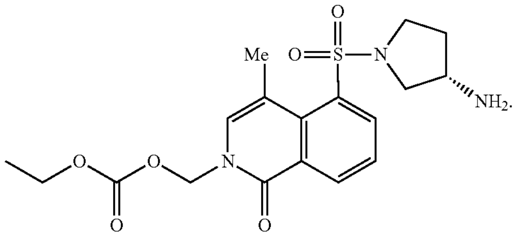

23. A pharmaceutical composition, comprising a therapeutically effective amount of the compound, the isomer thereof or the pharmaceutically acceptable salt thereof according to claim 1 and a pharmaceutically acceptable carrier.

24. A method of treating a disease associated with an ROCK protein kinase, comprising administrating a therapeutically effective amount of the compound, the isomer thereof or the pharmaceutically acceptable salt thereof according to claim 1 to a subject.

25. The method of claim 24, wherein the disease is selected from glaucoma or ocular hypertension.

* * * * *